US011851648B2

(12) United States Patent
Kawaoka et al.

(10) Patent No.: US 11,851,648 B2
(45) Date of Patent: Dec. 26, 2023

(54) HUMANIZED CELL LINE

(71) Applicants: Wisconsin Alumni Research Foundation (WARF), Madison, WI (US); The University of Tokyo, Tokyo (JP)

(72) Inventors: Yoshihiro Kawaoka, Middleton, WI (US); Kosuke Takada, Tokyo (JP); Masaki Imai, Kawasaki (JP)

(73) Assignees: Wisconsin Alumni Research Foundation (WARF), Madison, WI (US); The University of Tokyo, Tokyo (JP)

( * ) Notice: Subject to any disclaimer, the term of this patent is extended or adjusted under 35 U.S.C. 154(b) by 0 days.

(21) Appl. No.: 16/785,449

(22) Filed: Feb. 7, 2020

(65) Prior Publication Data

US 2020/0291384 A1 Sep. 17, 2020

Related U.S. Application Data

(60) Provisional application No. 62/803,266, filed on Feb. 8, 2019.

(51) Int. Cl.
| | |
|---|---|
| *C12N 5/10* | (2006.01) |
| *C12N 5/071* | (2010.01) |
| *C12N 9/10* | (2006.01) |
| *C12Q 1/04* | (2006.01) |
| *C12N 7/02* | (2006.01) |
| *C12N 15/10* | (2006.01) |

(52) U.S. Cl.
CPC ......... *C12N 15/102* (2013.01); *C12N 5/0602* (2013.01); *C12N 9/10* (2013.01); *C12Q 1/04* (2013.01); *C12Y 204/99001* (2013.01)

(58) Field of Classification Search
None
See application file for complete search history.

(56) References Cited

U.S. PATENT DOCUMENTS

| | | | |
|---|---|---|---|
| 4,071,618 A | 1/1978 | Konobe et al. |
| 4,659,569 A | 4/1987 | Mitsuhashi et al. |
| 5,166,057 A | 11/1992 | Palese et al. |
| 5,578,473 A | 11/1996 | Palese et al. |
| 5,716,821 A | 2/1998 | Wertz et al. |
| 5,750,394 A | 5/1998 | Palese et al. |
| 5,786,199 A | 7/1998 | Palese |
| 5,789,229 A | 8/1998 | Wertz et al. |
| 5,820,871 A | 10/1998 | Palese et al. |
| 5,840,520 A | 11/1998 | Clarke et al. |
| 5,854,037 A | 12/1998 | Palese et al. |
| 5,948,410 A | 9/1999 | Van Scharrenburg et al. |
| 5,994,526 A | 11/1999 | Meulewaeter et al. |
| 6,001,634 A | 12/1999 | Palese et al. |
| 6,033,886 A | 3/2000 | Conzelmann |
| 6,037,348 A | 3/2000 | Colacino et al. |
| 6,146,642 A | 11/2000 | Garcia-Sastre et al. |
| 6,169,175 B1 | 1/2001 | Frace et al. |
| 6,194,546 B1 | 2/2001 | Newton et al. |
| 6,270,958 B1 | 8/2001 | Olivo et al. |
| 6,271,011 B1 | 8/2001 | Lee et al. |
| 6,358,733 B1 | 3/2002 | Motwani et al. |
| 6,455,298 B1 | 9/2002 | Groner et al. |
| 6,544,785 B1 | 4/2003 | Palese et al. |
| 6,656,720 B2 | 12/2003 | Groner et al. |
| 6,825,036 B2 | 11/2004 | Makizumi et al. |
| 6,843,996 B1 | 1/2005 | Parkin et al. |
| 6,872,395 B2 | 3/2005 | Kawaoka |
| 6,890,710 B1 | 5/2005 | Palese et al. |
| 6,951,752 B2 | 10/2005 | Reiter et al. |
| 6,951,754 B2 | 10/2005 | Hoffmann |
| 6,974,695 B2 | 12/2005 | Vogels et al. |
| 7,037,707 B2 | 5/2006 | Webster et al. |
| 7,176,021 B2 | 2/2007 | Kawaoka |
| 7,211,378 B2 | 5/2007 | Kawaoka et al. |
| 7,226,774 B2 | 6/2007 | Kawaoka |
| 7,312,064 B2 | 12/2007 | Hoffmann |
| 7,335,356 B2 | 2/2008 | Hart et al. |
| 7,507,411 B2 | 3/2009 | Zhou et al. |
| 7,566,458 B2 | 7/2009 | Yang et al. |
| 7,585,657 B2 | 9/2009 | Kawaoka |
| 7,588,769 B2 | 9/2009 | Kawaoka |
| 7,601,356 B2 | 10/2009 | Jin et al. |
| 7,670,837 B2 | 3/2010 | Schwartz |
| 7,682,618 B2 | 3/2010 | Bavari et al. |
| 7,723,094 B2 | 5/2010 | Kawaoka et al. |
| 7,833,788 B2 | 11/2010 | Pau et al. |
| 7,883,844 B2 | 2/2011 | Nouchi et al. |
| 7,955,833 B2 | 6/2011 | Reiter et al. |
| 7,959,930 B2 | 6/2011 | De Wit et al. |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

Chung, C. (2016, Glycoengineering of Chinese Hamster Ovary Cells for Improving Biotherapeutics' Efficacies, A dissertation submitted to Johns Hopkins University, retrieved from the Internet «https://jscholarship.library.jne.edu/handle/1774.2/60731», retrieved on Mar. 1, 2022).*

(Continued)

*Primary Examiner* — Suzanne M Noakes
*Assistant Examiner* — Jae W Lee
(74) *Attorney, Agent, or Firm* — Schwegman Lundberg & Woessner, P.A.

(57) ABSTRACT

A mammalian or avian cell line that expresses high levels of human influenza virus receptors is provided. In one embodiment, the cell line supports human influenza virus, e.g., human A/H3 influenza virus, isolation and growth much more effectively than corresponding conventional (unmodified) cells or in corresponding human virus receptor-overexpressing cells, and the propagated viruses may maintain higher genetic stability than in the corresponding cells.

17 Claims, 19 Drawing Sheets

Figure 1A:
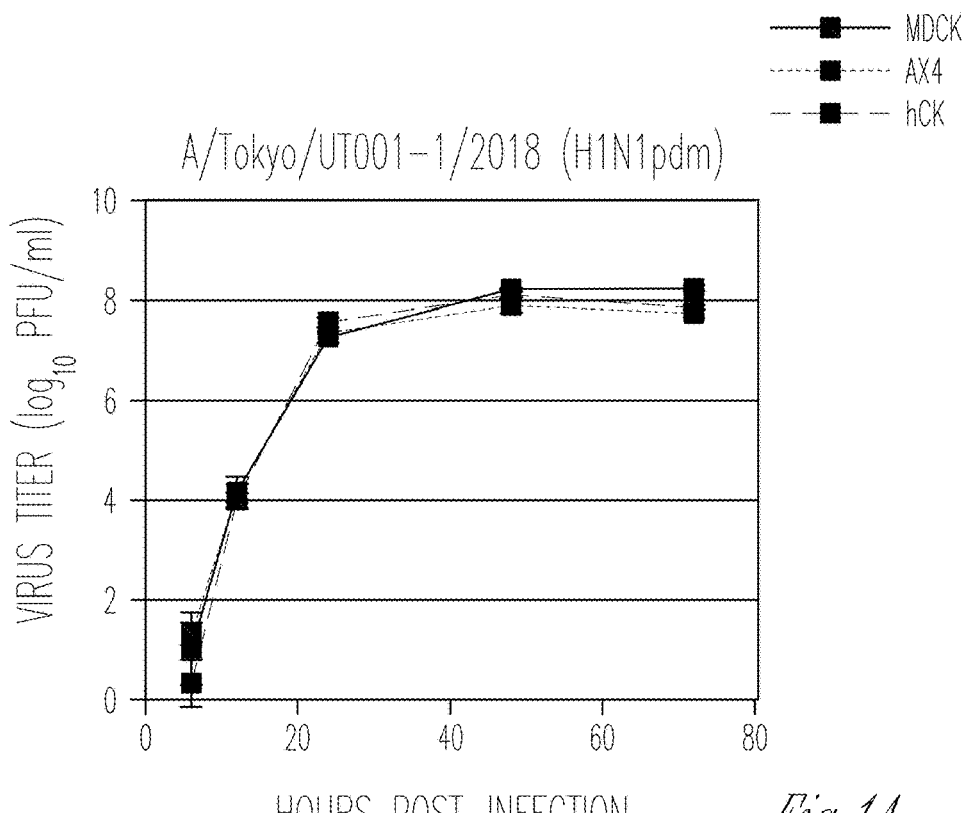

Specification includes a Sequence Listing.

(56) References Cited

U.S. PATENT DOCUMENTS

| | | |
|---|---|---|
| 7,968,101 B2 | 6/2011 | Kawaoka et al. |
| 7,972,843 B2 | 7/2011 | Hoffmann |
| 7,993,924 B2 | 8/2011 | Billeter et al. |
| 8,012,736 B2 | 9/2011 | Hoffman et al. |
| 8,043,856 B2 | 10/2011 | Kawaoka et al. |
| 8,048,430 B2 | 11/2011 | Yang et al. |
| 8,057,806 B2 | 11/2011 | Kawaoka et al. |
| 8,093,033 B2 | 1/2012 | Kemble et al. |
| 8,114,415 B2 | 2/2012 | Hoffmann et al. |
| 8,119,337 B2 | 2/2012 | Gregersen |
| 8,119,388 B2 | 2/2012 | Schwartz et al. |
| 8,298,805 B2 | 10/2012 | Kawaoka |
| 8,309,099 B2 | 11/2012 | Hoffmann |
| 8,354,114 B2 | 1/2013 | Lu et al. |
| 8,357,376 B2 | 1/2013 | Liu et al. |
| 8,409,843 B2 | 4/2013 | Kemble et al. |
| 8,460,914 B2 | 6/2013 | Gregersen |
| 8,465,960 B2 | 6/2013 | Kawaoka et al. |
| 8,475,806 B2 | 7/2013 | Kawaoka |
| 8,507,247 B2 | 8/2013 | Kawaoka et al. |
| 8,524,497 B2 | 9/2013 | Reiter et al. |
| 8,546,123 B2 | 10/2013 | Lewis |
| 8,574,591 B2 | 11/2013 | Hoffmann et al. |
| 8,574,593 B2 | 11/2013 | Yang et al. |
| 8,580,277 B2 | 11/2013 | Yang et al. |
| 8,591,914 B2 | 11/2013 | Yang et al. |
| 8,597,661 B2 | 12/2013 | Kawaoka et al. |
| 8,679,819 B2 | 3/2014 | Kawaoka |
| 8,877,209 B2 | 11/2014 | Kawaoka et al. |
| 8,900,595 B2 | 12/2014 | Kawaoka et al. |
| 9,101,653 B2 | 8/2015 | Kawaoka et al. |
| 9,109,013 B2 | 8/2015 | Kawaoka et al. |
| 9,222,118 B2 | 12/2015 | Kawaoka et al. |
| 9,254,318 B2 | 2/2016 | Kawaoka et al. |
| 9,284,533 B2 | 3/2016 | Bilsel et al. |
| 9,474,798 B2 | 10/2016 | Watanabe et al. |
| 9,757,446 B2 | 9/2017 | LeFebvre et al. |
| 9,890,363 B2 | 2/2018 | Kawaoka |
| 9,926,535 B2 | 3/2018 | Kawaoka et al. |
| 9,950,057 B2 | 4/2018 | Kawaoka et al. |
| 10,053,671 B2 | 8/2018 | Kawaoka et al. |
| 10,059,925 B2 | 8/2018 | Kawaoka et al. |
| 10,119,124 B2 | 11/2018 | Watanabe et al. |
| 10,130,697 B2 | 11/2018 | Watanabe |
| 10,172,934 B2 | 1/2019 | Kawaoka et al. |
| 10,246,686 B2 | 4/2019 | Kawaoka et al. |
| 10,358,630 B2 | 7/2019 | Kawaoka et al. |
| 10,494,613 B2 | 12/2019 | Kawaoka et al. |
| 10,513,692 B2 | 12/2019 | Kawaoka et al. |
| 10,633,422 B2 | 4/2020 | Kawaoka et al. |
| 10,808,229 B2 | 10/2020 | Kawaoka et al. |
| 11,007,262 B2 | 5/2021 | Watanabe et al. |
| 11,046,934 B2 | 6/2021 | Kawaoka et al. |
| 11,180,737 B2 | 11/2021 | Kawaoka et al. |
| 11,197,925 B2 | 12/2021 | Kawaoka et al. |
| 11,197,926 B2 | 12/2021 | Kawaoka et al. |
| 11,241,492 B2 | 2/2022 | Kawaoka et al. |
| 11,384,339 B2 | 7/2022 | Kawaoka et al. |
| 11,389,523 B2 | 7/2022 | Kawaoka et al. |
| 11,390,649 B2 | 7/2022 | Kawaoka et al. |
| 2002/0010143 A1 | 1/2002 | Barbosa et al. |
| 2002/0164770 A1 | 11/2002 | Hoffmann |
| 2002/0197705 A1 | 12/2002 | Kawaoka |
| 2003/0035814 A1 | 2/2003 | Kawaoka et al. |
| 2003/0044962 A1 | 3/2003 | Makizumi et al. |
| 2003/0073223 A1 | 4/2003 | Groner et al. |
| 2003/0119183 A1 | 6/2003 | Groner |
| 2003/0194694 A1 | 10/2003 | Kawaoka |
| 2003/0215794 A1 | 11/2003 | Kawaoka et al. |
| 2004/0002061 A1 | 1/2004 | Kawaoka |
| 2004/0029251 A1 | 2/2004 | Hoffman et al. |
| 2004/0057967 A1 | 3/2004 | Bavari et al. |
| 2004/0063141 A1 | 4/2004 | Lok |
| 2004/0077086 A1 | 4/2004 | Reiter et al. |
| 2004/0132164 A1 | 7/2004 | Doyle et al. |
| 2004/0142322 A1 | 7/2004 | Malcolm et al. |
| 2004/0219170 A1 | 11/2004 | Kawaoka |
| 2004/0241139 A1 | 12/2004 | Hobom et al. |
| 2004/0242518 A1 | 12/2004 | Chen et al. |
| 2005/0003349 A1 | 1/2005 | Kawaoka |
| 2005/0037487 A1 | 2/2005 | Kawaoka et al. |
| 2005/0095583 A1 | 5/2005 | Pekosz et al. |
| 2005/0118140 A1 | 6/2005 | Vorlop et al. |
| 2005/0158342 A1 | 7/2005 | Kemble et al. |
| 2005/0186563 A1 | 8/2005 | Hoffmann |
| 2005/0202553 A1 | 9/2005 | Groner et al. |
| 2005/0232950 A1 | 10/2005 | Kawaoka |
| 2005/0266023 A1 | 12/2005 | Bavari et al. |
| 2005/0266026 A1 | 12/2005 | Hoffmann et al. |
| 2006/0057116 A1 | 3/2006 | Kawaoka et al. |
| 2006/0088909 A1 | 4/2006 | Compans |
| 2006/0099609 A1 | 5/2006 | Bavari et al. |
| 2006/0134138 A1 | 6/2006 | Kawaoka et al. |
| 2006/0166321 A1 | 7/2006 | Kawaoka et al. |
| 2006/0188977 A1 | 8/2006 | Schwartz et al. |
| 2006/0216702 A1 | 9/2006 | Compans et al. |
| 2006/0240515 A1 | 10/2006 | Dimitrov et al. |
| 2006/0246092 A1 | 11/2006 | Neirynck et al. |
| 2007/0141699 A1 | 6/2007 | Kawaoka |
| 2007/0231348 A1 | 10/2007 | Kawaoka et al. |
| 2008/0009031 A1 | 1/2008 | Kawaoka |
| 2008/0187557 A1 | 8/2008 | Sambhara |
| 2008/0233560 A1 | 9/2008 | Hoffmann |
| 2008/0254067 A1 | 10/2008 | Trepanier et al. |
| 2008/0274141 A1 | 11/2008 | Groner et al. |
| 2008/0292658 A1 | 11/2008 | De Wit et al. |
| 2008/0293040 A1 | 11/2008 | Kawaoka et al. |
| 2008/0311148 A1 | 12/2008 | Hoffmann |
| 2008/0311149 A1 | 12/2008 | Hoffmann |
| 2009/0017444 A1 | 1/2009 | Kawaoka et al. |
| 2009/0047728 A1 | 2/2009 | Kawaoka et al. |
| 2009/0074812 A1 | 3/2009 | Watanabe et al. |
| 2009/0081252 A1 | 3/2009 | Gregersen |
| 2009/0181446 A1 | 7/2009 | Nouchi et al. |
| 2009/0311669 A1 | 12/2009 | Kawaoka |
| 2009/0324640 A1 | 12/2009 | Kawaoka et al. |
| 2010/0021499 A1 | 1/2010 | Bilsel et al. |
| 2010/0080825 A1 | 4/2010 | Kawaoka et al. |
| 2010/0112000 A1 | 5/2010 | Schwartz |
| 2010/0183671 A1 | 7/2010 | Gregersen et al. |
| 2010/0247572 A1 | 9/2010 | Kawaoka |
| 2010/0267116 A1 | 10/2010 | Kawaoka et al. |
| 2011/0020374 A1 | 1/2011 | Frazer |
| 2011/0027314 A1 | 2/2011 | Broeker |
| 2011/0045022 A1 | 2/2011 | Tsai |
| 2011/0081373 A1 | 4/2011 | Kawaoka et al. |
| 2011/0110978 A1 | 5/2011 | Kawaoka et al. |
| 2011/0159031 A1 | 6/2011 | Falkner et al. |
| 2011/0236417 A1 | 9/2011 | Watanabe et al. |
| 2011/0263554 A1 | 10/2011 | Kawaoka et al. |
| 2011/0300604 A1 | 12/2011 | Kawaoka et al. |
| 2012/0020997 A1 | 1/2012 | Hoffman et al. |
| 2012/0034600 A1 | 2/2012 | Gregersen |
| 2012/0058124 A1 | 3/2012 | Kurosawa et al. |
| 2012/0115206 A1 | 5/2012 | Schwartz et al. |
| 2012/0156241 A1 | 6/2012 | De Wit et al. |
| 2012/0207785 A1 | 8/2012 | Fabry et al. |
| 2013/0095135 A1 | 4/2013 | Collignon et al. |
| 2013/0183741 A1 | 7/2013 | Park et al. |
| 2013/0230552 A1 | 9/2013 | Kawaoka et al. |
| 2013/0243744 A1 | 9/2013 | Betenbaugh |
| 2013/0315929 A1 | 11/2013 | Bock |
| 2013/0316434 A1 | 11/2013 | Reiter et al. |
| 2014/0227310 A1 | 8/2014 | Li et al. |
| 2015/0017205 A1 | 1/2015 | Kawaoka et al. |
| 2015/0166967 A1 | 6/2015 | Kawaoka et al. |
| 2015/0307851 A1 | 10/2015 | Kawaoka et al. |
| 2015/0368621 A1 | 12/2015 | Kawaoka et al. |
| 2016/0024193 A1 | 1/2016 | Ayalon et al. |
| 2016/0024479 A1 | 1/2016 | Kawaoka et al. |
| 2016/0115518 A1 | 4/2016 | Kawaoka et al. |
| 2016/0208223 A1 | 7/2016 | Kawaoka et al. |
| 2016/0215040 A1 | 7/2016 | Kyratsous et al. |
| 2016/0355790 A1 | 12/2016 | Kawaoka et al. |

(56) References Cited

U.S. PATENT DOCUMENTS

| | | | |
|---|---|---|---|
| 2017/0058265 A1 | 3/2017 | Kawaoka et al. |
| 2017/0067029 A1 | 3/2017 | Kawaoka et al. |
| 2017/0096645 A1 | 4/2017 | Watanabe et al. |
| 2017/0097334 A1 | 4/2017 | Kawaoka et al. |
| 2017/0121391 A1 | 5/2017 | Kawaoka et al. |
| 2017/0258888 A1 | 9/2017 | Kawaoka |
| 2017/0298120 A1 | 10/2017 | Sasisekharan |
| 2017/0354730 A1 | 12/2017 | Kawaoka et al. |
| 2018/0245054 A1 | 8/2018 | Kawaoka et al. |
| 2018/0273588 A1 | 9/2018 | Kawaoka et al. |
| 2018/0340152 A1 | 11/2018 | Kawaoka et al. |
| 2019/0032023 A1 | 1/2019 | Kawaoka et al. |
| 2019/0048324 A1 | 2/2019 | Kawaoka et al. |
| 2019/0117759 A1 | 4/2019 | Wantanabe et al. |
| 2019/0167781 A1 | 6/2019 | Kawaoka et al. |
| 2020/0188506 A1 | 6/2020 | Kawaoka et al. |
| 2020/0237899 A1 | 7/2020 | Kawaoka et al. |
| 2020/0263142 A1 | 8/2020 | Kawaoka et al. |
| 2020/0263143 A1 | 8/2020 | Kawaoka et al. |
| 2021/0061862 A1 | 3/2021 | Kawaoka et al. |
| 2021/0102178 A1 | 4/2021 | Kawaoka et al. |
| 2021/0121545 A1 | 4/2021 | Knoll et al. |
| 2021/0228708 A1 | 7/2021 | Smith et al. |
| 2021/0246432 A1 | 8/2021 | Kawaoka et al. |
| 2021/0252130 A1 | 8/2021 | Watanabe et al. |
| 2021/0290754 A1 | 9/2021 | Kawaoka et al. |
| 2021/0299249 A1 | 9/2021 | Kawaoka et al. |
| 2022/0025339 A1 | 1/2022 | Kawaoka et al. |
| 2022/0202926 A1 | 6/2022 | Kawaoka et al. |
| 2022/0202927 A1 | 6/2022 | Kawaoka et al. |
| 2022/0241396 A1 | 8/2022 | Kawaoka et al. |
| 2023/0190913 A1 | 6/2023 | Kawaoka et al. |
| 2023/0192775 A1 | 6/2023 | Kawaoka et al. |

FOREIGN PATENT DOCUMENTS

| | | |
|---|---|---|
| AU | 2014290203 B2 | 12/2020 |
| AU | 2017221444 B2 | 11/2021 |
| AU | 2021201844 | 2/2023 |
| BR | PI0410702 B1 | 4/2022 |
| CA | 2379012 A1 | 1/2001 |
| CA | 2816242 C | 1/2019 |
| CA | 2525953 | 10/2023 |
| CN | 1826407 A | 8/2006 |
| CN | 101472941 A | 7/2009 |
| CN | 1826407 B | 9/2013 |
| CN | 105296356 A | 2/2016 |
| CN | 103540614 B | 2/2018 |
| CN | 109477074 A | 3/2019 |
| CN | 113874496 A | 12/2021 |
| CN | 114929269 A | 8/2022 |
| CN | 109477074 B | 1/2023 |
| EP | 0687471 A1 | 12/1995 |
| EP | 0700991 A1 | 3/1996 |
| EP | 0702085 A1 | 3/1996 |
| EP | 0704533 A1 | 4/1996 |
| EP | 1201760 A1 | 5/2002 |
| EP | 2010557 B1 | 2/2014 |
| EP | 1572910 B1 | 12/2015 |
| EP | 1631663 B1 | 8/2016 |
| EP | 2747778 B1 | 12/2017 |
| EP | 3009507 B1 | 6/2020 |
| EP | 2493912 B1 | 7/2020 |
| EP | 3022296 B1 | 12/2022 |
| IL | 171831 A | 5/2015 |
| JP | 07-203958 | 8/1995 |
| JP | H08510749 A | 11/1996 |
| JP | H10500113 A | 1/1998 |
| JP | 2002536992 A | 11/2002 |
| JP | 2003528570 A | 9/2003 |
| JP | 2004500842 A | 1/2004 |
| JP | 2004531232 A | 10/2004 |
| JP | 2005523698 A | 8/2005 |
| JP | 2005245302 A | 9/2005 |
| JP | 2005535288 A | 11/2005 |
| JP | 2006525815 A | 11/2006 |
| JP | 2007518395 A | 7/2007 |
| JP | 2007525175 A | 9/2007 |
| JP | 2007259758 | 10/2007 |
| JP | 2007529997 A | 11/2007 |
| JP | 2008500041 | 1/2008 |
| JP | 2008512443 | 4/2008 |
| JP | 2008520248 A | 6/2008 |
| JP | 2009511084 A | 3/2009 |
| JP | 2009514850 A | 4/2009 |
| JP | 2009523252 A | 6/2009 |
| JP | 2009532352 A | 9/2009 |
| JP | 2009539965 A | 11/2009 |
| JP | 2010530248 A | 9/2010 |
| JP | 2011530295 A | 12/2011 |
| JP | 4927290 | 5/2012 |
| JP | 4927290 B2 | 5/2012 |
| JP | 2013507990 A | 3/2013 |
| JP | 2013511280 A | 4/2013 |
| JP | 2013518059 | 5/2013 |
| JP | 2014039551 A | 3/2014 |
| JP | 2014131516 A | 7/2014 |
| JP | 2015501141 | 1/2015 |
| JP | 2016500007 A | 1/2016 |
| JP | 2016521553 A | 7/2016 |
| JP | 2016144463 A | 8/2016 |
| JP | 2016524915 A | 8/2016 |
| JP | 2016169225 A | 9/2016 |
| JP | 2017506903 | 3/2017 |
| JP | 2017527557 A | 9/2017 |
| JP | 2017197555 | 11/2017 |
| JP | 2018064493 A | 4/2018 |
| JP | 6352974 B2 | 6/2018 |
| JP | 637532982 | 7/2018 |
| JP | 2019510481 A | 4/2019 |
| JP | 2020010711 A | 1/2020 |
| JP | 2020114250 A | 7/2020 |
| JP | 2021500891 A | 1/2021 |
| JP | 2021036878 A | 3/2021 |
| JP | 2021184761 A | 12/2021 |
| JP | 2021533157 A | 12/2021 |
| JP | 2021536228 A | 12/2021 |
| JP | 2022066209 A | 4/2022 |
| JP | 2022522112 A | 4/2022 |
| JP | 2022527235 A | 6/2022 |
| JP | 2022172369 A | 11/2022 |
| JP | 2022551805 A | 12/2022 |
| JP | 2023011603 A | 1/2023 |
| JP | 7244455 | 3/2023 |
| JP | 2023511444 | 3/2023 |
| JP | 2023109845 | 8/2023 |
| KR | 101113432 B1 | 2/2012 |
| MX | 285206 | 3/2011 |
| NO | 341506 | 11/2017 |
| WO | WO-9610631 A1 | 4/1996 |
| WO | WO-9610632 A1 | 4/1996 |
| WO | WO-9640955 A1 | 12/1996 |
| WO | WO-9737000 A1 | 10/1997 |
| WO | WO-9802530 A1 | 1/1998 |
| WO | WO-9848834 A1 | 11/1998 |
| WO | WO-9853078 A1 | 11/1998 |
| WO | WO-9928445 A1 | 6/1999 |
| WO | WO-0053786 A1 | 9/2000 |
| WO | WO-0060050 A2 | 10/2000 |
| WO | WO-2000060050 A2 | 10/2000 |
| WO | WO-0060050 A3 | 1/2001 |
| WO | WO-2001004333 A1 | 1/2001 |
| WO | WO-2001025462 A1 | 4/2001 |
| WO | WO-0179273 A2 | 10/2001 |
| WO | WO-2001079273 A2 | 10/2001 |
| WO | WO-0183794 A2 | 11/2001 |
| WO | WO-2001083794 A2 | 11/2001 |
| WO | WO-0210143 A1 | 1/2002 |
| WO | WO-02064757 A2 | 8/2002 |
| WO | WO-02074795 A2 | 9/2002 |
| WO | WO-03068923 A2 | 8/2003 |
| WO | WO-2003068923 A2 | 8/2003 |
| WO | WO-03076462 A1 | 9/2003 |
| WO | WO-2003080846 A1 | 10/2003 |

(56) References Cited

FOREIGN PATENT DOCUMENTS

| | | |
|---|---|---|
| WO | WO-03091401 A2 | 11/2003 |
| WO | WO-2003091401 A2 | 11/2003 |
| WO | WO-2004094466 A2 | 11/2004 |
| WO | WO-04112831 A2 | 12/2004 |
| WO | WO-2004112831 A2 | 12/2004 |
| WO | WO-2004112831 A3 | 12/2004 |
| WO | WO-05028658 A2 | 3/2005 |
| WO | WO-05028658 A3 | 3/2005 |
| WO | WO-2005028658 A2 | 3/2005 |
| WO | WO-2005062820 A2 | 7/2005 |
| WO | WO-2006051069 A2 | 5/2006 |
| WO | WO-2007044024 A2 | 4/2007 |
| WO | WO-2007044024 A3 | 4/2007 |
| WO | WO-2007126810 A2 | 11/2007 |
| WO | WO-2007126810 A3 | 11/2007 |
| WO | WO-2007146057 A2 | 12/2007 |
| WO | WO-2007146057 A3 | 12/2007 |
| WO | WO-08156681 A3 | 12/2008 |
| WO | WO-2008147496 A2 | 12/2008 |
| WO | WO-2008147496 A3 | 12/2008 |
| WO | WO-2008156681 A2 | 12/2008 |
| WO | WO-2008156778 A2 | 12/2008 |
| WO | WO-2008156778 A3 | 12/2008 |
| WO | WO-2008157583 A1 | 12/2008 |
| WO | WO-09008921 A3 | 1/2009 |
| WO | WO-09008921 A9 | 1/2009 |
| WO | WO-2009007244 A2 | 1/2009 |
| WO | WO-2009008921 A2 | 1/2009 |
| WO | WO-2009014919 A2 | 1/2009 |
| WO | WO-2008156778 A9 | 2/2009 |
| WO | WO-09128867 A2 | 10/2009 |
| WO | 2009152181 | 12/2009 |
| WO | WO-2009128867 A3 | 3/2010 |
| WO | WO-2010053573 A2 | 5/2010 |
| WO | WO-2010053573 A3 | 7/2010 |
| WO | WO-2011014645 A1 | 2/2011 |
| WO | 2011063308 | 5/2011 |
| WO | WO-2011056591 A1 | 5/2011 |
| WO | WO-2011087839 A1 | 7/2011 |
| WO | WO-2011126370 A1 | 10/2011 |
| WO | WO-2011130627 A2 | 10/2011 |
| WO | WO-2012045882 A2 | 4/2012 |
| WO | WO-2012177924 A2 | 12/2012 |
| WO | WO-2013032942 A1 | 3/2013 |
| WO | WO-2013032942 A9 | 3/2013 |
| WO | WO-2013034069 A1 | 3/2013 |
| WO | WO-2013087945 A2 | 6/2013 |
| WO | WO-2013148302 A1 | 10/2013 |
| WO | WO-2014195920 A2 | 12/2014 |
| WO | WO-2015009743 A1 | 1/2015 |
| WO | 2015134488 | 9/2015 |
| WO | WO-2015142671 A2 | 9/2015 |
| WO | WO-2015196150 A2 | 12/2015 |
| WO | WO-2015196150 A3 | 12/2015 |
| WO | WO-2016144933 A1 | 9/2016 |
| WO | WO-2016207853 A2 | 12/2016 |
| WO | WO-2017007839 A1 | 1/2017 |
| WO | WO-2017040203 A1 | 3/2017 |
| WO | WO-2017136575 A1 | 8/2017 |
| WO | WO-2017143236 A1 | 8/2017 |
| WO | WO-2019084310 A1 | 5/2019 |
| WO | WO-2019241579 A1 | 12/2019 |
| WO | WO-2020033527 A2 | 2/2020 |
| WO | WO-2020041311 A1 | 2/2020 |
| WO | WO-2020/033527 A3 | 3/2020 |
| WO | WO-2020163804 A1 | 8/2020 |
| WO | WO-2020167432 A2 | 8/2020 |
| WO | WO-2020223699 A1 | 11/2020 |
| WO | WO-2020167432 A3 | 12/2020 |
| WO | WO-2020264141 A1 | 12/2020 |
| WO | WO-2021041624 A2 | 3/2021 |
| WO | WO-2021041624 A3 | 5/2021 |
| WO | WO-2021150874 A1 | 7/2021 |
| WO | WO-2021195410 A1 | 9/2021 |
| WO | WO-2021242597 A1 | 12/2021 |

OTHER PUBLICATIONS

ST3GAL6 Gene ID: 478535, <retrieved from the Internet << https://www.ncbi.nlm.nih.gov/gene/478535>>, retrieved on Sep. 14, 2022.*

Wang et al. (Glycoengineering of CHO Cells to Improve Product Quality, Methods in Molecular Biology book series (MIMB, vol. 1603), pp. 25-44, published online on May 11, 2017).*

"International Application Serial No. PCT US2020 017342, International Search Report dated Jun. 26, 2020", 6 pgs.

"International Application Serial No. PCT US2020 017342, Written Opinion dated Jun. 26, 2020", 6 pgs.

Matrosovich, M, "Overexpression of the [alpha]-2,6-sialyltransferase in MDCK cells increases influenza virus sensitivity to neuraminidase inhibitors", Journal of Virology, the American Society for Microbiology, US, vol. 77, No. 15, (Aug. 1, 2003), 8418-8425.

Takada, Kosuke, "A Humanized MDCK Cell Line for the Efficient Isolation and Propagation of Human Influenza Viruses", Nature Microbiology, Nature Publishing Group UK, London, vol. 4, No. 8, (Apr. 29, 2019), 1268-1273 (9 Pages).

"European Application Serial No. 20714015.3, Response to Communication persuant to Rules 161 and 162 filed Apr. 7, 2022", 10 pgs.

"International Application Serial No. PCT/US2020/017342, International Preliminary Report on Patentability dated Aug. 19, 2021", 8 pgs.

Result 1, NCBI Blast nucleotide search of SEQ ID No. 3, database "nr"; Result 4, NCBI Blast nucleotide search of SEQ ID No. 4, database "nr", (Jul. 22, 2006), 11 pgs.

Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.

Results 1, NCBI Blast nucleotide search of SEQ ID No. 7, database "nr"; Result 1, NCBI Blast nucleotide search of SEQ ID No. 8, database "nr", (Jul. 23, 2006), 8 pgs.

Result 17, NCBI Blast nucleotide search of SEQ ID No. 2, database "nr", (Jul. 18, 2006), 3 pgs.

Result 7, NCBI Blast nucleotide search of SEQ ID: 1, database "nr", (Jul. 18, 2006), 3 pgs.

FLUMIST™ Package Insert Template, [Online]. Retrieved from the Internet: http://www.fda.gov/downloads/BiologicsBloodVaccines!Vaccines/ApprovedProducts/UCM294307.pdf, (Mar. 1, 2012), 26 pgs.

"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.

"U.S. Appl. No. 10/855,975 Response filed Aug. 28, 2007 to Final Office Action datd Jun. 28, 2007", 16 pgs.

"2018-19 ACIP Background—Immunogenicity, Efficacy, and Effectiveness of Influenza Vaccines", [online]. [archived on Dec. 3, 2018]. Retrieved from the Internet: <URL: https://web.archive.org/web/20181203190316/https://www.cdc.gov/flu/professionals/acip/2018-2019/background/immunogenicity.htm>, (updated Aug. 23, 2018), 5 pgs.

"800.037US1 Final O.A Jun. 28, 2007", 5 pgs.

"Application Serial No. 04809419.7, Office Action dated Sep. 9, 2009", 3 pgs.

"U.S. Appl. No. 09/834,095, Advisory Action dated Jan. 8, 2004", 3 pgs.

"U.S. Appl. No. 09/834,095, Final Office Action dated Aug. 26, 2003", 12 pgs.

"U.S. Appl. No. 09/834,095, Non-Final Office Action dated Nov. 4, 2002", 12 pgs.

"U.S. Appl. No. 09/834,095, Notice of Allowance dated Sep. 27, 2004", 13 pgs.

"U.S. Appl. No. 09/834,095, Office Action dated Apr. 20, 2004", 11 pgs.

"U.S. Appl. No. 09/834,095, Response filed Feb. 4, 2003 to Office Action dated Nov. 4, 2002", 14 pgs.

(56) References Cited

OTHER PUBLICATIONS

"U.S. Appl. No. 09/834,095, Response filed Jun. 12, 2003 to Restriction Requirement dated Apr. 22, 2003", 2 pgs.
"U.S. Appl. No. 09/834,095, Response filed Jun. 18, 2004 to Office Action dated Apr. 20, 2004", 11 pgs.
"U.S. Appl. No. 09/834,095, Response filed Aug. 1, 2002 to Restriction Requirement dated Jul. 1, 2002", 3 pgs.
"U.S. Appl. No. 09/834,095, Response filed Nov. 26, 2003 to Final Office Action dated Aug. 26, 2003", 10 pgs.
"U.S. Appl. No. 09/834,095, Restriction Requirement dated Apr. 22, 2003", 5 pgs.
"U.S. Appl. No. 09/834,095, Restriction Requirement dated Jul. 1, 2002", 9 pgs.
"U.S. Appl. No. 09/834,095, Supplemental Amendment filed Aug. 4, 2004", 7 pgs.
"U.S. Appl. No. 10/081,170, Advisory Action dated Sep. 27, 2004", 3 pgs.
"U.S. Appl. No. 10/081,170, Final Office Action dated Apr. 12, 2006", 7 pgs.
"U.S. Appl. No. 10/081,170, Final Office Action dated Jul. 13, 2004", 8 pgs.
"U.S. Appl. No. 10/081,170, Non Final Office Action dated Jan. 15, 2004", 9 pgs.
"U.S. Appl. No. 10/081,170, Non Final Office Action dated Feb. 8, 2005", 9 pgs.
"U.S. Appl. No. 10/081,170, Non Final Office Action dated Aug. 24, 2005", 9 pgs.
"U.S. Appl. No. 10/081,170, Notice of Allowance dated Sep. 18, 2006", 8 pgs.
"U.S. Appl. No. 10/081,170, Preliminary Amendment filed May 20, 2003", 2 pgs.
"U.S. Appl. No. 10/081,170, Preliminary Amendment filed Jun. 6, 2002", 1 pg.
"U.S. Appl. No. 10/081,170, Response filed Jan. 24, 2006 to Non Final Office Action dated Aug. 24, 2005", 11 pgs.
"U.S. Appl. No. 10/081,170, Response filed Apr. 12, 2004 to Non Final Office Action dated Jan. 15, 2004", 12 pgs.
"U.S. Appl. No. 10/081,170, Response filed Jun. 8, 2005 to Non Final Office Action dated Feb. 8, 2005", 11 pgs.
"U.S. Appl. No. 10/081,170, Response filed Aug. 17, 2006 to Final Office Action dated Apr. 12, 2006", 9 pgs.
"U.S. Appl. No. 10/081,170, Response filed Sep. 13, 2004 to Final Office Action dated Jul. 13, 2004", 10 pgs.
"U.S. Appl. No. 10/081,170, Response filed Oct. 10, 2003 to Restriction Requirement dated Sep. 10, 2003", 3 pgs.
"U.S. Appl. No. 10/081,170, Restriction Requirement dated Sep. 10, 2003", 4 pgs.
"U.S. Appl. No. 10/353,856, Final Office Action dated Jun. 1, 2006", 10 pgs.
"U.S. Appl. No. 10/353,856, Non-Final Office Action dated Sep. 30, 2005", 9 pgs.
"U.S. Appl. No. 10/353,856, Non-Final Office Action dated Dec. 16, 2004", 11 pgs.
"U.S. Appl. No. 10/353,856, Notice of Allowance dated Oct. 18, 2006", 9 pgs.
"U.S. Appl. No. 10/353,856, Preliminary Amendment filed May 20, 2003", 2 pgs.
"U.S. Appl. No. 10/353,856, PTO Response to 312 Amendment dated Mar. 8, 2007", 2 pgs.
"U.S. Appl. No. 10/353,856, Response filed Feb. 28, 2006 to Non-Final Office Action dated Sep. 30, 2005", 10 pgs.
"U.S. Appl. No. 10/353,856, Response filed Apr. 7, 2005 to Non-Final Office Action dated Dec. 16, 2004", 10 pgs.
"U.S. Appl. No. 10/353,856, Response filed Aug. 17, 2006 to Final Office Action dated Jun. 1, 2006", 11 pgs.
"U.S. Appl. No. 10/353,856, Response filed Oct. 8, 2004 to Restriction Requirement dated Sep. 10, 2004", 2 pgs.
"U.S. Appl. No. 10/353,856, Restriction Requirement dated Sep. 10, 2004", 5 pgs.
"U.S. Appl. No. 10/353,856, Supplemental Amendment filed Jan. 9, 2007", 4 pgs.
"U.S. Appl. No. 10/353,856, Supplemental Preliminary Amendment filed Jun. 23, 2003", 4 pgs.
"U.S. Appl. No. 10/827,995, Final Office Action dated Nov. 15, 2006", 10 pgs.
"U.S. Appl. No. 10/827,995, Non-Final Office Action dated Jun. 2, 2006", 15 pgs.
"U.S. Appl. No. 10/827,995, Non-Final Office Action dated Oct. 25, 2007", 7 pgs.
"U.S. Appl. No. 10/827,995, Notice of Allowance dated Feb. 17, 2009", 9 pgs.
"U.S. Appl. No. 10/827,995, Notice of Allowance dated Jul. 2, 2008", 9 pgs.
"U.S. Appl. No. 10/827,995, Notice of Allowance dated Oct. 17, 2008", 7 pgs.
"U.S. Appl. No. 10/827,995, Notice of Non-Compliant Amendment dated Jul. 25, 2007", 4 pgs.
"U.S. Appl. No. 10/827,995, Proposed Examiner's Amendment dated Jun. 5, 2008", 6 pgs.
"U.S. Appl. No. 10/827,995, Response filed Mar. 3, 2008 to Office Action dated Oct. 25, 2007", 10 pgs.
"U.S. Appl. No. 10/827,995, Response filed May 14, 2007 Final Office Action dated Nov. 15, 2006", 16 pgs.
"U.S. Appl. No. 10/827,995, Response filed Aug. 13, 2007 to Notice of Non-Compliant Amendment dated Jul. 25, 2007", 16 pgs.
"U.S. Appl. No. 10/827,995, Response filed Aug. 17, 2006 Non-Final Office Action dated Jun. 2, 2006", 15 pgs.
"U.S. Appl. No. 10/855,875, Response filed May 17, 2012 to Non Final Office Action dated Mar. 15, 2012", 15 pgs.
"U.S. Appl. No. 10/855,875, Final Office Action dated Mar. 11, 2008", FOAR, 20 Pgs.
"U.S. Appl. No. 10/855,875, Final Office Action dated Aug. 2, 2006", 34 pgs.
"U.S. Appl. No. 10/855,875, Final Office Action dated Dec. 10, 2010", 15 pgs.
"U.S. Appl. No. 10/855,875, Non Final Office Action dated Mar. 15, 2012", 15 pgs.
"U.S. Appl. No. 10/855,875, Non-Final Office Action dated Feb. 19, 2010", 7 pgs.
"U.S. Appl. No. 10/855,875, Non-Final Office Action dated May 3, 2007", 13 pgs.
"U.S. Appl. No. 10/855,875, Non-Final Office Action dated Aug. 7, 2009", 32 pgs.
"U.S. Appl. No. 10/855,875, Non-Final Office Action dated Nov. 6, 2008", 12 pgs.
"U.S. Appl. No. 10/855,875, Non-Final Office Action dated Nov. 30, 2005", 13 pgs.
"U.S. Appl. No. 10/855,875, Notice of Allowance dated Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action dated Aug. 2, 2007", 14 pgs.
"U.S. Appl. No. 10/855,875, Response filed Mar. 18, 2011 to Final Office Action dated Dec. 10, 2010", 15 pgs.
"U.S. Appl. No. 10/855,875, Response filed Aug. 17, 2010 to Non Final Office Action dated Feb. 19, 2010", 20 pgs.
"U.S. Appl. No. 10/855,875, Response filed Dec. 7, 2009 to Non Final Office Action dated Aug. 7, 2009", 15 pgs.
"U.S. Appl. No. 10/855,875, Response filed Mar. 31, 2009 to Non Final Office Action dated Nov. 6, 2008", 14 pgs.
"U.S. Appl. No. 10/855,875, Response filed May 1, 2006 Non-Final Office Action dated Nov. 30, 2005", 13 pgs.
"U.S. Appl. No. 10/855,875, Response filed Aug. 18, 2008 to final Office Action dated Mar. 11, 2008", 15 pgs.
"U.S. Appl. No. 10/855,875, Response filed Sep. 20, 2005 to Restriction Requirement dated Jul. 26, 2005", 4 pgs.
"U.S. Appl. No. 10/855,875, Restriction Requirement dated Dec. 23, 2011", 9 pgs.
"U.S. Appl. No. 10/855,875, Restriction Requirement dated Jul. 26, 2005", 9 pgs.

(56) References Cited

OTHER PUBLICATIONS

"U.S. Appl. No. 10/855,975, Advisory Action dated Sep. 6, 2006", 3 pgs.

"U.S. Appl. No. 10/855,975, Advisory Action dated Sep. 13, 2007", 3 pgs.

"U.S. Appl. No. 10/855,975, Advisory Action dated Dec. 24, 2008", 4 pgs.

"U.S. Appl. No. 10/855,975, Final Office Action dated May 17, 2006", 7 pgs.

"U.S. Appl. No. 10/855,975, Final Office Action dated Jun. 28, 2007", 7 pgs.

"U.S. Appl. No. 10/855,975, Final Office Action dated Aug. 7, 2008", 5 pgs.

"U.S. Appl. No. 10/855,975, Non-Final Office Action dated Jan. 4, 2008", 10 pgs.

"U.S. Appl. No. 10/855,975, Non-Final Office Action dated Jan. 19, 2007", 7 pgs.

"U.S. Appl. No. 10/855,975, Non-Final Office Action dated May 29, 2009", 5 pgs.

"U.S. Appl. No. 10/855,975, Non-Final Office Action dated Nov. 30, 2005", 11 pgs.

"U.S. Appl. No. 10/855,975, Notice of Allowance dated Dec. 16, 2009", 19 pgs.

"U.S. Appl. No. 10/855,975, Response filed Jan. 29, 2009 to Advisory Action dated Dec. 24, 2008", 15 pgs.

"U.S. Appl. No. 10/855,975, Response filed Feb. 28, 2006 to Non-Final Office Action dated Nov. 30, 2005", 15 pgs.

"U.S. Appl. No. 10/855,975, Response filed Apr. 3, 2008 to Non Final Office Action dated Jan. 4, 2008", 16 pgs.

"U.S. Appl. No. 10/855,975, Response filed Apr. 19, 2007 to Non-Final Office Action dated Jan. 19, 2007", 16 pgs.

"U.S. Appl. No. 10/855,975, Response filed Aug. 13, 2009 to Non Final Office Action dated May 29, 2009", 19 pgs.

"U.S. Appl. No. 10/855,975, Response filed Aug. 17, 2006 to Final Office Action dated May 17, 2006", 13 pgs.

"U.S. Appl. No. 10/855,975, Response filed Aug. 28, 2007 to Final Office Action dated Jun. 28, 2007", 15 pgs.

"U.S. Appl. No. 10/855,975, Response filed Sep. 28, 2005 to Restriction Requirement dated Jul. 12, 2005", 3 pgs.

"U.S. Appl. No. 10/855,975, Response filed Dec. 11, 2008 to Final Office Action dated Aug. 7, 2008", 14 pgs.

"U.S. Appl. No. 10/855,975, Restriction Requirement dated Jul. 12, 2005", 8 pgs.

"U.S. Appl. No. 10/855,875, Response filed Nov. 2, 2007 to Office Action dated May 3, 2007", 16 pgs.

"U.S. Appl. No. 11/043,768 Non-Final Office Action dated Sep. 27, 2010", 8 pgs.

"U.S. Appl. No. 11/043,768, Final Office Action dated Jun. 27, 2008", 8 pgs.

"U.S. Appl. No. 11/043,768, Non-Final Office Action dated Feb. 23, 2010", 6 pgs.

"U.S. Appl. No. 11/043,768, Non-Final Office Action dated Feb. 23, 2009", 7 pgs.

"U.S. Appl. No. 11/043,768, Non-Final Office Action dated Nov. 28, 2007", 9 pgs.

"U.S. Appl. No. 11/043,768, Notice of Allowance dated Jun. 29, 2011", 12 pgs.

"U.S. Appl. No. 11/043,768, Response filed May 2, 2011 to Final Office Action dated Feb. 3, 2011", 11 pgs.

"U.S. Appl. No. 11/043,768, Response filed Jun. 15, 2010 to Non Final Office Action dated Feb. 23, 2010", 9 pgs.

"U.S. Appl. No. 11/043,768, Response filed Jun. 23, 2009 to Non-Final Office Action dated Feb. 23, 2009", 9 pgs.

"U.S. Appl. No. 11/043,768, Response filed Sep. 13, 2007 to Restriction Requirement dated Mar. 13, 2007", 10 pgs.

"U.S. Appl. No. 11/043,768, Response filed Oct. 26, 2010 to Non Final Office Action dated Sep. 27, 2010", 11 pgs.

"U.S. Appl. No. 11/043,768, Response filed Dec. 12, 2008 to Final Office Action dated Jun. 27, 2008", 9 pgs.

"U.S. Appl. No. 11/043,768, Response filed Mar. 10, 2008 to Office Action dated Nov. 28, 2007", 12 pgs.

"U.S. Appl. No. 11/043,768, Restriction Requirement dated Mar. 13, 2007", 9 pgs.

"U.S. Appl. No. 11/043,786, Final Office Action dated Feb. 3, 2011", 10 pgs.

"U.S. Appl. No. 11/283,498, Non Final Office Action dated Sep. 3, 2009", 5 pgs.

"U.S. Appl. No. 11/283,498, Non Final Office Action dated Jul. 9, 2007", 7 pgs.

"U.S. Appl. No. 11/283,498, Non-Final Office Action dated Jan. 23, 2008", 20 pgs.

"U.S. Appl. No. 11/283,498, Non-Final Office Action dated Apr. 29, 2010", 10 pgs.

"U.S. Appl. No. 11/283,498, Notice of Allowance dated Feb. 23, 2011", 9 pgs.

"U.S. Appl. No. 11/283,498, Response filed Jan. 4, 2010 to Non Final Office Action dated Sep. 3, 2009", 12 pgs.

"U.S. Appl. No. 11/283,498, Response filed Oct. 28, 2010 to Non Final Office Action dated Apr. 29, 2010", 13 pgs.

"U.S. Appl. No. 11/283,498, Response filed Nov. 7, 2007 to Office Action dated Jul. 9, 2007", 17 pgs.

"U.S. Appl. No. 11/283,498, Response filed Apr. 16, 2007 to Restriction Requirement dated Oct. 16, 2006", 17 pgs.

"U.S. Appl. No. 11/283,498, Response filed Jul. 22, 2008 to Non Final Office Action dated Jan. 23, 2008", 12 pgs.

"U.S. Appl. No. 11/283,498, Restriction Requirement dated Oct. 16, 2006", 6 pgs.

"U.S. Appl. No. 11/283,498, Supplemental Amendment Response to Non Final Office Action dated Oct. 28, 2010", 11 pgs.

"U.S. Appl. No. 11/509,249, Final Office Action dated Jun. 12, 2008", 5 pgs.

"U.S. Appl. No. 11/509,249, Non Final Office Action with Restriction Requirement dated Aug. 24, 2007", 8 pgs.

"U.S. Appl. No. 11/509,249, Notice of Allowance dated Apr. 9, 2009", 7 pgs.

"U.S. Appl. No. 11/509,249, Notice of Allowance dated Nov. 17, 2008", 4 pgs.

"U.S. Appl. No. 11/509,249, Response filed Feb. 20, 2008 to Non Final Office Action dated Aug. 24, 2007", 11 pgs.

"U.S. Appl. No. 11/509,249, Response filed Oct. 6, 2008 to Office Action dated Jun. 12, 2008", 11 pgs.

"U.S. Appl. No. 11/644,179 , Response filed Oct. 21, 2013 to Final Office Action dated May 21, 2013", 8 pgs.

"U.S. Appl. No. 11/644,179, Final Office Action dated May 21, 2013", 11 pgs.

"U.S. Appl. No. 11/644,179, Final Office Action dated Jul. 2, 2010", 8 pgs.

"U.S. Appl. No. 11/644,179, Non Final Office Action dated Nov. 29, 2012", 19 pgs.

"U.S. Appl. No. 11/644,179, Non Final Office Action dated Dec. 8, 2009", 7 pgs.

"U.S. Appl. No. 11/644,179, Notice of Allowance dated Nov. 1, 2013", 11 pgs.

"U.S. Appl. No. 11/644,179, Preliminary Amendment filed Dec. 22, 2006", 5 pgs.

"U.S. Appl. No. 11/644,179, Response filed Jan. 30, 2008 to Restriction Requirement dated Oct. 30, 2007", 5 pgs.

"U.S. Appl. No. 11/644,179, Response filed Apr. 8, 2010 to Non Final Office Action dated Dec. 8, 2009", 8 pgs.

"U.S. Appl. No. 11/644,179, Response filed Aug. 17, 2010 to Final Office Action dated Jul. 2, 2010", 8 pgs.

"U.S. Appl. No. 11/644,179, Restriction Requirement dated Oct. 30, 2007", 7 pgs.

"U.S. Appl. No. 11/644,179, Supplemental Preliminary Amendment filed Feb. 6, 2008", 6 pgs.

"U.S. Appl. No. 11/644,179. Response filed Feb. 20, 2013 to Non Final Office Action dated Nov. 29, 2012", 10 pgs.

"U.S. Appl. No. 11/654,863 Final Office Action dated Jul. 17, 2017", 11 pgs.

"U.S. Appl. No. 11/654,863 Restriction Requirement dated Sep. 3, 2010", 5 pgs.

(56) References Cited

OTHER PUBLICATIONS

"U.S. Appl. No. 11/654,863, Appeal Brief filed Apr. 30, 2014", 22 pgs.
"U.S. Appl. No. 11/654,863, Appeal Decision dated Aug. 3, 2016", 11 pgs.
"U.S. Appl. No. 11/654,863, Decision on Pre-Appeal Brief Request dated Dec. 5, 2013", 2 pgs.
"U.S. Appl. No. 11/654,863, Declaration of Dr. Heinz Feldmann dated Jan. 9, 2018", 2 pgs.
"U.S. Appl. No. 11/654,863, Declaration of Yoshihiro Kawaoka dated Apr. 18, 2012", 2 pgs.
"U.S. Appl. No. 11/654,863, Examiner's Answer to Appeal Brief dated Jun. 18, 2014", 10 pgs.
"U.S. Appl. No. 11/654,863, Final Office Action dated Jul. 11, 2013", 9 pgs.
"U.S. Appl. No. 11/654,863, Final Office Action dated Sep. 12, 2018", 12 pgs.
"U.S. Appl. No. 11/654,863, Final Office Action dated Oct. 25, 2011", 9 pgs.
"U.S. Appl. No. 11/654,863, Non Final Office Action dated Feb. 11, 2013", 10 pgs.
"U.S. Appl. No. 11/654,863, Non Final Office Action dated Mar. 29, 2018", 12 pgs.
"U.S. Appl. No. 11/654,863, Non Final Office Action dated Jun. 27, 2011", 9 pgs.
"U.S. Appl. No. 11/654,863, Non Final Office Action dated Dec. 2, 2010", 8 pgs.
"U.S. Appl. No. 11/654,863, Non Final Office Action dated Dec. 21, 2016", 14 pgs.
"U.S. Appl. No. 11/654,863, Pre-Appeal Brief Request filed Nov. 11, 2013", 5 pgs.
"U.S. Appl. No. 11/654,863, Preliminary Amendment filed May 7, 2007", 15 pgs.
"U.S. Appl. No. 11/654,863, Reply Brief filed Aug. 18, 2014", 6 pgs.
"U.S. Appl. No. 11/654,863, Response filed Jan. 17, 2018 to Final Office Action dated Jul. 17, 2017", 9 pgs.
"U.S. Appl. No. 11/654,863, Response filed Apr. 18, 2012 to Final Office Action dated Oct. 25, 2011", 8 pgs.
"U.S. Appl. No. 11/654,863, Response filed Jun. 2, 2011 to Non Final Office Action dated Dec. 2, 2010", 6 pgs.
"U.S. Appl. No. 11/654,863, Response filed Jun. 7, 2013 to Non Final Office Action dated Feb. 11, 2013", 10 pgs.
"U.S. Appl. No. 11/654,863, Response filed Jun. 21, 2017 to Non Final Office Action dated Dec. 21, 2016", 11 pgs.
"U.S. Appl. No. 11/654,863, Response filed Jul. 9, 2018 to Non Final Office Action dated Mar. 29, 2018", 10 pgs.
"U.S. Appl. No. 11/654,863, Response filed Sep. 28, 2010 to Restriction Requirement dated Sep. 3, 2010", 6 pgs.
"U.S. Appl. No. 11/654,863, Response filed Oct. 6, 2011 to Non Final Office Action dated Jun. 27, 2011", 9 pgs.
"U.S. Appl. No. 11/729,557, Advisory Action dated May 9, 2011", 3 pgs.
"U.S. Appl. No. 11/729,557, Advisory Action dated Dec. 24, 2014", 3 pgs.
"U.S. Appl. No. 11/729,557, Final Office Action dated Feb. 2, 2011", 14 pgs.
"U.S. Appl. No. 11/729,557, Final Office Action dated Aug. 20, 2009", 13 Pgs.
"U.S. Appl. No. 11/729,557, Final Office Action dated Sep. 12, 2014", 14 pgs.
"U.S. Appl. No. 11/729,557, Non Final Office Action dated Feb. 18, 2015", 13 pgs.
"U.S. Appl. No. 11/729,557, Non Final Office Action dated Feb. 26, 2014", 16 pgs.
"U.S. Appl. No. 11/729,557, Non-Final Office Action dated Jan. 30, 2009", 20 pgs.
"U.S. Appl. No. 11/729,557, Non-Final Office Action dated Feb. 22, 2010", 16 pgs.
"U.S. Appl. No. 11/729,557, Non-Final Office Action dated Aug. 23, 2010", 15 pgs.
"U.S. Appl. No. 11/729,557, Notice of Allowance dated Sep. 30, 2015", 11 pgs.
"U.S. Appl. No. 11/729,557, Respons filed Jun. 22, 2010 to Non Final Office Action dated Feb. 22, 2010", 33 pgs.
"U.S. Appl. No. 11/729,557, Response filed Apr. 27, 2011 to Final Office Action dated Feb. 2, 2011", 14 pgs.
"U.S. Appl. No. 11/729,557, Response filed Apr. 30, 2009 to Non Final Office Action dated Jan. 30, 2009", 18 pgs.
"U.S. Appl. No. 11/729,557, Response filed May 22, 2014 to Non Final Office Action dated Feb. 26, 2014", 13 pgs.
"U.S. Appl. No. 11/729,557, Response filed May 28, 2008 to Restriction Requirement dated Nov. 28, 2007", 13 pgs.
"U.S. Appl. No. 11/729,557, Response filed Jun. 22, 2010 to Non Final Office Action dated Feb. 22, 2010", 16 pgs.
"U.S. Appl. No. 11/729,557, Response filed Jun. 22, 2015 to non Final Office Action dated Feb. 18, 2015", 13 pgs.
"U.S. Appl. No. 11/729,557, Response filed Oct. 28, 2010 to Non Final Office Action dated Aug. 23, 2010", 13 pgs.
"U.S. Appl. No. 11/729,557, Response filed Dec. 1, 2009 to Final Office Action dated Aug. 26, 2009", 16 pgs.
"U.S. Appl. No. 11/729,557, Response filed Dec. 11, 2014 to Final Office Action dated Sep. 12, 2014", 15 pgs.
"U.S. Appl. No. 11/729,557, Restriction Requirement dated Nov. 28, 2007", 9 pgs.
"U.S. Appl. No. 11/810,956, Final Office Action dated Mar. 22, 2010", 8 pgs.
"U.S. Appl. No. 11/810,956, Non-Final Office Action dated Aug. 11, 2009", 9 pgs.
"U.S. Appl. No. 11/810,956, Response filed Jan. 11, 2010 to Non Final Office Action dated Aug. 11, 2009", 8 pgs.
"U.S. Appl. No. 11/810,956, Response filed Apr. 23, 2009 to Restriction Requirement dated Mar. 23, 2009", 6 pgs.
"U.S. Appl. No. 11/810,956, Restriction Requirement dated Mar. 23, 2009", 6 pgs.
"U.S. Appl. No. 12/058,389, Advisory Action dated Jan. 2, 2013", 2 pgs.
"U.S. Appl. No. 12/058,389, Final Office Action dated Jan. 22, 2010", 8 pgs.
"U.S. Appl. No. 12/058,389, Final Office Action dated Nov. 14, 2012", 7 pgs.
"U.S. Appl. No. 12/058,389, Non Final Office Action dated Aug. 10, 2012", 5 pgs.
"U.S. Appl. No. 12/058,389, Non Final Office Action dated Dec. 8, 2011", 8 pgs.
"U.S. Appl. No. 12/058,389, Non-Final Office Action dated Apr. 13, 2009", 12 pgs.
"U.S. Appl. No. 12/058,389, Notice of Allowability dated Mar. 22, 2013", 8 pgs.
"U.S. Appl. No. 12/058,389, Notice of Allowance dated Feb. 20, 2013", 9 pgs.
"U.S. Appl. No. 12/058,389, Preliminary Amendment filed Jun. 23, 2008", 7 pgs.
"U.S. Appl. No. 12/058,389, Respnse filed Nov. 6, 2012 to Non Final Office Action dated Aug. 10, 2012", 7 pgs.
"U.S. Appl. No. 12/058,389, Response filed Feb. 6, 2009 to Restriction Requirement dated Dec. 3, 2008", 7 pgs.
"U.S. Appl. No. 12/058,389, Response filed Apr. 10, 2012 to Non Final Office Action dated Dec. 8, 2011", 7 pgs.
"U.S. Appl. No. 12/058,389, Response filed Jun. 16, 2010 to Final Office Action dated Jan. 22, 2010" 6 pgs.
"U.S. Appl. No. 12/058,389, Response filed Oct. 13, 2009 to Non Final Office Action dated Apr. 13, 2009", 9 pgs.
"U.S. Appl. No. 12/058,389, Response filed Dec. 18, 2012 to Non Final Office Action dated Nov. 14, 2012", 7 pgs.
"U.S. Appl. No. 12/058,389, Restriction Requirement dated Dec. 3, 2008", 7 pgs.
"U.S. Appl. No. 12/113,690, Final Office Action dated Apr. 15, 2011", 10 pgs.
"U.S. Appl. No. 12/113,690, Non-Final Office Action dated Nov. 10, 2010", 11 pgs.

(56) References Cited

OTHER PUBLICATIONS

"U.S. Appl. No. 12/113,690, Notice of Allowability dated Aug. 19, 2013", 9 pgs.
"U.S. Appl. No. 12/113,690, Notice of Allowance dated Jul. 18, 2013", 14 pgs.
"U.S. Appl. No. 12/113,690, Preliminary Amendment filed Jul. 31, 2008", 14 pgs.
"U.S. Appl. No. 12/113,690, Response filed Jun. 23, 2011 to Final Office Action dated Apr. 15, 2011", 17 pgs.
"U.S. Appl. No. 12/113,690, Response filed Aug. 5, 2010 to Restriction Requirement dated Apr. 6, 2010", 14 pgs.
"U.S. Appl. No. 12/113,690, Response filed Dec. 22, 2010 to Non Final Office Action dated Nov. 10, 2010", 19 pgs.
"U.S. Appl. No. 12/113,690, Restriction Requirement dated Apr. 6, 2010", 10 pgs.
"U.S. Appl. No. 12/139,183, Non Final Office Action dated Jan. 6, 2011", 12 pgs.
"U.S. Appl. No. 12/139,183, Non-Final Office Action dated Jan. 4, 2010", 6 pgs.
"U.S. Appl. No. 12/139,183, Non-Final Office Action dated Jul. 13, 2010", 15 pgs.
"U.S. Appl. No. 12/139,183, Notice of Allowance dated Jun. 27, 2011", 11 pgs.
"U.S. Appl. No. 12/139,183, Preliminary Amendment filed Sep. 11, 2008", 17 pgs.
"U.S. Appl. No. 12/139,183, Response filed Mar. 22, 2011 to Non Final Office Action dated Jan. 6, 2011", 21 pgs.
"U.S. Appl. No. 12/139,183, Response filed Apr. 12, 2010 to Non Final Office Action dated Jan. 4, 2010", 17 pgs.
"U.S. Appl. No. 12/139,183, Response filed Aug. 18, 2009 to Restriction Requirement dated Jul. 24, 2009", 16 pgs.
"U.S. Appl. No. 12/139,183, Response filed Sep. 21, 2010 to Non Final Office Action dated Jul. 13, 2010", 21 pgs.
"U.S. Appl. No. 12/139,183, Restriction Requirement dated Jul. 24, 2009", 12 pgs.
"U.S. Appl. No. 12/214,414, Advisory Action dated Feb. 2, 2016", 5 pgs.
"U.S. Appl. No. 12/214,414, Advisory Action dated Apr. 15, 2015", 6 pgs.
"U.S. Appl. No. 12/214,414, Advisory Action dated Oct. 21, 2011", 5 pgs.
"U.S. Appl. No. 12/214,414, Examiner Interview Summary dated Dec. 11, 2015", 3 pgs.
"U.S. Appl. No. 12/214,414, Final Office Action dated Jan. 20, 2015", 28 pgs.
"U.S. Appl. No. 12/214,414, Final Office Action dated Aug. 2, 2011", 7 pgs.
"U.S. Appl. No. 12/214,414, Final Office Action dated Nov. 18, 2015", 17 pgs.
"U.S. Appl. No. 12/214,414, Non Final Office Action dated Jun. 12, 2014", 28 pgs.
"U.S. Appl. No. 12/214,414, Non Final Office Action dated Dec. 10, 2010", 6 pgs.
"U.S. Appl. No. 12/214,414, Non-Final Office Action dated Mar. 2, 2010", 9 pgs.
"U.S. Appl. No. 12/214,414, Notice of Allowance dated Jun. 7, 2016", 18 pgs.
"U.S. Appl. No. 12/214,414, Response filed Jan. 19, 2016 to Final Office Action dated Nov. 18, 2015", 14 pgs.
"U.S. Appl. No. 12/214,414, Response filed Feb. 18, 2016 to Final Office Action dated Nov. 18, 2015", 14 pgs.
"U.S. Appl. No. 12/214,414, Response filed Mar. 26, 2015 to Final Office Action dated Jan. 20, 2015", 13 pgs.
"U.S. Appl. No. 12/214,414, Response filed May 3, 2011 to Non Final Office Action dated Dec. 10, 2010", 12 pgs.
"U.S. Appl. No. 12/214,414, Response filed Jul. 20, 2015 to Advisory Action dated Apr. 15, 2015", 14 pgs.
"U.S. Appl. No. 12/214,414, Response filed Aug. 31, 2010 to Non Final Office Action dated Mar. 2, 2010", 11 pgs.

"U.S. Appl. No. 12/214,414, Response filed Oct. 3, 2011 to Non Final Office Action dated Aug. 2, 2011", 9 pgs.
"U.S. Appl. No. 12/214,414, Response filed Oct. 14, 2014 to Non Final Office Action dated Jun. 12, 2014", 16 pgs.
"U.S. Appl. No. 12/214,414, Response filed Dec. 21, 2011 to Advisory Action dated Oct. 21, 2011", 10 pgs.
"U.S. Appl. No. 12/245,296, Final Office Action dated Jul. 11, 2013", 15 pgs.
"U.S. Appl. No. 12/245,296, Final Office Action dated Dec. 17, 2010", 16 pgs.
"U.S. Appl. No. 12/245,296, Non Final Office Action dated Mar. 25, 2013", 14 pgs.
"U.S. Appl. No. 12/245,296, Non-Final Office Action dated Jun. 1, 2010", 13 pgs.
"U.S. Appl. No. 12/245,296, Notice of Allowance dated Aug. 1, 2014", 10 pgs.
"U.S. Appl. No. 12/245,296, Preliminary Amendment dated Jan. 28, 2009", 14 pgs.
"U.S. Appl. No. 12/245,296, Response filed Jan. 8, 2013 to Final Office Action dated Jul. 11, 2013", 10 pgs.
"U.S. Appl. No. 12/245,296, Response filed Apr. 8, 2010 to Restriction Requirement dated Mar. 9, 2010", 6 pgs.
"U.S. Appl. No. 12/245,296, Response filed May 17, 2011 to Final Office Action dated Dec. 17, 2010", 10 pgs.
"U.S. Appl. No. 12/245,296, Response filed Jun. 7, 2013 to Non Final Office Action dated Mar. 25, 2013", 9 pgs.
"U.S. Appl. No. 12/245,296, Response filed Oct. 1, 2010 to Non Final Office Action dated Jun. 1, 2010", 12 pgs.
"U.S. Appl. No. 12/245,296, Restriction Requirement dated Mar. 9, 2010", 6 pgs.
"U.S. Appl. No. 12/467,492, Restriction Requirement dated Nov. 22, 2010", 6 pgs.
"U.S. Appl. No. 12/470,287, Response filed Jan. 23, 2012 to Non Final Office Action dated Jul. 22, 2011", 13 pgs.
"U.S. Appl. No. 12/470,287, Response filed May 31, 2012 to Final Office Action dated Apr. 3, 2012". 14 pgs.
"U.S. Appl. No. 12/470,287, Corrected Notice of Allowability dated Sep. 11, 2012", 2 pgs.
"U.S. Appl. No. 12/470,287, Final Office Action dated Apr. 3, 2012", 7 pgs.
"U.S. Appl. No. 12/470,287, Non Final Office Action dated Jul. 22, 2011", 9 pgs.
"U.S. Appl. No. 12/470,287, Notice of Allowance dated Jun. 19, 2012", 5 pgs.
"U.S. Appl. No. 12/470,287, Response filed Apr. 28, 2011 to Restriction Requirement dated Dec. 29, 2010", 8 pgs.
"U.S. Appl. No. 12/470,287, Restriction Requirement dated Dec. 29, 2010", 6 pgs.
"U.S. Appl. No. 12/854,578, Response filed Oct. 1, 2012 to Non Final Office Action dated Jun. 29, 2012", 10 pgs.
"U.S. Appl. No. 12/854,578, Final Office Action dated Nov. 29, 2012", 8 pgs.
"U.S. Appl. No. 12/854,578, Non Final Office Action dated Jun. 29, 2012", 8 pgs.
"U.S. Appl. No. 12/854,578, Notice of Allowance dated Apr. 10, 2013", 6 pgs.
"U.S. Appl. No. 12/854,578, PTO Response to 312 Amendment dated Jul. 18, 2013", 2 pgs.
"U.S. Appl. No. 12/854,578, Response filed Feb. 28, 2013 to Final Office Action dated Nov. 29, 2012", 8 pgs.
"U.S. Appl. No. 12/854,578, Restriction Requirement dated Apr. 6, 2012", 6 pgs.
"U.S. Appl. No. 12/912,411, Advisory Action dated Feb. 5, 2014", 3 pgs.
"U.S. Appl. No. 12/912,411, Examiner Interview Summary dated Feb. 11, 2014", 2 pgs.
"U.S. Appl. No. 12/912,411, Final Office Action dated Jan. 14, 2015", 10 pgs.
"U.S. Appl. No. 12/912,411, Final Office Action dated Oct. 25, 2013", 11 pgs.
"U.S. Appl. No. 12/912,411, Non Final Office Action dated Jun. 7, 2013", 8 pgs.

(56) References Cited

OTHER PUBLICATIONS

"U.S. Appl. No. 12/912,411, Non Final Office Action dated Sep. 24, 2014", 11 pgs.
"U.S. Appl. No. 12/912,411, Notice of Allowability dated May 20, 2015", 7 pgs.
"U.S. Appl. No. 12/912,411, Notice of Allowance dated Apr. 8, 2015", 11 pgs.
"U.S. Appl. No. 12/912,411, Response filed Jan. 27, 2014 to Final Office Action dated Oct. 25, 2013", 11 pgs.
"U.S. Appl. No. 12/912,411, Response filed Feb. 18, 2013 to Restriction Requirement dated Oct. 17, 2012", 9 pgs.
"U.S. Appl. No. 12/912,411, Response filed Feb. 25, 2014 to Final Office Action dated Oct. 25, 2013", 11 pgs.
"U.S. Appl. No. 12/912,411, Response filed Mar. 16, 2015 to Final Office Action dated Jan. 14, 2015", 9 pgs.
"U.S. Appl. No. 12/912,411, Response filed Oct. 7, 2013 to Non Final Office Action dated Jun. 7, 2013", 10 pgs.
"U.S. Appl. No. 12/912,411, Response filed Dec. 31, 2014 to Non Final Office Action dated Sep. 24, 2014", 12 pgs.
"U.S. Appl. No. 12/912,411, Restriction Requirement dated Oct. 17, 2012", 9 pgs.
"U.S. Appl. No. 13/070,110 Response filed Feb. 14, 2017 to Final Office Action dated Sep. 14, 2016", 8 pgs.
"U.S. Appl. No. 13/070,110, Advisory Action dated Mar. 3, 2017", 5 pgs.
"U.S. Appl. No. 13/070,110, Examiner Interview Summary dated Jan. 16, 2018", 3 pgs.
"U.S. Appl. No. 13/070,110, Final Office Action dated Apr. 3, 2015", 18 pgs.
"U.S. Appl. No. 13/070,110, Final Office Action dated Jun. 12, 2013", 7 pgs.
"U.S. Appl. No. 13/070,110, Final Office Action dated Sep. 14, 2016", 12 pgs.
"U.S. Appl. No. 13/070,110, Non Final Office Action dated Jul. 21, 2017", 14 pgs.
"U.S. Appl. No. 13/070,110, Non Final Office Action dated Oct. 2, 2014", 24 pgs.
"U.S. Appl. No. 13/070,110, Non Final Office Action dated Dec. 11, 2015", 19 pgs.
"U.S. Appl. No. 13/070,110, Non Final Office Action dated Dec. 21, 2012", 7 pgs.
"U.S. Appl. No. 13/070,110, Notice of Allowance dated Mar. 26, 2018", 6 pgs.
"U.S. Appl. No. 13/070,110, Notice of Allowance dated Jul. 20, 2018", 7 pgs.
"U.S. Appl. No. 13/070,110, Preliminary Amendment filed Jun. 6, 2011", 4 pgs.
"U.S. Appl. No. 13/070,110, PTO Response to Rule 312 Communication dated Aug. 15, 2018", 2 pgs.
"U.S. Appl. No. 13/070,110, Response filed Jan. 22, 2018 to Non Final Office Action dated Jul. 21, 2017", 10 pgs.
"U.S. Appl. No. 13/070,110, Response filed Mar. 22, 2013 to Non Final Office Action dated Dec. 21, 2012", 8 pgs.
"U.S. Appl. No. 13/070,110, Response filed May 27, 2016 to Non Final Office Action dated Dec. 11, 2015", 13 pgs.
"U.S. Appl. No. 13/070,110, Response filed Jun. 20, 2017 to Advisory Action dated Mar. 3, 2017", 13 pgs.
"U.S. Appl. No. 13/070,110, Response filed Sep. 3, 2014 to Restriction Requirement dated Jul. 8, 2014", 7 pgs.
"U.S. Appl. No. 13/070,110, Response filed Oct. 2, 2015 to Final Office Action dated Apr. 3, 2015", 11 pgs.
"U.S. Appl. No. 13/070,110, Response filed Nov. 12, 2013 to Final Office Action dated Jun. 12, 2013", 9 pgs.
"U.S. Appl. No. 13/070,110, Response filed Dec. 30, 2014 to Non Final Office Action dated Oct. 2, 2014", 13 pgs.
"U.S. Appl. No. 13/070,110, Restriction Requirement dated Jul. 8, 2014", 7 pgs.
"U.S. Appl. No. 13/113,244, Final Office Action dated Feb. 27, 2014", 8 pgs.
"U.S. Appl. No. 13/113,244, Non Final Office Action dated Jul. 5, 2013", 6 pgs.
"U.S. Appl. No. 13/113,244, Non Final Office Action dated Oct. 1, 2012", 7 pgs.
"U.S. Appl. No. 13/113,244, Notice of Allowance dated Jun. 30, 2014", 9 pgs.
"U.S. Appl. No. 13/113,244, Preliminary Amendment filed Aug. 11, 2011", 4 pgs.
"U.S. Appl. No. 13/113,244, Response filed Jan. 30, 2012 to Restriction Requirement dated Oct. 31, 2011", 10 pgs.
"U.S. Appl. No. 13/113,244, Response filed Feb. 20, 2013 to Non Final Office Action dated Oct. 1, 2012", 12 pgs.
"U.S. Appl. No. 13/113,244, Response filed Jun. 13, 2014 to Final Office Action dated Feb. 27, 2014", 6 pgs.
"U.S. Appl. No. 13/113,244, Response filed Oct. 31, 2013 to Non Final Office Action dated Jul. 5, 2013", 12 pgs.
"U.S. Appl. No. 13/113,244, Restriction Requirement dated Oct. 31, 2011", 8 pgs.
"U.S. Appl. No. 13/127,951, Advisory Action dated Jul. 16, 2014", 3 pgs.
"U.S. Appl. No. 13/127,951, Final Office Action dated Apr. 9, 2014", 23 pgs.
"U.S. Appl. No. 13/127,951, Non Final Office Action dated Sep. 26, 2013", 18 pgs.
"U.S. Appl. No. 13/127,951, Notice of Allowance dated Jul. 20, 2015", 7 pgs.
"U.S. Appl. No. 13/127,951, Preliminary Amendment filed May 5, 2011", 7 pgs.
"U.S. Appl. No. 13/127,951, PTO Response to Rule 312 Communication dated Oct. 23, 2015", 2 pgs.
"U.S. Appl. No. 13/127,951, Response filed Mar. 18, 2014 to Non Final Office Action dated Sep. 26, 2013", 14 pgs.
"U.S. Appl. No. 13/127,951, Response filed Jul. 7, 2014 to Final Office Action dated Apr. 9, 2014", 10 pgs.
"U.S. Appl. No. 13/127,951, Response filed Aug. 30, 2013 to Restriction Requirement dated Apr. 30, 2013", Aug. 30, 2013.
"U.S. Appl. No. 13/127,951, Response filed Oct. 9, 2014 to Advisory Action dated Jul. 16, 2014", 10 pgs.
"U.S. Appl. No. 13/127,951, Restriction Requirement dated Apr. 30, 2013", 15 pgs.
"U.S. Appl. No. 13/594,611, Final Office Action dated Aug. 15, 2014", 7 pgs.
"U.S. Appl. No. 13/594,611, Non Final Office Action dated Apr. 24, 2014", 9 pgs.
"U.S. Appl. No. 13/594,611, Notice of Allowance dated Jan. 13, 2015", 7 pgs.
"U.S. Appl. No. 13/594,611, PTO Response to Rule 312 Communication dated Apr. 16, 2015", 2 pgs.
"U.S. Appl. No. 13/594,611, Response filed Feb. 25, 2014 to Restriction Requirement dated Jan. 27, 2014", 8 pgs.
"U.S. Appl. No. 13/594,611, Response filed Jul. 7, 2014 to Non Final Office Action dated Apr. 24, 2014", 9 pgs.
"U.S. Appl. No. 13/594,611, Response filed Dec. 15, 2014 to Final Office Action dated Aug. 15, 2014", 10 pgs.
"U.S. Appl. No. 13/594,611, Restriction Requirement dated Jan. 27, 2014", 8 pgs.
"U.S. Appl. No. 14/332,121, Non Final Office Action dated May 16, 2016", 9 pgs.
"U.S. Appl. No. 14/332,121, Notice of Allowance dated Feb. 15, 2017", 10 pgs.
"U.S. Appl. No. 14/332,121, Notice of Allowance dated Jun. 15, 2017", 8 pgs.
"U.S. Appl. No. 14/332,121, Notice of Allowance dated Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement dated Jul. 30, 2015", 9 pgs.
"U.S. Appl. No. 14/332,121, Response filed Sep. 7, 2017 to Notice of Allowability dated Jun. 15, 2017", 8 pgs.
"U.S. Appl. No. 14/332,121, Response filed Oct. 11, 2016 to Non Final Office Action dated May 16, 2016", 9 pgs.

(56) References Cited

OTHER PUBLICATIONS

"U.S. Appl. No. 14/332,121, Restriction Requirement dated Jul. 30, 2015", 9 pgs.
"U.S. Appl. No. 14/332,121, Supplemental Amendment filed Jan. 23, 2017", 10 pgs.
"U.S. Appl. No. 14/528,997, Advisory Action dated Aug. 9, 2017", 3 pgs.
"U.S. Appl. No. 14/528,997, Final Office Action dated Feb. 10, 2017", 9 pgs.
"U.S. Appl. No. 14/528,997, Non Final Office Action dated Jun. 16, 2016", 12 pgs.
"U.S. Appl. No. 14/528,997, Non Final Office Action dated Jun. 29, 2018", 7 pgs.
"U.S. Appl. No. 14/528,997, Notice of Allowance dated Mar. 8, 2019", 7 pgs.
"U.S. Appl. No. 14/528,997, PTO Response to Rule 312 Communication dated Jun. 19, 2019", 2 pgs.
"U.S. Appl. No. 14/528,997, Response filed Mar. 16, 2016 to Restriction Requirement dated Sep. 16, 2015", 11 pgs.
"U.S. Appl. No. 14/528,997, Response filed Jul. 27, 2017 to Final Office Action dated Feb. 10, 2017", 11 pgs.
"U.S. Appl. No. 14/528,997, Response filed Oct. 10, 2016 to Non Final Office Action dated Jun. 16, 2016", 12 pgs.
"U.S. Appl. No. 14/528,997, Response filed Nov. 16, 2018 to Non Final Office Action dated Jun. 29, 2018", 11 pgs.
"U.S. Appl. No. 14/528,997, Restriction Requirement dated Sep. 16, 2015", 8 pgs.
"U.S. Appl. No. 14/699,213, Advisory Action dated Mar. 7, 2018", 3 pgs.
"U.S. Appl. No. 14/699,213, Final Office Action dated Dec. 1, 2017", 11 pgs.
"U.S. Appl. No. 14/699,213, Non Final Office Action dated Jun. 2, 2017", 12 pgs.
"U.S. Appl. No. 14/699,213, Non-Final Office Action dated Jan. 11, 2019", 10 pgs.
"U.S. Appl. No. 14/699,213, Notice of Allowance dated Jul. 30, 2019", 8 pgs.
"U.S. Appl. No. 14/699,213, Preliminary Amendment filed Apr. 30, 2015", 8 pgs.
"U.S. Appl. No. 14/699,213, PTO Response to Rule 312 Communication dated Nov. 19, 2019", 2 pgs.
"U.S. Appl. No. 14/699,213, Response filed Feb. 15, 2017 to Restriction Requirement dated Aug. 15, 2016", 9 pgs.
"U.S. Appl. No. 14/699,213, Response filed Feb. 27, 2018 to Final Office Action dated Dec. 1, 2017", 34 pgs.
"U.S. Appl. No. 14/699,213, Response filed Aug. 22, 2017 to Non Final Office Action dated Jun. 2, 2017", 12 pgs.
"U.S. Appl. No. 14/699,213, Response filed Apr. 11, 2019 to Non-Final Office Action dated Jan. 11, 2019", 13 pgs.
"U.S. Appl. No. 14/699,213, Restriction Requirement dated Aug. 15, 2016", 10 pgs.
"U.S. Appl. No. 14/745,236, Advisory Action dated Nov. 15, 2017", 2 pgs.
"U.S. Appl. No. 14/745,236, Final Office Action dated Aug. 25, 2017", 16 pgs.
"U.S. Appl. No. 14/745,236, Non Final Office Action dated Feb. 2, 2017", 14 pgs.
"U.S. Appl. No. 14/745,236, Notice of Allowability dated Jul. 5, 2018", 4 pgs.
"U.S. Appl. No. 14/745,236, Notice of Allowance dated Feb. 5, 2018", 9 pgs.
"U.S. Appl. No. 14/745,236, PTO Response to Rule 312 Communication dated Jul. 10, 218", 2 pgs.
"U.S. Appl. No. 14/745,236, Response filed May 2, 2017 to Non Final Office Action dated Feb. 2, 2017", 10 pgs.
"U.S. Appl. No. 14/745,236, Response filed Nov. 6, 2017 to Final Office Action dated Aug. 25, 2017", 12 pgs.
"U.S. Appl. No. 14/745,236, Response filed Dec. 14, 2017 to Final Office Action dated Aug. 25, 2017", 12 pgs.
"U.S. Appl. No. 14/745,236, Response filed Dec. 23, 2016 to Restriction Requirement dated Sep. 23, 2016", 8 pgs.
"U.S. Appl. No. 14/745,236, Restriction Requirement dated Sep. 23, 2016", 8 pgs.
"U.S. Appl. No. 14/816,807, Non Final Office Action dated Oct. 3, 2017", 7 pgs.
"U.S. Appl. No. 14/816,807, Notice of Allowance dated Apr. 20, 2018", 8 pgs.
"U.S. Appl. No. 14/816,807, Preliminary Amendment filed Aug. 11, 2015", 8 pgs.
"U.S. Appl. No. 14/816,807, PTO Response to Rule 312 Communication dated Jul. 6, 2018", 2 pgs.
"U.S. Appl. No. 14/816,807, Response filed Jan. 3, 2018 to Non Final Office Action dated Oct. 3, 2017", 8 pgs.
"U.S. Appl. No. 14/816,807, Response filed May 1, 2017 to Restriction Requirement dated Nov. 1, 2016", 9 pgs.
"U.S. Appl. No. 14/816,807, Restriction Requirement dated Nov. 1, 2016", 8 pgs.
"U.S. Appl. No. 14/919,431, Preliminary Amendment filed Jan. 4, 2016", 8 pgs.
"U.S. Appl. No. 15/000,851, Non Final Office Action dated Jan. 26, 2017", 15 pgs.
"U.S. Appl. No. 15/000,851, Notice of Allowance dated Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action dated Jan. 26, 2017", 16 pgs.
"U.S. Appl. No. 15/000,851, Response filed Oct. 12, 2016 to Restriction Requirement dated May 12, 2016", 11 pgs.
"U.S. Appl. No. 15/000,851, Restriction Requirement dated May 12, 2016", 6 pgs.
"U.S. Appl. No. 15/000,851, Supplemental Amendment filed Apr. 4, 2016", 10 pgs.
"U.S. Appl. No. 15/170,556, Final Office Action dated Jul. 30, 2019", 6 pgs.
"U.S. Appl. No. 15/170,556, Non Final Office Action dated Feb. 8, 2019", 11 pgs.
"U.S. Appl. No. 15/170,556, Non Final Office Action dated Jul. 27, 2018", 10 pgs.
"U.S. Appl. No. 15/170,556, Notice of Allowability dated Jan. 29, 2020", 4 pgs.
"U.S. Appl. No. 15/170,556, Notice of Allowance dated Nov. 27, 2019", 8 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement dated Feb. 16, 2018", 8 pgs.
"U.S. Appl. No. 15/170,556, Response filed Oct. 29, 2018 to Non Final Office Action dated Jul. 27, 2018", 9 pgs.
"U.S. Appl. No. 15/170,556, Response filed Nov. 18, 2019 to Final Office Action dated Jul. 30, 2019", 8 pgs.
"U.S. Appl. No. 15/170,556, Response filed Apr. 15, 2019 to Non Final Office Action dated Feb. 8, 2019", 9 pgs.
"U.S. Appl. No. 15/170,556, Restriction Requirement dated Feb. 16, 2018", 7 pgs.
"U.S. Appl. No. 15/170,556, PTO Response to Rule 312 Communication dated Apr. 3, 2020", 2 pgs.
"U.S. Appl. No. 15/203,581, Examiners Interview Summary dated Sep. 11, 2017", 1 pg.
"U.S. Appl. No. 15/203,581, Notice of Allowance dated Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication dated Dec. 27, 2017", 2 pgs.
"U.S. Appl. No. 15/203,581, Response filed Aug. 15, 2017 to Restriction Requirement dated Jun. 16, 2017", 8 pgs.
"U.S. Appl. No. 15/203,581, Restriction Requirement dated Jun. 16, 2017", 8 pgs.
"U.S. Appl. No. 15/204,381, Advisory Action dated Feb. 7, 2019", 3 pgs.

(56) References Cited

OTHER PUBLICATIONS

"U.S. Appl. No. 15/204,381, Advisory Action dated Aug. 25, 2020", 3 pgs.

"U.S. Appl. No. 15/204,381, Final Office Action dated Feb. 27, 2020", 21 pgs.

"U.S. Appl. No. 15/204,381, Final Office Action dated Jul. 9, 2021", 14 pgs.

"U.S. Appl. No. 15/204,381, Final Office Action dated Sep. 21, 2018", 10 pgs.

"U.S. Appl. No. 15/204,381, Non Final Office Action dated Feb. 23, 2018", 10 pgs.

"U.S. Appl. No. 15/204,381, Non Final Office Action dated Jun. 13, 2019", 23 pgs.

"U.S. Appl. No. 15/204,381, Non Final Office Action dated Oct. 6, 2020", 15 pgs.

"U.S. Appl. No. 15/204,381, Preliminary Amendment filed Oct. 25, 2016", 74 pgs.

"U.S. Appl. No. 15/204,381, Response filed Jan. 2, 2019 to Final Office Action dated Sep. 21, 2018", 6 pgs.

"U.S. Appl. No. 15/204,381, Response filed Jan. 19, 2018 to Restriction Requirement dated Oct. 13, 2017", 6 pgs.

"U.S. Appl. No. 15/204,381, Response filed Apr. 6, 2021 to Non Final Office Action dated Oct. 6, 2020", 12 pgs.

"U.S. Appl. No. 15/204,381, Response filed May 30, 2018 to Non Final Office Action dated Feb. 23, 2018", 9 pgs.

"U.S. Appl. No. 15/204,381, Response filed Jul. 27, 2020 to Final Office Action dated Feb. 27, 2020", 11 pgs.

"U.S. Appl. No. 15/204,381, Response filed Aug. 27, 2020 to Advisory Action dated Aug. 25, 2020", 2 pgs.

"U.S. Appl. No. 15/204,381, Response Filed Nov. 14, 2019 to Non Final Office Action dated Jun. 13, 2019", 9 pgs.

"U.S. Appl. No. 15/204,381, Response Filed Mar. 21, 2019 to Advisory Action dated Aug. 25, 2020", 7 pgs.

"U.S. Appl. No. 15/204,381, Restriction Requirement dated Oct. 13, 2017", 10 pgs.

"U.S. Appl. No. 15/227,147, Preliminary Amendment filed Oct. 10, 2016", 7 pgs.

"U.S. Appl. No. 15/227,147, Restriction Requirement dated Jan. 19, 2017", 14 pgs.

"U.S. Appl. No. 15/247,006 Response filed Jun. 4, 2019 to Final Office Action dated Feb. 4, 2019", 7 pgs.

"U.S. Appl. No. 15/247,006, Examiner Interview Summary dated Nov. 27, 2017", 4 pgs.

"U.S. Appl. No. 15/247,006, Final Office Action dated Feb. 4, 2019", 8 pgs.

"U.S. Appl. No. 15/247,006, Non Final Office Action dated Apr. 20, 2018", 7 pgs.

"U.S. Appl. No. 15/247,006, Non Final Office Action dated Sep. 8, 2017", 8 pgs.

"U.S. Appl. No. 15/247,006, Notice of Allowance dated Jun. 24, 2019", 7 pgs.

"U.S. Appl. No. 15/247,006, Notice of Allowance dated Oct. 8, 2019", 7 pgs.

"U.S. Appl. No. 15/247,006, Preliminary Amendment filed Nov. 22, 2016", 3 pgs.

"U.S. Appl. No. 15/247,006, Response filed May 3, 2017 to Restriction Requirement dated Mar. 17, 2017", 12 pgs.

"U.S. Appl. No. 15/247,006, Response filed Oct. 22, 2018 to Non Final Office Action dated Apr. 20, 2018", 14 pgs.

"U.S. Appl. No. 15/247,006, Response filed Dec. 7, 2017 to Non Final Office Action dated Sep. 8, 2017", 13 pgs.

"U.S. Appl. No. 15/247,006, Restriction Requirement dated Mar. 17, 2017", 9 pgs.

"U.S. Appl. No. 15/292,595, Non Final Office Action dated Sep. 25, 2017", 13 pgs.

"U.S. Appl. No. 15/292,595, Notice of Allowance dated Feb. 28, 2018", 9 pgs.

"U.S. Appl. No. 15/292,595, Notice of Allowance dated Jun. 20, 2018", 9 pgs.

"U.S. Appl. No. 15/292,595, Preliminary Amendment filed Dec. 27, 2016", 5 pgs.

"U.S. Appl. No. 15/292,595, Response filed Dec. 22, 2017 to Non Final Office Action dated Sep. 25, 2017", 9 pgs.

"U.S. Appl. No. 15/436,245, Corrected Notice of Allowability dated Nov. 10, 2021", 2 pgs.

"U.S. Appl. No. 15/436,245, Final Office Action dated Mar. 24, 2021", 9 pgs.

"U.S. Appl. No. 15/436,245, Final Office Action dated Nov. 18, 2019", 9 pgs.

"U.S. Appl. No. 15/436,245, Non Final Office Action dated Apr. 19, 2019", 9 pgs.

"U.S. Appl. No. 15/436,245, Non Final Office Action dated Sep. 4, 2020", 9 pgs.

"U.S. Appl. No. 15/436,245, Notice of Allowance dated Aug. 3, 2021", 9 pgs.

"U.S. Appl. No. 15/436,245, Preliminary Amendment filed May 5, 2017", 3 pgs.

"U.S. Appl. No. 15/436,245, PTO Response to Rule 312 Communication dated Oct. 27, 2021", 2 pgs.

"U.S. Appl. No. 15/436,245, Response filed Apr. 27, 2020 to Final Office Action dated Nov. 18, 2019", 10 pgs.

"U.S. Appl. No. 15/436,245, Response filed Jun. 24, 2021 to Final Office Action dated Mar. 24, 2021", 11 pgs.

"U.S. Appl. No. 15/436,245, Response filed Dec. 4, 2020 to Non Final Office Action dated Sep. 4, 2020", 12 pgs.

"U.S. Appl. No. 15/436,245, Response filed Jul. 29, 2019 to Non-Final Office Action dated Apr. 19, 2019", 11 pgs.

"U.S. Appl. No. 15/436,245, Restriction Requirement dated Oct. 11, 2018", 9 pgs.

"U.S. Appl. No. 15/436,245, Supplemental Amendment filed Jul. 19, 2021", 10 pgs.

"U.S. Appl. No. 15/593,039, Non Final Office Action dated Feb. 6, 2018", 8 pgs.

"U.S. Appl. No. 15/593,039, Notice of Allowance dated Jul. 11, 2018", 5 pgs.

"U.S. Appl. No. 15/593,039, Preliminary Amendment filed Jul. 25, 2017", 7 pgs.

"U.S. Appl. No. 15/593,039, PTO Response to Rule 312 Communication dated Oct. 9, 2018", 2 pgs.

"U.S. Appl. No. 15/593,039, Response filed Apr. 30, 2018 to Non Final Office Action dated Feb. 4, 2018", 8 pgs.

"U.S. Appl. No. 15/593,039, Response filed Dec. 18, 2017 to Restriction Requirement dated Oct. 18, 2017", 8 pgs.

"U.S. Appl. No. 15/593,039, Restriction Requirement dated Oct. 18, 2017", 6 pgs.

"U.S. Appl. No. 15/593,039, Supplemental Preliminary Amendment filed Jul. 26, 2017", 4 pgs.

"U.S. Appl. No. 15/865,364, Notice of Allowance dated Nov. 15, 2018", 7 pgs.

"U.S. Appl. No. 15/865,364, Preliminary Amendment filed Apr. 10, 2018", 10 pgs.

"U.S. Appl. No. 15/905,454, Preliminary Amendment filed Nov. 2, 2018", 5 pgs.

"U.S. Appl. No. 15/905,454, Restriction Requirement dated Jan. 3, 2019", 6 pgs.

"U.S. Appl. No. 15/915,486 Supplemental Preliminary Amendment Filed Mar. 12, 2019", 15 pgs.

"U.S. Appl. No. 15/915,486, Advisory Action dated Jun. 28, 2021", 7 pgs.

"U.S. Appl. No. 15/915,486, Advisory Action dated Jul. 13, 2020", 3 pgs.

"U.S. Appl. No. 15/915,486, Final Office Action dated Jan. 11, 2022", 9 pgs.

"U.S. Appl. No. 15/915,486, Final Office Action dated Jan. 27, 2020", 8 pgs.

"U.S. Appl. No. 15/915,486, Final Office Action dated Feb. 1, 2021", 8 pgs.

"U.S. Appl. No. 15/915,486, Non Final Office Action dated Sep. 2, 2021", 8 pgs.

"U.S. Appl. No. 15/915,486, Non Final Office Action dated Sep. 15, 2020", 10 pgs.

(56) References Cited

OTHER PUBLICATIONS

"U.S. Appl. No. 15/915,486, Non Final Office Action dated Oct. 24, 2019", 10 pgs.
"U.S. Appl. No. 15/915,486, Response filed Jan. 3, 2020 to Non Final Office Action dated Oct. 24, 2019", 8 pgs.
"U.S. Appl. No. 15/915,486, Response filed Jun. 1, 2021 to Final Office Action dated Feb. 1, 2021", 10 pgs.
"U.S. Appl. No. 15/915,486, Response filed Jun. 23, 2020 to Final Office Action dated Jan. 27, 2020", 7 pgs.
"U.S. Appl. No. 15/915,486, Response filed Jul. 27, 2021 to Advisory Action dated Jun. 28, 2021", 10 pgs.
"U.S. Appl. No. 15/915,486, Response filed Nov. 30, 2021 to Non Final Office Action dated Sep. 2, 2021", 6 pgs.
"U.S. Appl. No. 15/915,486, Response filed Dec. 21, 2020 to Non Final Office Action dated Sep. 15, 2020", 7 pgs.
"U.S. Appl. No. 15/915,486, Restriction Requirement dated Aug. 5, 2019", 9 pgs.
"U.S. Appl. No. 15/966,092, Interview Summary dated Mar. 2, 2021", 2 pgs.
"U.S. Appl. No. 15/966,092, Non Final Office Action dated Jun. 26, 2020", 22 pgs.
"U.S. Appl. No. 15/966,092, Notice of Allowance dated Feb. 11, 2021", 5 pgs.
"U.S. Appl. No. 15/966,092, Response filed Oct. 26, 2020 to Non Final Office Action dated Jun. 26, 2020", 9 pgs.
"U.S. Appl. No. 16/046,250, Non Final Office Action dated Mar. 6, 2020", 10 pgs.
"U.S. Appl. No. 16/046,250, Notice of Allowance dated Jun. 15, 2020", 9 pgs.
"U.S. Appl. No. 16/046,250, Response filed Jun. 3, 2020 to Non Final Office Action dated Mar. 6, 2020", 10 pgs.
"U.S. Appl. No. 16/046,250, Response filed Oct. 25, 2019 to Restriction Requirement dated Jul. 25, 2019", 9 pgs.
"U.S. Appl. No. 16/046,250, Restriction Requirement dated Jul. 25, 2019", 7 pgs.
"U.S. Appl. No. 16/170,321, Advisory Action dated Feb. 23, 2021", 3 pgs.
"U.S. Appl. No. 16/170,321, Corrected Notice of Allowability dated Sep. 29, 2021", 2 pgs.
"U.S. Appl. No. 16/170,321, Final Office Action dated Dec. 14, 2020", 13 pgs.
"U.S. Appl. No. 16/170,321, Non Final Office Action dated Apr. 13, 2020", 13 pgs.
"U.S. Appl. No. 16/170,321, Notice of Allowance dated Aug. 4, 2021", 10 pgs.
"U.S. Appl. No. 16/170,321, PTO Response to Rule 312 Communication dated Sep. 1, 2021", 2 pgs.
"U.S. Appl. No. 16/170,321, Response filed Jan. 24, 2020 to Restriction Requirement dated Nov. 27, 2019", 9 pgs.
"U.S. Appl. No. 16/170,321, Response filed Jan. 26, 2021 to Final Office Action dated Dec. 14, 2020", 9 pgs.
"U.S. Appl. No. 16/170,321, Response filed Mar. 9, 2021 to Advisory Action dated Feb. 23, 2021", 9 pgs.
"U.S. Appl. No. 16/170,321, Response filed Sep. 11, 2020 to Non Final Office Action dated Apr. 13, 2020", 9 pgs.
"U.S. Appl. No. 16/170,321, Restriction Requirement dated Nov. 27, 2019", 10 pgs.
"U.S. Appl. No. 16/173,605 Preliminary Amendment Filed Nov. 18, 2019", 5 pgs.
"U.S. Appl. No. 16/173,605, Final Office Action dated Jul. 27, 2020", 7 pgs.
"U.S. Appl. No. 16/173,605, Non Final Office Action dated Mar. 13, 2020", 10 pgs.
"U.S. Appl. No. 16/173,605, Notice of Allowance dated Jan. 13, 2021", 6 pgs.
"U.S. Appl. No. 16/173,605, Response filed Jul. 13, 2020 to Non Final Office Action dated Mar. 13, 2020", 13 pgs.
"U.S. Appl. No. 16/173,605, Response filed Dec. 21, 2020 to Final Office Action dated Jul. 27, 2020", 7 pgs.
"U.S. Appl. No. 16/545,761, Final Office Action dated Oct. 20, 2021", 10 pgs.
"U.S. Appl. No. 16/545,761, Non Final Office Action dated Feb. 11, 2021", 12 pgs.
"U.S. Appl. No. 16/545,761, Notice of Allowance dated Mar. 9, 2022", 6 pgs.
"U.S. Appl. No. 16/545,761, Preliminary Amendment filed Feb. 7, 2020", 9 pgs.
"U.S. Appl. No. 16/545,761, PTO Response to Rule 312 Communication dated May 13, 2022", 2 pgs.
"U.S. Appl. No. 16/545,761, Response filed Feb. 16, 2022 to Final Office Action dated Oct. 20, 2021", 10 pgs.
"U.S. Appl. No. 16/545,761, Response filed Jun. 30, 2021 to Non Final Office Action dated Feb. 11, 2021", 13 pgs.
"U.S. Appl. No. 16/547,262, Non Final Office Action dated Mar. 31, 2021", 13 pgs.
"U.S. Appl. No. 16/547,262, Notice of Allowance dated Jul. 22, 2021", 7 pgs.
"U.S. Appl. No. 16/547,262, Response filed Jun. 30, 2021 to Non Final Office Action dated Mar. 31, 2021", 12 pgs.
"U.S. Appl. No. 16/547,262, Response filed Dec. 17, 2020 to Restriction Requirement dated Jul. 17, 2020", 12 pgs.
"U.S. Appl. No. 16/547,262, Restriction Requirement dated Jul. 17, 2020", 6 pgs.
"U.S. Appl. No. 16/694,748, Non Final Office Action dated Nov. 9, 2021", 6 pgs.
"U.S. Appl. No. 16/694,748, Notice of Allowance dated Mar. 3, 2022", 9 pgs.
"U.S. Appl. No. 16/694,748, Preliminary Amendment filed May 8, 2020", 7 pgs.
"U.S. Appl. No. 16/694,748, Response filed Feb. 9, 2022 to Non Final Office Action dated Nov. 9, 2021", 7 pgs.
"U.S. Appl. No. 16/694,748, Response filed Jul. 27, 2021 to Restriction Requirement dated Jan. 27, 2021", 8 pgs.
"U.S. Appl. No. 16/694,748, Restriction Requirement dated Jan. 27, 2021", 9 pgs.
"U.S. Appl. No. 16/749,910, Notice of Allowance dated Sep. 22, 2021", 10 pgs.
"U.S. Appl. No. 16/749,910, Response filed Jun. 17, 2021 to Restriction Requirement dated Apr. 19, 2021", 11 pgs.
"U.S. Appl. No. 16/749,910, Restriction Requirement dated Apr. 19, 2021", 9 pgs.
"U.S. Appl. No. 16/865,194, Notice of Allowance dated Mar. 3, 2022", 9 pgs.
"U.S. Appl. No. 16/865,194, Response filed Dec. 20, 2021 to Restriction Requirement dated Oct. 20, 2021", 11 pgs.
"U.S. Appl. No. 16/865,194, Restriction Requirement dated Oct. 20, 2021", 7 pgs.
"U.S. Appl. No. 17/004,583, Advisory Action dated Aug. 30, 2022", 2 pgs.
"U.S. Appl. No. 17/004,583, Final Office Action dated Jun. 9, 2022", 6 pgs.
"U.S. Appl. No. 17/004,583, Non Final Office Action dated Feb. 24, 2022", 5 pgs.
"U.S. Appl. No. 17/004,583, Non Final Office Action dated Sep. 29, 2022", 8 pgs.
"U.S. Appl. No. 17/004,583, Notice of Allowability dated Feb. 10, 2023", 4 pgs.
"U.S. Appl. No. 17/004,583, Notice of Allowance dated Feb. 1, 2023", 10 pgs.
"U.S. Appl. No. 17/004,583, Preliminary Amendment filed Dec. 21, 2020", 6 pgs.
"U.S. Appl. No. 17/004,583, Response filed Jan. 31, 2022 to Restriction Requirement dated Nov. 24, 2021", 7 pgs.
"U.S. Appl. No. 17/004,583, Response filed May 24, 2022 to Non Final Office Action dated Feb. 24, 2022", 9 pgs.
"U.S. Appl. No. 17/004,583, Response filed Aug. 9, 2022 to Final Office Action dated Jun. 9, 2022", 9 pgs.
"U.S. Appl. No. 17/004,583, Response filed Sep. 8, 2022 to Advisory Action dated Aug. 30, 2022", 15 pgs.
"U.S. Appl. No. 17/004,583, Response filed Dec. 29, 2022 to Non Final Office Action dated Sep. 29, 2022", 8 pgs.

(56) References Cited

OTHER PUBLICATIONS

"U.S. Appl. No. 17/004,583, Restriction Requirement dated Nov. 24, 2021", 10 pgs.
"U.S. Appl. No. 17/155,625, Advisory Action dated Jan. 20, 2023", 3 pgs.
"U.S. Appl. No. 17/155,625, Final Office Action dated Sep. 28, 2022", 18 pgs.
"U.S. Appl. No. 17/155,625, Non Final Office Action dated May 26, 2022", 10 pgs.
"U.S. Appl. No. 17/155,625, Response filed May 2, 2022 to Restriction Requirement dated Mar. 3, 2022", 7 pgs.
"U.S. Appl. No. 17/155,625, Response filed Aug. 29, 2022 to Non Final Office Action dated May 26, 2022", 8 pgs.
"U.S. Appl. No. 17/155,625, Response filed Dec. 28, 2022 to Final Office Action dated Sep. 28, 2022", 8 pgs.
"U.S. Appl. No. 17/155,625, Restriction Requirement dated Mar. 3, 2022", 9 pgs.
"U.S. Appl. No. 17/212,836, Non Final Office Action dated Feb. 16, 2023", 12 pgs.
"U.S. Appl. No. 17/212,836, Response filed Oct. 19, 2022 to Restriction Requirement dated Aug. 19, 2022", 6 pgs.
"U.S. Appl. No. 17/212,836, Restriction Requirement dated Aug. 19, 2022", 7 pgs.
"U.S. Appl. No. 17/229,001, Preliminary Amendment filed Apr. 26, 2021", 7 pgs.
"U.S. Appl. No. 17/352,845, Non Final Office Action dated Dec. 16, 2022", 15 pgs.
"U.S. Appl. No. 17/578,939, Preliminary Amendment filed Apr. 14, 2022", 9 pgs.
"U.S. Appl. No. 17/813,178, Preliminary Amendment filed Jan. 18, 2023", 7 pgs.
"U.S. Appl. No. 14/528,997, Preliminary Amendment filed Dec. 8, 2014", 3 pgs.
"U.S. Appl. No. 14/919,431, Restriction Requirement dated Feb. 3, 2016", 18 pgs.
"Australian Application Serial No. 2001255336, Examiner's First Report dated Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2003219745, Examiner's First Report dated Feb. 14, 2007", 2 pgs.
"Australian Application Serial No. 2003219745, Response filed Mar. 14, 2008 to Examiner's First Report dated Feb. 14, 2007", 24 pgs.
"Australian Application Serial No. 2004249133, First Examiner's Report dated May 5, 2008", 4 pgs.
"Australian Application Serial No. 2004249133, Response filed Mar. 30, 2009 to First Examiner's Report dated May 5, 2008", 30 pgs.
"Australian Application Serial No. 2004274860, Office Action dated May 21, 2008", 2 pgs.
"Australian Application Serial No. 2007245192, Office Action dated Aug. 25, 2011", 2 pgs.
"Australian Application Serial No. 2007245192, Response filed Feb. 28, 2012 to Office Action dated Aug. 25, 2011", 22 pgs.
"Australian Application Serial No. 2008203186, First Examiner Report dated Jan. 28, 2011", 2 pgs.
"Australian Application Serial No. 2008203186, Office Action Received dated Sep. 16, 2010", 1 page.
"Australian Application Serial No. 2008203186, Response filed Mar. 28, 2011 to First Examiner Report dated Jan. 28, 2011", 53 pgs.
"Australian Application Serial No. 2008203186, Response filed Aug. 29, 2011 to Official Action dated Apr. 13, 2011", 20 pgs.
"Australian Application Serial No. 2012204138, First Examiner Report dated Jul. 16, 2013", 4 pgs.
"Australian Application Serial No. 2012204138, Response filed Dec. 24, 2013 to First Examiner Report dated Jul. 16, 2013", 21 pgs.
"Australian Application Serial No. 2014202470, First Examiner Report dated Jul. 20, 2015", 2 pgs.
"Australian Application Serial No. 2014202470, Response filed Jul. 4, 2016 to Subsequent Examiners Report dated Feb. 1, 2016", 3 pgs.
"Australian Application Serial No. 2014202470, Response filed Jul. 20, 2016 to Subsequent Examiners Report dated Jul. 19, 2016", 15 pgs.
"Australian Application Serial No. 2014202470, Response filed Dec. 1, 2015 to First Examiner Report dated Jul. 20, 2015", 22 pgs.
"Australian Application Serial No. 2014202470, Subsequent Examiners Report dated Feb. 1, 2016", 2 pgs.
"Australian Application Serial No. 2014202470, Subsequent Examiners Report dated Jul. 19, 2016", 3 pgs.
"Australian Application Serial No. 2014290203, First Examination Report dated Oct. 10, 2019", 4 pgs.
"Australian Application Serial No. 2014290203, Response filed Mar. 13, 2020 to First Examination Report dated Oct. 10, 2019", 16 pgs.
"Australian Application Serial No. 2014290203, Response filed Jun. 24, 2020 to Subsequent Examiners Report dated Mar. 23, 2020", 16 pgs.
"Australian Application Serial No. 2014290203, Response filed Sep. 29, 2020 to Subsequent Examiners Report dated Jul. 21, 2020", 25 pgs.
"Australian Application Serial No. 2014290203, Response filed Dec. 9, 2020 to Subsequent Examiners Report dated Oct. 6, 2020", 14 pgs.
"Australian Application Serial No. 2014290203, Subsequent Examiners Report dated Mar. 23, 2020", 6 pgs.
"Australian Application Serial No. 2014290203, Subsequent Examiners Report dated Jul. 21, 2020", 5 pgs.
"Australian Application Serial No. 2014290203, Subsequent Examiners Report dated Oct. 6, 2020", 4 pgs.
"Australian Application Serial No. 2017221444, First Examination Report dated Jul. 8, 2020", 6 pgs.
"Australian Application Serial No. 2017221444, Fourth Examiners Report dated Jun. 29, 2021", 3 pgs.
"Australian Application Serial No. 2017221444, Response filed Jan. 25, 2021 to Subsequent Examiners Report dated Nov. 27, 2020", 18 pgs.
"Australian Application Serial No. 2017221444, Response filed Jun. 2, 2021 to Subsequent Examiners Report dated Feb. 24, 2021", 20 pgs.
"Australian Application Serial No. 2017221444, Response filed Jul. 6, 2021 to Fourth Examiners Report dated Jun. 29, 2021", 7 pgs.
"Australian Application Serial No. 2017221444, Response filed Nov. 13, 2020 to First Examination Report dated Jul. 8, 2020", 13 pgs.
"Australian Application Serial No. 2017221444, Subsequent Examiners Report dated Feb. 24, 2021", 4 pgs.
"Australian Application Serial No. 2017221444, Subsequent Examiners Report dated Nov. 27, 2020", 4 pgs.
"Australian Application Serial No. 2021201844, First Examination Report filed Sep. 29, 2022", 3 pgs.
"Australian Application Serial No. 2021201844, Response filed Feb. 3, 2023 to First Examination Report filed Sep. 29, 2022", Claims not amended in response filed, 4 pgs.
"Australian Application Serial No. 2021201844, Voluntary Amendment filed Dec. 6, 2021", 17 pgs.
"Australian Application Serial No. 2008203186, Subsequent Examiner Report dated Apr. 13, 2011", 2 pgs.
"Avian Inluenza", Queensland Government—Department of Primary Industries, (Observed Feb. 22, 2003), 2 pgs.
"Avian Inluenza", http://www.iah.bbsrc.ac.uk/reports/1997/ainf. html, (Observed Feb. 22, 2003), 2 pgs.
"Brazil Application Serial No. PI 0410702-0, Office Action dated Oct. 6, 2020", (w/ English Translation), 9 pgs.
"Brazil Application Serial No. PI 0410702-0, Response filed Dec. 14, 2020 to Office Action dated Oct. 6, 2020", (w/ English Translation of Claims), 42 pgs.
"Brazil Application Serial No. PI0307679-2, Office Action dated May 16, 2017", 2 pgs.
"Brazil Application Serial No. PI0307679-2, Response filed Jul. 13, 2017 to Office Action dated May 16, 2017", 9 pgs.

(56) References Cited

OTHER PUBLICATIONS

"Brazilian Application Serial No. PI 0307679-2, Office Action published in Patent Gazette No. 1871 dated Nov. 14, 2006", 2 pgs.
"Brazilian Application Serial No. PI 0307679-2, Petition filed Jan. 10, 2007 in response to publication dated Nov. 14, 2006", 6 pgs.
"Brazilian Application Serial No. PI 0410702-0, Office Action dated Nov. 1, 2019", (w/ English Translation), 6 pgs.
"Brazilian Application Serial No. PI 0410702-0, Response filed Feb. 6, 2020 to Office Action dated Nov. 1, 2019", (w/ English Translation of Claims), 92 pgs.
"Brazilian Application Serial No. PI0307679-2, Final Office Action dated Jul. 7, 2020", w/o English Translation, 6 pgs.
"Brazilian Application Serial No. PI0307679-2, Office Action dated May 13, 2019", (w/ English Translation), 17 pgs.
"Brazilian Application Serial No. PI0307679-2, Office Action dated Oct. 3, 2019", (w/ English Translation), 6 pgs.
"Brazilian Application Serial No. PI0307679-2, Office Action dated Dec. 20, 2016", 2 pgs.
"Brazilian Application Serial No. PI0307679-2, Response filed Feb. 1, 2017 to Office Action dated Dec. 20, 2016", 6 pgs.
"Brazilian Application Serial No. PI0307679-2, Response filed Aug. 16, 2019 to Office Action dated May 13, 2019", (w/ English Translation of Claims), 29 pgs.
"Brazilian Application Serial No. PI0307679-2, Response filed Dec. 11, 2019 to Office Action dated Oct. 3, 2019", w/ English Claims, 59 pgs.
"Brazilian Application Serial No. PI0410702-0, Office Action dated Feb. 23, 2012", w/ English Translation, 4 pgs.
"Brazilian Application Serial No. PI0410702-0, Office Action dated Apr. 1, 2020", (w/ English Summary), 6 pgs.
"Brazilian Application Serial No. PI0410702-0, Response filed May 7, 2012 to Office Action dated Feb. 23, 2012", w/ English Claims, 11 pgs.
"Brazilian Application Serial No. PI0410702-0, Response filed Aug. 28, 2020 to Office Action dated Apr. 1, 2020", (w/ English Translation of Claims), 86 pgs.
"Canadian Application No. 11/509,249, Response filed May 16, 2011 to Office Acttion dated Nov. 18, 2010", 15 pgs.
"Canadian Application Serial No. 2,406,180, Office Action dated Sep. 9, 2008", 5 pgs.
"Canadian Application Serial No. 2,406,180, Office Action dated Nov. 10, 2011", 3 pgs.
"Canadian Application Serial No. 2,406,180, Office Action dated Nov. 23, 2009", 3 pgs.
"Canadian Application Serial No. 2,406,180, Office Action dated Dec. 10, 2010", 2 Pgs.
"Canadian Application Serial No. 2,406,180, Response filed Jan. 26, 2009 to Official Action dated Sep. 9, 2008", 22 pgs.
"Canadian Application Serial No. 2,406,180, Response filed May 7, 2012 to Office Action dated Nov. 10, 2011", 11 pgs.
"Canadian Application Serial No. 2,406,180, Response filed May 21, 2010 to Office action dated Nov. 23, 2009", 13 pgs.
"Canadian Application Serial No. 2,406,180, Response filed Jun. 14, 2011 to Office Action dated Dec. 10, 2010", 10 pgs.
"Canadian Application Serial No. 2,406,180, Response dated Jun. 10, 2011 to Office Action dated Dec. 10, 2010", 10 pgs.
"Canadian Application Serial No. 2,492,097, Office Action dated Jan. 10, 2012", 4 pgs.
"Canadian Application Serial No. 2,492,097, Office Action dated Apr. 24, 2008", 3 pgs.
"Canadian Application Serial No. 2,492,097, Office Action dated Jul. 31, 2009", 3 pgs.
"Canadian Application Serial No. 2,492,097, Response filed Jan. 29, 2010 to Office Action dated Jul. 31, 2009", 13 pgs.
"Canadian Application Serial No. 2,492,097, Response filed May 2, 2012 to Office Action dated Jan. 10, 2012", 12 pgs.
"Canadian Application Serial No. 2,492,097, Response filed Oct. 23, 2008 to Office Action dated Apr. 24, 2008", 14 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action dated Jun. 6, 2011", 2 pgs.
"Canadian Application Serial No. 2,522,081, Office Action dated Aug. 30, 2010", 2 pgs.
"Canadian Application Serial No. 2,522,081, Office Action dated Oct. 8, 2009", 6 pgs.
"Canadian Application Serial No. 2,522,081, Response filed Feb. 28, 2011 to Office Action dated Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action dated Jun. 6, 2011", 11 pgs.
"Canadian Application Serial No. 2,525,953, Amendment and Response filed Feb. 1, 2017 to Office Action dated Aug. 1, 2016", 28 pgs.
"Canadian Application Serial No. 2,525,953, Non Final Office Action dated Mar. 30, 2022", 4 pgs.
"Canadian Application Serial No. 2,525,953, Office Action dated Jan. 21, 2016", 6 pgs.
"Canadian Application Serial No. 2,525,953, Office Action dated Jan. 29, 2020", 4 pgs.
"Canadian Application Serial No. 2,525,953, Office Action dated Apr. 28, 2021", 7 pgs.
"Canadian Application Serial No. 2,525,953, Office Action dated Jul. 31, 2012", 4 pgs.
"Canadian Application Serial No. 2,525,953, Office Action dated Aug. 1, 2016", 6 pgs.
"Canadian Application Serial No. 2,525,953, Office Action dated Aug. 16, 2013", 3 pgs.
"Canadian Application Serial No. 2,525,953, Office Action dated Oct. 3, 2017", 4 pgs.
"Canadian Application Serial No. 2,525,953, Office Action dated Nov. 2, 2018", 6 pgs.
"Canadian Application Serial No. 2,525,953, Office Action dated Nov. 6, 2014", 3 pgs.
"Canadian Application Serial No. 2,525,953, Office Action dated Jun. 22, 2011", 4 pgs.
"Canadian Application Serial No. 2,525,953, Office Action", 4 pgs.
"Canadian Application Serial No. 2,525,953, Response filed Jan. 31, 2013 to Office Action dated Jul. 31, 2012", 11 pgs.
"Canadian Application Serial No. 2,525,953, Response filed Feb. 1, 2017 to Office Action dated Aug. 1, 2016", 28 pgs.
"Canadian Application Serial No. 2,525,953, Response filed Feb. 14, 2014 to Office Action dated Aug. 16, 2013", 16 pgs.
"Canadian Application Serial No. 2,525,953, Response filed Apr. 3, 2018 to Office Action dated Oct. 3, 2017", 46 pgs.
"Canadian Application Serial No. 2,525,953, Response filed May 1, 2015 to Office Action dated Nov. 6, 2014", 23 pgs.
"Canadian Application Serial No. 2,525,953, Response filed May 2, 2019 to Office Action dated Nov. 2, 2018", 31 pgs.
"Canadian Application Serial No. 2,525,953, Response filed May 25, 2020 to Office Action dated Jan. 29, 2020", 35 pgs.
"Canadian Application Serial No. 2,525,953, Response filed Jul. 11, 2016 to Office Action dated Jan. 21, 2016", 21 pgs.
"Canadian Application Serial No. 2,525,953, Response filed Aug. 26, 2021 to Office Action dated Apr. 28, 2021", 16 pgs.
"Canadian Application Serial No. 2,525,953, Response filed Dec. 22, 2011 to Office Action dated Jun. 22, 2011", 17 pgs.
"Canadian Application Serial No. 2,647,985 , Response filed Sep. 30, 2013 to Office Action dated May 15, 2013", 20 pgs.
"Canadian Application Serial No. 2,647,985, Office Action dated May 15, 2013", 3 pgs.
"Canadian Application Serial No. 2,816,242, Office Action dated Jun. 16, 2014", 3 pgs.
"Canadian Application Serial No. 2,816,242, Office Action dated Jul. 12, 2017", 4 pgs.
"Canadian Application Serial No. 2,816,242, Office Action dated Sep. 16, 2016", 4 pgs.
"Canadian Application Serial No. 2,816,242, Office Action dated Oct. 5, 2015", 6 pgs.
"Canadian Application Serial No. 2,816,242, Response filed Jan. 3, 2018 to Office Action dated Jul. 12, 2017", 13 pgs.

(56) References Cited

OTHER PUBLICATIONS

"Canadian Application Serial No. 2,616,242, Response filed Mar. 10, 2017 to Office Action dated Sep. 16, 2016", 18 pgs.
"Canadian Application Serial No. 2,816,242, Response filed Apr. 5, 2016 to Office Action dated Oct. 5, 2015", 13 pgs.
"Canadian Application Serial No. 2,816,242, Response filed Dec. 16, 2014 to Office Action dated Jun. 16, 2014", 9 pgs.
"Canadian Application Serial No. 2492097, Office Action dated Nov. 18, 2010", 4 pgs.
"Canadian Application Serial No. 3,014,435, Office Action dated Oct. 26, 2021", 4 pgs.
"Canadian Application Serial No. 3,014,435, Office Action dated Nov. 6, 2020", 5 pgs.
"Canadian Application Serial No. 3,014,435, Office Action dated Nov. 13, 2019", 4 pgs.
"Canadian Application Serial No. 3,014,435, Response filed Feb. 25, 2022 to Office Action dated Oct. 26, 2021", 15 pgs.
"Canadian Application Serial No. 3,014,435, Response filed Mar. 5, 2021 to Office Action dated Nov. 6, 2020", 20 pgs.
"Canadian Application Serial No. 3,014,435, Response filed Mar. 13, 2020 to Office Action dated Nov. 13, 2019", 18 pgs.
"Chinese Application Serial No. 202080048487.4, Voluntary Amendment filed Dec. 5, 2022", w/ English Claims, 33 pgs.
"Chinese Application Serial No. 03808356.6, Office Action dated Sep. 5, 2008", (English Translation), 6 pgs.
"Chinese Application Serial No. 03808356.6, Office Action", (w/ English Translation of Office Action), 8 pgs.
"Chinese Application Serial No. 03808356.6, Reexamination Notice dated Nov. 26, 2012", (w/ English Translation), 9 pgs.
"Chinese Application Serial No. 03808356.6, Response filed Mar. 11, 2013 to Office Action dated Nov. 26, 2012", (w/ English Translation of Amended Claims), 9 pgs.
"Chinese Application Serial No. 03808356.6, Response filed Mar. 16, 2009 to Office Action dated Sep. 5, 2008", (w/ English Translation of Claims), 8 pgs.
"Chinese Application Serial No. 03808356.6, Response filed Oct. 14, 2011 to Office Action dated Jul. 1, 2011", (w/ English Translation of Amended Claims), 25 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action dated Mar. 1, 2010", (w/ English Translation of Claims), 16 pgs.
"Chinese Application Serial No. 200480017037.X, Response filed Aug. 4, 2009 to Second Office Action dated Mar. 20, 2009", (w/ English Translation of Amended Claims), 15 pgs.
"Chinese Application Serial No. 200480017037.X, Second Office Action dated Mar. 20, 2009", (English Translation), 7 pgs.
"Chinese Application Serial No. 200480017037.X, Third Office Action dated Mar. 1, 2010", (w/ English Translation), 9 pgs.
"Chinese Application Serial No. 200480021259.9 Office Action dated Sep. 11, 2009", (English Translation), 7 pgs.
"Chinese Application Serial No. 200480021259.9 Response filed Aug. 20, 2010 to Office Acton dated May 6, 2010", (w/ English Translation of Claims), 26 pgs.
"Chinese Application Serial No. 200480021259.9, First Offiice Action dated Aug. 24, 2007", (w/ English Translation), 9 pgs.
"Chinese Application Serial No. 200480021259.9, Notice of Reexamination dated Jul. 3, 2012", (w/ English Translation), 10 pgs.
"Chinese Application Serial No. 200480021259.9, Office Action dated Jan. 11, 2011", (w/ English Translation), 15 pgs.
"Chinese Application Serial No. 200480021259.9, Office Action dated May 6, 2010", (w/ English Translation), 12 pgs.
"Chinese Application Serial No. 200480021259.9, Office Action dated Jul. 3, 2012", (w/ English Translation), 10 pgs.
"Chinese Application Serial No. 200480021259.9, Reexamination Decision dated Mar. 25, 2013", (w/ English Translation), 17 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Office Action dated Aug. 24, 2007", (w/ English Translation of Claims), 13 pgs.
"Chinese Application Serial No. 200480021259.9, Response filed Oct. 16, 2012 to Office Action dated Jul. 3, 2012", (w/ English Translation of Claims), 13 pgs.
"Chinese Application Serial No. 200480022014, First Office Action dated Aug. 24, 2007", w/English Translation, 6 pgs.
"Chinese Application Serial No. 200580046922.5, Office Action dated Jul. 24, 2009", 12 pgs.
"Chinese Application Serial No. 200780020095.1, Decision on Rejection dated Jul. 22, 2013", w/ English Translation), 11 pgs.
"Chinese Application Serial No. 200780020095.1, First Office Action dated Jun. 24, 2011", (w/ (English Translation), 13 pgs.
"Chinese Application Serial No. 200780020095.1, Office Action dated Jan. 29, 2013", (w/ English Translation), 10 pgs.
"Chinese Application Serial No. 200780020095.1, Office Action dated Mar. 5, 2015", (w/ English Translation), 12 pgs.
"Chinese Application Serial No. 200780020095.1, Office Action dated Apr. 26, 2016", (w/ English Summary), 4 pgs.
"Chinese Application Serial No. 200780020095.1, Office Action dated May 3, 2012", (w/ English Translation), 10 pgs.
"Chinese Application Serial No. 200780020095.1, Office Action dated Nov. 2, 2016", (w/ English Translation), 11 pgs.
"Chinese Application Serial No. 200780020095.1, Response filed Jan. 6, 2017 to Office Action dated Nov. 2, 2016", (w/ English Translation of Claims), 15 pgs.
"Chinese Application Serial No. 200780020095.1, Response filed Jun. 9, 2013 to Office Action dated Jan. 29, 2013", (w/ English Translation of Claims), 10 pgs.
"Chinese Application Serial No. 200780020095.1, Response filed Jun. 23, 2015 to Office Action dated Mar. 5, 2015", (w/ English Translation of Claims), 16 pgs.
"Chinese Application Serial No. 200780020095.1, Response filed Jun. 30, 2016 to Office Action dated Apr. 26, 2016", (w/ English Translation of Claims), 22 pgs.
"Chinese Application Serial No. 200780020095.1, Response filed Sep. 17, 2012 to Office Action dated May 3, 2012", (w/ English Translation of Claims), 17 pgs.
"Chinese Application Serial No. 200780020095.1, Response filed Nov. 5, 2013 to to Decision on Rejection dated Jul. 22, 2013", (w/ English Translation of Claims), 12 pgs.
"Chinese Application Serial No. 200780020095.1, Response filed Nov. 8, 2011 to Office Action dated Jun. 24, 2011", (w/ English Translation of Amended Claims), 20 pgs.
"Chinese Application Serial No. 201310400039.8, Notice of Reexamination dated Aug. 26, 2016", (w/ English Translation), 7 pgs.
"Chinese Application Serial No. 201310400039.8, Office Action dated Feb. 12, 2015", (w/ English Translation), 10 pgs.
"Chinese Application Serial No. 201310400039.8, Office Action dated Feb. 15, 2016", (w/ English Translation), 12 pgs.
"Chinese Application Serial No. 201310400039.8, Office Action dated Apr. 1, 2017", (English Translation), 10 pgs.
"Chinese Application Serial No. 201310400039.8, Office Action dated Aug. 7, 2015", (w/ English Translation), 10 pgs.
"Chinese Application Serial No. 201310400039.8, Office Action dated Aug. 21, 2014", (w/ English Translation), 13 pgs.
"Chinese Application Serial No. 201310400039.8, Office Action Response dated Jun. 16, 2017", W/ English Claims, 8 pgs.
"Chinese Application Serial No. 201310400039.8, Response filed Jan. 4, 2015 to Office Action dated Aug. 21, 2014", (w/ English Translation of Claims), 10 pgs.
"Chinese Application Serial No. 201310400039.8, Response filed Apr. 27, 2015 to Office Action dated Feb. 12, 2015", (w/ English Translation of Claims), 16 pgs.
"Chinese Application Serial No. 201310400039.8, Response filed Jun. 1, 2016 to Office Action dated Feb. 15, 2016", (w/ English Translation of Claims), 9 pgs.

(56) References Cited

OTHER PUBLICATIONS

"Chinese Application Serial No. 201310400039.8, Response filed Oct. 10, 2016 to Notice of Reexamination dated Aug. 26, 2016", (w/ English Translation of Claims), 12 pgs.
"Chinese Application Serial No. 201310400039.8, Response filed Oct. 20, 2015 to Office Action dated Aug. 7, 2015", (w/ English Translation of Claims), 11 pgs.
"Chinese Application Serial No. 201310400039.8, Response filed Aug. 14, 2017 to Office Action Response dated Jun. 2016, 17", W/ English Claims, 11 pgs.
"Chinese Application Serial No. 201310400039.8, Response filed Aug. 7, 2017 to Office Action Response dated Jun. 16, 2017", W/ English Claims, 10 pgs.
"Chinese Application Serial No. 201780024821.0, Office Action dated Jun. 15, 2022", (w/ English Translation), 6 pgs.
"Chinese Application Serial No. 201780024821.0, Office Action dated Nov. 30, 2021", (w/ English Translation), 21 pgs.
"Chinese Application Serial No. 201780024821.0, Response filed Apr. 12, 2022 to Office Action dated Nov. 30, 2021", (w/ English Translation of Claims), 17 pgs.
"Chinese Application Serial No. 201780024821.0, Response filed Aug. 30, 2022 to Office Action dated Jun. 15, 2022", w/ English Claims, 18 pgs.
"Chinese Application Serial No. 201780024821.0, Response to Examiner Telephone Interview filed Sep. 26, 2022", w/ English Claims, 10 pgs.
"Chinese Application Serial No. 202080048487.4, Notification to Make Rectification dated Jan. 18, 2022", w/o English Translation, 1 pg.
"Chinese Application Serial No. 202080048487.4, Notification to Make Rectification dated May 26, 2022", w/o English translation, 1 pg.
"Chinese Application Serial No. 200480021259.9, Office Action dated May 8, 2009", (w/ English Translation), 6 pgs.
"Confirmed Cases of Avian Influenza A(H5N1)", World Health Organization, (Jan. 28, 2004), 1 pg.
"Declaration of Anne Koch Ballard dated Oct. 6, 2011", 1 pg.
"Eurasian Application No. 200501890, Notice of Allowance dated Jun. 23, 2009", 1 pg.
"Eurasian Application Serial No. 200501890, Office Action dated Mar. 23, 2007", (w English Translation), 2 pgs.
"Eurasian Application Serial No. 200501890, Office Action dated Sep. 4, 2008", (English Translation), 1 pg.
"Eurasian Application Serial No. 200501890, Office Action dated Dec. 17, 2007", (w/ English Translation), 6 pgs.
"Eurasian Application Serial No. 200501890, Response filed Mar. 26, 2008 to Office Action dated Dec. 17, 2007", (w/ English Translation of Claims), 15 pgs.
"Eurasian Application Serial No. 200501890, Response filed Jun. 14, 2007 to Office Action dated Mar. 23, 2007", (w/ English Translation of Claims), 11 pgs.
"Eurasian Application Serial No. 200501890, Response filed Dec. 17, 2008 to Office Action dated Sep. 4, 2008", (w/ English Translation of Claims), 14 pgs.
"Eurasian Application Serial No. 200701097, Office Action dated Sep. 4, 2008", OAR-MISC, 2 pgs.
"Eurasion Application Serial No. 200701097, Office Action dated Jun. 16, 2009", 3 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication dated Oct. 12, 2006", 4 pgs.
"European Application Serial 17709236.8 , Response filed Apr. 26, 2019 to Communication Pursuant to Rules 161(1) and 162 EPC dated Oct. 19, 2018", 9 pgs.
"European Application Serial No. 03716017.3, Office Action dated Aug. 23, 2012", 4 pgs.
"European Application Serial No. 01928486.8 Office Action dated Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action dated Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication dated Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action dated Oct. 1, 2009", 11 pgs.
"European Application Serial No. 02724994.5, Office Action dated Mar. 27, 2009", 2 pgs.
"European Application Serial No. 03716017.3, Communication and Supplementary European Search Report dated Jan. 2, 2008", 8 pgs.
"European Application Serial No. 03716017.3, Communication dated May 23, 2006", 3 pgs.
"European Application Serial No. 03716017.3, Communication dated Jul. 26, 2006", 2 pgs.
"European Application Serial No. 03716017.3, Communication dated Oct. 20, 2008", 7 pgs.
"European Application Serial No. 03716017.3, Further Written Submissions filed Mar. 19, 2015", 45 pgs.
"European Application Serial No. 03716017.3, Office Action dated Jul. 27, 2010", 4 pgs.
"European Application Serial No. 03716017.3, Response filed Feb. 4, 2011 to Office Action dated Jul. 27, 2010", 12 pgs.
"European Application Serial No. 03716017.3, Response filed Feb. 27, 2015 to Summons dated Nov. 3, 2014", 29 pgs.
"European Application Serial No. 03716017.3, Response filed Mar. 4, 2013 to Examination Notification Art. 94(3) dated Aug. 23, 2012", 19 pgs.
"European Application Serial No. 03716017.3, Response filed Mar. 24, 2015 to Office Action dated Nov. 3, 2014", 38 pgs.
"European Application Serial No. 03716017.3, Response filed Jul. 28, 2006 to Communication dated May 23, 2006", 5 pgs.
"European Application Serial No. 03716017.3, Response filed Aug. 19, 2009 to Communication dated Oct. 20, 2008", 17 pgs.
"European Application Serial No. 03716017.3, Response filed Sep. 28, 2015", 13 pgs.
"European Application Serial No. 03716017.3, Result of Consultation dated Mar. 17, 2015", 5 pgs.
"European Application Serial No. 03716017.3, Summons to Attend Oral proceedings mailed Nov. 3, 2014", 5 pgs.
"European Application Serial No. 04750333.9, Office Action dated Jan. 22, 2009", 5 pgs.
"European Application Serial No. 04750333.9, Response filed Oct. 21, 2008 to Communication dated Apr. 11, 2008", 15 pgs.
"European Application Serial No. 04750333.9, Response filed Nov. 17, 2009 to Communication dated Jan. 22, 2009", 17 pgs.
"European Application Serial No. 04750333.9, Summons to Attend Oral Proceedings mailed Aug. 3, 2011", 13 pgs.
"European Application Serial No. 04776133.3, Communication dated Mar. 30, 2006", 3 pgs.
"European Application Serial No. 04776133.3, Examination Notification Art. 94(3) dated Jul. 28, 2015", 4 pgs.
"European Application Serial No. 04776133.3, Examination Notification Art. 94(3) dated Nov. 25, 2013", 5 pgs.
"European Application Serial No. 04776133.3, Office Action dated Jan. 5, 2010", 4 pgs.
"European Application Serial No. 04776133.3, Response filed Jan. 25, 2007 to Communication dated Mar. 30, 2006", 20 pgs.

(56) References Cited

OTHER PUBLICATIONS

"European Application Serial No. 04776133.3, Response filed Apr. 30, 2014 to Examination Notification Art. 94(3) dated Nov. 25, 2013", 12 pgs.

"European Application Serial No. 04776133.3, Response filed Jul. 15, 2010 to Office Action dated Jan. 5, 2010", 9 pgs.

"European Application Serial No. 04776133.3, Response filed Sep. 18, 2015 to Examination Notification Art. 94(3) dated Jul. 28, 2015", 47 pgs.

"European Application Serial No. 04809419.7, Communication dated Apr. 3, 2007", 3 pgs.

"European Application Serial No. 04809419.7, Response filed Oct. 19, 2007 to Communication dated Apr. 3, 2007", 20 pgs.

"European Application Serial No. 07754132.4, Office Action dated Apr. 28, 2009", 4 pgs.

"European Application Serial No. 07754132.4, Office Action dated Sep. 5, 2011", 5 pgs.

"European Application Serial No. 07754132.4, Office Action dated Nov. 2, 2012", 4 pgs.

"European Application Serial No. 07754132.4, Response filed Feb. 5, 2010 to Office Action dated Apr. 28, 2009", 15 pgs.

"European Application Serial No. 07754132.4, Response filed Mar. 15, 2012 to Office Action dated Sep. 5, 2011", 21 pgs.

"European Application Serial No. 07754132.4, Response filed May 10, 2013 to Office Action dated Nov. 2, 2012", 14 pgs.

"European Application Serial No. 07754132.4, Response filed Jun. 26, 2013", 8 pgs.

"European Application Serial No. 10777154.5, Communication Pursuant to Article 94(3) EPC dated Apr. 4, 2018", 7 pgs.

"European Application Serial No. 10777154.5, Communication Pursuant to Article 94(3) EPC dated Jun. 11, 2019", 3 pgs.

"European Application Serial No. 10777154.5, Communication Pursuant to Article 94(3) EPC dated Oct. 12, 2017", 7 pgs.

"European Application Serial No. 10777154.5, Examination Notification Art. 94(3) dated Oct. 6, 2014". 7 pgs.

"European Application Serial No. 10777154.5, Office Action dated May 2, 2016", 6 pgs.

"European Application Serial No. 10777154.5, Office Action dated Jul. 4, 2012", 2 pgs.

"European Application Serial No. 10777154.5, Response field May 13, 2019 to Summons to Attend Oral Proceedings mailed Jan. 7, 2019", 35 pgs.

"European Application Serial No. 10777154.5, Response field Jun. 4, 2019 to Summons to Attend Oral Proceedings mailed Jan. 7, 2019", 9 pgs.

"European Application Serial No. 10777154.5, Response filed Jan. 14, 2013 to Office Action dated Jul. 4, 2012", 12 pgs.

"European Application Serial No. 10777154.5, Response filed Feb. 21, 2018 to Communication Pursuant to Article 94(3) EPC dated Oct. 12, 2017", 12 pgs.

"European Application Serial No. 10777154.5, Response filed Jul. 29, 2019 to Communication Pursuant to Article 94(3) EPC dated Jun. 11, 2019", 57 pgs.

"European Application Serial No. 10777154.5, Response filed Sep. 7, 2018 to Communication Pursuant to Article 94(3) EPC dated Apr. 4, 2018", 18 pgs.

"European Application Serial No. 10777154.5, Response filed Sep. 8, 2016 to Office Action dated May 2, 2016", 69 pgs.

"European Application Serial No. 10777154.5, Summons to Attend Oral Proceedings mailed Jan. 7, 2019", 5 pgs.

"European Application Serial No. 12761841.1, Communication pursuant to Article 94(3) EPC dated Dec. 23, 2016", 6 pgs.

"European Application Serial No. 12761841.1, Response filed Feb. 23, 2017 to Communication pursuant to Article 94(3) EPC dated Dec. 23, 2016", 9 pgs.

"European Application Serial No. 12761841.1, Voluntary Amendment filed Dec. 1, 2014", 5 pgs.

"European Application Serial No. 14745060.5, Communication Pursuant to Article 94(3) EPC dated Feb. 6, 2018", 5 pgs.

"European Application Serial No. 14745060.5, Communication Pursuant to Article 94(3) EPC dated Mar. 12, 2020", 4 pgs.

"European Application Serial No. 14745060.5, Communication Pursuant to Article 94(3) EPC dated Jul. 18, 2019", 5 pgs.

"European Application Serial No. 14745060.5, Communication Pursuant to Article 94(3) EPC dated Sep. 15, 2021", 4 pgs.

"European Application Serial No. 14745060.5, Communication Pursuant to Article 94(3) EPC dated Sep. 18, 2018", 4 pgs.

"European Application Serial No. 14745060.5, Communication Pursuant to Article 94(3) EPC dated Nov. 9, 2020", 4 pgs.

"European Application Serial No. 14745060.5, Office Action dated Feb. 23, 2016", 2 pgs.

"European Application Serial No. 14745060.5, Response filed Jan. 5, 2022 to Communication Pursuant to Article 94(3) EPC dated Sep. 15, 2021", 78 pgs.

"European Application Serial No. 14745060.5, Response filed Jan. 28, 2020 to Communication Pursuant to Article 94(3) EPC dated Jul. 18, 2019", 9 pgs.

"European Application Serial No. 14745060.5, Response filed Mar. 27, 2019 to Communication Pursuant to Article 94(3) EPC dated Sep. 18, 2018", 13 pgs.

"European Application Serial No. 14745060.5, Response filed May 12, 2021 to Communication Pursuant to Article 94(3) EPC dated Nov. 9, 2020", 12 pgs.

"European Application Serial No. 14745060.5, Response filed Jun. 15, 2018 to Communication Pursuant to Article 94(3) EPC dated Feb. 6, 2018", 14 pgs.

"European Application Serial No. 14745060.5, Response filed Jul. 17, 2020 to Communication Pursuant to Article 94(3) EPC dated Mar. 12, 2020", 52 pgs.

"European Application Serial No. 14745060.5, Response filed Dec. 22, 2016 to Communication pursuant to Rules 161(1) and 162 EPC dated Feb. 23, 2016", 6 pgs.

"European Application Serial No. 15197386.4, Communication Pursuant to Article 94(3) EPC dated Feb. 21, 2018", 5 pgs.

"European Application Serial No. 15197386.4, Communication Pursuant to Article 94(3) EPC dated Apr. 21, 2017", 5 pgs.

"European Application Serial No. 15197386.4, Communication Pursuant to Article 94(3) EPC dated Jun. 19, 2019", 4 pgs.

"European Application Serial No. 15197386.4, extended European Search Report dated Feb. 26, 2016", 11 pgs.

"European Application Serial No. 15197386.4, Response filed Jul. 3, 2018 to Communication Pursuant to Article 94(3) EPC dated Feb. 21, 2018", 7 pgs.

"European Application Serial No. 15197386.4, Response filed Aug. 27, 2019 to Communication Pursuant to Article 94(3) EPC dated Jun. 19, 2019", 61 pgs.

"European Application Serial No. 15197386.4, Response filed Oct. 20, 2016 to Extended European Search Report dated Feb. 26, 2016", 4 pgs.

"European Application Serial No. 15197386.4, Response filed Oct. 31, 2017 to Communication Pursuant to Article 94(3) EPC dated Apr. 21, 2017", 5 pgs.

"European Application Serial No. 16778485.9, Communication Pursuant to Article 94(3) EPC dated Feb. 18, 2022", 4 pgs.

"European Application Serial No. 16778485.9, Communication Pursuant to Article 94(3) EPC dated May 25, 2020", 5 pgs.

"European Application Serial No. 16778485.9, Communication Pursuant to Article 94(3) EPC dated Aug. 22, 2019", 5 pgs.

"European Application Serial No. 16778485.9, Office Action dated Apr. 30, 2018", 3 pgs.

"European Application Serial No. 16778485.9, Response filed Aug. 9, 2022 to Communication Pursuant to Article 94(3) EPC dated Feb. 18, 2022", 14 pgs.

"European Application Serial No. 16778485.9, Response filed Oct. 5, 2020 to Communication Pursuant to Article 94(3) EPC dated May 25, 2020", 14 pgs.

"European Application Serial No. 16778485.9, Response filed Nov. 8, 2018 to Office Action dated Apr. 30, 2018", 18 pgs.

"European Application Serial No. 16778485.9, Response filed Dec. 19, 2019 to Communication Pursuant to Article 94(3) EPC dated Aug. 22, 2019", 20 pgs.

(56) References Cited

OTHER PUBLICATIONS

"European Application Serial No. 17709236.8, Communication Pursuant to Article 94(3) EPC dated Jun. 8, 2022", 6 pgs.
"European Application Serial No. 17709236.8, Communication Pursuant to Article 94(3) EPC dated Jul. 6, 2021", 10 pgs.
"European Application Serial No. 17709236.8, Response filed Jan. 17, 2022 to Communication Pursuant to Article 94(3) EPC dated Jul. 6, 2021", 13 pgs.
"European Application Serial No. 17709236.8, Response filed Oct. 11, 2022 to Communication Pursuant to Article 94(3) EPC dated Jun. 8, 2022", 65 pgs.
"European Application Serial No. 18800815.5, Response to Communication pursuant to Rules 161(1) and 162 EPC filed Dec. 15, 2020", 14 pgs.
"European Application Serial No. 19778696.5, Response to Communication persuant to Rules 161 and 162 filed Oct. 15, 2021", 39 pgs.
"European Application Serial No. 20731609.2, Response to Communication persuant to Rules 161 and 162 filed Mar. 16, 2022", 17 pgs.
"European Application Serial No. 20768781.5, Response to Communication persuant to Rules 161 and 162 filed Oct. 17, 2022", 17 pgs.
"Evaluation of Medicines for human Use", EMEA/CPMP/BWP/2289/01, London the European Agency for the Evaluation of Medicinal Products, Committee for Proprietary Medicinal Products (CPMP), (Feb. 20, 2003), 14.
"FLUZONE Influenza Virus Vaccine", Sanofi Aventis Pasteur, Swiftwater, (Jul. 2005), 12 pgs.
"Gen Bank Accession AFP82914", matrix protein 1 [Influenza A virus (A/reassortant/IVR-148(Brisbane/59/2007 x Texas/1/1977) (H1N1))], (2012), 2 pgs.
"Gen Bank Accession JX414012", Influenza A virus (A/reassortant/IVR-148(Brisbane/59/2007 x Texas/1/1977)(H1 N1)) segment 7 matrix protein 2 (M2) and matrix protein 1 (M1) genes, complete cds, (2012), 2 pgs.
"Gen Bank Accessions QHU79173", surface glycoprotein [Severe acute respiratory syndrome coronavirus 2], (Mar. 17, 2020), 3 pgs.
"Genbank Accession # AAA43733, Neuraminidase Protein of Influenza B/Beijing/1/87 virus,", (1993), 4 pg.
"Genbank Accession # AAU94753, Neuraminidase Protein of Influenza B/Aichi/5/88 virus,", (2004), 7 pgs.
"Genbank Accession # ABA02233, Neuraminidase Protein of Influenza B/Perth/211/2001 virus", (2006), 3 pgs.
"Genbank Accession #,", neuraminidase influenza virus B/memphis/20/96,, (1999), 3 pgs.
"GFP antibody (ab6556) datasheet", (r) abcam. [online]. [retrieved on Dec. 5, 2004]. Retrieved from the Internet: <URL: http://www.abcam.com/index.html?datasheet=6556>, (2004), 5 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, (2006), 1 pg.
"https://www.abcam.com/gfp-antibody-ab6556", [online]. [accessed on Dec. 5, 2004]. Retrieved from the Internet: http://www.abcam.com/index.html?datasheet=6556, (Dec. 5, 2004), 5 pgs.
"Identification by siRNA of host proteins involved in Ebolavirus replication", Index of GLRCE: documents from 2007 Great Lakes Regional Center of Excellence Index, Retrieved from the Internet: URL:http://www.rcebiodefense.org/glrce/docs/2007/Kawaokja.pdf [retrieved on Jan. 14, 2010], (2007), 8 pgs.
"Indian Application Serial No. 02082/KOLNP/2005, Examination Report dated Mar. 17, 2008", 1 pg.
"Indian Application Serial No. 02082/KOLNP/2005, Examination Report dated Dec. 28, 2007", 1 pg.
"Indian Application Serial No. 02082/KOLNP/2005, First Examination Report dated Jan. 25, 2007", 9 pgs.
"Indian Application Serial No. 02082/KOLNP/2005, Response filed Jan. 22, 2008 to Examination Report dated Dec. 28, 2007", 13 pgs.
"Indian Application Serial No. 02082/KOLNP/2005, Response filed Jun. 10, 2008 to Examination Report dated Mar. 17, 2008", 3 pgs.
"Indian Application Serial No. 02082/KOLNP/2005, Response filed Nov. 19, 2007 to First Examination Report dated Jan. 25, 2007", 26 pgs.
"Indian Application Serial No. 1026/KOLNP/2009, First Examiner Report dated Mar. 13, 2014", 2 pgs.
"Indian Application Serial No. 2272/KOLNP/2005, First Examination Report dated Mar. 17, 2008", 10 pgs.
"Indian Application Serial No. 2272/KOLNP/2005, Response filed Mar. 16, 2009 to Subsequent Examination Report dated Mar. 6, 2009", 12 pgs.
"Indian Application Serial No. 2272/KOLNP/2005, Response filed Oct. 11, 2008 to First Examination Report dated Mar. 17, 2008", 27 pgs.
"Indian Application Serial No. 2272/KOLNP/2005, Subsequent Examination Report dated Mar. 6, 2009", 1 pg.
"Indian Application Serial No. 2388/KOLNP/2005, First Examination Report dated Mar. 28, 2007", 10 pgs.
"Influenza B/Ann Arbor/1/66 (cold-adapted) nonstructural protein (seg 8) RNA, complete cds", GenBank Accession M20224, (Aug. 2, 1993), 13 pgs.
"Influenza B/lee/40, neuraminidase & nb (seg 6) ma", Database Em_VI E.B.I. Hinxton U.K., (Jun. 13, 1985), 10 pgs.
"Influenza virus A/CHR/ 157/83 genomic RNA for haemagglutinin", (2012), 2 pgs.
"International Application No. PCT/US2004/016680, International Search Report", (dated Feb. 2, 2005), 7 pgs.
"International Application Serial No. PCT/US2021/033365, International Search Report dated Sep. 24, 2021", 6 pgs.
"International Application Serial No. PCT/US2021/033365, Written Opinion dated Sep. 24, 2021", 6 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report dated Oct. 15, 2002", 13 pgs.
"International Application Serial No. PCT/US01/11963, International Search Report dated May 7, 2002", 5 pgs.
"International Application Serial No. PCT/US01/11963, Response filed Sep. 9, 2002 to Written Opinion dated Aug. 7, 2002", 12 pgs.
"International Application Serial No. PCT/US01/11963, Written Opinion dated Jun. 14, 2002", 12 pgs.
"International Application Serial No. PCT/US01/11963, Written Opinion dated Aug. 7, 2002", 6 pgs.
"International Application Serial No. PCT/US02/05455, International Preliminary Examination Report dated Aug. 17, 2004", 4 pgs.
"International Application Serial No. PCT/US02/05455, International Search Report dated Mar. 25, 2003", 3 pgs.
"International Application Serial No. PCT/US03/04233, International Search Report dated Dec. 16, 2005", 7 pgs.
"International Application Serial No. PCT/US2004/012050, International Search Report dated Feb. 2, 2005", 8 pgs.
"International Application Serial No. PCT/US2004/012050, Written Opinion dated Feb. 2, 2005", 12 pgs.
"International Application Serial No. PCT/US2004/016649, International Preliminary Report on Patentability dated Dec. 15, 2005", 7 pgs.
"International Application Serial No. PCT/US2004/016649, International Search Report dated Apr. 18, 2005", 6 pgs.
"International Application Serial No. PCT/US2004/016680, International Preliminary Report on Patentability dated Dec. 15, 2005", 11 pgs.
"International Application Serial No. PCT/US2005/041991, International Search Report dated Jun. 4, 2007", 5 pgs.
"International Application Serial No. PCT/US2005/041991, Written Opinion dated Jun. 4, 2007", 6 pgs.
"International Application Serial No. PCT/US2007/007562, International Preliminary Report on Patentability dated Oct. 9, 2008", 5 pgs.
"International Application Serial No. PCT/US2007/007562, International Search Report dated Jan. 14, 2008", 8 pgs.

(56) References Cited

OTHER PUBLICATIONS

"International Application Serial No. PCT/US2007/007562, Written Opinion dated Jan. 14, 2008", 9 pgs.
"International Application Serial No. PCT/US2007/013407, International Search Report dated Oct. 24, 2008", 10 pgs.
"International Application Serial No. PCT/US2007/013407, Written Opinion dated Oct. 24, 2008", 14 pgs.
"International Application Serial No. PCT/US2008/004125, International Search Report dated Feb. 20, 2009", 6 pgs.
"International Application Serial No. PCT/US2008/004125, Written Opinion dated Feb. 20, 2009", 8 pgs.
"International Application Serial No. PCT/US2008/005641, International Preliminary Report on Patentability dated Nov. 10, 2009", 9 pgs.
"International Application Serial No. PCT/US2008/005641, International Search Report dated Feb. 4, 2009", 6 pgs.
"International Application Serial No. PCT/US2008/005641, Written Opinion dated Feb. 4, 2009", 8 pgs.
"International Application Serial No. PCT/US2008/007417, International Search Report dated Jan. 30, 2009", 20 pgs.
"International Application Serial No. PCT/US2008/007417, Written Opinion dated Jan. 30, 2009", 10 pgs.
"International Application Serial No. PCT/US2008/007582, International Preliminary Report on Patentability dated Jan. 7, 2010", 9 pgs.
"International Application Serial No. PCT/US2008/007582, International Search Report and Written Opinion dated Feb. 18, 2009", 16 pgs.
"International Application Serial No. PCT/US2009/000056, International Search Report dated Feb. 9, 2010", 3 pgs.
"International Application Serial No. PCT/US2009/000056, Written Opinion dated Feb. 9, 2010", 5 pgs.
"International Application Serial No. PCT/US2009/006019, International Preliminary Report on Patentability dated May 19, 2011", 8 pgs.
"International Application Serial No. PCT/US2009/006019, Invitation to Pay Additional Fee dated Apr. 6, 2010", 8 pgs.
"International Application Serial No. PCT/US2009/006019, Search Report dated Jun. 10, 2010", 7 Pgs.
"International Application Serial No. PCT/US2009/006019, Written Opinion dated Jun. 10, 2010", 6 pgs.
"International Application Serial No. PCT/US2010/054128, Preliminary Report on Patentability dated May 10, 2012", 10 pgs.
"International Application Serial No. PCT/US2010/054128, Search Report dated Feb. 23, 2011", 6 pgs.
"International Application Serial No. PCT/US2010/054128, Written Opinion dated Mar. 13, 2014", 8 pgs.
"International Application Serial No. PCT/US2012/052368, International Preliminary Report on Patentability dated Mar. 13, 2014", 8 pgs.
"International Application Serial No. PCT/US2012/052368, International Search Report dated Dec. 3, 2012", 4 pgs.
"International Application Serial No. PCT/US2012/052368, Written Opinion dated Dec. 3, 2012", 6 pgs.
"International Application Serial No. PCT/US2014/046731, International Preliminary Report on Patentability dated Jan. 28, 2016", 12 pgs.
"International Application Serial No. PCT/US2014/046731, International Search Report dated Nov. 25, 2014", 9 pgs.
"International Application Serial No. PCT/US2014/046731, Written Opinion dated Nov. 25, 2014", 10 pgs.
"International Application Serial No. PCT/US2015/036803, International Preliminary Report on Patentability dated Dec. 29, 2016", 10 pgs.
"International Application Serial No. PCT/US2015/036803, International Search Report dated Dec. 11, 2015", 8 pgs.
"International Application Serial No. PCT/US2015/036803, Invitation to Pay Add'l Fees and Partial Search Rpt dated Oct. 2, 2015", 8 pgs.
"International Application Serial No. PCT/US2015/036803, Written Opinion dated Dec. 11, 2015", 8 pgs.
"International Application Serial No. PCT/US2016/041172, International Preliminary Report on Patentability dated Jan. 18, 2018", 10 pgs.
"International Application Serial No. PCT/US2016/041172, International Search Report dated Oct. 27, 2016", 6 pgs.
"International Application Serial No. PCT/US2016/041172, Written Opinion dated Oct. 27, 2016", 8 pgs.
"International Application Serial No. PCT/US2016/048691, International Preliminary Report on Patentability dated Mar. 15, 2018", 7 pgs.
"International Application Serial No. PCT/US2016/048691, International Search Report dated Nov. 22, 2016", 7 pgs.
"International Application Serial No. PCT/US2016/048691, Written Opinion dated Nov. 22, 2016", 6 pgs.
"International Application Serial No. PCT/US2017/018443, International Preliminary Report on Patentability dated Aug. 30, 2018", 11 pgs.
"International Application Serial No. PCT/US2017/018443, International Search Report dated May 22, 2017", 9 pgs.
"International Application Serial No. PCT/US2017/018443, Written Opinion dated May 22, 2017", 9 pgs.
"International Application Serial No. PCT/US2018/057576, International Preliminary Report on Patentability dated May 7, 2020", 12 pgs.
"International Application Serial No. PCT/US2018/057576, International Search Report dated Mar. 25, 2019", 7 pgs.
"International Application Serial No. PCT/US2018/057576, Invitation to Pay Additional Fees and Partial Search Report dated Jan. 31, 2019", 16 pgs.
"International Application Serial No. PCT/US2018/057576, Written Opinion dated Mar. 25, 2019", 10 pgs.
"International Application Serial No. PCT/US2019/037084, International Preliminary Report on Patentability dated Dec. 24, 2020", 12 pgs.
"International Application Serial No. PCT/US2019/037084, International Search Report dated Nov. 14, 2019", 10 pgs.
"International Application Serial No. PCT/US2019/037084, Invitation to Pay Add'l Fees and Partial Search Report dated Sep. 24, 2019", 10 pgs.
"International Application Serial No. PCT/US2019/037084, Written Opinion dated Nov. 14, 2019", 10 pgs.
"International Application Serial No. PCT/US2019/045476, International Preliminary Report on Patentability dated Feb. 18, 2021", 13 pgs.
"International Application Serial No. PCT/US2019/045476, International Search Report dated Feb. 11, 2020", 8 pgs.
"International Application Serial No. PCT/US2019/045476, Invitation to Pay Additional Fees dated Dec. 17, 2019", 14 pgs.
"International Application Serial No. PCT/US2019/045476, Written Opinion dated Feb. 11, 2020", 13 pgs.
"International Application Serial No. PCT/US2019/047263, International Preliminary Report on Patentability dated Mar. 4, 2021", 8 pgs.
"International Application Serial No. PCT/US2019/047263, International Search Report dated Dec. 20, 2019", 5 pgs.
"International Application Serial No. PCT/US2019/047263, Written Opinion dated Dec. 20, 2019", 6 pgs.
"International Application Serial No. PCT/US2020/014659, International Preliminary Report on Patentability dated Aug. 5, 2021", 12 pgs.
"International Application Serial No. PCT/US2020/014659, International Search Report dated Nov. 6, 2020", 7 pgs.
"International Application Serial No. PCT/US2020/014659, Invitation to Pay Additional Fees dated Sep. 16, 2020", 11 pgs.
"International Application Serial No. PCT/US2020/014659, Written Opinion dated Nov. 6, 2020", 10 pgs.
"International Application Serial No. PCT/US2020/031176, International Preliminary Report on Patentability dated Nov. 11, 2021", 9 pgs.
"International Application Serial No. PCT/US2020/031176, International Search Report dated Jul. 22, 2020", 6 pgs.

(56) References Cited

OTHER PUBLICATIONS

"International Application Serial No. PCT/US2020/031176, Written Opinion dated Jul. 22, 2020", 7 pgs.
"International Application Serial No. PCT/US2020/048130, International Preliminary Report on Patentability dated Mar. 10, 2022", 11 pgs.
"International Application Serial No. PCT/US2020/048130, International Search Report dated Apr. 20, 2021", 9 pgs.
"International Application Serial No. PCT/US2020/048130, Invitation to Pay Additional Fees dated Jan. 13, 2021", 7 pgs.
"International Application Serial No. PCT/US2020/048130, Written Opinion dated Apr. 20, 2021", 9 pgs.
"International Application Serial No. PCT/US2021/014586, International Preliminary Report on Patentability dated Aug. 4, 2022", 10 pgs.
"International Application Serial No. PCT/US2021/014586, International Search Report dated May 20, 2021", 7 pgs.
"International Application Serial No. PCT/US2021/014586, Written Opinion dated May 20, 2021", 8 pgs.
"International Application Serial No. PCT/US2021/024200, International Preliminary Report on Patentability dated Oct. 6, 2022", 8 pgs.
"International Application Serial No. PCT/US2021/024200, International Search Report dated Jul. 16, 2021", 6 pgs.
"International Application Serial No. PCT/US2021/024200, Written Opinion dated Jul. 16, 2021", 6 pgs.
"International Application Serial No. PCT/US2021/033365, International Preliminary Report on Patentability dated Dec. 8, 2022", 8 pgs.
"Israel Application Serial No. 163,546, Office Action dated Nov. 12, 2009", w/English Translation, 1 pg.
"Israel Application Serial No. 163,546, Office Action dated Dec. 26, 2007", w/English Translation, 1 pg.
"Israel Application Serial No. 163,546, Response filed May 9, 2008 to Office Action dated Dec. 26, 2007", w/English Translation, 2 pgs.
"Israel Application Serial No. 163,546, Response filed Jun. 8, 2010 to Office Action dated Nov. 12, 2009", w/English Claims, 3 pgs.
"Israel Application Serial No. 163,546, Response filed Aug. 16, 2009 to Substantive Examination Report dated Feb. 23, 2009", w/English Claims, 4 pgs.
"Israel Application Serial No. 163,546, Response filed Oct. 20, 2010 to Office Action dated Jun. 8, 2010", w/English Claims, 8 pgs.
"Israel Application Serial No. 163,546, Response filed Nov. 27, 2008 to First Examination Report dated Jul. 28, 2008", w/English Claims, 13 pgs.
"Israel Application Serial No. 163546, Office Action dated Jun. 8, 2010", w/English Translation, 2 pgs.
"Israel Application Serial No. 183026, Office Action dated Feb. 9, 2009", w/English Translation, 2 pgs.
"Israel Application Serial No. 238584, Office Action dated Jul. 24, 2017", w/English Translation, 2 pgs.
"Israel Application Serial No. 238584, Response filed Nov. 21, 2017 to Office Action dated Jul. 24, 2017", W/English Translation, 2 pgs.
"Israeli Application Serial No. 171831, Notification of Defects dated Nov. 10, 2008", w/English Translation, 10 pgs.
"Israeli Application Serial No. 163,546, First Examination Report dated Jul. 28, 2008", (English Translation), 2 pgs.
"Israeli Application Serial No. 163,546, Substantive Examination Report dated Feb. 23, 2009", w/English Translation, 3 pgs.
"Israeli Application Serial No. 171372, Office Action dated Feb. 21, 2010", w/English Translation, 2 pgs.
"Israeli Application Serial No. 171372, Office Action dated Nov. 6, 2008", (Translation), 12 pgs.
"Israeli Application Serial No. 171372, Response filed Nov. 18, 2010 to Office Action dated Feb. 21, 2010", w/English Translation, 19 pgs.
"Israeli Application Serial No. 171831, Office Action dated Feb. 21, 2010", w/English Translation, 2 pgs.
"Israeli Application Serial No. 171831, Office Action dated Apr. 18, 2012", (English Translation), 2 pgs.
"Israeli Application Serial No. 171831, Response filed Jan. 20, 2011 to Office Action dated Feb. 21, 2021", w/English Translation, 18 pgs.
"Israeli Application Serial No. 171831, Response filed Jun. 24, 2009 to Notification of Defects dated Nov. 10, 2008", w/English Claims, 10 pgs.
"Israeli Application Serial No. 171831, Response filed Nov. 6, 2012 to Office Action dated Apr. 18, 2012", w/English Claims, 54 pgs.
"Israeli Application Serial No. 211324, Office Action dated Sep. 18, 2014", w/English Translation, 5 pgs.
"Israeli Application Serial No. 211324, Office Action dated Oct. 18, 2015", w/English Translation, 4 pgs.
"Israeli Application Serial No. 211324, Response filed Feb. 16, 2016 to Office Action dated Oct. 18, 2015", w/English Claims, 4 pgs.
"Israeli Application Serial No. 211324, Response filed Mar. 31, 2015 to Office Action dated Sep. 8, 2014", w/English Translation, 21 pgs.
"Israeli Application Serial No. 238584, Notification of Defects in Patent Application dated Jul. 21, 2019", (w/ English Translation), 5 pgs.
"Israeli Application Serial No. 238584, Office Action dated Apr. 2014, 16", (English Translation), 3 pgs.
"Israeli Application Serial No. 238584, Office Action dated Aug. 23, 2018", (w/ English Translation), 6 pgs.
"Israeli Application Serial No. 238584, Response filed Aug. 3, 2016 to Office Action dated Apr. 14, 2016", (English Translation of Claims), 19 pgs.
"Israeli Application Serial No. 238584, Response filed Nov. 21, 2017 to Office Action dated Jul. 24, 2017", (Translation), 2 pgs.
"Israeli Application Serial No. 238584, Response filed Nov. 21, 2019 to Notification of Defects in Patent Application dated Jul. 21, 2019", (w/ English Translation of Claims), 6 pgs.
"Israeli Application Serial No. 238584, Response Filed Dec. 10, 2018 to Office Action dated Aug. 23, 2018", (w/ English Translation of Claims), 10 pgs.
"Israeli Application Serial No. 171372,Office Action dated Feb. 20, 2011", (Translation), 2 pgs.
"Japanese Application No. 2001-576868, Office Action dated May 31, 2011", (w/ English Translation), 5 pgs.
"Japanese Application No. 2001-576868, Response filed Apr. 26, 2011 to Office Action dated Nov. 2, 2010", (w/ Translation of Amended Claims), 14 pgs.
"Japanese Application Serial No. 2022-144599, Voluntary Amendment filed Nov. 9, 2022", w/ English Claims, 14 pgs.
"Japanese Application Serial No. 2022-544779, Voluntary Amendment filed Sep. 9, 2022", w/ English Claims, 8 pgs.
"Japanese Application Serial No. 2001-576868, Office Action dated Nov. 2, 2010", w/ English Translation), 10 pgs.
"Japanese Application Serial No. 2001-576868, Response filed Dec. 1, 2011 to Office Action dated May 3, 2011", (w/ English Translation of Amended Claims), 37 pgs.
"Japanese Application Serial No. 2003-315106, Amended Claims filed Oct. 15, 2009 in Response to Office Action dated Jun. 24, 2009", (English Translation), 6 pgs.
"Japanese Application Serial No. 2003-315106, Notice of Allowance dated Jan. 5, 2010", (w/ English Translation), 5 pgs.
"Japanese Application Serial No. 2003-315106, Office Action dated Jun. 24, 2009", (w/ English Translation), 10 pgs.
"Japanese Application Serial No. 2003-568038, Amendment filed Aug. 19, 2005", (English Translation), 8 pgs.
"Japanese Application Serial No. 2003-568038, Notice of Allowance dated Nov. 30, 2009", w/out English Translation, 3 pgs.
"Japanese Application Serial No. 2003-568038, Office Action dated May 15, 2009", (w/ English Translation), 7 pgs.
"Japanese Application Serial No. 2003-568038, Office Action dated Jul. 10, 2008", (w/ English Translation), 11 pgs.
"Japanese Application Serial No. 2003-568038, Office Action dated Jul. 21, 2005", w/out English Translation, 3 pgs.
"Japanese Application Serial No. 2003-568038, Request for Examination filed Aug. 19, 2005 in Response to Official Action dated Jul. 21, 2005", (w/ Partial English Translation of Specification), 8 pgs.

(56) References Cited

OTHER PUBLICATIONS

"Japanese Application Serial No. 2003-568038, Response filed Sep. 14, 2009 to Office Action dated May 15, 2009", (w/ English Translation of Amended Claims), 10 pgs.

"Japanese Application Serial No. 2003-568038, Response filed Dec. 10, 2008 to Office Action dated Jul. 10, 2008", (w/ English Translation of Amended Claims), 15 pgs.

"Japanese Application Serial No. 2006-513125, Office Action dated Mar. 9, 2010", (English Translation), 11 pgs.

"Japanese Application Serial No. 2006-513125, Response filed Aug. 30, 2010 to Office Action dated Mar. 9, 2010", (w/ English Translation of Amended Claims), 60 pgs.

"Japanese Application Serial No. 2006-533439, Decision of Final Rejection dated Aug. 14, 2012", (w/ English Translation), 5 pgs.

"Japanese Application Serial No. 2006-533439, Office Action dated Mar. 9, 2010", (w/ English (Translations), 20 pgs.

"Japanese Application Serial No. 2006-533439, Office Action dated Mar. 27, 2012", w/ English Translation, 8 pgs.

"Japanese Application Serial No. 2006-533439, Response filed May 21, 2012 to Office Action dated Mar. 27, 2012", (w/ English Translation of Amended Claims), 19 pgs.

"Japanese Application Serial No. 2006-533439, Response filed Aug. 3, 2011 to Office Action dated Feb. 15, 2011", (w/ English Translation of Amended Claims), 18 pgs.

"Japanese Application Serial No. 2006-533439,Office Action dated Feb. 15, 2011", (w/ English Translation), 13 pgs.

"Japanese Application Serial No. 2006-533439; Office Action Response filed Jul. 9, 2010", (w/ English Translation of Claims), 25 pgs.

"Japanese Application Serial No. 2008-315106, Office Action dated Jun. 24, 2009", (w/ English Translation), 10 pgs.

"Japanese Application Serial No. 2008-315106, Response filed Oct. 15, 2009 to Office Action dated Jun. 24, 2009", w/English Translation, 103 pgs.

"Japanese Application Serial No. 2008-315106, Response filed Oct. 15, 2009 to Office Action dated Jun. 24, 2009", (w/ English Translation of Amended Claims), 103 pgs.

"Japanese Application Serial No. 2008-315106, Response filed Dec. 3, 2009 to Office Action dated Jun. 24, 2009", (w/ English Translation of Claims), 9 pgs.

"Japanese Application Serial No. 2009-238781, Office Action dated Oct. 11, 2011", (w/ English Translation), 3 pgs.

"Japanese Application Serial No. 2009-502945, Examiners Decision of Final Refusal dated Nov. 12, 2013", (w/ English Translation), 8 pgs.

"Japanese Application Serial No. 2009-502945, Office Action dated Oct. 23, 2012", (w/ English Translation), 16 pgs.

"Japanese Application Serial No. 2009-502945, Response filed Apr. 10, 2013 to Office Action dated Oct. 23, 2012", (w/ English Translation of Claims), 18 pgs.

"Japanese Application Serial No. 2011-111048, Office Action dated Jun. 25, 2013", (w/ English Translation), 7 pgs.

"Japanese Application Serial No. 2011-111048, Office Action dated Sep. 18, 2012", (w/ English Translation), 10 pga.

"Japanese Application Serial No. 2011-111048, Response filed Sep. 25, 2012 to Office Action dated Jun. 25, 2013", (w/ English Translation of Amended Claims), 18 pgs.

"Japanese Application Serial No. 2011-111048. Response filed Mar. 15, 2013", (w/ Translation of Amended Claims), 14 pgs.

"Japanese Application Serial No. 2012-273898, Office Action dated Jun. 10, 2014", (w/ English Translation), 7 pgs.

"Japanese Application Serial No. 2012-273898, Response filed Sep. 4, 2014 to Office Action dated Jun. 10, 2014", W/ English Claims, 9 pgs.

"Japanese Application Serial No. 2012-536963, Amendment and Argument filed Jun. 26, 2015 to Office Action dated Jan. 6, 2015", (w/ English Translation of Amended Claims), 12 pgs.

"Japanese Application Serial No. 2012-536963, Examiners Decision of Final Refusal dated Nov. 17, 2015", (w/ English Translation), 8 pgs.

"Japanese Application Serial No. 2012-536963, Office Action dated Jan. 6, 2015", (w/ English Translation), 14 pgs.

"Japanese Application Serial No. 2012-536963, Voluntary Amendment filed Jun. 27, 2012", (w/ English Translation of Amended Claims), 17 pgs.

"Japanese Application Serial No. 2013-198377, Office Action dated Jan. 6, 2015", (w/ English Translation), 9 pgs.

"Japanese Application Serial No. 2014-049025 Response filed Sep. 4, 2015 to Office Action dated Jun. 16, 2015", (w/ Amended Claims), 12 pgs.

"Japanese Application Serial No. 2014-049025, Examiners Decision of Final Refusal dated Feb. 2, 2016", W/ English Translation, 5 pgs.

"Japanese Application Serial No. 2014-049025, Office Action dated Jun. 16, 2015", (w/ English Translation), 6 pgs.

"Japanese Application Serial No. 2014-527339, Examiners Decision of Final Refusal dated Feb. 7, 2017", (w/ English Translation), 5 pgs.

"Japanese Application Serial No. 2014-527339, Office Action dated May 31, 2016", (w/ English Translation), 10 pgs.

"Japanese Application Serial No. 2014-527339, Response filed Sep. 16, 2016 to Office Action dated May 31, 2016", (w/ English Translation of Amended Claims), 33 pgs.

"Japanese Application Serial No. 2016-053990, Office Action dated Jun. 6, 2017", (w/ English Translation), 4 pgs.

"Japanese Application Serial No. 2016-053990, Response filed Dec. 6, 2017 to Office Action dated Jun. 6, 2017", (w/ English Translation of Amended Claims), 14 pgs.

"Japanese Application Serial No. 2016-110879, Office Action dated May 30, 2017", (w/ English Translation), 7 pgs.

"Japanese Application Serial No. 2016-110879, Response filed Nov. 30, 2017 to Office Action dated May 30, 2017", (w/ English Translation of Claims), 25 pgs.

"Japanese Application Serial No. 2016-527046, Examiners Decision of Final Refusal dated May 21, 2019", (w/ English Translation), 20 pgs.

"Japanese Application Serial No. 2016-527046, Reasons for Rejection dated Aug. 14, 2018", (w/ English Translation), 14 pgs.

"Japanese Application Serial No. 2016-527046, Response Filed Dec. 4, 2018 to Reasons For Rejection dated Aug. 14, 2018", (w/ English Translation of Amended Claims), 18 pgs.

"Japanese Application Serial No. 2017-111526, Office Action dated May 14, 2019", (w/ English Translation), 6 pgs.

"Japanese Application Serial No. 2017-111526, Office Action dated Jun. 26, 2018", (w/ English Translation), 5 pgs.

"Japanese Application Serial No. 2017-111526, Response Filed Dec. 21, 2018 to Office Action dated Jun. 26, 2018", (w/ English Translation of Amended Claims), 7 pgs.

"Japanese Application Serial No. 2018-510751, Examiners Decision of Final Refusal dated Dec. 17, 2019", w/ English Translation, 10 pgs.

"Japanese Application Serial No. 2018-510751, Notification of Reasons for Refusal dated Mar. 13, 2019", (w/ English Translation), 14 pgs.

"Japanese Application Serial No. 2018-510751, Response filed Apr. 17, 2020 to Examiners Decision of Final Refusal dated Dec. 17, 2019", w/ English Claims, 7 pgs.

"Japanese Application Serial No. 2018-510751, Response filed Aug. 9, 2019 to Notification of Reasons for Refusal dated Mar. 13, 2019", (w/ English Translation of Claims), 24 pgs.

"Japanese Application Serial No. 2018-543688, Notification of Reasons for Rejection dated Oct. 29, 2019", w/ English Translation, 14 pgs.

"Japanese Application Serial No. 2018-543688, Office Action dated Jun. 30, 2020", w/ English translation, 11 pgs.

"Japanese Application Serial No. 2018-543688, Response filed Apr. 28, 2020 to Notification of Reasons for Rejection dated Oct. 29, 2019", w/ English Claims, 12 pgs.

"Japanese Application Serial No. 2019-171818, Examiners Decision of Final Refusal dated Oct. 5, 2021", (w/ English Translation), 15 pgs.

(56) References Cited

OTHER PUBLICATIONS

"Japanese Application Serial No. 2019-171818, Notification of Reasons for Rejection dated Nov. 10, 2020", (w/ English Translation), 11 pgs.
"Japanese Application Serial No. 2019-171818, Preliminary Examination Report dated May 10, 2022" (w/ English Translation), 2 pgs.
"Japanese Application Serial No. 2019-171818, Response filed Feb. 4, 2022 to Examiners Decision of Final Refusal dated Oct. 5, 2021", (w/ English Translation of Claims), 21 pgs.
"Japanese Application Serial No. 2019-171818, Response filed May 10, 2021 to Notification of Reasons for Rejection dated Nov. 10, 2020", (w/ English Translation of Claims), 12 pgs.
"Japanese Application Serial No. 2019-171818, Response filed Dec. 2, 2022 to Preliminary Examination Report dated May 10, 2022", w/ English Claims, 44 pgs.
"Japanese Application Serial No. 2019-171818, Trial Brief filed Mar. 30, 2022", (w/ English Translation), 14 pgs.
"Japanese Application Serial No. 2020-073952, Examiners Decision of Final Refusal dated Aug. 4, 2022", w/ English translation, 3 pgs.
"Japanese Application Serial No. 2020-073952, Final Notification of Reasons for Refusal dated Jan. 25, 2022", w/ English Translation, 11 pgs.
"Japanese Application Serial No. 2020-073952, Notification of Reasons for Refusal dated May 20, 2021", w/o English Translation, 2 pgs.
"Japanese Application Serial No. 2020-073952, Response filed Apr. 20, 2022 to Final Notification of Reasons for Refusal dated Jan. 25, 2022", w/ English Claims, 40 pgs.
"Japanese Application Serial No. 2020-073952, Response filed Sep. 9, 2021 to Notification of Reasons for Refusal dated May 20, 2021", w/ English Claims, 27 pgs.
"Japanese Application Serial No. 2020-073952, Response filed Dec. 2, 2022 to Examiners Decision of Final Refusal dated Aug. 4, 2022", w/ English Claims, 36 pgs.
"Japanese Application Serial No. 2020-182549, Examiners Decision of Final Refusal dated Jun. 7, 2022", (w/ English Translation), 11 pgs.
"Japanese Application Serial No. 2020-182549, Notification of Reasons for Refusal dated Nov. 30, 2021", (w/ English Translation), 10 pgs.
"Japanese Application Serial No. 2020-182549, Response filed Feb. 28, 2022 to Notification of Reasons for Refusal dated Nov. 30, 2021", (w/ English Translation of Claims), 52 pgs.
"Japanese Application Serial No. 2020-182549, Response filed Oct. 6, 2022 to Examiners Decision of Final Refusal dated Jun. 7, 2022", w/ English Claims, 21 pgs.
"Japanese Application Serial No. 2020-523276, Examiners Decision of Final Refusal dated May 10, 2022", w/ English Translation, 13 pgs.
"Japanese Application Serial No. 2020-523276, Notification of Reasons for Refusal dated Jul. 27, 2021", w/ English Translation, 12 pgs.
"Japanese Application Serial No. 2020-523276, Response filed Jan. 12, 2022 to Notification of Reasons for Refusal dated Jul. 27, 2021", w/ English Claims, 27 pgs.
"Japanese Application Serial No. 2021-146743, Notification of Reasons for Rejection dated Aug. 17, 2022", w/ English Translation, 3 pgs.
"Japanese Application Serial No. 2021-506434, Examiners Decision of Final Refusal dated Jan. 10, 2023", w/ English Translation, 10 pgs.
"Japanese Application Serial No. 2021-506434, Notification of Reasons for Refusal dated May 10, 2022", w/ English translation, 10 pgs.
"Japanese Application Serial No. 2021-506434, Response filed Feb. 18, 2022 to Office Action dated Dec. 21, 2021", 135 pgs.
"Japanese Application Serial No. 2021-506434, Response filed Nov. 7, 2022 to Notification of Reasons for Refusal dated May 10, 2022", w/ English Claims, 13 pgs.

"Japanese Application Serial No. 2021-509824, Voluntary Amendment filed Aug. 18, 2022", w/ English Claims, 39 pgs.
"Japanese Application Serial No. 2021-542525, Notification of Reasons for Refusal dated Dec. 13, 2022", w/ English Translation, 14 pgs.
"Japanese Application Serial No. 2006-513125,Final Office Action dated Jan. 18, 2011", (English Translation), 4 pgs.
"Korean Application Serial No. 10-2005-7020077, Response filed Apr. 28, 2008 to Examination Report dated Dec. 28, 2007", (w/ English Translation of Revised Claims), 41 pgs.
"Korean Application Serial No. 10-2004-7012647, Office Action dated Feb. 26, 2010", (w/ English Translation), 7 pgs.
"Korean Application Serial No. 10-2004-7012647, Response filed Jun. 10, 2010 to Office Action dated Feb. 26, 2010", (w/ English Translation of Claims), 17 pgs.
"Korean Application Serial No. 10-2005-7020077, Examination Report dated Dec. 28, 2007", (w/ English Translation), 8 pgs.
"Korean Application Serial No. 10-2005-7020077, Notice of Preliminary Rejection dated Jun. 28, 2007", (w/ English Translation), 9 pgs.
"Korean Application Serial No. 10-2005-7020077, Response filed Aug. 28, 2007 to Notice of Preliminary Rejection dated Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action dated Aug. 6, 2008", W/ English Translation, 4 pgs.
"Korean Application Serial No. 10-2005-7022564, Response and Amendment filed Dec. 29, 2008 to Office Action dated Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action dated Aug. 6, 2008", (w/ English Translation of Claims), 16 pgs.
"Korean Application Serial No. 10-2010-7011520, Office Action dated Jul. 20, 2010", (w/ English Translation), 6 pgs.
"Korean Application Serial No. 10-2010-7011520, Response filed Oct. 20, 2010 to Office Actiion dated Jul. 20, 2010", (w/ English Translation of Amended Claims), 30 pgs.
"Korean Application Serial No. 10-2010-7011520, Amended Claims filed May 24, 2011 in Response to Office Action dated Feb. 24, 2011", (English Translation of Amended Claims), 22 pgs.
"Korean Application Serial No. 10-2010-7011520, Office Action dated Feb. 24, 2011", (w/ English Translation), 5 pgs.
"Mexican Application No. PA/a/2005/012712 Office Action dated Jul. 21, 2009", (w/ English Translation), 9 pgs.
"Mexican Application Serial No. MX/a/2009/006341, Office Action dated Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action dated May 19, 2015", (w/ English Translation of Claims), 21 pgs.
"Mexican Application Serial No. MX/a/2012/009249, Office Action dated Feb. 5, 2016", W/ English Claims, 2 pgs.
"Mexican Application Serial No. MX/a/2012/009249, Office Action dated May 19, 2015", (English Translation), 1 pg.
"Mexican Application Serial No. MX/a/2012/009249, Response filed Mar. 29, 2016 to Office Action dated Feb. 5, 2016", (English Translation of Claims), 18 pgs.
"Mexican Application Serial No. PA/a/2004/007914, Office Action dated Feb. 14, 2008", (w/ English Translation), 3 pgs.
"Mexican Application Serial No. PA/a/2004/007914, Office Action dated Feb. 22, 2008", (English Translation), 3 pgs.
"Mexican Application Serial No. PA/a/2004/007914, Response filed Jun. 11, 2008 to Office Action dated Feb. 22, 2008", (w/ English Translation of Claims), 68 pgs.
"Mexican Application Serial No. PA/a/2005/011250, Office Action dated Aug. 23, 2010", W/ English Translation, 4 pgs.

(56) References Cited

OTHER PUBLICATIONS

"Mexican Application Serial No. PA/a/2005/011250, Response Filed Dec. 20, 2010 to Office Action dated Aug. 23, 2010", (w/ English Translation of Claims), 14 pgs.
"Mexican Application Serial No. PA/a/2005/012712, Office Action dated Aug. 11, 2009", (English Translation), 5 pgs.
"Mexican Application Serial No. PA/a/2005/012712, Response filed Sep. 28, 2009 to Office Action dated Jul. 21, 2009", (w/ English Translation of Claims), 24 pgs.
"Mexican Application Serial No. PA/a/2005/012712, Office Action dated May 12, 2010", (w/ English Translation), 19 pgs.
"Mexican Application Serial No. PA/a/2005/012712, Office Action dated Jun. 9, 2010", (w/ English Translation), 11 pgs.
"Mexican Application Serial No. PA/a/2005/012712, Office Action dated Nov. 30, 2009", (w/ English Translation), 14 pgs.
"Mexican Application Serial No. PA/a/2005/012712, Official Action dated Mar. 5, 2009" (English Translation), 2 pgs.
"Mexican Application Serial No. PA/a/2005/012712, Response filed Feb. 3, 2010 to Office Action dated Nov. 30, 2009", (w/ English Translation of Amended Claims), 22 pgs.
"Mexican Application Serial No. PA/a/2005/012712, Response filed Sep. 27, 2010 to Office Action dated May 12, 2010", (w/ English Translation of Claims), 19 pgs.
"Mexico Application Serial No. PA/a/2005/012712, Response filed Jun. 12, 2009 to Official Action dated Mar. 5, 2009", (w/ English Translation of Claims), 11 pgs.
"Neuraminidase [Influenza A virus (A/Aichi/2/1968 (H3N2))]", GenBank: BAD16642.1, NCBI, [online]. Retrieved from the Internet: <URL: http://www.ncbi.nlm.nih.gov/protein/46401580>, (2008), 3 pgs.
"Neuraminidase [Influenza B virus]", GenBank: CAB71147.1, NCBI, [online]. Retrieved from the Internet: <URL: http://www.ncbi.nlm.nih.gov/protein/6851026>, (2005), 3 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 542935, Examination Report dated Feb. 25, 2008", 2 pgs.
"New Zealand Application Serial No. 542935, Examination Report dated Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report dated Feb. 29, 2008", 2 pgs.
"New Zealand Application Serial No. 543446, Examination Report dated May 12, 2008", 1 pg.
"New Zealand Application Serial No. 543446, Response dated Mar. 20, 2008 to Examination Report dated Feb. 29, 2008", 2 pgs.
"New Zealand Application Serial No. 543587, Examination Report dated Mar. 1, 2007", 1 pg.
"New Zealand Application Serial No. 543587, Examination Report dated Jul. 7, 2006", 2 pgs.
"New Zealand Application Serial No. 543587, Response filed Aug. 7, 2007 to Examination Reports dated Jul. 7, 2006 and Mar. 1, 2007", 24 pgs.
"New Zealand Application Serial No. 543587, Second Examination Report dated Feb. 25, 2008", 2 pgs.
"New Zealand Application Serial No. 555245, First Examination Report dated Aug. 26, 2008", 2 pgs.
"New Zealand Application Serial No. 555245, Subsequent Examiner Report dated Jul. 3, 2009", 1 pg.
"Nonstructural protein 1 [influenza B virus (B/Hong Kong/330/2001)]", GenBank AAT69443.1, (2006), 1 pg.
"Norway Application Serial No. 20056074, Office Action dated Jan. 17, 2017", (English Translation), 5 pgs.
"Norway Application Serial No. 20056074, Office Action dated Apr. 25, 2017", (w English Translation), 3 pgs.
"Norway Application Serial No. 20056074, Office Action Response dated Apr. 18, 2017", W/ English Claims, 27 Pgs.
"Norway Application Serial No. 20056074, Response filed Jul. 25, 2017 to Office Action dated Apr. 25, 2017", (w/ English Translation of Amended Claims), 111 pgs.
"Norweigan Application No. 20056074, Office Action dated Apr. 25, 2017", (Translation), 3 pgs.
"Nucleotide sequences of influenza virus segments 1 and 3 reveal mosaic structure of a small viral RNA segment", Database Uniprot, (Nov. 14, 2001), 2 pgs.
"Nucleotides Sequences of Influenza Virus Segments 1 and 3 Reveal Mosaic Structrure of Small Viral RNA Segment", Database UniProt EBI / Accession No. NC_002023, (Jul. 10, 2008), 15 pgs.
"PCT Application Serial No. PCT/US2005/041991, International Preliminary Report on Patentability / Written Opinion dated Jul. 19, 2007", 8 pgs.
"Polymerase acidic [influenza A virus (A/swine/Shizuoka/120/97(H3N2))]", GenBank AAO15329.1, (2003), 1 pg.
"Polymerase PA [Influenza A virus (A/swine/Yangzhou/Jan.2008(H9N2))]", GenBank: ADK98493.1, [Online]. Retrieved from the Internet: <URL: https://www.ncbi.nlm.nih.gov/protein/ADK98493.1/>, 9 pgs.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"RecName: Full=Non-structural protein 1; Short=NS1; AltName: Full=NS1 B", GenPept Accesion P08013, (Dec. 9, 2015).
"RNA World", http://faculty.uca.edu/~benw/biol4415/lecture10a/tsld003.htm, (Observed Feb. 25, 2003), 1 pg.
"Russian Federation Application No. 2005136233, Office Action dated Dec. 25, 2007", 2 pgs.
"Russian Federation Application No. 2005136233, Response filed May 29, 2008 to Office Action dated Dec. 25, 2007", (w/ Partial English Translation), 7 pgs.
"Russian Federation Application Serial No. 2005136233, First Office Action dated Feb. 27, 2007", (w/ English Translation), 5 pgs.
"Russian Federation Application Serial No. 2005136233, Response filed Jun. 14, 2007 to First Office Action dated Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singapore Application Serial No. 200507467-9, Invitation to Respond to Written Opinion dated Jun. 19, 2007", 5 pgs.
"Singaporean Application Serial No. 200506858-0, Examination Report dated Feb. 9, 2007", 4 pgs.
"Singaporean Application Serial No. 200506858-0, Response filed Dec. 22, 2006 to Written Opinion dated Jul. 26, 2006", 18 pgs.
"Singaporean Application Serial No. 200506858-0, Written Opinion dated Jul. 26, 2006", 8 pgs.
"Singaporean Application Serial No. 200507468-7, Examination Report dated Mar. 19, 2008", 5 pgs.
"Singaporean Application Serial No. 200507468-7, Invitation to Respond to Written Opinion dated Jun. 12, 2007", 6 pgs.
"Singaporean Application Serial No. 200507468-7, Response filed Nov. 7, 2007 to Invitation to Respond to Written Opinion dated Jun. 12, 2007", 9 pgs.
"The Influenza Virus: Structure and Replication", Rapid Reference to Influenza. Elsevier Ltd, [Online]. Retrieved from the Internet: http://www.rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainese Application Serial No. 200512619, Response filed Jan. 21, 2010 to Office Action dated Jun. 17, 2009", W/ English Claims, 14 pgs.

(56) References Cited

OTHER PUBLICATIONS

"Ukrainian Application Serial No. 200512619, Office Action dated Feb. 27, 2009", (w/ English (Translation), 21 pgs.
"Ukrainian Application Serial No. 200512619, Office Action dated Jun. 17, 2009", (w/ English Translation), 4 pgs.
"Ukrainian Application Serial No. 200512619, Response filed Apr. 8, 2009 to Office Action dated Feb. 27, 2009", (w/ English Translation of Claims), 9 pgs.
Abram, M. E, et al., "Nature, position, and frequency of mutations made in a single cycle of HIV-1 replication", J Virol., 84(19), (Oct. 2010), 9864-78.
Air, Gillian M., et al., "Antigenic, Sequence, and Crystal Variation in Influenza B Neuraminidase", Virology, 177(2), (1990), 578-587.
Air, Gillian M., et al., "Antigenic, Sequence, and Crystal Variation in Influenza B Neuraminidase", Virology vol. 177, (1990), 578-587.
Akarsu, H., et al., "Crystal structure of the M1 protein-binding domain of the influenza A virus nuclear export protein (NEP/NS2).", EMBO J., 22(18), (Sep. 15, 2003), 4646-55.
Albo, C., et al., "The 5' Ends of Thogoto Virus (Orthomyxoviridae) mRNAS Are Homogeneous in both Length and Sequence", Journal of Virology, 70(12), (1996), 9013-9017.
Alonso-Caplen, et al., "Efficient Transcription, Not Translation, Is Dependent on Adenovirus Tripartite Leader Sequences at Late Times of Infection", Journal of Virology, vol. 62, No. 5, 1606-1616, (1988), 11 pgs.
Author Unknown, "New Approaches to Influenza Vaccine", Medscape—Infections in Medicine, http://www.medscape.com/viewarticle/417404_3, (Observed Feb. 26, 2003), 4 pgs.
Avetisyan, G, et al., "Cell-mediated immune responses to influenza vaccination in healthy volunteers and allogeneic stem cell transplant recipients", Bone Marrow Transplant 411-415, (2005), 5 pgs.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bai, B., et al., "Virus-Like Particles of SARS-Like Coronavirus Formed by Membrane Proteins from Different Origins Demonstrate Stimulating Activity in Human Dendritic Cells", PloS One, 3(7): e2685, (2008), 1-12.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Bedford, M. T, et al., "FBP WW domains and the Abl SH3 domain bind to a specific class of proline-rich ligands", EMBO J., 16(9), (May 1, 1997), 2376-83.
Betakova, T., et al., "The NB protein is an integral component of the membrane of influenza B virus.", J Gen Virol., 77 ( Pt 11), (Nov. 1996), 2689-94.
Biere, Barbara, et al., "Differentiation of Influenza B Virus Lineages Yamagata and Victoria by Real-Time PCR", Journal of Clinical Microbiology, vol. 48, No. 4 1425-1427, (2010), 3 pgs.

Bilsel, P., et al., "Mutations in the Cytoplasmic Tail of Influenza A Virus Neuraminidase Affect Incorporation into Virions", Journal of Virology, 67(11), (Nov. 30, 1993), 6762-6767.
Blount, K. F., et al., "The Hammerhead Ribozyme", Biochemical Society Transactions, 30(6), (2002), 1119-1122.
Bourmakina, S. V, et al., "Reverse genetics studies on the Filamentous morphology of influenza A Virus", Journal of General Virology (2003) 84,, (2003), 517-527.
Bowie, et al., "Deciphering the Message in Protein Sequences: Tolerance to Amino Acid Substitutions", Science, 247, (Mar. 1990), 1306-1310.
Bowie, J. U., et al., "Deciphering the Message in Protein Sequences: Tolerance to Amino Acid Substitutions", Science, 247(4948) 1306-1310, (1990), 5 pgs.
Boyer, J. C., et al., "Infectious transcripts and cDNA clones of RNA viruses", Virology, 198(2), (Feb. 1994), 415-426.
Bradfute, S. B., "The Early Clinical Development of Ebola Virus Treatments", Exp. Opin. Invest. Drugs 26(1):, (2017), 5 pgs.
Bradsher, K., "Cases of New Bird Flue in Hong Kong Prompt Worldwide Alerts", The New York Times web site, (Observed Feb. 22, 2003), 3 pgs.
Bradsher, K., "Man's Death of 'Bird Flu' in Hong Kong Raises Fears", The New York Times web site, (Observed Feb. 22, 2003), 3 pgs.
Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.
Brands, R., et al., "Influvac: A Safe Madin Darby Canine Kidney (MDCK) Cell Culture-Based Influenza Vaccine", Dev. Biol. Stand., 98, (1999), 93-100.
Brassard, D.L., et al., "Influenza B virus NB glycoprotein is a component of the virion", Virol., 220(2), No Document, (1996), 350-360.
Bridgen, A., et al., "Rescue of a Segmented Negative-Strand RNA Virus Entirely From Cloned Complementary DNAs", Proc. Natl. Acad. Sci. USA, 93, (1996), 15400-15404.
Broecker, Felix, et al., "A mosaic hemagglutinin-based influenza virus vaccine candidate protects mice from challenge with divergent H3N2 strains", npj Vaccines (2019) 31, www.nature.com/npjvaccines Published in partnership with the Sealy Center for Vaccine Development, (Jul. 19, 2019), 9 pages.
Broecker, Felix, et al., "Extending the Stalk Enhances Inmunogenicity of the Influenza Virus Neuraminidase", Journal of Virology, 93(18), e00840-19, (Sep. 1, 2019), 1-12.
Broecker, Felix, et al., "Immunodominance of Antigenic Site B in the Hemagglutinin of the Current H3N2 In?uenza Virus in Humans and Mice", Journal of Virology, 92(20): e01100-18, (Oct. 2018), 1-13.
Brooke, C B, "Biological activities of 'noninfectious' influenza A virus particles", Future Virol 9(1) 41-51, (Jan. 2014), 16 pgs.
Brown, E. G., et al., "Genetic analysis of mouse-adapted influenza A virus identifies roles for the NA, PB1, and PB2 genes in virulence", Virus Research, 61(1), (May 1999), 63-76.
Brown, TA, "Studying DNA", Genomes—NCBI Bookshelf, Brown TA. Genomes. 2nd edition. Oxford: Wiley-Liss; 2002, (2002), 26 pgs.
Bruhl, P., et al., "Humoral and Cell-Mediated Immunity to Vero Cell-Derived Influenza Vaccine", Vaccine, 19, (2001), 1149-1158.
Buchholz, U. J., et al., "Generation of Bovine Respiratory Syncytial Virus (BRSV) From cDNA: BRSV NS2 is Not Essential for Virus Replication in Tissue Culture, and the Human RSV Leader Region Acts as a Functional BRSV Genome Promoter", Journal of Virology, 73(1), (1999), 251-259.
Bukreyev, A., et al., "Chimeric human parainfluenza virus bearing the Ebola virus glycoprotein as the sole surface protein is immunogenic and highly protective against Ebola virus challenge", Virology, 383(2), (Abstract Only), (2009), 1 pg.
Bukreyev, A., et al., "Recovery of infectious respiratory syncytial virus expressing an additional, foreign gene", Journal of Virology, 70(10), (Oct. 1996), 6634-6641.
Bullido, R., et al., "Influenza A Virus NEP (NS2 protein) Downregulates RNA Synthesis of Model Template RNAs", Journal of Virology, 75(10), (May 2001), 4912-4917.

(56) References Cited

OTHER PUBLICATIONS

Bullido, R., et al., "Influenza A virus NEP(NS2 protein) downregulates RNA synthesis of model template RNAs", Journal of Virology, vol. 75 4912-4917, (May 2001), 6 pgs.

Burmeister, W. P., et al., "The 2.2 A resolution crystal structure of influenza B neuraminidase and its complex with sialic acid", The EMBO Journal, 11(1), (1992), 49-56.

Cannon, Joseph G., "Chapter Nineteen—Analog Design", In: Burger's Medicinal Chemistry and Drug Discovery, Fifth Edition, vol. I: Principles and Practice, Wiley-Interscience, (1995), 783-802.

Cao, S., et al., "Characterization of the Nucleocytoplasmic Shuttle of the Matrix Protein of Influenza B Virus", Journal of Virology., 88(13), (Jul. 2014), 7464-7473.

Cardona, C. J., "Avian Influenza", http://www.vetmed.ucdavis.edu/vetex/INF-PO_AvianInfluenzaFS.html, ((Observed Feb. 22, 2003), 3 pgs.

Castrucci, M. R, et al., "Attenuation of Influenza A Virus by Insertion of a Foreign Epitope into the Neuraminidase", Journal of Virology, 66(8), (1992), 4647-4653.

Castrucci, M. R., et al., "Biologic Importance of Neuraminidase Stalk Length in Influenza A Virus", Journal of Virology, 67(2), (1993), 759-764.

Castrucci, M. R, et al., "Protection against Lethal Lymphocytic Choriomeningitis Virus (LCMV) Infection by Immunization of Mice with an Influenza Virus Containing an LOMV Epitope Recognized by Cytotoxic T Lymphocytes", Journal of Virology, 68(6), (1994), 3486-3490.

Castrucci, Maria R., et al., "Reverse genetics system for generation of an influenza A virus mutant containing a deletion of the carboxyl-terminal residue of M2 protein.", J Virol., 69(5), (May 1995), 2725-8.

Catchpole, A P, et al., "Alternative base pairs attenuate influenza A virus when introduced into the duplex region of the conserved viral RNA promoter of either the NS or the PA gene", Journal of General Virology, 84, (2003), 507-515.

Chan, Winnie, et al., "The cold adapted and temperature sensitive influenza A/AnnArbor/6/60 virus, the master donor virus for live attenuated influenza vaccines, has multiple defects in replication at the restrictive temperature", Virology, 380(2), (2008), 304-311.

Chang, M. W., et al., "Analysis of HIV Wild-Type and Mutant Structures via in Silico Docking against Diverse Ligand Libraries", J. Chem. Inf. Model., 47(3), (2007), 1258-1262.

Chen, H, et al., "Generation and evaluation of a high-growth reassortant H9N2 influenza A virus as a pandemic vaccine candidate", Vaccine, 21(17-18), (May 16, 2003), 1974-9.

Chen, Z., et al., "Influenza A Virus NS1 Protein Targets Poly(A)-Binding Protein II of the Cellular 3'-End Processing Machinery", The EMBO Journal, 18(8), (1999), 2273-2283.

Chevalie, Christophe, et al., "PB1-F2 Influenza A Virus Protein Adopts a Bℓ-Sheet Conformation and Forms Amyloid Fibers in Membrane Environments", The of Biological Chemistry, 285(17), (2010), 13233-13243.

Chiba, Shiho, et al., "Multivalent nanoparticle-based vaccines protect hamsters against SARS-CoV-2 after a single immunization", Communications Biology, 4: 597, (2021), 1-9.

Cho, Alice, et al., "Implications of Broadly Neutralizing Antibodies in the Development of a Universal Influenza Vaccine", Current Opinion In Virology, vol. 17 110-115, (Apr. 1, 2016), 6 pgs.

Chothia, Cyrus, et al., "Canonical Structures for the Hypervariable Regions of Immunoglobulins.", J Mol Biol., 196(4), (1987), 901-917.

Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41), (1994), 25856-25864.

Claas, E C. J., et al., "Human Influenza A H5N1 Virus Related to a Highly Pathogenic Avian Influenza Virus", The Lancet, 351, (1998), 472-477.

Clarke, D. K., et al., "Rescue of Mumps Virus From cDNA", Journal of Virology, 74(10), (2000), 4831-4838.

Cohen, Alexander A., et al., "Mosaic nanoparticles elicit cross-reactive immune responses to zoonotic coronaviruses in mice", Science, 371(6530), and Supplementary Materials, (2021), 735-741 (30 pgs).

Coleman, P. M., et al., "Sequence and Structure Alignment of Paramyxovirus Hemagglutinin-Neuraminidase with Influenza Virus Neuraminidase", Journal of Virology, 67(6), (1993), 2972-2980.

Collins, P. L., et al., "Chapter 41—Parainfluenza Viruses", In: Fields Virology, edited by Fields, B. N., et al. (3rd Edition, 1996, Lippincott—Raven Publishers, Philadelphia, PA, 1205-1241.

Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.

Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.

Conzelmann, K.-K., "Genetic Engineering of Animal RNA Viruses", Trends in Microbiology, 4(10), (1996), 386-393.

Conzelmann, K.-K., "Genetic manipulation of non-segmented negative-strand RNA viruses", Journal of General Virology, 77(Pt. 3), (Mar. 1996), 381-389.

Conzelmann, K.-K., "Nonsegmented Negative-Strand RNA Viruses: Genetics and Manipulation of Viral Genomes", Annu. Rev. Genet., 32, (1998), 123-162.

Conzelmann, K.-K., "Rescue of Synthetic Genomic RNA Analogs of Rabies Virus by Plasmid-Encoded Proteins", Journal of Virology, 68(2), (1994), 713-719.

Craven, R. C., et al., "Late Domain Function Identified in the Vesicular Stomatitis Virus M Protein by Use of Rhabdovirus-Retrovirus Chimeras", Journal of Virology, 73(4), (1999), 3359-3365.

Crescenzo-Chaigne, B., et al., "Comparative Analysis of the Ability of the Polymerase Complexes of Influenza Viruses Type A, B and C to Assemble into Functional RNPs that Allow Expression and Replication of Heterotypic Model RNA Templates In Vivo", Virology, 265(2), (1999), 342-353.

Cunningham, Brian C, et al., "High-Resolution Epitope Mapping of hGH-Receptor Interactions by Alanine-Scanning Mutagenesis", Science 244:4908, (1989), 6 pgs.

Da Silva, Diogo V, et al., "Assembly of Subtype 1 Influenza Neuraminidase Is Driven by Both the Transmembrane and Head Domains", Journal of Biological Chemistry, 288(1), (Jan. 1, 2013), 644-653.

Daddario-Dicaprio, K. M, et al., "Cross-protection against Marburg virus strains by using a live, attenuated recombinant vaccine", J Virol., 80(19), (Oct. 2006), 9659-66.

De, B. P., et al., "Requirements and Functions of Vesicular Stomatitis Virus L and NS Proteins in the Transcription Process in Vitro", Biochemical and Biophysical Research Communications, 126(1), (1985), 40-49.

De, B. P., et al., "Rescue of synthetic analogs of genome RNA of human parainfluenza virus type 3", Virology, 196(1), (Sept. 1993), 344-348.

De, B. P., et al., "Reverse Genetics of Negative Strand RNA Viruses", Indian Journal of Biochemistry & Biophysics, 31, (1994), 367-375.

De Filette, Marina, et al., "An influenza A vaccine based on tetrameric ectodomain of matrix protein 2", J Biol Chem. 2008 ; 283 (17):, (Feb. 5, 2008), 11382-7.

De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.

De La Luna, S., et al., "Influenza Virus NS1 Protein Enhances the Rate of Translation Initiation of Viral mRNAs", Journal of Virology, 69(4), (1995), 2427-2435.

(56) References Cited

OTHER PUBLICATIONS

Del Guidice, G., et al., "What are the limits of adjuvanticity?", (Abstract), Vaccine, 20(Suppl 1), S38-S41, (2001), 1 pg.
Desheva, J. A, et al., "Characterization of an influenza A H5N2 reassortant as a candidate for live-attenuated and inactivated vaccines against highly pathogenic H5N1 viruses with pandemic potential", Vaccine, 24, (2006), 6859-6866.
Desselberger, Ulrich, et al., "The 3' and 5'-terminal sequences of influenza A, B and C virus RNA segments are highly conserved and show partial inverted complementarity", Gene, 8 (3), (Feb. 1980), 315-328.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dollenmaier, G., et al., "Membrane-Associated Respiratory Syncytial Virus F Protein Expressed From a Human Rhinovirus Type 14 Vector Is Immunogenic", Virology, 281(2), (Mar. 15, 2001), 216-230.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Du, Q., "Ribozyme Enzymology", http://academic.brooklyn.cuny.edu/chem/zhuang/QD/toppage1.htm, (Observed Feb. 25, 2003), 8 pgs.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Duhaut, S., et al., "Approximately 150 Nucleotides from the 5' End of an Influenza a segment 1 Defective Virion RNA Are needed for Genome Stability during passage of Defective Virus in Infected Cells", Virology, 275(2) 278-285 Academic Press, Orlando, US, (Sep. 30, 2000), 8 pgs.
Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.
Duhaut, S. D, et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", Virology, 248(2), Academic Press, Orlando, US, (Sep. 1, 1998), 241-253.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Dumoulin, Mireille, et al., "Single-domain antibody fragments with high conformational stability", Protein Science, 11, (2002), 500-515.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P, et al., "Human Parainfluenza Virus Type 3 (PIV3) Expressing The Hemagglutinin Protein of Measles Virus Provides a Potential Method for Immunization Against Measles Virus and PIV3 in Early Infancy", Journal of Virology, 74(15), (Aug. 2000), 6821-6831.
Durbin, A. P., et al., "Recovery of infectious human parainfluenza virus type 3 from cDNA", Virology, 235(2), (Sep. 1, 1997), 323-332.
Dyall, J., et al., ""Identification of inhibitors of Ebola virus with a subgenomic replication system"", Antiviral Research, 70(1), 19th International Conference on Antiviral Research, San Juan, PR (May 7-11, 20006), (May 2006), p. A39.
Elhefnawi, M, et al., "Identification of novel conserved functional motifs across most (Influenza A viral strains", Virology Journal, 8:44, (2011), 10 pages.
Elliott, R. M., "Emerging Viruses: The Bunyaviridae", Molecular Medicine, 3(9), (1997), 572-577.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, K., et al., "Influenza virus NS1 protein stimulates translation of the M1 protein", Journal of Virology, 68 1432-1437, (1994), 6 pgs.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Enterlein, S., et al., "Antiviral Strategies Against : Exploring Gene Silencing Mechanisms to Identify Potential Antiviral Targets", Antiviral Research, 70(1), (Abstract 33), 19th International Conference on Antiviral Research, San Juan, PR (May 7-11, 2006), (May 2006), p. A38.
Enterlein, S., et al., "Untersuchungen zur Replikation und Transkription von Marburgund Ebolavirus", [Online]. 2005, Philipps-Universitat Marburg , XP002563470, Retrieved from the Internet: <URL:http://deposit.ddb.de/cgi-bin/dokserv?>idn=977005607&dok_var=d1&dok_ext=pdf&filename=977005607 .pdf> [retrieved on Jan. 15, 2010], (2005), p. 70-p. 84.
Essere, Boris, et al., "Critical role of segment-specific packaging signals in genetic reassortment of influenza A viruses", Proc. Natl. Acad. Sci. USA, 110(40), (2013), E3840-E3848.
Fahey, J. L., et al., "Status of Immune-Based Therapies in HIV Infection and Aids", Clininical and Experimental Immunology, 88(1), (1992), 1-5.
Fan, J, et al., "Preclinical study of influenza virus A M2 peptide conjugate vaccines in mice, ferrets, and rhesus monkeys", Vaccine, 22, (2004), 2993-3003.
Feng, L., et al., "The mouse Pol I terminator is more efficient than the hepatitis delta virus ribozyme in generating influenza-virus-like RNAs with precise 3' ends in a plasmid-only-based virus rescue system", Arch Virol., 154(7), (2009), 1151-6.
Fields, S., et al., "Nucleotides Sequences of Influenza Virus Segments 1 and 3 Reveal Mosaic Structure of Small Viral RNA Segment", Cell, 28, (1982), 303-313.
Fischer, W. B, et al., "Viral ion channels: structure and function.", Biochim Biophys Acta., 1561(1), (Mar. 19, 2002), 27-45.
Flandorfer, A., et al., "Chimeric Influenza A Viruses with a Functional Influenza B Virus Neuraminidase or Hemagglutinin", Journal of Virology, 77(17), (2003), 9116-9123.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Fodor, E., et al., "Rescue of Influenza A Virus from Recombinant DNA", Journal of Virology, 73(11), XP002151487; ISSN:0022-538X, (Nov. 1999), 9679-9682.

(56) References Cited

OTHER PUBLICATIONS

Forbes, Nicole E, et al., "Multifunctional Adaptive NS1 Mutations Are Selected upon Human Influenza Virus Evolution in the Mouse", Plos One, vol. 7, No. 2, (Feb. 21, 2012), 20 pgs.
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fouchier, R. A. M., et al., "Avian Influenze A Virus (H7N7) Associated With Human Conjunctivitis and a Fatal Case of Acute Respiratory Distress Syndrome", Proc. Natl. Acad. Sci. USA, 101(5) 1356-1361, (2004), 6 pgs.
Friers, et al., "Soluble recombinant influenza vaccines", Phil. Trans. R. Soc. Lond. B (2001). vol. 356 1961-1963, (2001), 4 pgs.
Fuji, Y., et al., "Selective incorporation of influenza virus RNA segments into virions", Proc. Natl. Acad. Sci. USA, 100(4) 2002-2007, (2003), 6 pgs.
Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.
Fujii, Y, et al., "The packaging of influenza viral genome", Virus, 52 (1), Uirusu (Japanese Journal Name), (Jun. 2002), 203-206.
Gao, Qinshan, et al., "A Nine-Segment In?uenza A Virus Carrying Subtype H1 and H3 Hemagglutinins †", Journal of Virology, 84(16), (Aug. 2010), 8062-8071.
Gao, Qinshan, et al., "A Seven-Segmented Influenza A Virus Expressing the Influenza C Virus Glycoprotein HEF", Journal of Virology, 82(13), (Jul. 2008), 6419-6426.
Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.
Garay, R. P, et al., "Cancer relapse under chemotherapy: why TLR2/4 receptor agonists can help", Eur J Pharmacol., 563(1-3), (Jun. 1, 2007), 1-17.
Garcia-Sastre, A., et al., "Genetic Manipulation of Negative-Strand RNA Virus Genomes", Annu. Rev. Microbiol., 47, (1993), 765-790.
Garcia-Sastre, A., et al., "Introduction of Foreign Sequences into the Genome of Influenza A Virus", Dev. Biol. Stand. vol. 82, (1994), 237-246.
Garcia-Sastre, A., et al., "Introduction of Foreign Sequences into the Genome of Influenza A Virus", In: Recombinant Vectors in Vaccine Development. Dev. Biol. Stand., 82, Fred Brown, Editor, (1994), 237-246.
Garcia-Sastre, A., et al., "Introduction of foreign sequences into the genome of influenza A virus.", Dev Biol Stand., 82, (1994), 237-246.
Garcia-Sastre, A., et al., "The cytoplasmic tail of the neuraminidase protein of influenza A virus does not play an important role in the packaging of this protein into viral envelopes", (Virus Research, 37(1), (1995), 37-47.
Garcia-Sastre, A., et al., "Use of a mammalian internal ribosomal entry site element for expression of a foreign protein by a transfectant influenza virus.", Journal of Virology, 68(10), (1994), 6254-6261.
Garcia-Sastre, Adolfo, et al., "Use of a Mammalian Internal Ribosomal Entry Site Element for Expression of a Foreign Protein by a Transfectant Influenza Virus", Journal of Virology, 68(10) 6254-6261, (Jun. 30, 1994), 8 pgs.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Garrett, L., "Deadly Ebola, Avian Influenza Re-Emerging", Newsday.com, (Feb. 20, 2003), 3 pgs.
Genbank, "", ABD36884.1, (2007).
Genbank, "", CY002484.1, (2005).
Gerdil, C., "The Annual Production Cycle for Influenza Vaccine", Vaccine, 21 1776-1779, (2003), 4 pgs.
Ghate, Anita A, et al., "Influenza Type B Neuraminidase Can Replace the Function of (Type A Neuraminidase", Virology, 264 (2), (Nov. 1999), 265-277.
Giddings, A M, et al., "The matrix protein of HIV-1 is not sufficient for assembly and release of virus-like particles", Virology, 248(1), (1998), 108-16.
Giles, Brendan Michael, "Development of Broadly Reactive Vaccine for Highly Pathogenic H5N1 Influenza", Retrieved from the Internet: URL<http//search.proquest.com/docview/928138363>, (Jan. 1, 2011), 283 pgs.
Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.
Gomez-Puertas, P., et al., "Influenza Virus Matrix Protein Is the Major Driving Force in Virus Budding", Journal of Virology, 74 11538-11547, (Dec. 1, 2000), 10 pgs.
Gorman, O T, et al., "Evolution of influenza A virus PB2 genes: implications for evolution of the ribonucleoprotein complex and origin of human influenza A virus", J. Virol., 64(10), (Oct. 1990), 4893-4902.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Goto, Hideo, et al., "The Genome-Packaging Signal of the Influenza A Virus Genome Comprises a Genome Incorporation Signal and a Genome-Bundling Signal", Journal of Virology; vol. 87 No. 21, (Nov. 2013), 11316-11322.
Govorkova, E A, et al., "Replication of Influenza A Viruses in a Green Monkey Kidney Continuous Cell Line (Vero)", J. Infect. Dis. 172(1), (1995), 250-253.
Grambas, S., et al., "Influence of amantadine resistance mutations on the pH regulatory function of the M2 protein of influenza A viruses", Virology, 191(2), (Dec. 1992), 541-549.
Green, R. F., et al., "Glycosylation Does Not Determine Segregation of Viral Envelope Proteins in the Plasma Membrane of Epithelial Cells", J. Cell Biol., 89(2), (1981), 230-239.
Groseth, A., "13. Generation of Recombinant Ebola Viruses Using Reverse Genetics", In: Hoenen T., et al. (eds), Ebolaviruses: Methods and Protocols, Methods in Molecular Biology, vol. 162, (2017), 177-187.
Groseth, A., et al., "RNA Polymerase I-Driven Minigenome System for Ebola Viruses", Journal of Virology, 79(7), (2005), 4425-4433.
Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Gubareva, "Molecular mechanisms of influenza virus resistance to neuraminidase inhibitors", Virus Research, vol. 103, (2004), pp. 199-203.
Gunther, S, et al., "Application of real-time PCR for testing antiviral compounds against Lassa virus, SARS coronavirus and Ebola virus in vitro", Antiviral Research, Elsevier BV, NL, vol. 63, No. 3, XP004580000 ISSN: 0166-3542, (Sep. 1, 2004), 209-215.
Hagen, M., et al., "Recombinant Influenza Virus Polymerase: Requirement of both 5' and 3' Viral Ends for Endonuclease Activity", Journal of Virology, 68(3), (1994), 1509-1515.
Hai, Rong, et al., "Influenza B Virus NS1-Truncated Mutants: Live-Attenuated Vaccine Approach", Journal of Virology, 82(21), (2008), 10580-10590.
Halfmann, P., et al., "Generation of biologically contained Ebola viruses", Proceedings of the National Academy of Sciences of the United States of America 1129-1133, vol. 105, No. 4, XP002563467 ISSN: 1091-6490 the whole document, (Jan. 29, 2008), 6 pgs.
Halfmann, P., et al., "Replication-Deficient Ebolavirus as a Vaccine Candidate", Journal of Virology, vol. 83, No. 8 3810-3815, XP002563468; ISSN: 1098-5514; the whole document, (Apr. 2009), 6 pgs.

(56) References Cited

OTHER PUBLICATIONS

Halfmann, Peter J., et al., "Potent neutralization of SARS-CoV-2 including variants of concern by vaccines presenting the receptor-binding domain multivalently from nanoscaffolds", Bioengineering & Translational Medicine, 6(3): e10253, (2021), 8 pgs.

Halperin, S. A., et al., "Safety and Immunogenicity of a Trivalent, Inactivated, Mammalian Cell Culture-Derived Influenza Vaccine in Healthy Adults, Seniors, and Children", Vaccine, 20 1240-1247, (2002), 8 pgs.

Halstead, Scott B,, et al., "Dengue Antibody-Dependent Enhancement: Knowns and Unknowns", Microbiology Spectrum, 2(6), (2014), 1-18.

Harding, Alfred T, et al., "Rationally Designed Influenza Virus Vaccines That Are Antigenically Stable during Growth in Egg", MBIO, vol. 8, No. 3, e00669-17, (Jul. 5, 2017), 1-16.

Harmsen, M. M., et al., "Properties, production, and applications of camelid single-domain (antibody fragments", Appl Microbiol Biotechnol, 77, (2007), 13-22.

Harty, R. N, et al., "A PPxY Motif within the VP40 Protein of Ebola Virus Interacts Physically and Functionally with a Ubiquitin Ligase: Implications for Filovirus Budding", Proc. Natl. Acad. Sci, 97 (25), (Dec. 5, 2000), 13871-13876.

Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.

Harvey, K. F, et al., "All three WW domains of murine Nedd4 are involved in the regulation of epithelial sodium channels by intracellular Na+.", J Biol Chem., 274(18), (Apr. 30, 1999), 12525-30.

Hatada, E., et al., "Binding of Influenza A Virus NS1 Protein to dsRNA in vitro", Journal of General Virology, 73, (1992), 3325-3329.

Hatakeyama, S., et al., "Dissection and identification of regions required to form pseudoparticles by the interaction between the nucleocapsid (N) and membrane (M) proteins of SARS coronavirus", Virology, 380(1), (2008), 99-108.

Hatakeyama, S., et al., "Emergence of Influenza B Viruses With Reduced Sensitivity to Neuraminidase Inhibitors", Journal of the American Medical Association, 297(13) 1435-1442, (Apr. 4, 2007), 8 pgs.

Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8), (2005), 4139-4146.

Hatakeyma, S., et al., "The molecular basis of resistance to anti-influenza drugs", Japanese Journal of Clinical Medicine—Nippon Rinsho, 64(10) 1845-1852, (Oct. 1, 2006), 8 pgs.

Hatta, M., et al., "The NB protein of influenza B virus is not necessary for virus replication in vitro", Journal of Virology, 77(10), (May 2003), 6050-6054.

Hay, A. J., et al., "The role of the M2 protein in influenza A virus infection", Proceedings of the International Conference on Options for the Control of Influenza, Courchevel, (1992), 281-288.

He, B., et al., "Recovery of infectious SV5 from cloned DNA and expression of a foreign gene", Virology, 237(2), (1997), 249-260.

He, X., et al., "Generation of SARS-CoV-2 reporter replicon for high-throughput antiviral screening and testing", Proc. Natl. Acad. Sci. USA, 118(15): e2025866118, (2021), 8 pgs.

Helenius, A., "Unpacking the Incoming Influenza Virus", Cell, 69, (May 1992), pp. 577-578.

Hevey, Michael, et al., "Marburg virus vaccines based upon alphavirus replicons protect guinea pigs and nonhuman primates", Virology, 251(1), (Nov. 10, 1998), 28-37.

Hickman, Danielle, et al., "An avian live attenuated master backbone for potential use in epidemic and pandemic influenza vaccines", Journal of General Virology, 89(Part 11), (2008), 2682-2690.

Hiromoto, Y., et al., "Phylogenetic Analysis of the Three Polymerase Genes (PB1, PB2 and PA) of Influenza B Virus", Journal of General Virology, 81, (Apr. 2000), 929-937.

Hiti, A. L., et al., "P03470—Neuraminidase", Entrez Protein Database, http://www.ncbi.nlm.nih.gov/entrez/viewer.fcgi?db=protein&val=84028231, (1982), 730-734.

Hiti, A. L., et al., "P03470—Neuraminidase", Entrez Protein Database, [online]. [retrieved on Aug. 30, 2006]. Retrieved from the Internet: <URL: http://www.ncbi.nlm.nih.gov/entrez/viewer.fcgi?db=protein&val=84028231>, (1982), 730-734 (8 pgs.).

Ho, Y., et al., "Assembly of human severe acute respiratory syndrome coronavirus-like particles", Biochem Biophys Res Commun, 318(4), (2004), 833-838.

Hoenen, T., et al., "11. Reverse Genetics Systems for Filoviruses", In: Perez, Daniel (Ed.), Reverse Genetics of RNA Viruses: Methods and Protocols, Methods in Molecular Biology, vol. 1602, (2017), 159-170.

Hoenen, Thomas, et al., "Minigenomes, Transcription and Replication Competent Virus-Like Particles and Beyong: Reverse Genetics Systgems for Filoviruses and other Negative Stranded Hemorrhagic Fever Viruses", Antiviral Res., 91:195, (2011), 30.

Hoffman, E., et al., "Ambisense Approach for the Generation of Influenza A Virus: vRNA and mRNA Synthesis from One Template", Virology 267(2) 310-317, (Feb. 15, 2006), 8 pgs.

Hoffman, Lucas R, et al., "Structure-Based Identification of an Inducer of the Low-pH Conformational Change in the Influenza Virus Hemagglutinin: Irreversible Inhibition of Infectivity", Journal of Virology, vol. 71, No. 11, (Nov. 1997), 8808-8820.

Hoffman, M. A., et al., "An Infectious Clone of Human Parainfluenza Virus Type 3", Journal of Virology, 71(6), (1997), 4272-4277.

Hoffmann, E., et al., "A DNA transfection system for generation of influenza A virus from eight plasmids", Proc Natl Acad Sci U S A., 97(11), (May 23, 2000), 6108-13.

Hoffmann, E., et al., "Ambisense Approach for the Generation of Influenza A Virus: vRNA and mRNA Synthesis from One Template", Virology, 267, (2000), 310-317.

Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.

Hoffmann, E., et al., "Rescue of Influenza B Virus from Eight Plasmids", Proceedings of the National Academy of Sciences of USA, National Academy of Science, 99(17), (Aug. 20, 2002), 11411-11416.

Hoffmann, Erich, et al., "A DNA transfection system for generation of influenza A virus from eight plasmids", Proceedings of the National Academy of Sciences, vol. 97, No. 11, (2000), 6108-6113.

Holmes, E. C, et al., "Whole-Genome Analysis of Human Influenza A Virus Reveals Multiple Persistent Lineages and Reassortment Among Recent H3N2 Viruses", PLoS Biology, 3(9) 1579-1589, (2005), 11 pgs.

Holsinger, L. J., et al., "Influenza A Virus M2 Ion Channel Protein: a Structure-Function Analysis", Journal of Virology, 68 (3), (1994), pp. 1551-1563.

Honda, A., et al., "RNA Polymerase of Influenza Virus: Role of NP in RNA Chain Elongation", The Journal of Biochemistry. 104(6), (1988), 1021-1026.

Honda, Ayae, et al., "Differential Roles of Viral RNA and cRNA in Functional Modulation of the Influenza Virus RNA Polymerase", The Journal of Biological Chemistry, 276(33), (2001), 31179-31185.

Horimoto, "Designing Vaccines for Pandemic Influenza", Current Topics Microbiol Immunol 333, (2009), 165-176.

Horimoto, T., et al., "Enhanced growth of seed viruses for H5N1 influenza vaccines", Virology, 366(1), (Sep. 15, 2007), 23-27.

Horimoto, T., et al., "Generation of Influenza A Viruses with Chimeric (Type A/B) Hemagglutinins", Journal of Virology, 77(14) 8031-8038, (2003), 11 pgs.

Horimoto, T., et al., "Reverse Genetics Provides Direct Evidence for a Correction of Hemagglutinin Cleavability and Virulence of an Avian Influenza A Virus", Journal of Virology, 68(5), (1994), 3120-3128.

Horimoto, T., et al., "The Development and Characterization of H5 Influenza Virus Vaccines Derived from a 2003 Human Isolate", Vaccine, 24(17) 3669-3676, (2006), 8 pgs.

(56) References Cited

OTHER PUBLICATIONS

Hossain, M. J., et al., "Establishment and Characterization of a Madin-Darby Canine Kidney Reporter Cell Line for Influenza A Virus Assays", J Clin Microbiol, 48(7), (2010), 2515-2523.

Hsieh, P.-K., et al., "Assembly of Severe Acute Respiratory Syndrome Coronavirus RNA Packaging Signal into Virus-Like Particles Is Nucleocapsid Dependent", J Virol., 79(22), (2005), 13848-13855.

Huang, T. S, et al., "Determinaton of Influenza Virus Proteins Required for Genome Replication", Jounal of Virology, vol. 64 5669-5673, (1990), 5 pgs.

Huang, T.-S., et al., "Determination of Influenza Virus Proteins Required for Genome Replication", Journal of Virology, 64(11), (1990), 5669-5673.

Huang, Y., et al., "Generation of Synthetic Severe Acute Respiratory Syndrome Coronavirus Pseudoparticles: Implications for Assembly and Vaccine Production", J. Virol,, 78(22), (Nov. 2004), 12557-12565.

Huddleston, J. A., et al., "The Sequence of the Nucleoprotein Gene of Human Influenza A Virus, Strain A/NT/60/68", Nucleic Acids Research, 10(3), (1982), 1029-1038.

Huggins, J., et al., "Antiviral drug therapy of filovirus infections: S-adenosylhomocysteine hydrolase inhibitors inhibit Ebola virus in vitro and in a lethal mouse model.", Journal of Infectious Diseases, vol. 179, NR (Suppl 1), XP002574255 ISSN: 0022-1899 'abstract, (Feb. 1999), 240-247.

Hughes, M. T., et al., "Adaptation of Influenza A Viruses to Cells Expressing Low Levels of Sialic Acid Leads to Loss of Neuraminidase Activity", Journal of Virology, 75(8), (2001), 3766-3770.

Hughes, M. T., et al., "Influenza A Viruses Lacking Sialidase Activity Can Undergo Multiple Cycles of Replication in Cell Culture, Eggs, or Mice", Journal of Virology, 74 (11), (2000), 5206-5212.

Hughes, M. T, et al., "Influenza A Viruses Lacking Sialidase Activity Can Undergo Multiple Cycles of Replication in Cell Culture, Eggs, or Mice", Journal of Virology, 74(11) 5206-212, (2000), 7 pgs.

Huisman, W., et al., "Vaccine-induced enhancement of viral infections", Vaccine, 27(4), (2009), 505-512.

Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.

Hurt, A. C, et al., "Identification of a human influenza type B strain with reduced sensitivity to neuraminidase inhibitor drugs", Virus Research, vol. (103), (2004), 205-211.

Hutchinson, Edward C., et al., "Genome packaging in influenza A virus", Journal of General Virology, 91(Pt 2), (2010), 313-328.

Hwang, Jung-Shan, et al., "Expression of Functional Influenza Virus RNA Polymerase in the Methylotrophic Yeast Pichia pastoris", Journal of Virology, 74(9), (2000), 4074-4084.

Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.

Ito, T, et al., "Differences in Sialic Acid-Galactose Linkages in the Chicken Egg Amnion and Allantois Influence Human Influenza Virus Receptor Specificity and Variant Selection", Journal of Virology, 71 (4), (Apr. 1997), 3357-3362.

Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.

Iwatsuki-Horimoto, K., et al., "The cytoplasmic tail of the influenza A virus M2 protein plays a role in viral assembly.", J Virol., 80(11), (Jun. 2006), 5233-40.

Jackson, et al., "Characterization of recombinant influenza B viruses with key neuraminidase inhibitor resistance mutations,", Journal of Antimicrobial Chemotherapy, vol. (55), (2005), 162-169.

Jackson, D., et al., "A reverse genetics approach for recovery of recombinant influenza B viruses entirely from cDNA.", J Virol., 76(22), (Nov. 2002), 11744-7.

Jahrling, P. B., et al., "Ebola Hemorrhagic Fever: Evaluation of Passive Immunotherapy in Nonhuman Primates", J. Infect. Dis. 196, (2007), 4 pgs.

Jang, S.-W., et al., "Deoxygedunin, a Natural Product with Potent Neurotrophic Activity in Mice", PLoS ONE 5(7): e11528, (2010), 1-15.

Jasenosky, Luke D, et al., "Ebola Virus VP40-Induced Particle Formation and Association with the Lipid Bilayer", Journal of Virology, 75 (110, (Jun. 2001), 5205-5214.

Jennings, Philip A., et al., "Does the Higher Order Structure of the Influenza Virus Ribonucleoprotein Guide Sequence Rearrangements in Influenza Viral RNA?", Cell, 34, (Sep. 1983), 619-627.

Jiang, H, et al., "Influenza virus genome C4 promoter/origin attenuates its transcription and replication activity by the low polymerase recognition activity", Virology, 408(2), (2010), 190-196.

Jiang, Y., et al., "Genome wide analysis of protein protein interactions and involvement of viral proteins in SARS CoV 2 replication", Cell Biosci, 11:140, 2021, 16 pgs., (2021), 16 pgs.

Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", Journal of Virology, 78(2), (2004), 995-998.

Jin, H., et al., "Influenza virus hemagglutinin and neuraminidase cytoplasmic tails control particle shape", The EMBO Journal, 16(6), (1997), 1236-1247.

Jin, H., et al., "The influenza virus hemagglutinin cytoplasmic tail is not essential for virus assembly or infectivity", The EMBOL Journal, 13(22), (1994), 5504-5515.

Johnson, David A, et al., "TLR4 Agonists as Vaccine Adjuvants", Vaccine Adjuvants and Delivery Systems, (2007), 131-156.

Johnson, R. F., et al., "Ebola Virus VP35-VP40 Interaction Is Sufficient for Packaging 3E-5E Minigenome RNA into Virus-Like Particles", Journal of Virology, 80(11), (Jun. 2006), 5135-5144.

Ju, X., et al., "A novel cell culture system modeling the SARS-CoV-2 life cycle", PloS Pathogens, 17(3): e1009439, (2021), 23 pgs.

Justice, P. A., et al., "Membrane Vesiculation Function and Exocytosis of Wild-Type and Mutant Matrix Proteins of Vesicular Stomatitis Virus", Journal of Virology, 69(5), (1995), 3156-3160.

Kang, Byoung-Hoon, et al., "Ultrafast and Real-Time Nanoplasmonic On-Chip Polymerase Chain Reaction for Rapid and Quantitative Molecular Diagnostics", ACS Nano, 15(6), (2021), 10194-10202.

Kaplan, G., et al., "In vitro Synthesis of Infectious Poliovirus RNA", Proc. Natl. Acad. Sci. USA, 82, (1985), 8824-8428.

Katinger, D., et al., "Attenuated Influenza Viruses as a Vector for Mucosal Immunization Against HIV-1", Vaccines, 97, Cold Spring Harbor, (1997), 315-319.

Kato, A., et al., "Initiation of Sendai Virus Multiplication From Transfected cDNA or RNA With Negative or Positive Sense", Genes to Cells, 1, (1996), 569-579.

Kawaoka, Y, et al., "Sequence requirements for cleavage activation of influenza virus hemagglutinin expressed in mammalian cells", Proc Natl Acad Sci., 85(2), (1988), 324-328.

Kawaoka, Y., "Identification by siRNA of host proteins involved in Ebolavirus replication", Great Lakes Regional Center of Excellence for Biodefense and Emerging Infectious Diseases Research, [Online]; Retrieved from the Internet: URL:http://www.rcebiodefense.org/glrce/docs/2007/Kawaoka.pdf> [retrieved on Jan. 13, 2010] p. 10, under item C, -& Anonymous: "Index of GLRCE: documents from 2007" Great Lakes Regional Center of Excellence Index, [Online] 2007, XP002563469 Retrieved from the Internet: URL:http://www.rcebiodefense.org/glrce/docs/2007/> [retrieved on Jan. 14, 2010] -& Kawaoka Y:, (2007), pp. 1-19.

Kawaoka, Y., "Mutant Cells With Altered Sialic Acid", U.S. Appl. No. 11/644,179 filed Dec. 22, 2006, 51 pgs.

Kawaoka, Y., "Prevention and Control of Ebola Virus Infection (Ongoing Research)", Great Lakes Regional Center of Excellence (GLRCE) Annual Meeting Schedule, (Abstract), [online] [retrieved

(56) References Cited

OTHER PUBLICATIONS on Jan. 14, 2010]. Retrieved from the Internet: <URL:http://www.rcebiodefense.org/glrce/annualmeeting/2007Agenda.pdf>, (Nov. 29, 2007), 4 pgs.

Keitel, W. A., et al., "Chapter 28—Live Cold-Adapted, Reassortant Influenza Vaccines (USA)", In: Textbook of Influenza, Nicoholson, K. G., et al., Editors, Blackwell Science Ltd., (1998), 373-390.

Kijima, H., et al., "Therapeutic Application of Ribozymes", Pharmac. Ther., 68(2), (1995), 247-267.

Kilbourne, E. D, et al., "Related studies of a recombinant influenza-virus vaccine. I. Derivation and characterization of virus and vaccine", J Infect Dis., 124(5), (Nov. 1971), 449-62.

Kim, H., et al., "Cold adaptation generates mutations associated with the growth of influenza B vaccine viruses", Vaccine, 33(43), (2015), 5786-5793.

Kim, Min-Chul, et al., "Supplementation of Influenza Split Vaccines with Conserved M2 Ectodomains Overcomes Strain Specificity and Provides Long-term Cross Protection", Molecular Therapy, 22(7), (2014), 1364-1374.

Kimura, N., et al., "An In Vivo Study of the Replication Origin in the Influenza Virus Complementary RNA", The Journal of Biochemistry, 113(1), (1993), 88-92.

Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.

Kiseleva, I., et al., "Role of individual genes of the A-Leningrad/134/17/57 (H2N2) cold-adapted don

(56) References Cited

OTHER PUBLICATIONS

Leal, et al., "New challenges in therapeutic vaccines against HIV infection", Expert Review of Vaccines, vol. 16, No. 6, (2017), 587-600.
Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.
Lee, D.-H., et al., "H9N2 avian influenza virus-like particle vaccine provides protective immunity and a strategy for the differentiation of infected from vaccinated animals", Vaccine, vol. 29, (2011), 4003-4007.
Lee, Dong-Hun, et al., "Progress and hurdles in development of influenza virus-like particle vaccines for veterinary use", Korean Vaccine Society, (2014), 133-139.
Lee, Jeffrey E., et al., "Complex of a Protective Antibody with Its Ebola Virus GP Peptide Epitope: Unusual Features of a V?x Light Chain", J. Mol. Biol., 375, (2007), 202-216.
Lee, Jong-Soo, et al., "The Highly Conserved HA2 Protein of the Influenza A Virus Induces a Cross Protective Immune Response", Journal of Virological Methods, 194(1-2), (2013), 280-288.
Lee, M. S, et al., "Genetic and pathogenic characterization of H6NI avian influenza viruses isolated in Taiwan between 1972 and 2005", Avian Diseases, 50(4), (Dec. 2006), 561-571.
Lefranc, Marie-Paule, et al., "IMGT unique numbering for immunoglobulin and T cell receptor variable domains and Ig superfamily V-like domains", Developmental & Comparative Immunology, 27, (2003), 55-77.
Lembo, A, et al., "Administration of a synthetic TLR4 agonist protects mice from pneumonic tularemia.", J Immunol., 180(11), 7574-81.
Levis, R., et al., "Deletion Mapping of Sindbis Virus DI RNAs Derived From cDNAs Defines the Sequences Essential for Replication and Packaging", Cell, 44, (1986), 137-145.
Li, et al., "Selection of antigenically advanced variants of seasonal influenza viruses", Nature Microbiology, 1 (6), (2016), 1-10.
Li, Feng, et al., "Generation of Replication-Competent Recombinant Influenza A Viruses Carrying a Reporter Gene Harbored in the Neuraminidase Segment", Journal of Virology, 84(22), (Nov. 2010), 12075-12081.
Li, Junwei, et al., "Engineering Influenza Viral Vectors", Bioengineered, vol. 4, No. 1, (Jan. 1, 2013), 9-14.
Li, K. S., et al., "Genesis of a highly pathogenic and potentially pandemic H5N1 influenza virus in eastern Asia", Nature, vol. 430, (2004), 209-213 pgs.
Li, K. S, et al., "Genesis of a highly pathogenic and potentially pandemic H5NI influenza virus in eastern Asia", Nature, 430(6996), (Jul. 8, 2004), 209-213.
Li, Qi, et al., "Screening of the high yield influenza B virus on MDCK cell and cloning of its whole genome", (English Abstract), Chinese Journal of Virology, 3, (Sep. 30, 2004), 1 pg.
Li, Qi, et al., "Screening of the high yield influenza B virus on MDCK cell and cloning of its whole genome", International Congress Series 1263, (2004), 610-614.
Li, S., et al., "Electroporation of Influenza Virus Ribonucleoprotein Complexes for Rescue of the Nucleoprotein and Matrix Genes", Virus Research, 37(2), (1995), 153-161.
Li, S., et al., "Influenza A Virus Transfectants with Chimeric Hemagglutinins Containing Epitopes from Different Subtypes", Journal of Virology, 66(1), (1992), 399-404.
Li, S., et al., "Recombinant Influenza A Virus Vaccines for the Pathogenic Human A/Hong Kong/97 (H5N1) Viruses", J Infect Dis., 179(5), (1999), 1132-1138.
Li, Shengqiang, et al., "Influenza A Virus Transfectants with Chimeric Hemagglutinins containing Epitopes from different subtypes", Journal of Virology 399-404, (1992), 6 pgs.
Li, Y, et al., "The I binding specificity of human VH4-34 (VH4-21) encoded antibodies is determined by both VH framework region 1 and complementarity determining region 3", J. Mol. Biol. 256 577-589, (1996), 13 pgs.
Li, Y, et al., "Viral liposomes released from insect cells infected with recombinant baculovirus expressing the matrix protein of vesicular stomatitis virus", Journal of Virology, 67 (7), (1993), 4415-4420.
Lin, Y P, et al., "Adaptation of egg-grown and transfectant influenza viruses for growth in mammalian cells: selection of hemagglutinin mutants with elevated pH of membrane fusion", Virology, 233(2), (1997), 402-410.
Lin, Yi Pu, et al., "Adaptation of Egg-Grown and Transfectant Influenza Viruses for Growth in Mammalian Cells: Selection of Hemagglutinin Mutants with Elevated pH of Membrane Fusion", Virology, vol. 233, Issue 2, (1997), 402-410.
Liu, Bo, et al., "Comparison of three methods in construction fusion gene of influenza A virus Nucleoprotein", (English Abstract), Zhonghua Shi Yan He Lin Chuang Bing Du Xue Za Zhi, 26(1), 70-74, (Feb. 2012), 1 pg.
Liu, C., et al., "Influenza type A virus neuraminidase does not play a role in viral entry, replication, assembly, or budding.", Journal of Virology, 69(2), (1995), 1099-1106.
Liu, C., et al., "Selection and Characterization of a Neuraminidase-Minus Mutant of Influenza Virus and its Rescue by Cloned Neuraminidase Genes", Virology, 194(1), (1993), 403-407.
Liu, Y., et al., "A live-attenuated SARS-CoV-2 vaccine candidate with accessory protein deletions", bioRxiv [online]. [retrieved Jun. 10, 2022]. Retrieved from the Internet: <URL:https://www.biorxiv.org/content/10.1101/2022.02.14.480460v1.full.pdf>, (2022), 44 pgs.
Liu, Z, et al., "Fine mapping of the antigen-antibody interaction of scFv215 A recombinant antibody inhibiting RNA polymerase II from *Drosophila melanogaster*", J. Mol. Recog. 12:103-111, (1999), 9 pgs.
Lobo, Ingrid A., "Predicting Vaccine Effectiveness Using Systems Biology", Nature Education, 8(3):9, [online]. Retrieved from the Internet: <URL: https://www.nature.com/scitable/nated/topicpage/predicting-vaccine-effectiveness-using-systems-biology-132628443>, (2015), 4 pgs.
Longnecker, R., et al., "WWW- and SH3-domain interactions with Epstein-Barr virus LMP2A", Exp Cell Res., 257(2), (Jun. 15, 2000), Abstract Only.
Lott, W. B., et al., "A Two-Metal Ion Mechanism Operates in the Hammerhead Ribozyme-Mediated Cleavage of an RNA Substrate", Proc. Natl. Acad. Sci. USA, 95, (1998), 542-547.
Lu, Xiuhua, et al., "Cross-protective immunity in mice induced by live-attenuated or linactivated vaccines against highly pathogenic influenza A (H5N1) viruses", Vaccine, 24(44-46), (2006), 6588-6593.
Lugovtsev, V. Y., et al., "Genetic Composition and Mutational Pattern of Influenza B Viruses Adapted to Replication in Embryonated Eggs", GenBank: AAT69446.1, (2005), 1 pg.
Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Luytjes, W., "Amplification, Expression, and Packaging of a Foreign Gene by Influenza Virus", Cell, 59(6), (1989), 1107-1113.
Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.
Manicassamy, Balaji, et al., "Analysis of in vivo dynamics of influenza virus infection in mice using a GFP reporter virus", Proc Natl Acad Sci. USA, 107(25), (2010), 11531-11536.
Mansky, L. M, "Retrovirus mutation rates and their role in genetic variation", J Gen Virol., 79 (Pt 6), (Jun. 1998), 1337-45.
Manz, Benjamin, et al., "Disruption of the Viral Polymerase Complex Assembly as a Novel Approach to Attenuate Influenza A Virus", The Journal of Biological Chemistry, 286(10), (2011), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.

(56) References Cited

OTHER PUBLICATIONS

Marsh, Glenn A., et al., "Specific Residues of the Influenza A Virus Hemagglutinin Viral RNA Are Important for Efficient Packaging into Budding Virions", Journal of Virology, 81(18), (Sep. 2007), 9727-9736.

Martin, J., et al., "Studies of the Binding Properties of Influenza Hemagglutinin Receptor-Site Mutants", Virology, 241(1), (Feb. 1, 1998), 101-111.

Martinez-Sobrido, L., et al., "Hemagglutinin-Pseudotyped Green Fluorescent Protein-Expressing Influenza Viruses for the Detection of Influenza Virus Neutralizing Antibodies", J Virol., 84(4), (2010), 2157-2163.

Martorelli Di, Genova B., et al., "Intestinal delta-6-desaturase activity determines host range for Toxoplasma sexual reproduction", Plos Biology, vol. 17, No. 8, E3000364, (Aug. 20, 2019), XP055619380, (Aug. 20, 2019), 1-19.

Masuda, H., et al., "Substitution of Amino Acid Residue in Influenza A Virus Hemagglutinin Affects Recognition of Sialyl-Oligosaccharides Containing N-Glycolylneuraminic Acid", FEBS Letters, 464, (1999), 71-74.

Matsuoka, et al., "Neuraminidase Stalk Length and Additional Glycosylation of the Hemagglutinin Influence the Virulence of Influenza H5N1 Viruses for Mice", Journal of Virology, vol. 83, No. 9,, (2009), pp. 4704-4708.

Matsuzaki, Y., et al., "Epitope Mapping of the Hemagglutinin Molecule of A/(H1N1)pdm09 (Influenza Virus by Using Monoclonal Antibody Escape Mutants", Journal of Virology, 88(21) 12364-12373, (2014), 10 pgs.

Matta, M, et al., "Cell-surface sialoglycoconjugate structures in wild-type and mutant Crithidia fasciculata", Parasitol. Res., 85(4), (1999), 293-299.

McCown, M F, et al., "The influenza A virus M2 cytoplasmic tail is required for infectious virus production and efficient genome packaging.", J Virol., 79(6), (Mar. 2005), 3595-605.

McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.

McCullers, et al., "Multiple Genotypes of Influenza B Virus Circulated between 1979 and 2003,", Journal of Virology, vol. (78), No. (23) 12817-12828, (2004), 13 pgs.

McCullers, Jonathan A., et al., "A single amino acid change in the C-terminal domain of the matrix protein M1 of influenza B virus confers mouse adaption and virulence", Virology, 336(2) 318-326, (Jun. 5, 2005), 9 pgs.

McKee, Dwight L, et al., "Candidate drugs against SARS-CoV-2 and COVID-19", Pharmacological Research, Academic Press, London, GB, vol. 157, (Apr. 29, 2020), 9 pgs.

McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.

McSharry, J. J, et al., "Phenotypic Drug Susceptibility Assay for Influenza Virus Neuraminidase Inhibitors", Cinical and Diagnostic Laboratory Immunology vol. (11), No. (2),, (2004), 10 pgs.

Mebatsion, Teshome, et al., "Budding of Rabies Virus Particles in the Absence of the Spike Glycoprotein", Cell, 84(6), (1996), 941-951.

Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.

Mena, I., "Rescue of a Synthetic Choramphenicol Acetyltransferase RNA into influenza Virus-Like Particles obtained from recombinant plasmids", Journal of Virology, 70(8), (1996), 5016-5024.

Mena, I., et al., "Synthesis of biologically active influenza virus core proteins using a vaccinia virus-T7 RNA polymerase expression system", Journal of General Virology, 75 2109-2114, (1994), 6 pgs.

Mena, I., et al., "Synthesis of Biologically Active Influenza Virus Core Proteins Using a Vaccinia Virus-T7 RNA Polymerase Expression System", Journal of General Virology, 75, (1994), 2109-2114.

Mishin, V. P, et al., "Protection afforded by intranasal immunization with the neuraminidase-lacking mutant of influenza A virus in a ferret model", Vaccine, 23(22), (Apr. 22, 2005), 2922-7.

Mitnaul, et al., "The Cytoplasmic Tail of Influenza a Virus Neuraminidase (NA) Affects NA Incorporation into Virons, Viron Morphology, and Virulence in Mice but is not essential for (Virus Replication", Journal of Virology, 70 (2), (1996), 873-879.

Mitnaul, L. J., et al., "Balanced Hemagglutinin and Neuraminidase Activities are Critical for Efficient Replication of Influenza A Virus", Journal of Virology, 74 (13), (2000), 6015-6020.

Mittler, E., et al., "Role of the transmembrane domain of marburg virus surface protein GP in assembly of the viral envelope.", J Virol., 81(8), (Apr. 2007), 3942-8.

Miyoshi, H., et al., "Development of Self-Inactivating Lentivirus Vector", Journal of Virology, 72(10), (1998), 8150-8157.

Monto, A. S, et al., "Detection of influenza viruses resistant to neuraminidase inhibitors in global surveillance during the first 3 years of their use", Antimicrobal Agents and Chemotherapy, 50(7) 2395-2402, (2006), 8 pgs.

Monto, Arnold S, et al., "Comparative efficacy of inactivated and live attenuated influenza vaccines.", N Engl J Med., 361(13) 1260-7, (Sep. 24, 2009), 8 pgs.

Morita, S., et al., "Plat-E: an efficient and stable system for transient packaging of retroviruses", Gene Therapy, 7(12), (2000), 1063-1066.

Moss, B., et al., "New Mammalian Expression Vectors", Nature, 348, (1990), 91-92.

Moyer, S. A., et al., "Assembly and Transcription of Synthetic Vesicular Stomatitis Virus Nucleocapsids", Journal of Virology, 65(5), (1991), 2170-2178.

Muhlberger, E., et al., "Comparision orf the Transcription and Replication Strategies of Marburg Virus and Ebola Virus by Using Artificial Replication Systems", Journal of Virology, 73(3) 2333-2342, (1999), 10 pgs.

Muhlberger, E., et al., "Three of the four nucleocapsid proteins of Marburg virus,NP , VP35, and L, are sufficient to mediate replication and transcription of Marburg virus-specific monocistronic minigenomes", Journal of Virology, 72(11) 8756-8764, (1998), 11 pgs.

Muhlberger, Elke, "Filovirus replication and transcription", Future Virol., 2:205, (2007), 16 pgs.

Murakami, Shin, et al., "Enhanced Growth of Influenza Vaccine Seed Viruses in Vero Cells Mediated by Broadening the Optimal pH Range for Virus Membrane Fusion", J Virol 86(3), (2012), 1405-1410.

Murakami, Shin, et al., "Growth Determinants for H5N1 Influenza Vaccine Seed Viruses in MDCK Cells", Journal of Virology, vol. 82, No. 21, (Nov. 2008), 10502-10509.

Muramoto, Y., et al., "Hierarchy among Viral RNA (vRNA) Segments in Their Role in VRNA Incorporation into Influenza A Virions", J. Virol., 80(5), (2006), 2318-2325.

Muramoto, Yukiko, "Hierarchy among Viral RNA (vRNA) Segments in Their Role in VRNA Incorporation into Influenza A Virions", Journal of Virology, 80(5), (2006), 2318-2325.

Murphy, B. R, et al., "An influenza A live attenuated reassortant virus possessing three temperature-sensitive mutations in the PB2 polymerase gene rapidly loses temperature sensitivity following replication in hamsters", Vaccine, 15(12-13) 1372-8, (1997), 7 pgs.

Murphy, Brian R, et al., "Virulence of Avian Influenza A Viruses for Squirrel Monkeys", Infection and Immunity 37 (3), (Sep. 1982), 1119-1126.

Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.

Muyldermans, S, "Nanobodies: Natural single-domain antibodies", Ann. Rev. Biochem. 82, (2013), 1 pg.

Naim, H. Y., et al., "Basis for Selective Incorporation of Glycoproteins into the Influenza Virus Envelope", Journal of Virology, 67(8), (1993), 4831-4841.

(56) References Cited

OTHER PUBLICATIONS

Naito, S., et al., "Function and Structure of RNA Polymerase From Vesicular Stomatitis Virus", The Journal of Biological Chemistry, 251(14), (1976), 4307-4314.
Nara, et al., "", PLoS Biology, 8 (12), (2010), e1000571.
Inara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "A Decade After the Generation of a Negative-Sense RNA Virus From Cloned cDNA-What Have We Learned?", Journal of General Virology, 83(11), (Nov. 2002), 2635-2662.
Neumann, G., et al., "An Improved Reverse Genetics System for Influenza A Virus Generation and Its Implications for Vaccine Production", Proc. Natl. Acad. Sci. USA, 102(46) 16825-16829, (2005), 5 pgs.
Neumann, G., et al., "An improved reverse genetics system for influenza A virus generation and its implications for vaccine production", Proc. Natl. Acad. Sci. USA. 102(46), (2005), 16825-16829.
Neumann, G., et al., "Emergence and pandemic potential of swine-origin H1N1 influenza virus", Nature (London), 459(7249), (Jun. 2009), 931-939.
Neumann, G., et al., "Generation of influenza A virus from cloned cDNAs—historical perspective and outlook for the new millenium. ", Rev Med Virol., 12(1), XP002314285, (Jan.-Feb. 2002), 13-30.
Neumann, G., et al., "Generation of influenza A viruses entirely from cloned cDNAs", Proc. Natl. Acad. Sci. USA., 96(16), (1999), 9345-9350.
Neumann, G., et al., "Genetic Engineering of Influenza and Other Negative-Strand RNA Viruses Containing Segmented Genomes", Advances in Virus Research, 53, (1999), 265-300.
Neumann, G., et al., "Influenza A virus NS2 protein mediates vRNP nuclear export through NES-independent interaction with hCRM1", The EMBO Journal, 19 (24), (2000), 6751-6758.
Neumann, G., et al., "Mutational analysis of influenza virus promoter elements in vivo", Journal of General Virology, 76 1709-1717, (1995), 9 pgs.
Neumann, G., et al., "Nuclear Import and Export of Influenza Virus Nucleoprotein", Journal of Virology, 71 (12), (1997), 9690-9700.
Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.
Neumann, G., et al., "Reverse genetics of influenza virus.", Virology, 287(2), (Sep. 1, 2001), 243-50.
Neumann, G., et al., "Reverse Genetics of Influenza Viruses—Applications in Research and Vaccine Design", Monographs in Virology, 27, (2008), 118-133.
Neumann, G., et al., "RNA Polymerase I-Mediated Expression of Influenza Viral RNA Molecules", Virology, 202(1), (1994), 477-479.
Neumann, G., et al., "Synthesis of Influenza Virus: New impetus from an old enzyme, RNA polymerase I", Virus Research 82(1-2), (Jan. 30, 2002), 153-158.
Neumann, Gabriele, "Minireview Reverse Genetics of Influenza Virus", Virology, vol. 287, (2001), 243-250.
Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.

Nicolson, C., et al., "Generation of Influenza Vaccine Viruses on Vero Cells by Reverse Genetics: an H5N1 Candidate Vaccine Strain Produced Under a Quality System", Vaccine, 23 2943-2952, (2005), 10 pgs.
Niwa, H., et al., "Efficient Selection for High-Expression Transfectants With a Novel Eukaryotic Factor", Gene, 108(2), (1991), 193-199.
Noda, Takeshi, et al., "Three-dimensional analysis of ribonucleoprotein complexes in influenza A virus", Nature Communications, 3, (2012), 1-6.
Odagiri, T., et al., "Nucleotide Sequence of the PA Gene of Influenza A/WSN/33 (H1N1)", Nucleic Acids Research, 18 (3), Department of Virology, (Jan. 9, 1990), 1 pg.
Odagiri, Takato, et al., "Segment-Specific Noncoding Sequences of the In?uenza Virus Genome RNA Are Involved in the Speci?c Competition between Defective Interfering RNA and Its Progenitor RNA Segment at the Virion Assembly Step", Journal of Virology, 71(3), (1997), 2138-2145.
Olivo, P. D, et al., "Detection and quantitation of human respiratory syncytial virus (RSV) using minigenome cDNA and a Sindbis virus replicon: a prototype assay for negative-strand RNA viruses.", Virology, 251(1), (Nov. 10, 1998), 198-205.
Onishi, M., et al., "Applications of retrovirus-mediated expression cloning", Experimental Hematology, 24(2), (1996), 324-329.
Orkin, S. H, et al., "Report and Recommendations of the Panel to Assess the NIH Investment in Research on Gene Therapy", http://www.nih.gov/news/panelrep.html, (Dec. 7, 1995), 37 pgs.
Ozaki, "Generation of High-Yielding Influenza A Viruses in African Green Monkey Kidney (Vero) Cells by Reverse Genetics", J Virol 78(4), (2004), 1851-1857.
Ozaki, H., et al., "Generation of High-Yielding Influenza A Viruses in African Green Money Kidney (Vero) Cells by Reverse Genetiics", Journal of Virology, 78(4) 1851-1857, (2004), 6 pgs.
Ozawa, M., et al., "An adenovirus vector-mediated reverse genetics system for Influenza A virus generation", Journal of Virology, The American society For Microbiology, US vol. 81 (17), XP002471230, ISSN: 0022-538X, (Jun. 27, 2007), 9556-9559.
Ozawa, M., et al., "Replication-incompetent influenza A viruses that stably express a foreign gene", Journal of General Virology, 92(Part 12)., (2011), 2879-2888.
Palache, A. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98 133-134 abstract, (1999), 1 pg.
Palese, P., et al., "47. Orthomyxoviridae: The Viruses and Their Replication", In: Fields Virology (5th Edition), (2007), 90 pgs.
Palese, P., "Negative-Strand RNA Viruses: Genetic Engineering and Applications", Proc. Natl. Acad. Sci. USA, 93(21), (1996), 11354-11358.
Park, Eun K., et al., "The M2 Ectodomain is important for its incorporation into influenza A virions", J. of Virology, vol. 72, No. 3, XP002196797, (Mar. 1998), 2449-2455.
Park, K. H., et al., "Rescue of a Foreign Gene by Sendai Virus", Proc. Natl. Acad. Sci. USA, 88, (1991), 5537-5541.
Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.
Pattnaik, A. K., et al., "The Termini of VSV DI Particle RNAs are Sufficient to Signal RNA Encapsidation, Replication, and Budding to Generate Infectious Particles", Virology, 206, (1995), 760-764.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Peiris, J. S. M., et al., "Re-Emergence of Fatal Human Influenza A Subtype H5N1 Disease", The Lancet, 363 617-619, (2004), 3 pgs.
Pekosz, A., "Commentary—Reverse Genetics of Negative-Strand RNA Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.

(56) References Cited

OTHER PUBLICATIONS

Pelet, T., et al., "High throughput screening assay for negative single stranded RNA virus polymerase inhibitors", Journal of Virological Methods, 128 29-36, (2005), 8 pgs.
Percy, N., et al., "Expression of a Foreign Protein by Influenza A Virus", Journal of Virology, 68(7), (1994), 4486-4492.
Perdue, M., et al., "Virulence and the Avian Influenza Virus Hemagglutinin Gene", United States Department of Agriculture—Agriculture Research Service, http://www.nps.ars.usda.gov/publications/publications.htm?SEQ_NO_155=106036, (Observed Feb. 22, 2003), 1 pg.
Perez, D. R., et al., "The Matrix 1 Protein of Influenza A Virus Inhibits the Transcriptase Activity of a Model Influenza Reporter Genome in Vivo", Virology, 249(1), (1998), 52-61.
Perez, Jasmine T., et al., "Unit 15G.4—Insertion of a GFP Reporter Gene in Influenza Virus", Curr Protoc Microbiol., (2013), 20 pgs.
Peterson, B. C., et al., "Homologous sequences other than insertion elements can serve as recombination sites in plasmid drug resistance gene amplification", Journal of Bacteriology, Oct. 1983. 156(1) 177-185, (1983), 5 pgs.
Piatti, G., "Identification of immunodominant epitopes in the filamentous Hemagglutinin of Bordetella pertusis", FEMS Immunology and Medical Microbiology, 23(3), (1999), 235-241.
Piller, S C., et al., "Vpr protein of human immunodeficiency virus type 1 forms cation-selective channels in planar lipid bilayers", PNAS, 93, (1996), 111-1115.
Ping, J., et al., "Development of high-yield influenza B virus vaccine viruses", Proc. Natl. Acad. Sci. USA, 113(51), (Dec. 5, 2016), E8296-E8305.
Ping, Jihui, et al., "Development of high-yield influenza A virus vaccine viruses", Nature Communications, [online]. Retrieved from the Internet: <http://www.nature.com/article-assets/npg/ncomms/2015/150902/ncomms9148/extref/ncomms9148-sl.pdf>, (Sep. 2, 2015), 50 pgs.
Pinto, L. H., et al., "Influenza Virus M2 Protein Has Ion Channel Activity", Cell, 69, (May 1992), pp. 517-528.
Pittman, Kelly J., et al., "Z-DNA Binding Protein Mediates Host Control of Toxoplasma gondii Infection", Infection and Immunity, 84(10), (Oct. 2016), 3063-3070.
Plant, E P, et al., "Mutations to A/PuertoRico/8/34 PB1 gene improves seasonal reassortant influenza A virus growth kinetics", Vaccine, 31(1), (Dec. 1, 2012), 207-212.
Pleschka, S., et al., "A Plasmid-Based Reverse Genetics System for Influenza A Virus", Journal of Virology, 70(6), (1996), 4188-4192.
Pley, H. W., et al., "Three-Dimensional Structure of a Hammerhead Ribozyme", Nature, 372, (1994), 68-74.
Popova, Lyubov, et al., "Immunodominance of Antigenic Site B over Site of Hemagglutinin of Recent H3N2 Influenza Viruses", Plos One, vol. 7 No. 7, (Jul. 25, 2012), e41895.
Portela, A., et al., "Replication of orthomyxoviruses", Advances in Virus Research, 54, (1999), 319-348.
Potter, C. W., "Chapter 1—Chronicle of Influenza Pandemics", In: Textbook of Influenza, Nicoholson, K. G., et al., Editors, (Blackwell Scientific Publication), (1998), 3-18.
Powell, Robin H., et al., "WRN conditioned media is sufficient for in vitro propagation of intestinal organoids from large farm and small companion animals", Biology Open, vol. 6, No. 5, (Mar. 27, 2017), XP055620505, (Mar. 27, 2017), 698-705.
Preston, Andrew, "Choosing a Cloning Vector", Methods in Molecular Biology, vol. 235, *E. coli* Plasmid Vectors 19-27, Edited by: N. Casali and A. Preston, (2003), 9 pgs.
Pushko, P., et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 page.
Puzelli, S., et al., "Changes in the Hemagglutinins and Neuraminidase of Human Influenza B Viruses Isolated in Italy During the Feb. 2001, Mar. 2002, and Apr. 2003 Seasons", Journal of Medical Virology, 74(4) 629-640, (2004), 12 pgs.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981), 4 pgs.
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Ramanunninair, Manojkumar, et al., "Molecular Signature of High Yield (Growth) Influenza A Virus Reassortants Prepared as Candidate Vaccine Seeds", PLoS One, 8(6): e65955, (2013), 1-16.
Ray, M. K., et al., "A Novel Glycosylation Phenotype Expressed by Lec23, a Chinese Hamster Ovary Mutant Deficient in alpha-Glucosidase I", Journal of Biological Chemistry, 266(34), (1991), 22818-22825.
Rayner, J., et al., "Alphavirus vectors and vaccination", Reviews in Medical Virology, 12, (2002), 279-296.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Restifo, N. P., et al., "Transfectant Influenza A Viruses are Effective Recombinant Immunogens in the Treatment of Experimental Cancer", Virology, 249(1), (1998), 89-97.
Ricardo-Lax, I., et al., "Replication and single-cycle delivery of SARS-CoV-2 replicons", Science, 374(6571), (2021), 1099-1106 (9 pgs).
Rimmelzwaan, G. F., et al., "Use of GFP-expressing influenza viruses for the detection of influenza virus A/H5N1 neutralizing antibodies", Vaccine, 29(18), (2011), 3424-3430.
Roberts, A., et al., "Minireview—Recovery of Negative-Strand RNA Viruses From Plasmid DNAs: A Positive Approach Revitalizes a Negative Field", Virology, 247(1), (1998), 1-6.
Robison, C. S, et al., "The Membrane-Proximal Stem Region of Vesicular Stomatitis Virus G Protein Confers Efficient Virus Assembly", Journal of Virology, 74 (5), (Mar. 2000), 2239-2246.
Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol, 153(10), (1994), 4636-4648.
Romanova, J., et al., "Live cold-adapted influenza A vaccine produced in Vero cell line", Virus Research, 103, (2004), 187-193.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Ruigrok, R W, et al., "Characterization of three highly purified influenza virus strains by electron microscopy", J Gen Virol 65 (Pt 4) 799-802, (Apr. 1984), 4 pgs.
Ruigrok, R W, et al., "Structural Characterization and Membrane Binding Properties of the Matrix Protein VP40 of Ebola Virus", Journal of Molecular Biology, 300(1), (2000), 103-112.
Ruiz-Arguello, M. B, et al., "Phosphatidylinositol-Dependent Membrane Fusion Induced by a Putative Fusogenic Sequence of Ebola Virus", Journal of Virology, 72(3), (Mar. 1998), 1775-1781.
Sansom, M. S., et al., "Influenza virus M2 Protein: a molecular modelling study of the ion channel", Protein Engineering, 6 (1), (1993), pp. 65-74.
Saphire, E. O., et al., "Feverish Quest for Ebola Immunotherapy: Straight or Cocktail", Trends Microbial, 24(9), (Sep. 2016), 684-686.
Satterlee, B., "Production of H5N1 avian influenza virus vaccine by plasmid-based reverse genetics technology", Basic Biotechnology eJournal, vol. 4, pp. 93-98, (2008), 93-98 Pgs.
Saunders, Kevin O., et al., "Neutralizing antibody vaccine for pandemic and pre-emergent coronaviruses", Nature, 594, (2021), 553-559 (27 pgs.).
Schares, G., et al., "Oocysts of Neospora caninum, Hammondia heydorni, Toxoplasma gondii and Hammondia hammondi in faeces

(56) References Cited

OTHER PUBLICATIONS collected from dogs in Germany", International Journal of Parasitology, vol. 35, No. 14, (Dec. 1, 2005), XP027737007, (Dec. 1, 2005), 1525-1537.
Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.
Schmidt, Kristina Maria, et al., "Marburg Virus Reverse Genetics Systems", Viruses 2016, 8, 178; doi: 10.3390 / v8060178, www.mdpi.com/journal/viruses, (2016), 17 pgs.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17 (5), (1998), 1289-1296.
Schotsaert, M, et al., "Universal M2 ectodomain-based influenza A vaccines: preclinical and clinical developments", Expert Rev Vaccines. Apr. 2009;8(4):, 499-508.
Schultz-Cherry, S., et al., "Influenza Virus NS1 Protein Induces Apoptosis in Cultured Cells", Journal of Virology, 75(17), (2001), 7875-7881.
Seong, B. L., et al., "A New Method for Reconstituting Influenza Polymerase and RNA in Vitro: A Study of the Promoter Elements for cRNA AND vRNA Synthesis in Vitro and Viral Rescue in Vivo", Virology, 186(1), (1992), 247-260.
Sheridan, Cormac, et al., "Innovators target vaccines for variants and shortages in global South", Nature Biotechnology, 39(4), (Apr. 2021), 393-396.
Shi, Pei-Yong, "Infectious cDNA Clone of the Epidemic West Nile Virus from New York City", Journal of Virology 5847-5856, (Jun. 2002), 10 pgs.
Shimojima, M., et al., "Tyro3 family-mediated cell entry of Ebola and Marburg viruses", J Virol., 80(20), (Oct. 2006), 10109-16.
Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.
Shortridge, K. F., et al., "Characterization of Avian H5N1 Influenza Viruses From Poultry in Hong Kong", Virology, 252 331-342, (1998), 12 pgs.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Silvas, J. A., et al., "Contribution of SARS-CoV-2 Accessory Proteins to Viral Pathogenicity in K18 Human ACE2 Transgenic Mice", J Virol, 95(17): e00402-21, (Sep. 2021), 1-14.
Siu, Y. L., et al., "The M, E, and N Structural Proteins of the Severe Acute Respiratory Syndrome Coronavirus Are Required for Efficient Assembly, Trafficking, and Release of Virus-Like Particles", J Virol., 82(22), (2008), 11318-11330.
Skehel, J. J., et al., "On the Mechanism of Inhibition of Influenza Virus Replication by Amantadine Hydrochloride", The Journal of General Virology, 38 (1), (1977), pp. 97-110.
Smatti, Maria K., et al., "Viral-Induced Enhanced Disease Illness", Front Microbiol, vol. 9: Article 2991, (Dec. 2018), 1-19.
Smeenk, et al., "Mutations in the Hemagglutinin and Matrix Genes of a Virulent Influenza (Virus Variant, A/FM/1/47-MA, Control Different Stages in Pathogenesis", Virus Research 44, (1996), 79-95.
Smura, T, "Surface glycoprotein [Severe acute respiratory syndrome coronavirus 2]", Gen Bank Accessions QH062107, (Feb. 11, 2020), 2 pgs.
Stray, S. J., et al., "Influenza virus infection of desialylated cells", Glycobiology, 10(7), (2000), 649-658.
Strobel, I., et al., "Efficient Expression of the Tumor-Associated Antigen MAGE-3 In Human Dendritic Cells, Using an Avian Influenza Virus Vector", Human Gene Therapy, 11(16), (2000), 2207-2218.
Stroud, Chad K., et al., "Disruption of FADS2 gene in mice impairs male reproduction and causes dermal and intestinal ulceration", Journal of Lipid Research, vol. 50, (2009), 1870-1880.
Subbarao, E. K., et al., "Rescue of an InfluenzaA Virus Wild-Type PB2 Gene and a Mutant Derivative Bearing a Site-Specific Temperature-Sensitive and Attenuating Mutation", Journal of Virology, 67(12), (1993), 7223-7228.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Characterization of an Avian Influenza A (H5N1) Virus Isolated From a Child With a Fatal Respiratory Illness", Science, 279, (1998), 393-396.
Subbarao, K., et al., "Evaluation of a Genetically Modified Reassortant H5N1 Influenza A (Virus Vaccine Candidate Generated by Plasmid-based Reverse Genetics", Virology, vol. 305(1), (Jan. 5, 2003), 192-200.
Sugawara, K., et al., "Development of Vero Cell-Derived Inactivated Japanese Encephalities Vaccine", Biologicals, 30 303-314, (2002), 12 pgs.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.
Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sun, Weina, et al., "Development of Influenza B Universal Vaccine Candidates Usingthe "Mosaic" Hemagglutinin Approach", American Society for Microbiology, Journal of Virology, Vaccines and Antiviral Agents, vol. 93, Issue 12, (Jun. 2019), 17 pgs.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Taira, K., et al., "Construction of a novel RNA-transcript-trimming plasmid which can be used both in vitro in place of run-off and (G)-free transcriptions and in vivo as multi-sequences transcription vectors", Nucleic Acids Research, 19(19), (1991), 5125-5130.
Takada, A., et al., "Downregulation of beta1 integrins by Ebola virus glycoprotein: implication for virus entry", Virology, 278(1), (Dec. 2000), Abstract Only.
Takada, Ayato, et al., "A system for functional analysis of Ebola?virus?glycoprotein", Proc. Natl. Acad. Sci. USA, 94(26), (1997), 14764-14769.
Takada, Ayato, et al., "Antibody-dependent enhancement of viral infection: molecular mechanisms and in vivo implications", Rev Med Virol, 13(6), (2003), 387-398.
Takada, Ayato, et al., "Epitopes Required for Antibody-Dependent Enhancement of Ebola Virus Infection", J Infect Dis, 196 (Suppl 2), (2007), S347-S356.
Takada, Ayato, et al., "Identification of Protective Epitopes on Ebola Virus Glycoprotein at the Single Amino Acid Level by Using Recombinant Vesicular Stomatitis Viruses", Journal of Virology, 77(2), (2003), 1069-1074.
Takada, Ayato, et al., "Infectivity-Enhancing Antibodies to Ebola Virus Glycoprotein", Journal of Virology, 75(5), (2001), 2324-2330.
Takada, Ayato, et al., "Protective efficacy of neutralizing antibodies against Ebola virus infection", Vaccine, 25(6), (2007), 993-999.

(56) References Cited

OTHER PUBLICATIONS

Takada, Ayato, et al., "The pathogenesis of Ebola hemorrhagic fever", Trends in Microbiology, 9(10), (2001), 506-511.

Takeda, M., et al., "Influenza a virus M2 ion channel activity is essential for efficient replication in tissue culture.", J Virol., 76(3), (Feb. 2002), 1391-9.

Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.

Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.

Tan, Tiong Kit, et al., "A COVID-19 vaccine candidate using SpyCatcher multimerization of the SARS-CoOV-2 spike protein receptor-binding domain induces potent neutralising antibody responses", Nature Communications, 12: 542, (2021), 1-16.

Tang, et al., "Recombinant adenovirus encoding the HA gene from swine H3N2 influenza virus partially protects mice from challenge with heterologous virus: AIHK/1/68 (H3N2)", Archives of Virology, vol. 147 2125-2141, (2002), 17 pgs.

Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.

Taylor, J., et al., "Newcastle Disease Virus Fusion Protein Expressed in a Fowlpox Virus Recombinant Confers Protection in Chickens", Journal of Virology, 64(4), (1990), 1441-1450.

Terry, G., et al., "The Contruction of Defective Interfering Rubella Virus Particles", Archives of Virology, 145(3), (2000), 625-633.

Tetsutani, K., et al., "Adjuvants in Influenza Vaccines", Vaccine 2012, vol. 30, (2012), 4 pgs.

Theriault, S., "The role of reverse genetics systems in determining filovirus pathogenicity", Archives of Virology, Supplementum. 157-177, (2005), 22 pgs.

Thi, T., et al., "Rapid reconstruction of SARS-CoV-2 using a synthetic genomics platform", Nature, vol. 582, (2020), 561-565 (24 pgs).

Thompson, Christine M, et al., "Critical assessment of influenza VLP production in Sf9 and HEK293 expression systems", BMC Biotechnology, 15(1), (May 16, 2015), 12 pgs.

Thompson, W. W., et al., "Mortality Associated With Influenza and Respiratory Syncytial Virus in the United States", JAMA, 289(2) 179-186, (2003), 8 pgs.

Tobler, K, et al., "Effect of cytoplasmic tail truncations on the activity of the M(2) ion channel of influenza A virus", J Virol., 73(12), (Dec. 1999), 9695-9701.

Towner, J S, et al., "Generation of eGFP express ing recombinant Zaire ebolavirus for analysis of early pathogenesis events and high-throughput antiviral drug screening", Virology, Academic Press ,Orlando, US , vol. 332, No. 1 20-27, XP004715289 ISSN: 0042-6822 the whole document, (Feb. 5, 2005), 8 pgs.

Treanor, J. J, et al., "The B allele of the NS gene of avian influenza viruses, but not the A allele, attenuates a human influenza a virus for squirrel monkeys", Virology, 171(1), (1989), 11-9.

Uraki, R., et al., "A Bivalent Vacine Based on a PB2-Knockout Influenza Virus Protects Mice From Secondary Pneumoccal Pneumonia", The Journal of Infectious Diseases, 212(12), (2015), 1939-1948.

Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.

Vaishnava, Shipra, et al., "The Antibacterial Lectin RegIIIg Promotes the Spatial Segregation of Microbiota and Host in the Intestine", Science, 334, (2011), 255-258.

Vanessa, Monteil, "Inhibition of SARS-CoV-2 Infections in Engineered Human Tissues Using Clinical-Grade Soluble Human ACE2", Cell, vol. 181, Retrieved from the Internet: <URL:https://www.ncbi.nlm.nih.gov/pmc/articles/PMC7181998/pdf/main.pdf>, (Apr. 24, 2020), 905-913.

Varner, Chad, "Developing Synthetic Multivalent Cellular Effectors", Thesis, School of Chemical and Biomolecular Engineering, Georgia Institute of Technology, (Aug. 2017), 88 pgs.

Verma, I. M, et al., "Gene Therapy—Promises, Problems and Prospects", Nature, 389, (1997), 239-242.

Via, L. E, et al., "Isolation of restriction fragments from large plasmids recovered from bacteria with multiple plasmids", Biotechniques, 11(4), (Oct. 1991), Abstract Only.

Victor, Sylvia, et al., "A Replication-Incompetent PB2-Knockout Influenza A Virus Vaccine Vector", Journal of Virology, vol. 86, No. 8, (Apr. 2012), 4123-4128.

Victor, Sylvia T., et al., "A Replication-Incompetent PB2-Knockout Influenza A Virus Vaccine Vector", Journal of Virology, 2012, 86(8):4123; DOL: 10.1128/JVI.06232-11. Journals.ASM.org;, Downloaded from http://jvi.asm.org/ on Aug. 20, 2012 by Univ. of Wisonsin—Mad, (Feb. 1, 2012), 7.

Vincke, C, et al., "Introduction to heavy chain antibodies and derived nanobodies", Meth. Mol. Biol. 911, (2012), 13 pgs.

Voeten, J. T, et al., "Characterization of high-growth reassortant influenza A viruses generated in MDCK cells cultured in serum-free medium", Vaccine, vol. 17, (1999), 1942-1950.

Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.

Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.

Waap, Helga, et al., "isolation and seroprevalence ofin stray cats and pigeons in Lisbon, Portugal", Veterinary Parasitology, vol. 187, No. 3, (Jan. 17, 2012), XP028492469, (Jan. 17, 2012), 542-547.

Wagner, R., et al., "Interdependence of hemagglutinin glycosylation and neuraminidase as regulators of influenza virus growth: a study by reverse genetics", Journal of Virology, 74 (14), (Jul. 2000), 6316-6323.

Walker, W. S, et al., "HEL-Flu: an influenza virus containing the hen egg lysozyme epitope recognized by CD4+ T cells from mice transgenic for an alphabeta TCR", J. Immunol., 159(6), (Sep. 1997), 2563-2566.

Wan, Yushun, et al., "Molecular mechanism for Antibody-Dependent Enhancement of Coronavirus EntrM", Journal of Virology, 94(5): e02015-19, (2019), 1-15.

Wang, B., et al., "Construction of Non-infectious SARS-CoV-2 Replicons and Their Application in Drug Evaluation", Virologica Sinica, 36, (2021), 890-900.

Wang, C., et al., "Ion Channel Activity of Influenza A Virus M2 Protein: Characterization of the Amantadine Block", Journal of Virology, 67 (9), (Sep. 1993), pp. 5585-5594.

Wang, Sheng-Fan, et al., "Antibody-dependent SARS coronavirus infection is mediated by antibodies against spike proteins", Biochem Biophys Res Commun, 451, (2014), 208-214.

Wang, Weijia, et al., "Identification of Critical Residues in the Hemagglutinin and Neuraminidase of Influenza Virus H1N1pdm for Vaccine Virus Replication in Embryonated Chicken Eggs", Journal of Virology, 87(8), (2013), 4642-4649.

Wang, Wenlig, et al., "Robust Immunity and Heterologous Protection against Influenza in Mice Elicited by a Novel Recombinant NP-M2e Fusion Protein Expressed in E. coli", PLoS One 7(12): e52488, (Dec. 2012), 1-13.

Wanitchang, Asawin, et al., "Characterization of influenza A virus pseudotyped with the spike protein of porcine epidemic diarrhea virus", Archives of Virology, 163(12), (2018), 3255-3264.

Ward, C. D., et al., "Direct Measurement of the Poliovirus RNA Polymerase Error Frequency In Vitro", Journal of Virology, 62(2), (1988), 558-562.

Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.

Warfield, et al., "", PNAS, vol. 100(26), (2003), pp. 5889-15894.

(56) References Cited

OTHER PUBLICATIONS

Watanabe, S., et al., "Ebola virus (EBOV) VP24 inhibits transcription and replication of the EBOV genome", J Infect Dis., 196(Suppl 2), (Nov. 15, 2007), S284-90.
Watanabe, S., et al., "Influenza A Virus Lacking M2 Protein as a Live Attenuated Vaccine". Journal of Virology, 83(11), (2009), 5947-5950.
Watanabe, S., et al., "Production of Novel Ebola Virus-Like Particles from CDNAs: an Alternative to Ebola Virus Generation by Reverse Genetics", Journal of Virology, 78(2), (Jan. 2004), 999-1005.
Watanabe, T., et al., "Influenza A virus can undergo multiple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, T., et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.
Weber, F., et al., "Conserved vRNA end sequences of Thogotoorthomyxovirus suggest a new panhandle structure", Archives of Virology, 142(5), (1997), 1029-1033.
Weber, F., et al., "Nucleoprotein Viral RNA and mRNA of Thogoto Virus: a Novel "Cap-Stealing" Mechanism in Tick-Borne Othomyxoviruses?", Journal of Virology, 70(12), (1996), 8361-8367.
Webster, R G, et al., "Evolution and molecular epidemiology of H9N2 influenza A viruses (from quail in southern China", XP002744257, retrieved from EBI accession No. UNIPROT:A3R6C9 Database accession No. A3R6C9 the whole document, (Apr. 3, 2007), 1 pg.
Wei, Hung-Ju, et al., "Fabrication of influenza virus-like particles using M2 fusion proteins for imaging single viruses and designing vaccines", Vaccine, 29, (2011), 7163-7172.
Wei, Kai, et al., "Influenza A Virus Acquires Enhanced Pathogenicity and Transmissibility after Serial Passages in Swine", Journal of Virology, 88(20), (Oct. 2014), 11981-11994.
Wentworth, D E, et al., "The NIAID Influenza Genome Sequencing Project", XP002744258, retrieved from EBI accession No. UNIPROT:U3S198 Database accession No. U3S198 the whole document, (Dec. 11, 2013), 1 pg.
Whelan, S. P. J., et al., "Efficient Recovery of Infectious Vesicular Stomatitis Virus Entirely from cDNA Clones", Proc. Natl. Acad. Sci. USA, 92, (1995), 8388-8392.
Wiedmer, T., et al., "Identification of three new members of the phospholipid scramblase gene family", Biochim Biophys Acta, 1467(1), (Jul. 31, 2000), Abstract Only.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wills, J. W., et al., "An Assembly Domain of the Rous Sarcoma Virus Gag Protein Required Late in Budding", Journal of Virology, 68(10), (1994), 6605-6618.
Wilson, et al., "Vaccine Potential of Ebola Virus VP24, VP30, VP35 and VP40 Proteins", Virology 286, (2001), 384-90.
Wilson, Julie A, et al., "Epitopes Involved in Antibody-Mediated Protection from Ebola Virus", Science, 287(5458), (Mar. 2000), 1664-1666.
Winkler, K, et al., "Changing the antigen binding specificity by single point mutations of an anti-p24 (HIV-1) antibody", J. Immunol. 165, (2000), 4505-4514.
Winter, G., et al., "The use of synthetic oligodeoxynucleotide primers in cloning and sequencing segment 8 of influenza virus (A/PR/8/34)", Nucleic Acids Res., 9(2), (1981), 237-245.

Wood, J. M., et al., "From Lethal Virus to Life-Saving Vaccine: Developing Inactivated Vaccines for Pandemic Influenza", Nature Reviews Microbiology, 2(10), (2004), 842-847.
Wu, Rui, et al., "A live bivalent influenza vaccine based on a H9N2 virus strain", Vaccine, 28, (2010), 673-680.
Wu, Tai Te, et al., "An Analysis of the Sequences of the Variable Regions of Bence Jones Proteins and Myeloma Light Chains and Their Implications for Anti-body complementarity", J. Exp. Med., 132(2), (1970), 211-250.
Xiang, J, et al., "Modification in framework region I results in a decreased affinity of chimeric anti-Tag72 antibody", Mol. Immunol. 28(1/2), (1991), 141-148.
Xu, Jiayu, et al., "The Cold-Adapted, Temperature-Sensitive SARS-Co V-2 Strain TS11 Is Attenuated in Syrian Hamsters and a Candidate Attenuated Vaccine", Viruses 2023, 15, 95. https://doi.org/10.3390/v15010095, (2023), 23.
Xu, Ruodan, et al., "Construction of SARS-CoV-2 Virus-Like Particles by Mammalian Expression System", Frontiers in Bioengineering and Technology, 8:862, (2020), 1-6.
Xu, X., et al., "Reassortment and evolution of current human influenza A and B viruses", Virus Research, 103, (2004), 55-60.
Yagi, Y., et al., "In silico panning for a non-competitive peptide inhibitor", BMC Bioinformatics, 8(11), (2007), 11 pgs.
Yamamoto, K., et al., "Orientation Dependence in Homologous Recombination", Genetics May 1996; 143(1): 27-36, (1996), 27-36.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yang, P., et al., "Hemagglutinin Specificity and Neuraminidase Coding Capacity of Meuraminidase-Deficient Influenza Viruses", Virology, 229(1), (1997), 155-165.
Yang, Z. Y, et al., "Identification of the Ebola virus glycoprotein as the main viral determinant of vascular cell cytotoxicity and injury", Nat Med., 6(8), (Aug. 2000), Abstract Only.
Yannarell, Dean A., et al., "Factors affecting the yield of cold-adapted influenza virus vaccine", Journal of Virological Methods, vol. 64, 161-169, (1997), 1 pg.
Yasuda, J., "Growth Control of Influenza A Virus by M1 Protein: Analysis of Transfectant Viruses Carrying the Chimeric M Gene", Journal of Virology, 68(12), (1994), 8141-8146.
Yen, H L, et al., "Neuraminidase Inhibitor-Resistant Recombinant A/Vietnam/1203/04 (K5N1) Influenza Viruses Retain Their Replication Efficiency and Pathogenicity In Vitro and In Vivo", Journal of Virology., vol. 81, No. 22, (Nov. 15, 2007), 12418-12426.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
Yip, Ming S., et al., "Antibody-dependent infection of human macrophages by severe acute respiratory syndrome", Virology Journal, 11: 82, (2014), 11 pgs.
Yonezawa, A., et al., "Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha", Journal of Virology, 79(2), (2005), 918-926.
Yu, Q., et al., "Functional cDNA Clones of the Human Respiratory Syncytial (RS) Virus N, P, and L Proteins Support Replication of RS Virus Genomic RNA Analogs and Define Minimal (trans-Acting Requirements for RNA Replication", Journal of Virology, 69(4), (1995), 2412-2419.
Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.
Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.
Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.

(56) References Cited

OTHER PUBLICATIONS

Zanin, M., et al., "An Amino Acid in the Stalk Domain of N1 Neuraminidase Is Critical for Enzymatic Activity", Journal of Virology, 2017, Vo. 91, No. 2, (Jan. 2017), 12 pgs.
Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.
Zeitlin, L., et al., "Antibody Therapeutics for Ebola Virus Disease", Curr. Opin. Viral. 17:, (2016), 11 pgs.
Zhang, Baoshan, et al., "A platform incorporating trimeric antigens into self-assembling nanoparticles reveals SARS-CoV-2-spike nanoparticles to elicit substantially higher neutralizing responses than spike alone", Scientific Reports 10, Article No. 18149, (2020), 13 pgs.
Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.
Zhang, Q.-Y., et al., "SARS-CoV-2 replicon for high-throughput antiviral screening", J Gen Virol,, 102(5), (2021), 1-4.
Zhang, V. Q, et al., "Easy two-step method for randomizing and cloning gene fragments", Methods Mol Biol., 634, (2010), Abstract Only.
Zhang, Xuming, et al., "Expression of Interferon-y by a Coronavirus Defective-Interfering RNA Vector and its Effect on Viral Replication, Spread, and Pathogenicity", Medical Institute, University of Southern California School of Medicine, (May 1997), 327-338.
Zhang, Y., et al., "A bacterial artificial chromosome (BAC)-vectored noninfectious replicon of SARS-CoV-2", Antiviral Research, vol. 185, 104974, (Jan. 2021), 1-9.
Zhao, Lili, et al., "New Insights into the Nonconserved Noncoding Region of the Subtype-Determinant Hemagglutinin and Neuraminidase Segments of Influenza A aViruses", Journal of Virology, 88(19), (Oct. 2014), 11493-11503.
Zhou, Yan, "Membrane-Anchored Incorporation of a Foreign Protein in Recombinant Influenza Virions", Virology 246(1), (1998), 83-94.
Zobel, A., et al., "RNA Polymerase I Catalysed Transcription of Insert Viral cDNA", Nucleic Acids Research, 21(16), (1993), 3607-3614.
"U.S. Appl. No. 17/004,583, PTO Response to Rule 312 Communication dated Feb. 23, 2023", 4 pgs.
"Japanese Application Serial No. 2021-146743, Response filed Feb. 17, 2023 to Notification of Reasons for Rejection dated Aug. 17, 2022", w English Claims, 34 pgs.
"U.S. Appl. No. 17/155,625, Response filed Feb. 28, 2023 to Advisory Action dated Jan. 20, 2023", 8 pgs.
"U.S. Appl. No. 17/813,200, Preliminary Amendment filed Mar. 7, 2023", 10 pgs.
"U.S. Appl. No. 17/266,049, Non Final Office Action dated Mar. 14, 2023", 12 pgs.
"U.S. Appl. No. 17/004,583, 312 Amendment filed Mar. 16, 2023", 7 pgs.
"Japanese Application Serial No. 2020-182549, Preliminary Examination Report dated Jan. 17, 2023", w English Translation, 3 pgs.
"U.S. Appl. No. 17/004,583, Supplemental Amendment filed Mar. 28, 2023", 6 pgs.
"Australian Application Serial No. 2021204721, First Examination Report dated Mar. 16, 2023", 6 pgs.
"U.S. Appl. No. 17/004,583, PTO Response to Rule 312 Communication dated Apr. 6, 2023", 3 pgs.
"European Application Serial No. 21705801.5, Response to Communication pursuant to Rules 161 and 162 filed Mar. 28, 2023", 13 pgs.
"U.S. Appl. No. 17/155,625, Notice of Allowance dated Apr. 12, 2023", 11 pgs.
"U.S. Appl. No. 17/578,939, Non Final Office Action dated Apr. 21, 2023", 5 pgs.
"Japanese Application Serial No. 2021-546853, Notification of Reasons for Refusal dated Apr. 18, 2023", w English Translation, 11 pgs.
"U.S. Appl. No. 17/004,583, Notice of Allowance dated May 15, 2023", 7 pgs.
"U.S. Appl. No. 17/352,845, Response filed May 16, 2023 to Non Final Office Action dated Dec. 16, 2022", 8 pgs.
"U.S. Appl. No. 17/212,836, Response filed May 16, 2023 to Non Final Office Action dated Feb. 16, 2023", 7 pgs.
"European Application Serial No. 18800815.5, Communication Pursuant to Article 94(3) EPC dated May 9, 2023", 6 pgs.
"U.S. Appl. No. 17/546,967, Restriction Requirement dated May 23, 2023", 10 pgs.
"Japanese Application Serial No. 2022-016436, Notification of Reasons for Refusal dated Apr. 11, 2023", w English translation, 13 pgs.
"Japanese Application Serial No. 2021-542525, Response filed May 18, 2023 Notification of Reasons for Refusal dated Dec. 13, 2022", w English Claims, 58 pgs.
"U.S. Appl. No. 17/229,001, Non Final Office Action dated Jun. 6, 2023", 15 pgs.
"U.S. Appl. No. 17/352,845, Notice of Allowance dated Jun. 7, 2023", 5 pgs.
"U.S. Appl. No. 17/266,049, Response filed Jun. 14, 2023 to Non Final Office Action dated Mar. 14, 2023", 10 pgs.
"European Application Serial No. 16778485.9, Communication Pursuant to Article 94(3) EPC dated Jun. 9, 2023", 4 pgs.
"U.S. Appl. No. 17/212,836, Final Office Action dated Jun. 22, 2023", 15 pgs.
"U.S. Appl. No. 18/173,535, Preliminary Amendment filed Jun. 26, 2023", 16 pgs.
"Japanese Application Serial No. 2022-513269, Notification of Reasons for Refusal dated Jun. 6, 2023", w English Translation, 15 pgs.
Abdoli, Mohsen, "Intranasal administration of cold-adapted live-attenuated SARS-CoV-2 candidate vaccine confers protection against SARS-CoV-2", Virus Research 319 198857, (2022), 10 pgs.
Faizuloev, Evgeny, "Cold-adapted SARS-CoV-2 variants with different sensitivity exhibit an attenuated phenotype and confer protective immunity", Science Direct Vaccine 41 892-902, (2023), 12 pgs.
Lu, Shan, "The SARS-CoV-2 nucleocapsid phosphoprotein forms mutually exclusive condensates with RNA and the membrane-associated M protein", nature communications 12:502, (2021), 15 pgs.
Marzi, "An Ebola whole-virus vaccine is protective in nonhuman primates", Science 348(6233) 439-442, (Apr. 2015), 4 pgs.
Matrosovich, "Early Alteration of the Receptor-Binding Properties of H1, H2, and H3 Avian Influenza Virus Hemagglutinins after Their Introduction to Mammals", J. Virology, 74(18) 8502-8512, (Sep. 2000), 11 pgs.
Plescia, Caroline B, "SARS-CoV-2 viral budding and entry can be modeled using BSL-2 level virus-like particles", JBC Research Article, (Nov. 19, 2020), 10 pgs.
Seo, Sang Heui, "Cold-Adapted Live Attenuated SARS-CoV-2 Vaccine Completely Protects Human ACE2 Transgenic Mice from SARS-Cov-2 Infection", Vaccines 2020 8, 584, (10 3 2020), 17 pgs.
Swann, Heather, "Minimal system for assembly of SARS CoV 2 virus like particles", Scientific Reports 10:21877 nature portfolio, (2020), 1-5.
Wolff, "Downstream porcessing of cell culture-derived virus particles", Expert Rev. Vaccines 10(10) 1451-1475, (2011), 25 pgs.
Zhang, Zhikuan, "Structure of SARS-CoV-2 membrane protein essential for virus assembly", nature communications 13:4399, (Aug. 5, 2022), 12 pgs.
"Japanese Application Serial No. 2021-546853, Response filed Jul. 13, 2023 to Notification of Reasons for Refusal dated Apr. 18, 2023", W English Claims, 12 pgs.
"U.S. Appl. No. 17/004,583, Notice of Allowability dated Aug. 1, 2023", 2 pgs.
"Japanese Application Serial No. 2021-542525, Examiners Decision of Final Refusal dated Aug. 1, 2023", w English Translation, 7 pgs.

(56) References Cited

OTHER PUBLICATIONS

"Japanese Application Serial No. 2022-144599, Notification of Reasons for Refusal dated Aug. 22, 2023", w English translation, 19 pgs.
"Japanese Application Serial No. 2021-546853, Office Action dated Aug. 29, 2023", w English Translation, 10 pgs.
"Japanese Application Serial No. 2021-546853, Notification of Reasons for Refusal dated Aug. 29, 2023", w English Translation, 6 pgs.
"Japanese Application Serial No. 2021-536228, Notification of Reasons for Rejection dated Aug. 22, 2023", W English Translation, 13 pgs.
"Japanese Application Serial No. 2022-161803, Notification of Reasons for Refusal dated Sep. 12, 2023", w English Translation, 4 pgs.
"Japanese Application Serial No. 2022-544779, Notification of Reasons for Refusal dated Aug. 22, 2023", w English Translation, 10 pgs.
Matrosovich, Mikhail, "Overexpression of the a-2,6-Sialyltransferase in MDCK Cells Increases Influenza Virus Sensitivity to Neuraminidase Inhibitors", Journal of Virology, Aug. 2003, p. 8418-8425, (2003), 9 pgs.

\* cited by examiner

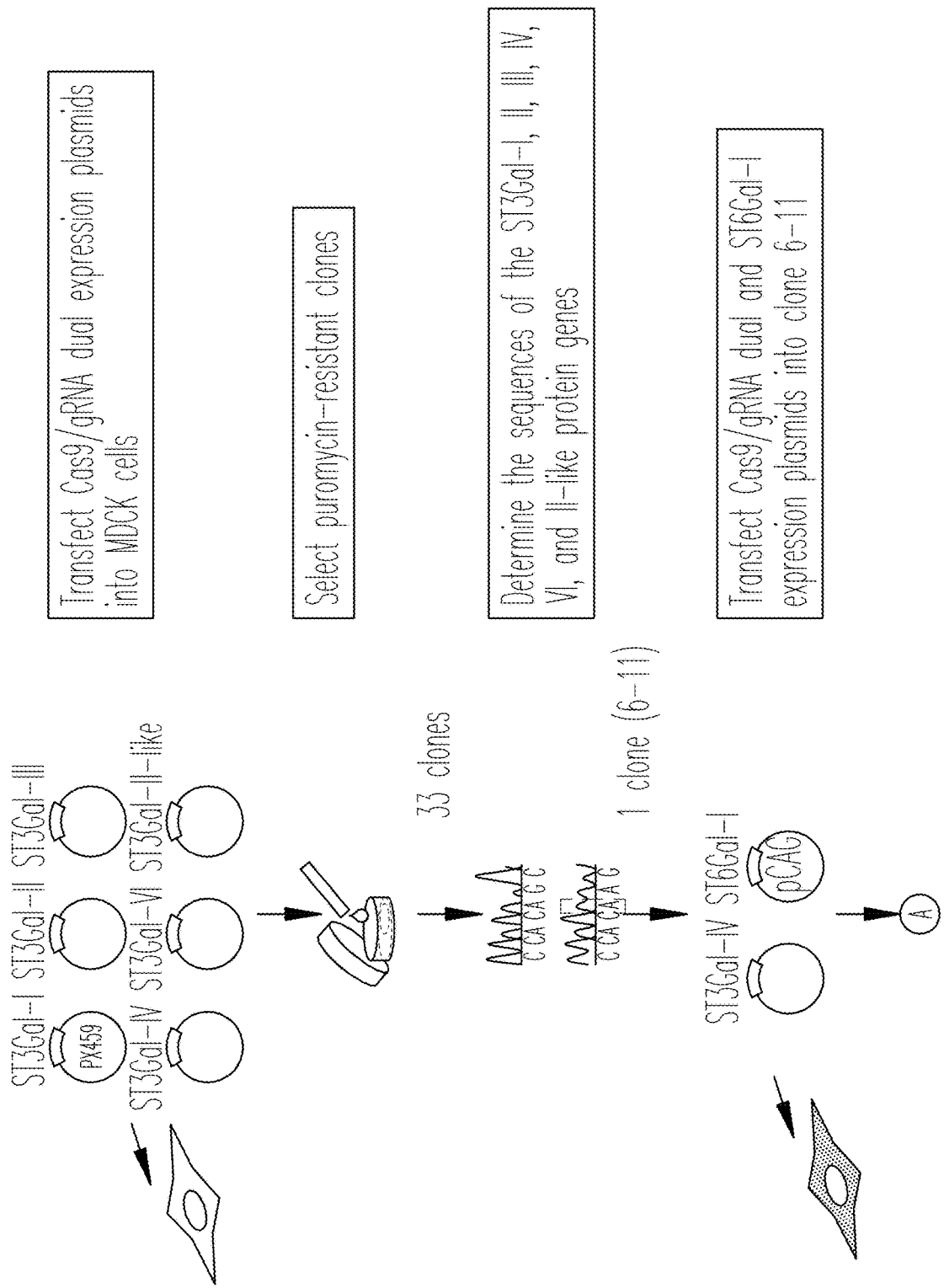

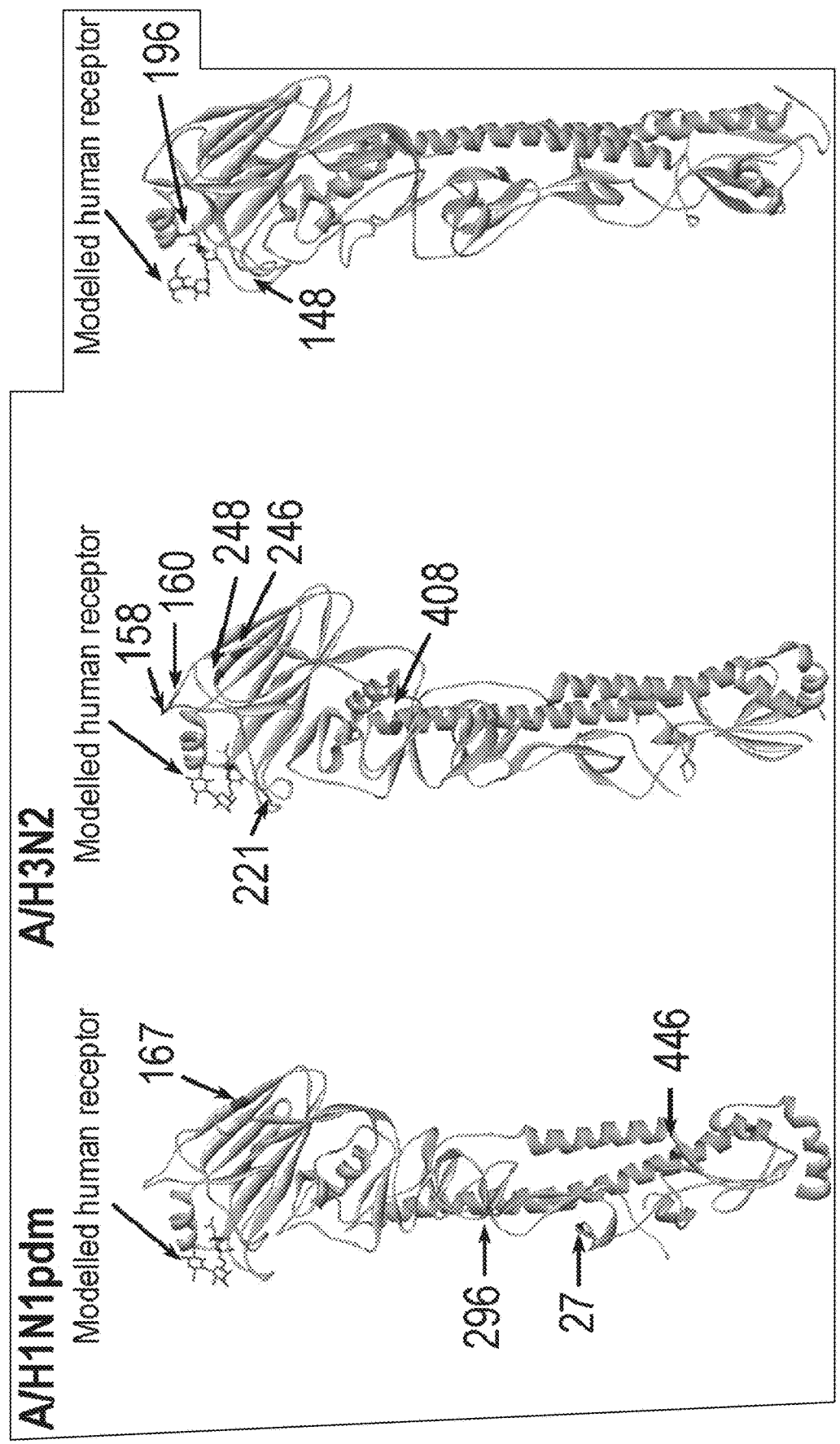

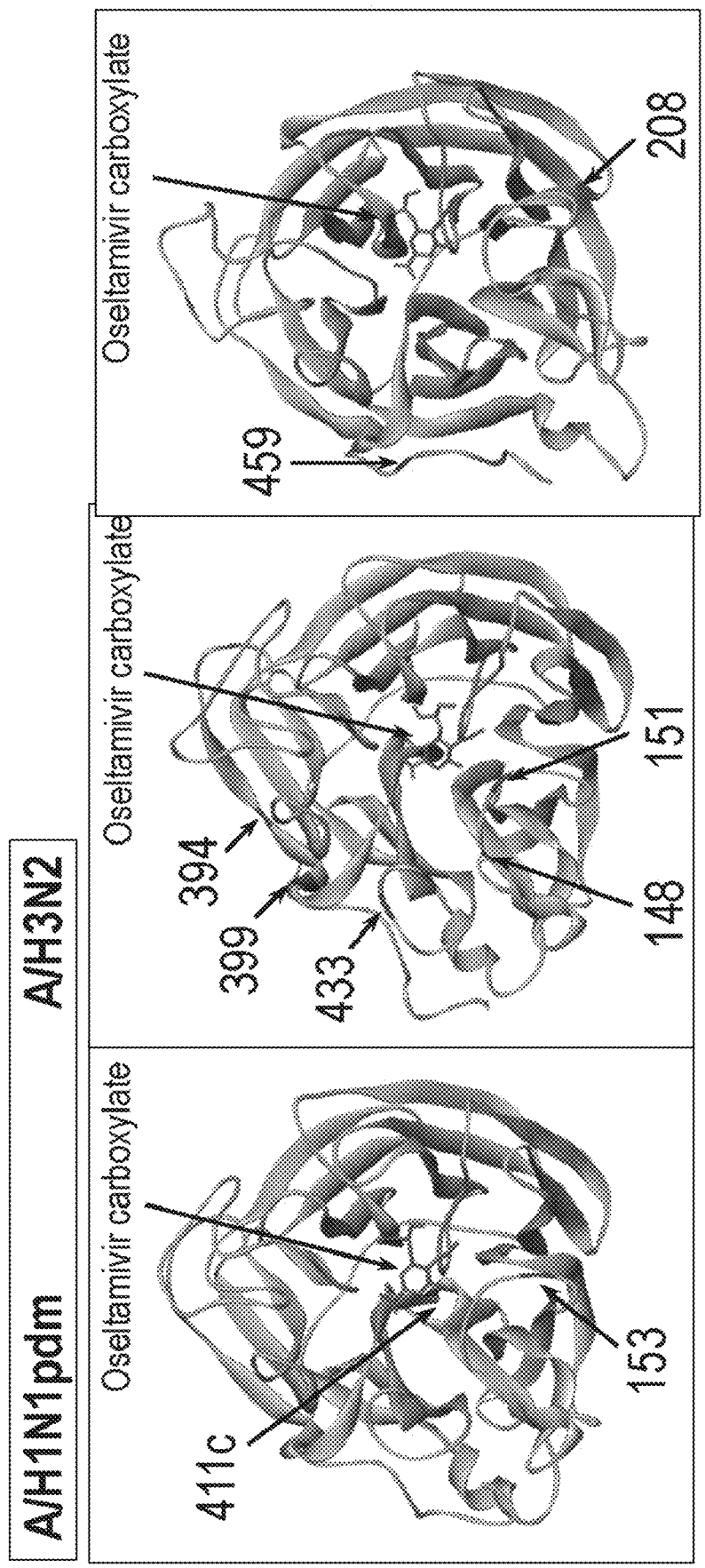

HUMANIZED CELL LINE

CROSS-REFERENCE TO RELATED APPLICATIONS

This application claims the benefit of the filing date of U.S. application No. 62/803,266, filed on Feb. 8, 2019, the disclosure of which is incorporated by reference herein.

STATEMENT OF GOVERNMENT RIGHTS

This invention was made with government support under HHSN272201400008C awarded by the National Institutes of Health. The government has certain rights in the invention.

BACKGROUND

The influenza A and B viruses possess two major surface glycoproteins, hemagglutinin (HA) and neuraminidase (NA). HA recognizes sialic acid-containing receptors on the cell surface, while NA cleaves sialic acids from receptors on cellular surfaces to facilitate the release of progeny virions from the surface of infected cells (Gamblin and Skehel, 2010). HA is also the major antigen stimulating the host's protective immunity, specifically the production of neutralizing antibodies.

Virus isolation from clinical specimens is an essential tool for the identification and characterization of circulating viruses. Currently, two subtypes of influenza A viruses (A/H1N1 and A/H3N2) and two lineages of influenza B viruses (B/Yamagata- and B/Victoria-lineage) are cocirculating in the human population and cause epidemics of seasonal influenza. Madin-Darby canine kidney (MDCK) cells are the most widely used cell line for isolation and propagation of human influenza viruses. This cell line shows high susceptibility to influenza viruses; however, it supports the growth of recent A/H3N2 viruses poorly. Furthermore, passaging of influenza viruses in MDCK cells often leads to the selection of variants with mutations in their HA and/or NA genes (Chambers et al., 2014; Lee et al., 2013; Tamura et al., 2013; Lin et al., 2017; Li et al., 2009; Oh et al., 2008). The emergence of such variants carrying mutations relevant to adaptation of influenza viruses to cell culture could distort the evaluation of the antigenic, genetic, and antiviral properties of circulating influenza viruses. For example, the emergence of mutations that confer receptor-binding activity to the NA of A/H3N2 viruses, such as the aspartic acid-to-glycine substitution at position 151 (D151G) (Mob et al., 2015; Lin et al., 2010; Zhu et al., 2012), is problematic for characterization of HA antigenicity by means of hemagglutination-inhibition, virus-neutralization, and focus reduction assays because the receptor-binding activity of NA contributes to the results of these assays. Nevertheless, many laboratories use MDCK cells to isolate A/H3N2 viruses. A GISAID EpiFlu database analysis by Lee et al. (2013) showed that approximately 30% of MDCK-cultured A/H3N2 isolates possess an amino acid change at position 151. Therefore, currently circulating A/H3N2 strains should be isolated and propagated in cell lines that can faithfully maintain their characteristics.

The HAs of human influenza viruses prefer to bind to glycans that end with sialic acid linked to galactose by α2,6-linkages, whereas avian virus HAs preferentially bind to glycans that terminate with sialic acid linked to galactose by α2,3-linkages (Connor et al., 1994; Rogers and Paulson, 1983; Stevens et al., 2006). Correspondingly, epithelial cells in the human upper respiratory tract express predominantly α2,6-sialoglycans (van Riel et al., 2006; Shinya et al., 2006). Although MDCK cells expressing both α2,6- and α2,3-sialoglycans are suitable for the isolation of influenza viruses from multiple animal species, this cell line has been shown to express relatively low levels of α2,6-sialoglycans (Lin et al., 2017; Hatakeyama et al., 2005; Matrosovich et al., 2003). Previously, our group and others engineered MDCK cells to overexpress α2,6-sialoglycans (Hatakeyama et al., 2005; Matrosovich et al., 2003). These modified MDCK cells (designated AX4 or MDCK-SIAT1) displayed a higher sensitivity for human influenza virus isolation than a conventional MDCK cell line (Oh et al., 2008; Hatakeyama et al., 2005), yet they still expressed α2,3-sialoglycans. Importantly, as with conventional MDCK cells, variants with mutations in either HA or NA have been detected when seasonal influenza viruses were passaged through MDCK-SIAT1 cells (Tamura et al., 2013; Li et al., 2009). Therefore, an alternative cell line that supports efficient isolation and propagation of human influenza viruses without any cell culture-adaptive mutations is necessary for accurate characterization of circulating viruses and possibly for efficient vaccine production in cells.

SUMMARY

The present disclosure relates to a mammalian or avian cell line that is genetically modified to support, for example, more efficient isolation and/or amplification (propagation) of human influenza viruses, and in particular human H3 influenza viruses. The disclosed cell lines may be genetically modified to decrease expression of alpha-2,3-linked sialic acids on the cell surface and to increase expression of alpha-2,6-linked sialic acids relative to a parental cell lines that are not modified to alter expression of alpha-2,3-linked sialic acids, alpha-2,6-linked sialic acids, or both. In one embodiment, the modified mammalian or avian cell lines are modified to express high levels of human influenza virus receptors and low levels of avian influenza virus receptors. In one embodiment, the cell line is a mammalian cell line, e.g., a non-human cell line such as a primate cell line, or a canine cell line. In one embodiment, the modified cell line is a modified MDCK cell line that has decreased expression of alpha-2,3-linked sialic acid relative to AX-4, or increased expression of alpha-2,6-linked sialic acid relative to unmodified MDCK cells. In one embodiment, the modified cell line is hCK, which supports more efficient isolation and amplification of human influenza viruses compared to MDCK and AX-4 cells. In one embodiment, the decrease in expression of alpha-2,3-linked sialic acids is due to a genetic modification that decreases or eliminates expression of one or more sialyltransferases that produce alpha-2,3-linked sialic acids, a genetic modification including but not limited to an insertion of one or more nucleotides, a deletion of one or more nucleotides, a substitution of one or more nucleotides, or any combination thereof, in one or more sialyltransferase genes. In one embodiment, the genetic modification includes an insertion of one or more nucleotides in one or more sialyltransferase genes. In one embodiment, the genetic modification includes a deletion of one or more nucleotides in one or more sialyltransferase genes. In one embodiment, the genetic modification includes a substitution of one or more nucleotides in one or more sialyltransferase genes. In one embodiment, the genetic modification includes an insertion of one or more nucleotides in at least one sialyltransferase gene. In one embodiment, the genetic modification includes a deletion of one or more nucleotides in at least one sialyltransferase gene. In one embodiment, the genetic modification includes a substitution of one or more nucleotides in at least one sialyltransferase gene. The genetic modifications that decrease expression of alpha-2,3-linked sialic acids may be the result of any method that "knocks down" or "knocks out" expression, methods including the uses of recombinase systems such as CRISPR/Cas, TALEN or zinc finger binding proteins. In one embodiment, the increase in expression of alpha-2,6-linked sialic acids is due to a genetic modification that increase expression of one or more sialyltransferases that produce alpha-2,6-linked sialic acids, a genetic modification including but not limited to an expression cassette comprising a nucleotide sequence encoding a sialyltransferase that that produces alpha-2,6-linked sialic acids, e.g., a human β-galactoside α2,6-sialyltransferase I (ST6Gal I) gene.

In one embodiment, an isolated recombinant mammalian or avian cell comprising a reduced amount of cell surface β-galactoside α2,3 sialyl residues and an increased amount of human β-galactoside α2,6 sialyl residues relative to a corresponding non-recombinant mammalian or avian cell is provided. In one embodiment, the isolated recombinant cell is a non-human mammalian cell. In one embodiment, the isolated recombinant cell is a canine or non-human primate cell. In one embodiment, the reduced amount of surface β-galactoside α2,3 sialyl residues is the result of a reduced amount or activity of one or more α2,3 sialyltransferases, e.g., a reduction in the amount or activity of one or more α2,3 sialyltransferases of at least 5%, 10%, 20%, 50%, 70%, 80%, 90%, 95% or more, which may result in a reduction of at least 5%, 10%, 20%, 50%, 70%, 80%, 90%, 95% or more in α2,3 sialyl residues, in the recombinant cell. In one embodiment, the amount or activity of α2,3 sialyltransferases, or the amount of α2,3 sialyl residues, in the recombinant cell is undetectable. In one embodiment, the α2,3 sialyltransferase gene that is modified encodes an α2,3 sialyltransferase that has at least 80%, 85%, 87%, 90%, 92%, 95%, 96%, 97%, 98%, or 99% amino acid sequence identity to any one of SEQ ID Nos. 6, 8, 10, 12, 14, 16 or 18, or a nucleotide sequence having at least 80%, 85%, 87%, 90%, 92%, 95%, 96%, 97%, 98%, or 99% nucleotide acid sequence identity to any one of SEQ ID Nos. 5, 7, 9, 11, 13, 15, or 17. In one embodiment, the isolated recombinant cell comprises an expression cassette encoding human β-galactoside α2,6 sialyltransferase I (ST6Gal-I) or ST6Gal-II. In one embodiment, the ST6Gal-I or ST6Gal-II comprises a protein having at least 80% amino acid sequence identity to any one of SEQ ID Nos. 1-4, 101 or 150. In one embodiment, the α2,6 sialyltransferase gene encodes an α2,6 sialyltransferase that has at least 85%, 87%, 90%, 92%, 95%, 96%, 97%, 98%, or 99% amino acid sequence identity to any one of SEQ ID Nos. 1-4, 101 or 150, or a nucleotide sequence having at least 80%, 85%, 87%, 90%, 92%, 95%, 96%, 97%, 98%, or 99% nucleotide acid sequence identity to SEQ ID Nos. 101 or 151. In one embodiment, the human β-galactoside α2,6 sialyltransferase amount or activity in the recombinant cell in creased by at least 1%, 5%, 10%, 20%, 50%, 70%, 80%, 90%, 95% or more. In one embodiment, one or more β-galactoside α2,3 sialyltransferase genes are mutated so as to reduce the amount of cell surface β-galactoside α2,3 sialyl residues. In one embodiment, two or more of ST3Gal-I, ST3Gal-II, ST3Gal-III, ST3Gal-IV, ST3Gal-V, ST3Gal-VI, or ST3Gal-II-like genes are mutated. In one embodiment, three, four, five, six or seven of ST3Gal-I, ST3Gal-II, ST3Gal-III, ST3Gal-IV, ST3Gal-V, ST3Gal-VI, or ST3Gal-II-like genes are mutated. In one embodiment, the ST3 genes have at least 80% nucleic acid sequence identity to any one of SEQ ID Nos. 5, 7, 9, 11, 13, 15, or 17. In one embodiment, the reduction in cell surface β-galactoside α2,3 sialyl residues is the result of reduced expression of one or more ST3 sialyltransferases. In one embodiment, the one or more ST3 sialyltransferases have at least 80% amino acid sequence identity to any one of SEQ ID Nos. 6, 8, 10, 12, 14, 16, or 18. In one embodiment, influenza H3 viruses replicate more efficiently in the recombinant cell relative to the non-recombinant cell.

Further provided is an isolated recombinant mammalian or avian cell, comprising a reduced amount of cell surface β-galactoside α2,3 sialyl residues relative to a corresponding non-recombinant mammalian or avian cell. In one embodiment, one or more of ST3Gal-I, ST3Gal-II, ST3Gal-III, ST3Gal-IV; ST3Gal-V, ST3Gal-VI, or ST3Gal-II-like genes in the recombinant cell are mutated. In one embodiment, a combination of ST3Gal-I, ST3Gal-II, ST3Gal-III, ST3Gal-IV, ST3Gal-V; ST3Gal-VI, or ST3Gal-II-like genes in the recombinant cell are mutated. In one embodiment, ST3Gal-I, ST3Gal-II, ST3Gal-III, ST3Gal-IV, ST3Gal-V, ST3Gal-VI, and ST3Gal-II-like genes in the recombinant cell are mutated.

The recombinant cells described herein are useful, for example, in virus isolation, vaccine production and in diagnostics. For example, the recombinant cells allow for isolation and/or amplification of progeny viruses. Moreover, HA assays generally are not used to detect human H3N2 viruses. The recombinant cells may be advantageous in that regard, e.g., to amplify virus.

Further, recombinant cells that have increased β-galactoside α2,6 sialyl residues can be used as a source of isolated β-galactoside α2,6 sialyl, which in turn may be used to coat surfaces such as beads, to inhibit galectin(s), to isolate or detect *Sambucus nigra* agglutinin (SNA), *Sambucus sieboldiana* (SSA) or *Trichosanthes japonica* agglutinin I (TJA-I).

In one embodiment, a method of modifying the amount of cell surface β-galactoside α2,3 sialyl residues and human β-galactoside α2,6 sialyl residues on a mammalian or an avian cell is provided. In one embodiment, the method includes mutating one or more β-galactoside α2,3 sialyltransferase (ST3Gal) genes, and overexpressing a human β-galactoside α2,6 sialyltransferase (ST6Gal) gene, in a parental mammalian or avian cell so as to result in a modified mammalian or avian cell having a reduced amount of cell surface β-galactoside α2,3 sialyl residues and an increased amount of human β-galactoside α2,6 sialyl residues on the surface of the modified cell relative to the corresponding parental cell. In one embodiment, the one or more ST3Gal genes are mutated using a genome editing system, e.g., a CRISPR/Cas9, Zinc Finger Nuclease (ZFN) or transcription activator-like effector nuclease (TALEN) system. In one embodiment, the mutations include one or more nucleotide insertions or one or more nucleotide deletions, or both, in one or more ST3 genes. In one embodiment, the modified cell comprises an expression cassette comprising a ST6Gal open reading frame. In one embodiment, the modified cell is a kidney cell. In one embodiment, the modified cell is a canine cell.

Methods of using the recombinant cell include a method of propagating an influenza virus, e.g., a human influenza virus, for vaccine production. In one embodiment, the influenza virus is an influenza A virus. In one embodiment, the influenza virus is an influenza B virus. In one embodiment, the influenza virus is a H3 virus. In one embodiment, the virus is A/H1N1, A/H3N2, a B/Yamagata-lineage influenza B virus or a B/Victoria-lineage influenza B virus.

A further method which employs the recombinant cell is a method of isolating an influenza virus. The method includes providing a sample from an avian or a mammal suspected of being infected with an influenza virus; and contacting the recombinant cell with the sample. In one embodiment, the method further includes determining whether the sample is infected with an influenza virus. In one embodiment, the method further includes identifying the HA and/or NA subtype of the virus.

In one embodiment, the cell line is a modified MDCK cell line, 'hCK' for 'humanized MDCK' cells, which was prepared using CRISPR/Cas-mediated gene knock-out methods to down-regulate sialyltransferases that catalyze the synthesis of alpha-2,3-linked sialic acids, and overexpression of a sialyltransferase that catalyzes the synthesis of alpha-2,6-linked sialic acids. hCK cells express low levels of alpha-2,3-linked sialic acids and high levels of alpha-2,6-linked sialic acids (similar to human epithelial cells in the upper respiratory tract). As disclosed herein, hCK cells allow for the isolation of H3N2 human influenza viruses 10-100 better than the AX-4 cell line. Efficient isolation and amplification of influenza viruses including human influenza viruses is advantageous for vaccine production (possibly supporting better replication), e.g., for seasonal influenza virus vaccine production, as seasonal human influenza viruses often replicate inefficiently in unmodified MDCK cells and even in MDCK (AX-4) cells overexpressing alpha-2,6-linked sialic acids on their surface, to which human influenza viruses bind efficiently. In one embodiment, the titer of human influenza viruses on the modified cell line disclosed herein is at least one log, at least two logs, at least three logs or greater than in unmodified MDCK cells, MDCK (AX-4) cells or MDCK-SIAT1 cells (Li et al., 2009).

BRIEF DESCRIPTION OF THE FIGURES

FIGS. 1A-IP. Sensitivity of hCK cells to human influenza virus growth and isolation. A-L) Growth kinetics of seasonal influenza viruses in MDCK, AX-4, and hCK cells. MDCK, AX4, and hCK cells were infected with viruses at a multiplicity of infection (MOI) of 0.002. The supernatants of the infected cells were harvested at the indicated times, and virus titers were determined by means of plaque assays in hCK cells. Error bars indicate standard deviations from three independent experiments. P values were calculated by using the linear mixed model described in the Methods section (*P<0.05; **P<0.01). Red and blue asterisks indicate the comparison of hCK and AX4 cells with MDCK cells; gray asterisks indicate the comparison between the cell lines depicted in red and blue. M-P) Comparative sensitivity of hCK and AX4 cells to seasonal influenza viruses. Serial 2-fold dilutions ($2^1$ to $2^{20}$) of clinical samples were prepared and inoculated into AX4 and hCK cells. Cells were observed for the development of cytopathic effect (CPE) for 7 days. Three wells were inoculated with each virus dilution. The highest dilution showing CPE in all three wells is shown by the horizontal bar. The number at the end of each horizontal bar indicates the ratio of the hCK highest dilution to the AX4 highest dilution.

FIGS. 2A-2B. Schematic overview of the generation of MDCK cells expressing markedly low levels of α2,3-linked sialic acid and high levels of α2,6-linked sialic acid.

FIGS. 3A-3C. Flow cytometric analysis of the cell surface expression of α2,6- and α2,3-linked Sias. A-B) Clone 6-11 (orange line open profiles) and parental MDCK cells (black line open profiles) were incubated with biotinylated *Maackia amurensis* II agglutinin (MAL II) lectin (specific for α2,3-linked sialic acid) or *Sambucus nigra* agglutinin (SNA) lectin (specific for α2,6-linked Sias), followed by Alexa 488-conjugated streptavidin, and then analyzed by flow cytometry. C) Unstained cells served as negative controls (no lectin).

FIGS. 4A-4J. Characterization of MDCK cells expressing markedly low levels of α2,3-linked sialic acid and high levels of α2,6-linked sialic acid. MDCK cells carrying mutations in seven different β-galactoside α2,3 sialyltransferase (ST3Gal) genes were generated by using the CRISPR/Cas9 genome-editing system, as described in the Methods section. The edited MDCK cells were further modified to overexpress the human β-galactoside α2,6 sialyltransferase I (ST6Gal-I) by transfection of plasmids containing the ST6Gal-I gene. The modified cell clones were selected with puromycin and blasticidin, and characterized. A-D) Flow cytometric analysis of the cell surface expression of α2,6- and α2,3-linked Sias. Modified MDCK cells (green and red line open profiles) and parental MDCK cells (black line open profiles) were incubated with biotinylated *Maackia Amurensis* II agglutinin (MAL II) lectin (specific for α2,3-linked sialic acid) or *Sambucus nigra* agglutinin (SNA) lectin (specific for α2,6-linked Sias), followed by Alexa 488-conjugated streptavidin, and then analyzed by flow cytometry. E-G) Immunofluorescence analysis of the expression of α2,3-linked sialic acid. Modified MDCK and parental MDCK cells were fixed and stained with a monoclonal antibody (green) that recognizes Siaα2,3Galβ1,4GlcNAc. Nuclei were stained with Hoechst dye (blue). H-J) Flow cytometric analysis of the cell surface expression of α2,6-linked Sias. Modified MDCK cells (red line open profiles), parental MDCK cells (black line open profiles), and AX4 cells (blue line open profiles) were incubated with SNA lectin or *Sambucus sieboldiana* (SSA) lectin (specific for α2,6-linked Sias), followed by Alexa 488-conjugated streptavidin, and then analyzed by flow cytometry. D) Flow cytometric analysis of the cell surface expression of α2,3-linked Sias. Modified MDCK cells (red line open profiles), parental MDCK cells (black line open profiles), and AX4 cells (blue line open profiles) were incubated with MAL II lectin, followed by Alexa 488-conjugated streptavidin, and then analyzed by flow cytometry.

FIGS. 5A-5F. Localization of amino acid changes in HA and NA proteins. A-C) Shown are the three-dimensional structures of A/California/04/2009 (H1N1pdm) HA (PDB ID: 3UBN), A/Wyoming/3/2003 (H3N2) HA (PDB ID: 6BKR), and B/Hong Kong/8/1973 HA (PDB ID: 2RFU) in complex with human receptor analogues. Mutations identified in this study are shown in red. Mutations in influenza A virus HA are shown with H3 numbering. D-F) Shown are the three-dimensional structures of A/California/04/2009 (H1N1 pdm) NA (PDB ID: 3TI6), A/Tanzania/205/2010 (H3N2) NA (PDB ID: 4GZP), and B/Brisbane/60/2008 NA (PDB ID: 4CPM) in complex with oseltamivir carboxylate. Mutations identified in this study are shown in red. All mutations are shown with N2 numbering. Images were created with the DS Visualizer v 17.2.

DETAILED DESCRIPTION

Definitions

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest, may comprise sequences for introducing mutations into a host cell genome, or both. Vectors include, for example, plasmids, viral vectors (such as adenoviruses, adeno-associated viruses (AAV), lentiviruses, herpesvirus and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective (biologically contained), requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include at least a portion of an open reading frame of a gene which is partly or entirely heterologous (i.e., foreign) to the transgenic organism, or may represent at least a portion of an open reading frame of a gene homologous to an endogenous gene of the organism, which portion optionally encodes a polypeptide with substantially the same activity as the corresponding full-length polypeptide or at least one activity of the corresponding full-length polypeptide.

By "transgenic cell" is meant a cell containing a transgene. For example, a cell stably or transiently transformed with a vector containing an expression cassette is a transgenic cell that can be used to produce a population of cells having altered phenotypic characteristics. A "recombinant cell" is one which has been genetically modified, e.g., by insertion, deletion or replacement of sequences in a nonrecombinant cell by genetic engineering.

The term "wild-type" or "native" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector such as a replication-defective viral vector.

The term "heterologous" as it relates to nucleic acid sequences such as gene sequences encoding a protein and control sequences, denotes sequences that are not normally joined together, and/or are not normally associated with a particular cell, e.g., are from different sources (for instance, sequences from a virus are heterologous to sequences in the genome of an uninfected cell). Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "gene," "polynucleotide," "coding region," "sequence," "segment," "fragment" or "transgene" which, in one embodiment, "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide may be chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, at least about 90%, or at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide, virus or cell refers to a nucleic acid sequence, peptide, polypeptide, virus or cell that is identified and separated from at least one contaminant nucleic acid, polypeptide or other biological component with which it is ordinarily associated in its natural source, e.g., so that it is not associated with in vivo substances, or is substantially purified from in vitro substances. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

As used herein, the term "recombinant nucleic acid" or "recombinant DNA sequence, molecule or segment" refers to a nucleic acid, e.g., to DNA, that has been derived or isolated from a source, that may be subsequently chemically altered in vitro, and includes, but is not limited to, a sequence that is naturally occurring, is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use, by the methodology of genetic engineering.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less such as 2 bases or less. When using oligonucleotides as probes or treatments, the sequence homology between the target nucleic acid and the oligonucleotide sequence is generally not less than 17 target base matches out of 20 possible oligonucleotide base pair matches (85%); not less than 9 matches out of 10 possible base pair matches (90%), or not less than 19 matches out of 20 possible base pair matches (95%).

Generally, the nucleic acid sequence homology between the polynucleotides, oligonucleotides, and fragments, and a nucleic acid sequence of interest is at least 65%, and more typically with y increasing homologies of at least about 70%, about 90%, about 95%, about 98%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less such as 2 or less. Alternatively, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof may be considered homologous if their amino acids are greater than or equal to 50% identical when optimally aligned using the ALIGN program.

The term "corresponds to" is used herein to mean that a polynucleotide sequence is homologous (e.g., is identical, not strictly evolutionarily related) to all or a portion of a reference polynucleotide sequence that encodes a polypeptide or its complement, or that a polypeptide sequence is identical in sequence or function to a reference polypeptide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by using local homology algorithms or by a search for similarity method, by computerized implementations of these algorithms (GAP, BESTFIT, FASTA, and TFASTA Genetics Software Package or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least about 80% sequence identity, at least about 90% sequence identity, at least about 95% percent sequence identity, and or at least about 99% sequence identity.

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present. Generally, a substantially pure composition will comprise more than about 80 percent of all macromolecular species present in the composition, more than about 85%, about 90%, about 95%, and about 99%. The object species may be purified to essential homogeneity (contaminant species cannot be detected in the composition by conventional detection methods) wherein the composition consists essentially of a single macromolecular species.

"Transfected," "transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

Exemplary Cells and Modifications Thereof

Most influenza vaccines are produced in embryonated chicken eggs, but increasingly influenza vaccines are produced in other systems. MDCK (Madin-Darby Canine Kidney) cells are one of two mammalian cell lines that have been approved for influenza vaccine production. Virus production in cells may be enhanced by altering the host cell or the virus. However, for vaccine production, virus modification during passage is not advantageous.

As disclosed herein, the genome of cells, e.g., avian cells or mammalian cells including but not limited to canine, feline, equine, bovine, caprine, swine, human or non-human primate, cells may be modified to enhance influenza virus isolation, propagation, or both. For example, certain HA subtypes (HA subtypes H1-H18) may not bind well to certain species or types of cells due to the number of or composition of cell surface receptors for HA. Those cells may be modified by increasing the number of cell surface receptors or modifying the type of molecules found on cell surface receptors, or both. For example, in mammals there are about 20 sialyltransferases that transfer sialic acid residues to oligosaccharide side chains of glycoconjugates. The genes encoding one or more of those enzymes may be modified to decrease, e.g., decrease by 1%, 5%, 10%, 50%, 70%, 80%, 90% or more, or eliminate expression of the encoded enzyme, or the open reading frame for one or more of those enzymes may be expressed in the cell from an exogenously introduced expression cassette, e.g., a plasmid having that expression cassette. For example, α2,6-sialyltransferases transfer sialic acid with an α2,6-linkage to terminal Gal (ST6GalI and II) or GalNAc (ST6GalNAcI-VI); α2,8-sialyltransferases transfer sialic acid with an α2,8-linkage (STSiaI-IV); and α2,3-sialyltransferases transfer sialic acid with an α2,3-linkage to terminal Gal residues (ST3Gal). ST3GalI-II and IV transfer to the Gal residue located on terminal Galβ1-3GlcNAc, ST3GalIV and VI transfer to the Gal residue located on terminal Galβ1-4GlcNAc, ST3GalV transfers to the Gal residue located on terminal Galβ1-4Glc-Cer, and ST3GalIII transfers to the Gal residue located on terminal Galβ1-3GlcNAc or Galβ1-3GlcNAc. Thus, each of the genes for these sialyltransferases may be employed to prepare a cell disclosed herein. In one embodiment, one or more α2,3-sialyltransferase genes in the genome of a host cell are modified to decrease, e.g., eliminate, expression of the encoded enzyme, and one or more α2,6-sialyltransferase genes are expressed from a recombinant expression vector introduced to the host cell. To decrease expression of a sialyltransferase, one or more vectors, or a combination of vectors and isolated protein, may be introduced to a cell. The vectors and/or protein may be part of a recombinase system that can be targeted to a specific gene in the cell, systems including CRISPR/Cas, TALEN and zinc finger nucleases.

To prepare expression cassettes (to express RNA such as gRNA or a protein including a recombinase or a sialyltransferase) for transformation herein, the recombinant DNA sequence or segment may be circular or linear, double-stranded or single-stranded. A DNA sequence which encodes an RNA sequence that is substantially complementary to a mRNA sequence encoding a gene product of interest is typically a "sense" DNA sequence cloned into a cassette in the opposite orientation (i.e., 3' to 5' rather than 5' to 3'). Generally, the DNA sequence or segment is in the form of chimeric DNA, such as plasmid DNA, that can also contain coding regions flanked by control sequences which promote the expression of the DNA in a cell. As used herein, "chimeric" means that a vector comprises DNA from at least two different species, or comprises DNA from the same species, which is linked or associated in a manner which does not occur in the "native" or wild-type of the species.

Aside from DNA sequences that serve as transcription units, or portions thereof, a portion of the DNA may be untranscribed, serving a regulatory or a structural function. For example, the DNA may itself comprise a promoter that is active in eukaryotic cells, e.g., mammalian cells, or in certain cell types, or may utilize a promoter already present in the genome that is the transformation target of the lymphotropic virus. Such promoters include the CMV promoter, as well as the SV40 late promoter and retroviral LTRs (long terminal repeat elements), e.g., the MMTV, RSV, MLV or HIV LTR, although many other promoter elements well known to the art may be employed.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant DNA to be introduced into the cells may contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, puro, hyg, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Exemplary reporter genes include the chloramphenicol acetyl transferase gene (cat) from Tn9 of *E. coli*, the beta-glucuronidase gene (gus) of the uidA locus of *E. coli*, the green, red, or blue fluorescent protein gene, and the luciferase gene. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, Sambrook et al., *Molecular Cloning: A Laboratory Manual* (2002) provides suitable methods of construction.

The recombinant DNA can be readily introduced into the host cells, e.g., mammalian, yeast or insect cells, by transfection with an expression vector comprising the recombinant DNA by any procedure useful for the introduction into a particular cell, e.g., physical or biological methods, to yield a transformed (transgenic) cell having the recombinant DNA so that the DNA sequence of interest is expressed by the host cell. In one embodiment, at least one of the recombinant DNA which is introduced to a cell is maintained extrachromosomally. In one embodiment, at least one recombinant DNA is stably integrated into the host cell genome.

Physical methods to introduce a recombinant DNA into a host cell include calcium-mediated methods, lipofection, particle bombardment, microinjection, electroporation, and the like. Biological methods to introduce the DNA of interest into a host cell include the use of DNA and RNA vectors. Viral vectors, e.g., retroviral or lentiviral vectors, have become a widely used method for inserting genes into eukaryotic, such as mammalian, e.g., human, cells. Other viral vectors useful to introduce genes into cells can be derived from poxviruses, e.g., vaccinia viruses, herpes viruses, adenoviruses, adeno-associated viruses, baculoviruses, and the like.

To confirm the presence of the recombinant DNA sequence in the host cell, a variety of assays may be performed. Such assays include, for example, molecular biological assays well known to those of skill in the art, such as Southern and Northern blotting, RT-PCR and PCR; biochemical assays, such as detecting the presence or absence of a particular gene product, e.g., by immunological means (ELISAs and Western blots) or by other molecular assays.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the recombinant DNA segment is being expressed. Expression may be evaluated by specifically identifying the peptide products of the introduced DNA sequences or evaluating the phenotypic changes brought about by the expression of the introduced DNA segment in the host cell.

For vectors that are used to knock down or knock out expression of one or more sialyltransferases, the vectors harbor sequences that result in one or more mutations in the genome of the cell. The mutation is effective to inhibit or prevent production of at least one functional sialyltransferase. In one embodiment, the mutation is a deletion from 1, 10, 20, 50, 100, 500 and up to thousands of nucleotides, e.g., 1%, 10%, 50%, 90% or more of sequences corresponding to a sialyltransferase gene are deleted, e.g., a deletion in the coding region for a sialyltransferase, e.g., a 2,3-sialyltransferase (ST3). In one embodiment, the deleted sequences correspond to sequences with a substantial identity, e.g., at least 80% or more, e.g., 85%, 90% or 95% and up to 100% or any integer in between, nucleic acid sequence identity, to SEQ ID Nos. 5, 7, 9, 11, 13, 15 or 17, or any combination thereof. In one embodiment, the mutation is an insertion from 1, 2, 3, 5, 10, 20, 50, 100, 500 and up to thousands of nucleotides or more into sequences corresponding to a sialyltransferase gene such as an insertion into the coding region for a sialyltransferase, e.g., a 2,3-sialyltransferase (ST3). In one embodiment, the insertion is in sequences corresponding to sequences with a substantial identity, e.g., at least 80% or more, e.g., 85%, 90% or 95% and up to 100% or any integer in between, nucleic acid sequence identity, to SEQ ID Nos. 5, 7, 9, 11, 13, 15 or 17, or any combination thereof. In one embodiment, the mutation include one or more nucleotide substitutions, e.g., 1, 2, 3, 4, 5, 6, 10 or up to hundreds of nucleotide substitutions in sequences corresponding to the coding region for a sialyltransferase, e.g., a 2,3-sialyltransferase (ST3) such as substitutions in SEQ ID Nos. 5, 7, 9, 11, 13, 15 or 17, or any combination thereof. In one embodiment, a combination of insertions, nucleotide substitutions, and/or deletions in sequences with a substantial identity, e.g., at least 80% or more, e.g., 85%, 90% or 95% and up to 100% or any integer in between, nucleic acid sequence identity, SEQ ID Nos. 5, 7, 9, 11, 13, 15 or 17, or any combination thereof, are in a host cell. In one embodiment, the mutation(s) result in the host cell having reduced expression of one or more ST3 genes, e.g., encoding a protein having at least 80% or more, e.g., 85%, 90% or 95% and up to 100% or any integer in between, amino acid sequence identity to any of SEQ ID Nos. 6, 8, 10, 12, 14, 16, or 18.

In one embodiment, the host cell expresses one or more ST6 genes, e.g., encoding a protein having at least 80% or more, e.g., 85%, 90% or 95% and up to 100% or any integer in between, amino acid sequence identity to any of SEQ ID Nos. 1-4.

The CRISPR/Cas System

The Type II CRISPR is a well characterized system that carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system. The primary products of the CRISPR loci appear to be short RNAs that contain the invader targeting sequences, and are termed guide RNAs "Cas1" polypeptide refers to CRISPR associated (Cas) protein. Cas1 (COG 1518 in the Clusters of Orthologous Group of proteins classification system) is the best marker of the CRISPR-associated systems (CASS). Based on phylogenetic comparisons, seven distinct versions of the CRISPR-associated immune system have been identified (CASS1-7). Cas1 polypeptide used in the methods described herein can be any Cas polypeptide present in any prokaryote. In certain embodiments, a Cas1 polypeptide is a Cas1 polypeptide of an archaeal microorganism. In certain embodiments, a Cas1 polypeptide is a Cas1 polypeptide of a Euryarchaeota microorganism. In certain embodiments, a Cas1 polypeptide is a Cas1 polypeptide of a Crenarchaeota microorganism. In certain embodiments, a Cas1 polypeptide is a Cas1 polypeptide of a bacterium. In certain embodiments, a Cas1 polypeptide is a Cas1 polypeptide of a gram negative or gram positive bacteria. In certain embodiments, a Cas1 polypeptide is a Cas1 polypeptide of *Pseudomonas aeruginosa*. In certain embodiments, a Cas1 polypeptide is a Cas1 polypeptide of *Aquifex aeolicus*. In certain embodiments, a Cas1 polypeptide is a Cas1 polypeptide that is a member of one of CASs1-7. In certain embodiments, Cas1 polypeptide is a Cas1 polypeptide that is a member of CASS3. In certain embodiments, a Cas1 polypeptide is a Cas1 polypeptide that is a member of CASS7. In certain embodiments, a Cas1 polypeptide is a Cas1 polypeptide that is a member of CASS3 or CASS7.

In some embodiments, a Cas polypeptide is encoded by a nucleotide sequence provided in GenBank at, e.g., GeneID number: 2781520, 1006874, 9001811, 947228, 3169280, 2650014, 1175302, 3993120, 4380485, 906625, 3165126, 905808, 1454460, 1445886, 1485099, 4274010, 888506, 3169526, 997745, 897836, or 1193018 and/or an amino acid sequence exhibiting homology (e.g., greater than 80%, 90 to 99% including 91%, 92%, 93%, 94%, 95%, 96%, 97%, 98% or 99%) to the amino acids encoded by these polynucleotides and which polypeptides function as Cas polypeptides.

There are three types of CRISPR/Cas systems which all incorporate RNAs and Cas proteins. Types I and III both have Cas endonucleases that process the pre-crRNAs, that, when fully processed into crRNAs, assemble a multi-Cas protein complex that is capable of cleaving nucleic acids that are complementary to the crRNA.

In type II CRISPR/Cas systems, crRNAs are produced using a different mechanism where a trans-activating RNA (tracrRNA) complementary to repeat sequences in the pre-crRNA, triggers processing by a double strand-specific RNase III in the presence of the Cas9 protein. Cas9 is then able to cleave a target DNA that is complementary to the mature crRNA however cleavage by Cas9 is dependent both upon base-pairing between the crRNA and the target DNA, and on the presence of a short motif in the crRNA referred to as the PAM sequence (protospacer adjacent motif)). In addition, the tracrRNA must also be present as it base pairs with the crRNA at its 3' end, and this association triggers Cas9 activity.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand.

The requirement of the crRNA-tracrRNA complex can be avoided by use of an engineered "single-guide RNA" (sgRNA) that comprises the hairpin normally formed by the annealing of the crRNA and the tracrRNA (see Jinek, et al. (2012) Science 337:816 and Cong et al. (2013) Sciencexpress/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA "Cas polypeptide" encompasses a full-length Cas polypeptide, an enzymatically active fragment of a Cas polypeptide, and enzymatically active derivatives of a Cas polypeptide or fragment thereof. Suitable derivatives of a Cas polypeptide or a fragment thereof include but are not limited to mutants, fusions, covalent modifications of Cas protein or a fragment thereof.

RNA Components of CRISPR/Cas

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong, et al. (2013) Sciencexpress 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek, ibid and Cong, ibid).

Chimeric or sgRNAs can be engineered to comprise a sequence complementary to any desired target. The RNAs comprise 22 bases of complementarity to a target and of the form G[n19], followed by a protospacer-adjacent motif (PAM) of the form NGG. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence that conforms to the G[n20]GG formula.

Donors

As noted above, insertion of an exogenous sequence (also called a "donor sequence" or "donor" or "transgene" or "gene of interest"), for example for correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Alternatively, a donor may have no regions of homology to the targeted location in the DNA and may be integrated by NHEJ-dependent end joining following cleavage at the target site. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded and/or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang, et al. (1987) Proc. Natl. Acad. Sci. USA 84:4959-4963; Nehls, et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted (e.g., highly expressed, albumin, AAVS1, HPRT, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an albumin or other locus such that some (N-terminal and/or C-terminal to the transgene encoding the lysosomal enzyme) or none of the endogenous albumin sequences are expressed, for example as a fusion with the transgene encoding the lysosomal sequences. In other embodiments, the transgene (e.g., with or without additional coding sequences such as for albumin) is integrated into any endogenous locus, for example a safe-harbor locus. See, e.g., U.S. Patent Publication Nos. 2008/0299580; 2008/0159996; and 2010/0218264.

When endogenous sequences (endogenous or part of the transgene) are expressed with the transgene, the endogenous sequences (e.g., albumin, etc.) may be full-length sequences (wild-type or mutant) or partial sequences. In one embodiment, the endogenous sequences are functional. Non-limiting examples of the function of these full length or partial sequences (e.g., albumin) include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Other nucleases, such as zinc finger nucleases (ZFNs), transcription activator-like effector nucleases (TALENs), or others that are specific for targeted genes and can be utilized such that the transgene construct is inserted by either homology directed repair (HDR) or by end capture during non-homologous end joining (NHEJ) driven processes.

Exemplary Embodiments

In one embodiment, an isolated recombinant mammalian or avian cell is provided comprising a reduced amount of cell surface β-galactoside α2,3 sialyl residues and an increased amount of human β-galactoside α2,6 sialyl residues relative to a corresponding non-recombinant mammalian or avian cell. In one embodiment, the isolated recombinant cell is a non-human cell. In one embodiment, the isolated recombinant cell is a canine or primate cell. In one embodiment, the isolated recombinant cell comprises an expression cassette encoding human β-galactoside α2,6 sialyltransferase I (ST6Gal-I) or ST6Gal-II. In one embodiment, the ST6Gal-I or ST6Gal-II comprises a protein having at least 80% amino acid sequence identity to any one of SEQ ID Nos. 1-4 or 101. In one embodiment, the one or more β-galactoside α2,3 sialyltransferase genes are mutated in the recombinant cell so as to reduce the amount of cell surface β-galactoside α2,3 sialyl residues. In one embodiment, two or more of ST3Gal-I, ST3Gal-II, ST3Gal-II, ST3Gal-IV, ST3Gal-V, ST3Gal-VI, or ST3Gal-II-like genes are mutated in the recombinant cell. In one embodiment, the ST3 genes have at least 80% nucleic acid sequence identity to any one of SEQ ID Nos. 5, 7, 9, 11, 13, 15, or 17. In one embodiment, the reduction in cell surface β-galactoside α2,3 sialyl residues is the result of reduced expression of one or more ST3 sialyltransferases. In one embodiment, the one or more ST3 sialyltransferases have at least 80% amino acid sequence identity to any one of SEQ ID Nos. 6, 8, 10, 12, 14, 16, or 18. In one embodiment, influenza H3 viruses replicate more efficiently in the recombinant cell relative to the non-recombinant cell.

In one embodiment, an isolated recombinant mammalian or avian cell is provided comprising a reduced amount of cell surface β-galactoside α2,3 sialyl residues relative to a corresponding non-recombinant mammalian or avian cell. In one embodiment, one or more of ST3Gal-I, ST3Gal-II, ST3Gal-III, ST3Gal-IV, ST3Gal-1; ST3Gal-VI, or ST3Gal-II-like genes are mutated in the recombinant cell. In one embodiment, a combination of ST3Gal-I, ST3Gal-II, ST3Gal-III, ST3Gal-IV, ST3Gal-V, ST3Gal-VI, or ST3Gal-II-like genes are mutated in the recombinant cell. In one embodiment, ST3Gal-I, ST3Gal-II, ST3Gal-III, ST3Gal-IV, ST3Gal-V, ST3Gal-VI, and ST3Gal-II-like genes are mutated.

In one embodiment, a method of modifying the amount of cell surface β-galactoside α2,3 sialyl residues and human β-galactoside α2,6 sialyl residues on a mammalian or an avian cell is provided. In one embodiment, the method includes mutating one or more β-galactoside α2,3 sialyltransferase (ST3Gal) genes, and overexpressing a human β-galactoside α2,6 sialyltransferase (ST6Gal) gene, in a parental mammalian or avian cell so as to result in a modified mammalian or avian cell having a reduced amount of cell surface β-galactoside α2,3 sialyl residues and an increased amount of human β-galactoside α2,6 sialyl residues on the surface of the modified cell relative to the corresponding parental cell. In one embodiment, the one or more ST3Gal genes are mutated using a genome editing system. In one embodiment, the genome editing system comprises a CRISPR/Cas9, Zinc Finger Nuclease (ZFN) or transcription activator-like effector nuclease (TALEN). In one embodiment, the mutations include one or more nucleotide insertions or one or more nucleotide deletions, or both, in one or more ST3 genes. In one embodiment, the modified cell comprises an expression cassette comprising a ST6Gal open reading frame. In one embodiment, the modified cell is a kidney cell. In one embodiment, the modified cell is a canine cell. In one embodiment, the modified cell is a Madin-Darby canine kidney (MDCK) cell.

In one embodiment, a method of propagating an influenza virus is provided. The method includes infecting the recombinant cell with an influenza virus; and collecting progeny virus. In one embodiment, the influenza virus is a human influenza virus. In one embodiment, the influenza virus is an influenza A virus. In one embodiment, the influenza virus is an influenza B virus. In one embodiment, the influenza virus is a H3 virus. In one embodiment, the virus is A/H1N1, A/H3N2, a B/Yamagata-lineage influenza B virus or a B/Victoria-lineage influenza B virus.

In one embodiment, a method of isolating an influenza virus is provided which includes providing a sample from an avian or a mammal suspected of being infected with an influenza virus; and contacting the recombinant cell with the sample. In one embodiment, the method includes determining whether the sample is infected with an influenza virus. In one embodiment, the method includes identifying the HA and/or NA subtype of the virus.

In one embodiment, a method of diagnosing an influenza virus infection is provided. The method includes contacting the recombinant cell with a sample from an avian or a mammal suspected of being infected with an influenza virus; and determining if the cell is infected with virus. In one embodiment, a plaque assay is employed to determine the presence of amount of virus. In one embodiment, a nucleic acid amplification assay is employed to determine the presence of amount of virus, e.g., in the supernatant of the infected cell.

Exemplary Sialyltransferase Sequences

Sialyltransferases in higher vertebrates are glycosyltransferases that mediate the transfer of sialic acid residues from activated sugar donors (CMP-β-Neu5Ac, CMP-β-Neu5Gc, and CMP-β-KDN) to terminal non-reducing positions of oligosaccharide chains of glycoproteins and glycolipids. The vertebrate sialyltransferase superfamily is divided into four families, ST6Gal, ST3Gal, ST6GalNAc, and ST8Sia, depending on the glycosidic linkage formed and the monosaccharide acceptor used. Members of the mammalian and avian ST6Gal family catalyze the transfer of sialic acid residues to the terminal galactose residues of the type 2 disaccharide (Gal(NAc)β1,4GlcNAc), resulting in the formation of an α2-6 glycosidic linkage. Unlike the other sialyltransferase families, this family comprises only two paralogs in the human genome named ST6GAL1 and ST6GAL2, respectively. The human ST6GAL1 gene is ubiquitously expressed in a broad variety of tissues, whereas the ST6GAL2 gene is expressed in a tissue-specific (adult brain) and stage-specific (embryonic) manner. Mammalian st6gal1 gene expression is regulated by multiple promoters governing the expression of several transcripts encoding an identical polypeptide enzyme.

In one embodiment, one or more ST3 genes in an avian or a mammalian cell, e.g., a canine or non-human primate cell, are modified so as to result in decreased expression of α-2,3-linked sialic acids on the cell surface. In one embodiment, one or more human ST6 genes are introduced to a canine or a non-human primate cell. In one embodiment, one or more ST3 genes are modified before one or more ST6 genes are introduced to the cell. In one embodiment, one or more ST6 genes are introduced before ST3 genes are modified in the cell. In one embodiment, concurrently or sequentially ST3 genes are modified and ST6 genes are introduced to the cell.

In one embodiment, the ST6Gal that is expressed comprises human ST6 (Accession No. KJ897554) comprising (SEQ ID NO: 1)

```
MIHTNLKKKFSCCVLVFLLFAVICVWKEKKKGSYYDSFKLOTKE

FQVLKSLGKLAMGSDSQSYSSSSTQDPHRGRQTLGSLRGLAKAKPEASFQVIVNKDSSS

KNLIPRLOKIWKNYLSNINKYKVSYKGPGPGIKFSAEALRCHLRDIIVNVSMVEVTDFPF

NTSENVEGYLPKESIRTKAGPWGRCAVVSSAGSLKSSQLGREIDDHDAVLUNGAPTAN
```

```
FQQDVGTKTTIRLMNSQLVTTEKRFLKDSLYNEGILIVWDPSVYHSDIPKWYQNPDYN

FFNNYKTYRKLHPNQPFYILKPQMPWELWDILQEISPEEIQPNPPSSGMLGIIIMIVITL

CDQVDIYEFLPSKRKTDVCYYYQKFFDSACTMGAYHPLLYEKNLVKHLNQGTDEDIYL

LGKATLPURTIHC or
                                                                (SEQ ID NO: 150)
MIHTNLKKKFSCCVLVFLLFAVICVWKEKKKGSYYDSFKLQTKEFQVLKSL

GKLAMGSDSQSVSSSSTQDPHRGRQTLGSLRGLAKAKPEASFQVWNKDSSS

KNLIPRLQKIWKNYLSMNKYKVSYKGPGPGIKFSAEALRCHLRDHVNVSM

VEVTDFPFNTSEWEGYLPKESIRTKAGPWGRCAVVSSAGSLKSSQLGREIDD

HDAVLRFNGAPTANFQQDVGTKTTIRLMNSQLVTTEKRFLKDSLYNEGILIV

WDPSVYHPDIPKWYQNPDYNFFNNYKTYRKLHPNQPFYILKPQMPWELWD

ILQEISPEEIQPNPPSSGMLGIIIMMTLCDQVDIYEFLPSKRRTDVCYYYQKFF

DSACTMGAYHPLITEKNLVKHLNQGTDEDIYLLGKATLPGFRTIHC, which is encoded by
                                                                (SEQ ID NO: 151)
ATGATTCACACCAACCTGAAGAAAAAGTTCAGCTGCTGCGTCCTGGTCT

TTCTTCTGTTTGCAGTCATCTGTGTGTGGAAGGAGAAGAAGAAAGGGAG

TTACTATGATTCCTTTAAATTGCAAACCAAGGAATTCCAGGTGTTAAAGA

GTCTGGGGAAATTGGCCATGGGGTCTGATTCCCAGTCTGTATCCTCAAGC

AGCACCCAGGACCCCCACAGGGGCCGCCAGACCCTCGGCAGTCTCAGAG

GCCTAGCCAAGGCCAAACCAGAGGCCTCCTTCCAGGTGTGGAACAAGGA

CAGCTCTTCCAAAAACCTTATCCCTAGGCTGCAAAAGATCTGGAAGAAT

TACCTAAGCATGAACAAGTACAAAGTGTCCTACAAGGGGCCAGGACCA

GGCATCAAGTTCAGTGCAGAGGCCCTGCGCTGCCACCTCCGGGACCATG

TGAATGTATCCATGGTAGAGGTCACAGATTTTCCCTTCAATACCTCTGAA

TGGGAGGGTTATCTGCCCAAGGAGAAGCATTAGGACCAAGGCTGGGCCTT

GGGGCAGGTGTGCTGTTGTGTCGTCAGCGGGATCTCTGAAGTCCTCCCA

ACTAGGCAGAGAAATCGATGATCATGACGCAGTCCTGAGGTTTAATGGG

GCACCCACAGCCAACTTCCAACAAGATGTGGGCACAAAAACTACCATTC

GCCTGATGAACTCTCAGTTGGTTACCACAGAGAAGCGCTTCCTCAAAGA

CAGTTTGTACAATGAAGGAATCCTAATTGTATGGGACCCATCTGTATACC

ACCCAGATATCCCAAAGTGGTACCAGAATCCGGATTATAATTTCTTTAAC

AACTACAAGACTTATCGTAAGCTGCACCCCAATCAGCCCTTITACATCCT

CAAGCCCCAGATGCCTTGGGAGCTATGGGACATTCTTCAAGAAATCTCC

CCAGAAGAGATTCAGCCAAACCCCCCATCCTCTGGGATGCTTGGTATCA

TCATCATGATGACGCTGTGTGACCAGGTGGATATTTATGAGTTCCTCCCA

TCCAAGCGCAGGACTGACGTGTGCTACTACTACCAGAAGTTCTTCGATA

GTGCCTGCACGATGGGTGCCTACCACCCGCTGCTCTTTGAGAAGAATTTG

GTGAAGCATCTCAACCAGGGCACAGATGAGGACATCTACCTGCTTGGAA

AAGCCACACTGCCTGGCTTCCGGACCATTCACTGCTAA;
```

-continued a human ST6 (Accession No. BAC24793) comprising
(SEQ ID NO: 2)
mkphlkqwrq rmlfgifawg llfllifiyf tdsnpaepvp sslsfletrr llpvqgkqra imgaahepsp pggldargal prahpagsth agpgdlqkwa qsqdgfehke ffssqvgrks qsafypeddd yffaagqpgw hshtqgtlgf pspgepgpre gafpaaqvqr rrvklahrrq rrshvleegd dgdrlyssms raflyrlwkg nvsskmlnpr lqkamkdylt ankhgvrfrg kreaglsraq llcqlrsrar vrtldgteap fsalgwrrlv pavplsqlhp rglrscavvm sagailnssl geeidshdav lrfnsaptrg yekdvgnktt iriinsqilt npshhfidss lykdvilvaw dpapysanln lwykkpdynl ftpyiqhrqr npnqpfyilh pkfiwqlwdi iqentkekiq pnppssgfig ilimmsmcre vhvyeyipsv rqtelchyhe lyydaactlg ayhpllyekl lvqrinmgtq gdlhrkgkvv lpgfqavhcp apspviphs;

a human ST6 (Accession No. SJL87798) comprising
(SEQ ID NO: 3)
aamgsdsqsv sssstqdphr grqtlgslrg lakakpeasf qvwnkdsssk nliprlqkiw knylsmnkyk vsykgpgpgi kfsaealrch lrdhynysmv evtdfpfnts ewegylpkes irtkagpwgr cavvssagsl kssqlgreid dhdavlrfng aptanfqqdv gtkttirlmn sqlvttekrf lkdslynegi livwdpsyyh sdipkwyqnp dynffnnykt yrklhpnqpf yilkpqmpwe lwdilqeisp eeiqpnppss gmlgiiimmt lcdqvdiyef lpskrktdvc yyyqkffdsa ctmgayhpll yeknlvkhln qgtdediyll gkatlpgfit ihc; or a human ST6 Gal-II
(SEQ ID NO : 4)
MKPHLKQWRQRMLFGIFAWGLLFLLIFINTTDSNPAEPVPSSLS

FLETRRLLPVQGKQRAIMGAAHEPSPPGGLDARQALPRAHPAGSFHAGPGDLQKWAQS

QDGFEHKEFFSSQVGRKSQSAFYPEDDDYFFAAGQPGWHSHTQGTLGFPSPGEPGPRE

GAFPAAQVQRRRVKKRHRRQRRSHNTEEGDDGDRLYSSIVISRAFLYRLWKGNVSSKMLN

PRLQKAMKDYLTANKHGVRFRGKREAGLSRAQLLCQLRSRARVRTLDGTEAPFSALGW

RRINPAVPLSQLHPRGLRSCAVVMSAGAILNSSLGEE1DSHDAVLRFNSAPTRGYEKD

VGNKTTIRTINSQILTNPSHHFIDSSLYKDVILVAWDPAPYSANLNLWYKKPDYNLFT

PYIQHRQRNPNQPFYILHPKFIWQLWDITQENTKEKIQPNPPSSGFIGILIMMSIVICRE

VIWYEYIPSVRQTELCHYHELYYDAACTLGAYHPLLYEKLLVQRLNIVIGTQGDLHRKGK

VVLPGFQAVHCPAPSPVIPHS human ST6Gal1 encoded by
(SEQ ID NO: 100)
ATGATTCACACCAACCTGAAGAAAAAGTTCAGCTGCTGCGTCCTGGTCTTTCTTCTGTTTGCAGTCA

TCTGTGTGTGGAAGGAGAAGAAGAAAGGGAGTTACTATGATTCCTTTAAATTGCAAACCAAGGAA

TTCCAGGTGTTAAAGAGTCTGGGGAAATTGGCCATGGGGTCTGATTCCCAGTCTGTATCCTCAAGC

AGCACCCAGGACCCCCACAGGGGCCGCCAGACCCTCGGCAGTCTCAGAGGCCTAGCCAAGGCCAA

ACCAGAGGCCTCCTTCCAGGTGTGGAACAAGGACAGCTCTTCCAAAAACCTTATCCCTAGGCTGCA

AAAGATCTGGAAGAATTACCTAAGCATGAACAAGTACAAAGTGTCCTACAAGGGGCCAGGACCAG

GCATCAAGTTCAGTGCAGAGGCCCTGCGCTGCCACCTCCGGGACCATGTGAATGTATCCATGGTA

GAGGTCACAGATTTTCCCTTCAATACCTCTGAATGGGAGGGTTATCTGCCCAAGGAGAGCATTAGG

ACCAAGGCTGGGCCTTGGGGCAGGTGTGCTGTTGTGTCGTCAGCGGGATCTCTGAAGTCCTCCCA

ACTAGGCAGAGAAATCGATGATCATGACGCAGTCCTGAGGTTTAATGGGGCACCCACAGCCAACT

TCCAACAAGATGTGGGCACAAAAACTACCATTCGCCTGATGAACTCTCAGTTGGTTACCACAGAGA

AGCGCTTCCTCAAAGACAGTTTGTACAATGAAGGAATCCTAATTGTATGGGACCCATCTGTATACC

-continued

```
ACCCAGATATCCCAAAGTGGTACCAGAATCCGGATTATAATTTCTTTAACAACTACAAGACTTATCG

TAAGCTGCACCCCAATCAGCCCTTTTACATCCTCAAGCCCCAGATGCCTTGGGAGCTATGGGACAT

TCTTCAAGAAATCTCCCCAGAAGAGATTCAGCCAAACCCCCCATCCTCTGGGATGCTTGGTATCATC

ATCATGATGACGCTGTGTGACCAGGTGGATATTTATGAGTTCCTCCCATCCAAGCGCAGGACTGAC

GTGTGCTACTACTACCAGAAGTTCTTCGATAGTGCCTGCACGATGGGTGCCTACCACCCGCTGCTC

TTTGAGAAGAATTTGGTGAAGCATCTCAACCAGGGCACAGATGAGGACATCTACCTGCTTGGAAA

AGCCACACTGCCTGGCTTCCGGACCATTCACTGCTAA;
``` human ST6Gal I comprising (SEQ ID NO: 101)
```
MIHTNLKKKFSCCVLVFLLFAVICVWKEKKKGSYYDSFKLQTKEFQVLKSLGKLAMGSDSQSVSSSSTQD

PHRGRQTLGSLRGLAKAKPEASFQVWNKDSSSKNLIPRLQKIWKNYLSMNKYKVSYKGPGPGIKFSAE

ALRCHLRDHVNVSMVEVTDFPFNTSEWEGYLPKESIRTKAGPWGRCAVVSSAGSLKSSQLGREIDDHD

AVLRFNGAPTANFQQDVGTKTTIRLMNSQLVTTEKRFLKDSLYNEGILIVWDPSVYHPDIPKWYQNPD

YNFFNNYKTYRKLHPNQPFYILKPQMPWELWDILQEISPEEIQPNPPSSGMLGIIIMMTLCDQVDIYEFL

PSKRRTDVCYYYQKFFDSACTMGAYHPLLFEKNLVKHLNQGTDEDIYLLGKATLPGFRTIHC;
``` or a protein having at least 80%, 85%, 87%, 90%, 92%, 95%, 96%, 97%, 98%, or 99% amino acid sequence identity to any one of SEQ ID Nos. 1-4, 101 or 150 or a nucleotide sequence having at least 80%, 85%, 87%, 90%, 92%, 95%, 96%, 97%, 98%, or 99% nucleotide acid sequence identity to any one of SEQ ID Nos. 100 or 151.

In one embodiment, the ST3 gene that is mutated has at least 80%, 85%, 87%, 90%, 92%, 95%, 96%, 97%, 98%, or 99% nucleic acid sequence identity to a canine ST3GalI comprising (Accession No. XM_022426722)

(SEQ ID NO: 5)
```
gtcaggtctc agaaaagtct agaataaggc ttacaggcac tttgttcagt tgtggaacac atggaaactt catacaccgc cccctcctt gcagaccgga gagctctctg ctctaatttg ggcacaggcg cccaaccttg gccccagag gaagcctgtt ctactcccag gccaacgct caattgcttg ataacttgac acccacactg ttccaggctc tggtctcaat ttcactctct gcaaaatgag aggctcagag ttccgctgac atggcctcgg ggccgttaaa acctttcttc atgaagacag cctgcaccct tcctgcttct gctccaggtc catcctcaga accttccaga aagtcctggc acgtcagata acagggccaa cccggcagtg atgccccacc ccccaccct tcccttactc atagagcctg ctccagactc tcagagccca cacccacttg gtgaagtcat ttgccagtaa ttcttcgcac tggacattga gaggtttcag accccagaag tctcaggcgc tgggtctgaa agtgggcaga gcccaggtga catttgtgga gactctcagt ggtgcgtata gccgccggga ccattttcag actcaaccct tctgacctgg aaatgccaat agaagtaatc atcatcgcca agggctgtag tgagcaaatg cttagagctc tgtggccaag gcagtttcat ttgaggacca gagatggaca atccctcagc ctactgagat gaagaaactg agtctcagag aggttaagga actcccccga ggttgcacca ctgaggaaga ttgacctgac ttcccaagac catacatctg gtaaaccgga acctgcacct gcgccatctc aagcctactc tggaggcccg aggctaattg gcagagtttg aaggctgaga tgacagacaa ccctcagtgc cttcatcgga cgggctgctt acctgcacat ccctggtgac agcatgggaa agaccgcttc taattaagcg
```

```
tcatcacaca tcacccttttt ccggaggaag agaggcaaag acagctcccc tctatcctgc actgtgaacc ttcctccgag gtcctcccct caccccgag agtccttgcc ctgtcaccaa gattaattac ccctcaaccc ctttgaatgg caaaggcagt cattttatta agtttaatta aagcttcaag agacattgcc ggatgtttca ggactgctga caaagcagcc tgcttgtttc ctgaaaagac caattatatg caagaagcgt cagccccact ccccgagggg tccacttagc ctccgaccac cacagggtga tgtccagcgc accggtgtgg ccatcacctg gcgggagtga ggtcggccgt agcaagtctg gaggcccccc tgcaagtccc tgcctcaccc tatgactgaa cctctcgtct ctgggaattt tgttccaaat tccccgtcta ccaggtgtga tttcctccag ccccaccagc cctgggaggc gcccatccag agagcagaga tagtgaccat gagaaaaagg actctcaaag tactcaccct cctcgtcctc ttcatcttcc tcacctcctt cttcctaaat tactcccaca ccatggtgac caccacctgg tttcccaagc agatggttgt cgagctctca gagaacttta agaagttcat gaaatacact cacaggcctt gcacctgtgc ccgctgcatc gggcagcaga aggtctcgac ctggttcgat gagaggttca accggtccat gcagccgctg ctgaccgccc agaacgccct cttggaggag gacacctaca gctggtggct gaggctccag cgggagaagc aacccaacaa cttgaacgat accatcaggg agctgttcca ggtggtgccc gggaacgtgg acccctgct gaagaagagg tcggtggact gccgacgctg cacagtcgta ggcaactctg gcaacctccg aaagtcctgg tacgggcctc agatcgacag ccacgacttc gtgctcagga taaacaaggc ccccacagcg ggcttcgaga tagatgtcga gagcaaaacc acccaccacc tggtgtaccc cgagagcttc agggagctgg cggagaatgt cagcatggtc ctggtgccct tcaagaccac cgacctggag tgggtggtca gtgccaccac cacaggcacc atctctcaca cctatgttcc tgttcctgca aagatcaaag tgaaaaagaa taagatcctc atctaccacc cggccttcat caagtacgtc ttcgacagct ggctgcaggg ccacgggcgg tacccgtcca ccggcatcct ctccgtcatc ttctcgctgc acatctgcga cgaggtggac ttgtacggct tcggggcaga cagtaagggg aactggcatc actactggga gaacaatcca tcggcggagg ctttccgcaa gaccggggtg cacgacgaag actttgagtc caacgtgaca gccaccttgg catccatcaa taagatccgg atatttaagg gaagatgaca ctgccgagga gcaccggagc ccgcctcttt ggccagcccc agcctctgct ggagccgatc tgtgctgggg gctttgaggg ccagcctcgg gggcgtgttc aggtgcccct gftgccccct cgcaccccga catttggcag catcgactca gcaagacccc agaaccccgc tgggtctgca gagcgagtgt cagaactgat cttggatggg gacaccccc ctccacctcc ctgcaccgcc actgctgtcc tggagcaggg ggcaggtggg gagacgcggg aggaggtccg gtctccaaac gctcaagtca tttcggcttt gggggcaga ggggagata tcgaagactc tgtgttctaa agtgaaggac actggccctg gcaaaggggg tcccgggctg actctctaac tctgatgctt gctgggtgaa gacgacctcg gaacagagcc acatcgagcc acgtagacgc tagggtgaa aaggcaccct cctctgcacg atgcccggcc cctccctcac cgcctctgcg gtcttcccga agctcctccg tggcggccag gagaggcgcc ctgcgccgag ggtcctcaca gatgcttggc caagtgtttc agactccagc aggtgtcttc ttcgcaagct gagactccct tgagtgatcg atctttgtgg ccataaataa tggctaagag caaatctgac tacttccacg tgcctttgtg tctggggag agctgtgcgc attggctgaa ataaggcaaa gccttaatt cgggagtggg gagctccccc ctctccccgc ccccagcaat gccacccct tgctctggag ctgggtaaca tctttactag tttcctgagg cggtaccgga gctggaatga agctaggatg atgctcaacg gcgtccagaa
```

-continued

```
gtgcatcagc cacggcacgt cattcttagg ttcacagact gatggattta gggcccatga
ccttccaagg ccacacacag aacctccacc agccagcact ttgccccagg agcccaccct
ccaggccaag tccctccggg ccacctgcac agtgtcctgg ggtttgtggg gccatcccag
gaacatgacc ctcggagcag gagaaaacat acctcatcct ctcacttctg ggctgctctg
attcctcctc atgattattt attgattttt ttttaattca gctgacattg cgtgcacttt
gtggctccgt ggctggtcct gatgttttaa ttaagcttgc tctcgcttca cctggcagcc
ggggcatggg gggcttaagt caaggtttgc aggagtcctc agacttggga gggggatgca
tatctagggc ttgggggctc gtcggtgggc aaatgccagg gtttcaggtt ggtaggttct
ccgagtgctc tgtacctcct tcccctcagc tctgcctccc ttctccatca ttgcggattg
ggatcattct caggctaaga atctgcaaaa cccagtgaga cggccttggg gccaggtggg
gagtggagtc acacaggcag ggcagcgatg gttggctccg gttgctgaca ctgaatcaga
aaatccacgt ttcctattga gagcatttcc taacaggcca ctgctacttc gaggaggtgt
gacagtgtcc tggctgtcac gggggcccgt ctectgtgct ccttgcagca gcactccggc
aagttctgct ctcctggctt cagtctctgc ctctgcaaac ggagagggag gcatttgggg
agctcagggg gccacaggtg gtttcagggg gttcacaagc gtccccagag agagcacacc
acgcccgtgt tttaccccaa gcctgtgtgt atgagcatat attcctgggg aacggtgcca
tagcgttcat tcaattgtca gaggttcaga acccagacaa tggtttacaa aaacacgaaa
cgacagcaag caaacaaaaa cccgttcgag ctttaaaatc ctccaacact tagactctct
tgacccctaa aggctcataa atcactacga ggtcagcaag ctgatcataa atcccaaaga
ctatatagca ggcatctgtg ggttggctga tgaatccgct gagagaagtg ggtgcggagc
ggcctccgag ctcctcccg agtcctggaa gagccgagtc cagtcagaac tgatgagtcc
agagcgctca gcctgcgtcg ggactgtgct gagtcaggac aggtccccag agtaaggggg
ggggtctctc tccctcccca ccccactgag ccgtccaggc tgttgagagg acttcccacc
tgccttccca tgtaacactt gagaaaagcg aggcccggag aagggaagtg gcttgcaaag
tgaacccatg gtgctggaca acgcaagtca gacccttcga gcaaagatag aacacgatta
ctacatgttg aacacacctc gaggtgggct ttcccagccg gcttccatcc agcctcccca
aggactgtga ccgggcacag gtgggctcct caggctgcac gtggtggccc ccgcaagctc
cggtgtctgc cttttccccc catccctcca gtgagggaga cacccttgct cttccctcag
ccccagcaaa cttgtctttg tgttcattgg cttagcaaag aggtctgacc cgaatacacc
aacgggcttc agcccctgg catctgtacc tggggtaagg gtggctgaga atccaaccag
agtatttccc ccagagctcg tggctgtggg caggttaacg agaaccaccc gcccccccca
ctcggaggag gctcctgaat gcccacccca gtgttgggct cccagcctag ggccctgctt
gctcctcaag cacaaagctc ccttggaggc cagtcctaga cccctgggca gagagcagaa
gcatccctgc ctctctcagt gctgagcccg aagccaggaa gaccagggcc gaggagagag
agagagattt taacaccctc cccggccctg gggagccagg agctggagtc acctgccgca
aatgcaaggc ctggttccac gtgccccct ccgccctgt cctcacccc ttgttagggt
gggtttgtag cgtctggctc ccagaaccat cagacaaaaa agaaagttct taaagagatg
cttttagggg cctgtgctta gtgggagaag ccagattcaa gaaaatggga cttaaaacgg
ggaagccaga cgagaaggtg gggggggggt tgtccgggtg tgattcttac aagtgctgag
gccagaagga tggaccctct ccaggtccag agtagagtgg agtcaacggg gaatatttag
```

```
gactgtgatg tttgcagtaa tagtcctctt caaggcaacc tggacacaaa gcaaaatcga aaacagaaaa gaactcacca tcccttgcgt gggtaggacc aaaacagctt tctccaggga ggcgcaagcc ctgagtggcc gccgtctggc caaagccggc ctcgtgccat cgggaaccgg ccaccgccca tgcccctccg gagagctcgg ggtcgtcatc gtgtccacca cgggcatctg gtcagaagca aacgttccca caggccactg gctagtcatc atccctgtg gtctgagctg accggtttga gaccaagtcc gctgccttgc tccggcctgt cctgaagaca ccagcgcccc ggcctgtggg gtgccccgtg atgcctccat gcagggaaga gcaggggacc agggaggaag agcagagaca ggtgaagcga cagtccccgc gtcccagcct cagcattcgc atcctcttgg cccctacttt tcctctccgc ccagcagaca tctgccctgc ccttgccctt gaccccattg ctgcgcttcc ctcaaggacg ggcctggcct tggtggccac ctgcggacag ccctgcgccc gacgcccgct tcaccccggg gcccgggtct ggaggggccg cccccaggac gaacgcggct gccccacggg gccggcccct caccggcttc gcgtccaagc caaagtttct cgagcacttt tttgttcttt gcaatcatgt tgggttcatt gttggtgttt taaaattttg cttccctctc cctctggcct cgctcctgtg tgtgttttgt agccgagcgc taacctggat gctttttga atgacctttg caagagcctg ccttcctcgg cctctgctct gttttattta ttgttgaata tttccaatga tccaaatcaa agtgaattaa aacaaagcta ttttatcgtt;
``` a ST3 gene encoding a protein having at least 80%, 85%, 87%, 90%, 92%, 95%, 96%, 97%, 98%, or 99% amino acid sequence identity to

```
(SEQ ID NO: 6; Accession No. XP_022282430)
mvtmrkrtlk vitilvlfif ltsfflnysh tmvtttwfpk qmvvelsenf kkfmkythrp ctcarcigqq rvsawfderf nrsmqpilta qnalleedty swwirlqrek qpnnindtir elfqvvpanv dpliekrsvg crrcavvgns gnireswygp qidshdfvlr mnkaptagfe mdvgsktthh lvypesfrel aenvsmvlvp fkttdlewvv satttgtish tyvpvpakik vkkdkiliyh pafikyvfds wlqghgryps tgilsvifsl hicdevdivg fgadskgnwh hywennpsag afrktgvhdg dfesnvtati asinkirifk gr;
``` a ST3 gene having at least 80%, 85%, 87%, 90%, 92%, 95%, 96%, 97%, 98%, or 99% nucleic acid sequence identity to a canine ST3GalI gene comprising

```
(Accession No. XM_014114023)
                                              (SEQ ID NO: 7)
cggctcgctc cgggagggca gagccggcaa gggcgggact ggcctgctgc gggcggacgg gggagccgcg gagctaacgg gtccggacgt cgccagcggc ggagctttct gcacgggcgg aggcggcagc aggaacggca aacatggccc gcgcggcacc cggcactgac taagggtcat gctgggcag cctggcgcct gacgagtgag ggggaacctg ccagggatt actgctagca cgagctaaca gcaggacagc aggcctcagg ggagtgggga tgggcatagc agcctgcctg caacgctggg ccagtggcac caaggaggcc caggccctgg cagggagctc ggcacacgct cagctgaccc agacagcatt caaagcaggt ccctgctgag cagcagctat tccaagccc tggaggaccg caaacgcctc agcaaccaca tttgggctg tgaccatcag gagaagggac caacacctcg aatgggaagc agaagggcag aacctgctgc caggaggatc ttggtctctg cagcaaagtc ttccgacacc cgtggagctt cttgggtttc tcctctcagg actgggcct tgtttcctcc tctgatggag gaggtaggcc aggagggcca gctgaggtgg gaacgactct
```

-continued

```
cggatggaat ccaggccact tgaagcccat gggctctctg ctgtgattgg ggttcgaggg cttocccact gcaggggacg aggggccgcc tccgtgtctg ctcatgaacc acaaggaccc cgaatgctcc agactggacc atttcgagcc accaaagagt ggggccccca gagctggcag ccaacagctc caagggacta gagagctggg atgaactgac ctcccoctca ccaggacatt aggagagtca gagcctctgt ggcccagcta gtgacagaga gacccgatga ggccataagc tggcacccga gtgactcagg gacaggagag ccactcctgc ctactgtgct ttctctttac attgagggag ggtgtggtaa gggacccctg cctctgttcc ctcctcagca cgtgcccta tgccotttgc acgtagtgcc aagagacgca ggctacactg tggctggccc atcagtgggc tgggaaggga gtggccacgg tgacacccac ccgcccacca ggctggtggt ctagoccccc ggggcgccaa accatgaagt gctocctgcg ggtgtggttc ctotctgtgg cottcctgct ggtgttcatc atgtcactgc tctttaccta ctcccaccac agcatggcca cottgoccta cctggactca ggggccctgg gcggtaccca ccgggtgaag ctggtgcctg gctatgctgg tctgcagcgc ctcagcaagg aggggctcac cggtaagagc tgtgcctgcc gccgctgcat gggtgacact agcgcctctg actggtttga cagccactt caacagcaaca tttoccctgt gtggacccga gagaatatgg atctgcctcc agatgtccag aggtggtgga tgatgctgca gocccagttc aagtcacaca acaccaacga ggtactggag aagctgttcc agatagtacc aggcgagaac cootaccgtt tcogggaccc ccaccagtgc cggcactgtg cagtagtgga gaactcaagc aacctgcggg gctctggcta cggcccaaat gtggatgggc ataacttcat catgaggatg aatcaggcgc caaccgtggg cttttgagcag gatgttggca gccgaactac ccaccattc atgtacccog agagtgccaa gaaccttcct gccaacgtca gctttgtgtt ggtgccottc aaagctctgg acctactatg gattgccagc gctttgtcca cagggcaaat cagattcacc tatgcgccag tgaagtcctt ccttcgagtg aacaaagaaa aggttcagat ctacaacccg gcattcttca agtacatcca cgaccggtgg acagagcatc acgggcggta ccottccaca gggatgctgg tgctottctt tgccctgcat gtttgtgatg aggtgaacgt gtacgggttc ggggccgaca gccggggcaa ctggcaccac tactgggaga ataaccggta tgcgggcaag ttccagaaga caggagtgca cgacgccaac ttcgaggccc acatcatcga catgctggcc aaggccagca agatcgaggt ctaccgaggc aactgagccc ggcctcgccg cgacccttcc ggcccagccg cgaggctgcg acgctcgctc cgcagccggg actcccggcc agcccgaggg cggcggcctt ggcgagggcg cggcgccogg ttgggcgtct ccagccctgg gagcgacgcc aagtcgcgat ctggaccaat catactgcaa atccagcgag cgccgactgt ccoccgccaa tcaggagact ttgggggctg gcccaggcct ggcacccaat cagcgctgca gtgggagcgg aggctctttc tcccagccaa tcatgcgact caaggagaac ttccggcgct gggcccggtc toctccaatc aatggccttc ggaggcgggc cggccgccgc tgaatcocca ctoccotatg ctttaggtag gattttattt tatgctttt aaggagtagt gattggttcc ggcctcagtg gagtactttc ctcaggctct gcgggaggag tgttggtggc ctgtcggcgg tactcggcca ggggcaccga ggaggaagcg ggggggaagg tgcggggcag cagcggctgg gcctccottg gccgggggcc cctcgcgacc tcggggcggg cggggggcg ggggcgttgg cctcccgctt ctggaggtcc gggggaaatc aggtggtttc cggggagcac gctttcatcc ccgggaagag ctagatccct ctcaaaccctt tcaggcctc agagcactct agaccgcgta tttcctttat ctgtcgggcc cagatgggtg agtgtaaacc caccaaagaa aggcagtgga
```

-continued

```
gcgtgggtcc cctcgtoctc ccttgtoccc atccccacct ttggccaccc tatgggatgg cottcctaac caggacattg aacatcccac ctggaaacta gaactgtatt cacccgttgc tagggctcgg agttcgccga tggcctaact cgagcgcagg ggtaaggaac agggcagggg acccggaagc cccgtcactt cagatgtaag gtgcttctca ctctcgtgta ctctcgcggc cccttactgt tcgcccacaa ctttttagt gtcccttctt aagocctggg cctcctcacc agcctgctcg tcctgggatt gggggtgggg ggtagggcac tgctggcttc tccaaccocc taccoctoct cgctcgtott tagccggctc tagggagagg aaggcaggct ggagatgggg agcccagctg cctggtgcat gcaccgtttt cctccgccca tcaccccaaa gaggagtagg aaacctcttg cttggggtg gaatttgctt tggtctccta atttagttaa cttgaggtta ccagggatgg ctgaccaaca aagattottt taaaattcca ggctgqccat gcaaattgct gggatcctag ctggggagga gtcgactgac ttgcccgcct tacatgtotc ctctoctgcc cctgcgtocc ctocctotgc cacgctcact toctacctca totctccaac ccattttcca tttcagctc tagaagggca gggacgctta caaacaggag ttacatctgq aagttacttc caagactgaa cccagcttaa gtccctagag gaagctgctg atgatattct caccottcaa ggttgggaa atttcggaag gggaaagtgc ttctgtgaag cttccaaacc actaatagga tccoccttcc caacaatgag gaacacaaac accacccttt atcttagttg ataccaccaa gcagcctcct ggccattggg gtaattcctg cagctggctg gggtaaccag caqgggagta tattagaaga ggattggggc aaggcagtgg gcaccoctaa agttaatata ttgagaactt agcttaaacc taagtcttag ttcottocca attccaaaag taggaggagc aacgagtgga ggtgaatttg gaggggccta tcctggaatg cctotctcag gacttocccc accatttag agagtcaagg caccagccat tcatgccagt ctcctctcag tqcttcctga agaggctgtt tggaqtgttc gqaaaatgaa aaaaacaatg caattatgcc aaacagtatt gagcagaata atttatttct tttttgttcc tttttcttct ttttgttttg tttaaaacat taataaatcc cotttctgaa agaggtaggt cccagcatcc agcccagatc tocttttctg caatagttat ttaaacaaat gtttgtttgt tttttattt tcttcccttt ctctctottt ctgaattaaa aaaaaagaaa actccta;
``` a ST3 gene encoding a protein having at least 80%, 85%, 87%, 90%, 92%, 95%, 96%, 97%, 98%, or 99% amino acid sequence identity to

```
(Accession No. XP_013969498)
                                                (SEQ ID NO: 8)
mkcslrvwfl svafllvfim sllftyshhs matlpyldsg alggthrvkl vpgyaglgrl skegltgksc acrrcmgdtg asdwfdshfn snispvwtre nmdippdvqr wwmmlqpqfk shntnevlek lfqivpgenp vrfrdphqcr rcavvgnsgn lrgsgygpdv dghnfimrmn gaptvgfegd vgsrtthhfm ypesaknlpa nvsfvlvpfk aldilwiasa istgqirfty apvksfirvd kekvqiynpa ffkyibdrwt ehhgrypstg mlviffaihv cdevnvygfg adsrgnwhhy wennryagef rktgvhdadf eahiidmlak askievyrgn;
``` a ST3 gene having at least 80%, 85%, 87%, 90%, 92%, 95%, 96%, 97%, 98%, or 99% nucleic acid sequence identity to a canine ST3GalIII gene comprising (Accession No. XM_025420404)
(SEQ ID NO: 9)

```
ttgatggtcg cgctccgccc gccgctgcgt cccaccatg acggcgcccg tgcagcccac
cgcgtcgtag gcgcccgccg ggctccccog cggctgtgac ggccgcccgc gcctggcct
ccgcctcccc gcccgcgccg gccogggcgc cgcctccccg ctgcctccgt ctccgctgcg
qtcatgtaqg aaatcqtaaa tcatgtgaag atgggactct ggtatttgt acqcaatctg
ctgctagccc tctgccttt tctggtactg ggattttgt attattctgc gtggaagcta
catttactcc aatgggagga ctccaattca gtggttcttt cotttgactc cgctggacaa
acactaggct cagagtatga tcggttgggt ttcctcctga agctggactc taaactgcct
gctgagttag ccaccaagta tgcaaacttt tcagagggag cttgcaagcc tggctatgct
tcgaccttga tgactgccat ctttccoggg ttctccaagc cagcacccat gttcctggat
aactctttcc gcaagtgggc taagattcgg aagtttgtac cgccttttgg gatcaaaggt
caagacaatc tgatcaaagc catcttgtca gtcaccaaag agtaccgcct gaccccctgcc
ttggacagcc tcagctgccg ccqctgcatc atcgtgggca acggaggtgt cctagccaac
aagtctctqg ggtcacgaat tgatgactat qacattgtqg tcagactgaa ctccgcacca
gtgaaaggct ttgagaagga cgtgggcagc aaaactacac tqcgcatcac ctaccctgag
ggcgccatgc aqcggcctga gcaatatgaa cgcgattctc tatttgtcct cgctggcttc
aagtqgcagg acttcaagtq gttgaaqtac atcgtctaca aggagagagt gctctgqgcc
cgcagggata cctgccaatc tgtctgqgcc catccocctc toccotccac cagctgtcac
caqccacccc aggggaqqag tcctqcagag ttcaggccat tottottcca atacccgagc
ctcctactqg aggagaatga tgacagacag cctctggcga caagtqcatc agatggcttc
tggaaatccg tggccacacg agtgcccaag gagccccctg agattcgcat cctcaacccg
tacttcatcc agqaagccgc cttcaccotc atcggactgc ccttcaacaa cagcctcata
ggccgcqaga acatcccgac ccttggcaqt gtggcaqtga ccatagcgct acacggctgt
gatgaggtgg cagtcgcagq ctttggctac gacatgagca cacccaacgc gccoctqcac
tactatgaga ccgtgcgcat ggcagccatc aaagaggtca ccagcgactc agctcaaggc
tgccaaatcc aqtggacaca tggaagcctc atctttcctg acctcccaga aatgcttttt
ctqttgacca ctccttcctc tttqaaactt ttectgctca aactgtcctg gacacacaat
atccagcgag agaaagagtt tctgcgcaag ctggtgaaqg cgcgcqtcat caccgaccta
accagcggca tctgaggtgg gcccagcaca tggccacgga ggtcctggca ccqccaagag
gaagccgcag ccactgccac ctgtccactt cattggcctc ggtctqgctc tgcctgaaag
gcgcaggaqt cttcaqaccc agagaaggac agtgccaaqg gg;
``` a ST3 gene encoding a protein having at least 80%, 85%, 87%, 90%, 92%, 95%, 96%, 97%, 98%, or 99% amino acid sequence identity to (Accession No. XE 025276189)
(SEQ ID NO: 10)

```
mgilvfvrnl llalclfivl gflyvsawkl hllqwedsns vvlsfdsagq tlgsevdrlg flikldsklp aelatkyanf segackpgya salmtaifpr fskpapmfld dsfrkwarir efvppfgikg qdnlikails vtkeyrltpa ldslscrrci ivgnggvian kslgsriddv
```

-continued

```
divvrinsap vkgfekdvgs kttlritype gamqrpeqve rdslfvlagf kwqdfkwlkv ivykervlwa rrdtcqsvwa hpplpstsch qppqgrgpae frpfffqyps illeenddrq platsasdgf wksvatrvpk eppeirilnp yfigeaaftl iglpfnnglm grgniptlgs vavtmalhgc devavagfgv dmstpnaplh yyetvrmaai kevtsdsaqg cqiqwthgsl ifpdlpemlf llttpsslkl fllrlswthn iqrekeflrk lvkarvitdl tsgi;
``` a ST3 gene which has at least 80%, 85%, 87%, 90%, 92%, 95%, 96%, 97%, 98%, or 99% nucleic acid sequence identity to a canine ST3GalIV gene comprising (Accession No. XM_014113293)

(SEQ ID NO: 11)
```
gccctacagg cccgagctgc cagggtcggg cctccccagg ttcccgctcc caggtcctcc tggacacacc gacctggcct ggctcccggg gaactctcgt ctgctagcga ggagcctccc tccgcctcgc ccacgggcac ccctcccacc cagtatcctt ggcctcttgc aggtggcccg aggcagccgg gatgacagct ctccccagga accctgctac cctctgagaa acatgatcag caaatcccgc tggaagctcc tggccatgtt ggctctggtc ctggtcgtca tggtgtggta ttccatctcc cgagaagaca ggtacattga acttttttat tttcccatcc caaagaagaa ggaaccgtgc ttccaggggtg agcagagag aaaggcctct aagctctttg caactactc ccgagatcag cccatcttcc tgcagatgaa ggattatttc tgggtcaaga caccgtctgc ctacgagctg ccctatggga ccaaggggag cgaagacctg ctcctccggg ttctagccat caccagctac tccattccag agagcatcca gagtctcaag tgtcgccgct gcgtggtggt gggcaatggg catcggctgc gcaacagctc gctgggagat gccatcaaca gtacgacgt ggtcatcaga ctgaacaacg cccccgtggc tggctacgag ggtgacgtgg gctcgaagac caccatgcgt ctcttctacc cggagtcagc ccacttcaac cccaaagtgc agaacaaccc agacacactt ctcgtcctag tggccttcaa ggcaatggac ttccactgaa ttgagaccat cctgagtgat aagaagaggg tacgaaaggg cttctggaag cagcctcccc tcatctggga cgtcaacccc aggcaggttc ggattctcaa cccttcttt atggagattg cagctgacaa actgctgaac ctgccaatga acagccacg caagatttcc cagaagccca ccacgggcct gctggccatc acgctggctc tccacctctg cgacctgatg cacatcgccg gcttcggcta cccggacgcc cacaacagga agcagaccat tcactactat gaacagatca cgctcaagtc catggcgggg tcaggccaca acgtctccca ggaggccctg gccatcaagc ggatgctgga gatcggagca gtcaagaacc tcacgttctt ctgacgggga caggagctct agccgtcagt ctgcccgccc tgccgcctaa gcgaccaacc acgactgtgg aggcgccgac gtgacctgct tggattcccc ctccccgtgt ggagagggg cctggtacag gcgggccctg agatggggcc gcgcccctgg ctgctcttgg ggcggccgga tccagtcagg gtggaggccc cgggtggcgg gaggccttcc gaggcgcggg gtgtgtggct gaggcacccc ttctcaccag ccccgggagc ttatttaatg ggctatttaa ttaaaagggt aggaatgtgc ctcgagctgg tcccatggca tccggaaacg ggggcatagc acagtggtct gcccactgtg gataaaaaca cacaagtgct tggcccacta gagcctagag ccagagcagg cctcccagga gggcagggc gtctggagcg ggtgggtgcc ctccagagag gggctgctac ctcccagcgg gcatgggaag agcattggga tgaagtccca cggagaatag gacctcatgt agaaaagagg tttgaaacct aacattaaac tatttttttcc taaaacggaa;
``` a ST3 gene encoding a protein having at least 80%, 85%, 87%, 90%, 92%, 95%, 96%, 97%, 98%, or 99% amino acid sequence identity to (Accession No. NP_013968768)

(SEQ ID NO: 12)
```
misksrwkll amlalvlvvm vwysisredr yielfyfpip ekkepcfqge aerkasklfg
nysrdqpifl qmkdyfwvkt psayelpygt kgsedlllry laitsysipe siqsikorrc
vvvgnghrlr nssigdaink ydvvirinna pvagyegdvg skttmrlfvp esahfnpkve
nnpdtlivlv afkamdfhwi etilsdkkry rkgfwkqppl iwdvnprqvr ilnpffmeia
adkllnipmk qprkisqkpt tgllaitlai hladlvhiag fgypdahnrk atihyyeqit
lksmagsahn vsqealaikr mleigavkni tff;
``` a ST3 gene having at least 80%, 85%, 87%, 90%, 92%, 95%, 96%, 97%, 98%, or 99% nucleic acid sequence identity to a canine GalV comprising (Accession No. XM_022404744)

(SEQ ID NO: 13)
```
cgctctggaa ccacttacag ccacctggtg catcctcctt tggggtgcgt ttqgagggcc
tggttcctqc tcagccacat cttctgccac tttcaccaqc aatgcccagt gaqtataact
atgtaaaact gagaaqcgat cgctcaagac cctctctgca atggtacacc cgagctcaaa
acaagataag aaqacccaac ttgttgttaa aagacatcct taaqtgtaca ttgcttgtqt
ttggagtgtg gatcctttat attctcaagt taaattatac tactgaagaa tgtgacatga
aaaaaatgca ttatgtggac ccagaccgtg taaagagagc tcagaaatat gctcagcaag
tcttgcaaaa ggagtqccga cccaagtttg cgaagaagtc gatggcgcag ttqttcgagc
acagatacag cacggactta ccacctttcg tgaaagagac coccaaaata aatgaaaccg
agtacaagta taatcctcct tttggattcc gaaaattctc cagtgaagtc cagaccctgt
tggaaatact gcccgagcat gacatgcccg aacacttgag aqcaaagagc tgtaggcgtt
gtgtqgtcat cqgaagcggt ggcatactcc acggactagc actgggccaq gccctcaacc
aattcgatgt agtgataaag ttaaacagtg caccagttga aggatattct gagcatgttg
gtaataaaac tactataagg atgacttatc cagagggcgc gccactgtct gaccttgaat
attattccaa tgacttgttt gttgctgttt tattcaagag tgttgacttc aactggcttc
aagcaatagt aaaaaatgaa accctgccat tttggatacg gctottcttt tagaagcaga
tggcgaaaaa aatcccacta cagccaaaac atttcagaat tttgaatcca gttattatca
aagaaactgc ctttgacatc cttcaatact cagaacccca gtcaaggttc tggggccgag
ataaqaacgt gcccaccatt ggtgtcattg ccgttgtott aqccacacat ctgtgtqatg
aagtcagctt gqcaggcttt ggatatqacc tcaatcaacc caaaacacct ttgcactact
ttgacaatct ctgcatagct gccataaact ttcaaaccat acataatgtg acaacagaga
ccaggttcct cctcaagctg gtcaaagagg acgtggtgaa ggatctcagc ggaggcatcc
attgtgaatt ttgaacacag ggaaacctca tgtgacaatg caactctgac tctgaaggct
qttttcgta gccttctcga tgcagcgcat cctgcaaaat acttagaggt gcagctgggg
ttttt;
``` a ST3 gene encoding a protein having at least 80%, 85%, 87%, 90%, 92%, 95%, 96%, 97%, 98%, or 99% amino acid sequence identity to (Accession No. XP_022260452)

(SEQ ID NO: 14)

mpseynvvkl rsdrsrpslq wvtraqnkmr rpnlllkdil kctllvfgvw ilyilkinvt teecdmkkmh yvdpdrvkra akyaqqvlqk ecrpkfakks maqlfehrys tdlppfvket pkmneaeyky dppfafrkfs sevqtlleil pehdmpehlr akscrrovvi gsggilhgla lggalnqfdv virinsapve gysehvgnkt tirmtypega plsdleyysn dlfvavlfks vdfnwlqamv knetlpfwvr lffwkqvaek iplqpkhfri lnpviiketa fdilaysepq srfwgrdknv ptigviavvl athlcdevsl agfgydinqp ktpihyfdnl cmaamnfqtm hnvttetrfl lklvkegyvk dlsggihcef;

a ST3 gene having at least 80%, 85%, 87%, 90%, 92%, 95%, 96%, 97%, 98%, or 99% nucleic acid sequence identity to a canine GalVI comprising (Accession No. XM_005639375)

(SEQ ID NO: 15)

ggtcgattgc cccttggctg ctgtggaggc tgtgatgacc tccaaggccg cagccctcca ggcgatgctt ctccagggqc tgaggccaac gcagaactcc catggcaccc actcggactc gcggcgtgtt cacatgtggq gttttattaa atcctcccac caaccgtgtq agacagqaac agttagcccc gqtgtgtccq ccaagattgc cccgcacaag tqgctccgga tggatcacac gaaacacttg caagtgaaaa agcagcacag ccotttatct tgggctattt cctgtagaga aactccaaca atttaacagc caagctcctg agcctctgag accctcacca catcacatcc ttcaccttca ggagcagagc gcctttggga aacagacttc taaaaqtgca ggtgggccag ccatgagaqg gtacctagtg gccatattcc tgagtgctqt ctttctctat tatgtgctgc attgtatatt gtggagaaca acatctatt gggtgccacc tgtgaaaatg aagcggagaa ataaaatcca gccttgttta gcgaagccag cttttgcctc tctoctgaga tttcatcagt ttcacccttt tctgtgtgca gctgatttta aaaaqattgc ttccttgtat ggtagcqata agtttgatct gccctatggg ataagaacat cagcggaata ttttcqactc gctctttcaa aactacagag ttgtgatctc tttgataagt ttgacaatgt gccgtgtaaa aagtgcatgg tggttggtaa tagaggagtt ctgaagaata agacattagg aaaaaaaatt gactcctatg atgtcataat aagaatgaat aatggtcctg ttttaggaca tqaagaggaa gttgggagaa ggacaacctt ccgactttt tatccaqaat ctgtttttc aqatcccaat cacaatgatc ctaatactac agcgattctc actgctttta agccgcttga cttaaagtag ctgtgagaag tgttgacggg tggcaaaata aacactaatg gtttttggaa gaaaccagct ttaaacttga tctacaaacc ttatcaaatc agaatattag atcctttcat tatcagaatg gcagcttatg aactgcttca cttccaaaaa gtatttccca aaaaccaaaa acccaaacac caacaacaa gaattattgc catcacgctg gcctttcaca tatgtcacga agttcacctt gctggtttta aatacaattt ttctgacctc aagagccott tacactatta taggaacgca accatgtctt tgatqaataa gaatgcgtat cacaatqtga cagcqgaaca gctottttg aaggacattc tagaaaaaaa ctttgtaatc aacttgactg aagattgacc ctacagactc tgcagatgat gctaagagta ttagtttat ttttatactg caattttag tttatttta aatatattgg atgcacttat caaaaaattg tgtatagtca atctattgct gcctgatgat tcataaccac cagcttaatt tctgtgaata tatttaattt ataaaaaccca agaagatatg cttagatatc cgggaagttt tgattgcgtt ggttttaaaa caaccttaqt tctctqaagt gtttttaaac -continued

```
atcttttta  atagttactt  catctttgac  ttctgagagc  atgtaacgtc  caagtaagga gctttagctt  gaccaccaca  aactctaaac  agagttggtg  gcggattcga  ctactgtaaa ttggtgggga  atagccatgt  gattgtgcaa  actggaaccg  gtttaggcaa  gtatcgagtt cctttttact  gaacccgagq  aaacggattt  gaatcttaaa  gcaggcccaa  ccatagcagt aggtacggtt  atgaaatcta  agatcataat  ggtttcatta  agcttttttt  cctgtaagta aaccagatta  taaaatgaaa  ggtgtttgtt  tttaaggtag  aggaaacagg  ctacatgtga aattctggat  gagtaaacaa  cctaggaatg  caattactaa  agtctggtgg  ctgcattatt ttaaagttca  tacaaagaag  cagagctagg  ccacctcaag  gagacagttc  ttaaacgtca tcttttgcct  gccttaatat  gttaaaattt  ggaagtttac  tatttgaaat  aagaaagata aatacggcac  aataggtaaa  tocttcagac  tcctcaggct  gtttttggat  ttaaatagtc ctttcgtgaa  aaatctcact  tgtccacggt  gaaatcccat  cttcaaaggg  aaggcttacc cggctaccta  gqgtgcatca  gagaagagtc  ctgctggatg  cagacaagtc  aaaaccagcc tgtccaacaa  acgtgcgccc  gtotctcttc  tcaaagaggg  atggaatgaa  cagctctcag aagaggtaag  agttgaagga  cttgttatcc  tctgagcgat  aatcgtcatg  gagagacact gctggtattc  ctgaaaacca  gcctgcctct  gagtctcaga  gacaaaatat  gagagcagcc actgggataa  atcgtqaagc  acqgcataag  qggggagaag  cctcgtagtt  gattgaaccc atgtctacgt  ggcttcagct  gattcccctg  taacggaagt  ggaaagttcc  cacacgtaca cagctgcacg  ctgcagccta  gcggctagga  ttccatgggt  gaactcattc  agggtacaaa gacagtcctg  gctgcaaagt  gaaaaacccc  aggtggcatt  ttcaagtgtt  tatggactga aataatggct  gtacggtatc  tggcggatgc  tcaacttgag  gaatcggcat  ttttgtacag tggaagctga  agctataaac  ctcagcgtgg  cttcacataa  accagaagaa  actctcagcc cgatacatat  gtacaatta  ttaaaaacac  atgaacacat  taaaatctca  ctatttatac aatctacatt  ctagcaacat  atacaaatac  cgagtgacta  cagtacatgc  cgaggtaaga aaagtacatt  cggggagact  atcactgaca  ctcaagccat  ttttatttcc  aatatgtttt gctttcacct  ttcccagtgc  caaaaaaaa  aaaaaaaa;
``` a ST3 gene4 encoding a protein having at least 80%, 85%, 87%, 90%, 92%, 95%, 96%, 97%, 98%, or 99% amino acid sequence identity to (Accession No. XP_005639432)

(SEQ ID NO: 16)

```
mrgylvaifl  savflyyvin  cilwgtniyw  vppvemkrrn  kiqpclakpa  fasllrfhaf hpflcaadfk  kiaslygsdk  fdlpygirts  aeyfrlalsk  lqscdlfdef  dnvpckkcvv vgnggviknk  tlgekidsvd  viirmnngpv  lgheeevarr  ttfrlfypes  vfsdpnhndp nttailtafk  pldikwlwev  itggkintng  fwkkpainli  ykpyqirild  pfiirmaaye llhfpkvfpk  nqkpknpttg  iiaitlafhi  chevhlagfk  vnfsdlkspl  hyygnatmsl mnknayhnvt  aeqlflkdil  eknfvinite  d;
``` a ST3 gene having at least 80%, 85%, 87%, 90%, 92%, 95%, 96%, 97%, 98%, or 99% nucleic acid sequence identity to a canine ST3GalII-like comprising (Accession No. XM_025469036)

(SEQ ID NO: 17)

```
aaagacttca ctgggtatca gtgtcctttg ggagaccaca ggacacgtgt cacctctccc atcctctcag cctccagccc agaccttggc agagttcctt ttaggagtta gcaagtggct gaggaggcaa gaggtgccag agccaatcta ctatctgctg ggggatgatt gccagggcca gagatgaggg ctcaatactt gaagtagggt ctgatagctg cctgtataat tacgttatgg ctgatgatga tgaacttcct ggaccaggag ttcaaacaga atgacttccc taaaaagaca agaatacaat tatgccactg coccaggaac tctttcagaa agtgtaggtg ttcgtttgag atccgcaagt gctctgcctg cctccgcgta cgtggaacgt ctgtctggtt tgatgaacgc ttcgaaacgg ctattgagcc tatgcagaga ccagaagatc ccatatcctc taatgctcta atattgtggt taggtatcca atcaaagagg gagtttgaga ctcagaagcc aatagaagag cctcctgggc aaccactggg ctacgtggag tccagttgtc ggacctgtgc agtggttgga aactcaaggt gcctacgagg ctctggccat ggattcagga ttaaccaaaa tgacatggtc ctcaggatga accaggcccc cgtccaagga tttaagatgg atgtgggggaa cacaaccacc atgcgcataa tgtaccccga tatggctagc acgcagaatc ctggcaccaa attgctgctg cttcctctga attcatctgg tctaaagtgg tttatggaag tactacagga acagagcttc agaaagccca taaaccctgg atttcagata gtccagtttc ctgatggaag taacacgagc aaagacgagg tcttagtgat cagcctcacc tttcttcagt acatccagga tcattggcta cgaaaacgtc atcgttttcc atcottaggg tttgtgggtc tattatatgc cctgcacact tgtgaccagg tatccttatt tggttttggg acagatcagc tcatgaggtg gtcccattac tgggatgata aatatcggtt cgagagtaac atgcacagtt tcaaagaaga gcagaagctc atcctccagc tgcaatgtaa ggggaagatt gttatctaca actgacatat ttctgtoctg ttcagcccac tggaggcccc aggaggctga caggtagtca aggggaccac agagtgtcag agagggactg gggcttcaag tggaccctgg atatagatca gtctgctgct aaataaaact acagcttatt tctccca;
``` or
a ST3 gene that encodes a protein having at least 80%, 85%, 87%, 90%, 92%, 95%, 96%, 97%, 98%, or 99% amino acid sequence identity to (Accession No. XP_025324321)

(SEQ ID NO: 18)

```
mragylkwql vaacivtiwl mmmnfldqef kqndfpkktr iqlchcprns frkcrcsfei rkcsacirvr gtsvwfderf etaiepvqrp edpissdali lwlgvqskre fetqkpieep pgqplgyves scrtcavvgn srclrgsghg frinqndmvl rmnqapvqgf emdvgntttm rimvpdmast qnpgtkllll pinssglkwf mevlqeqsfr kpinpgfqiv qfpggsntsk devlvisltf lqyiqdhwlr krhrfpslgf vgilyaihtc dqvslfgfgt dqlmrwshyw ddkyrfesnm hsfkeeqkli lqlqcegkiv iys.
```

The invention will be further described by the following non-limiting example.

EXAMPLE

Methods

Cells.

MDCK and AX4 cells were maintained in Eagle's minimal essential media (MEM) containing 5% newborn calf serum (NCS) or 10% fetal calf serum (FCS). All cells were incubated at 37° C. with 5% $CO_2$, and regularly tested for *mycoplasma* contamination by using PCR and were confirmed to be *mycoplasma*-free.

Clinical Specimens.

Respiratory specimens were obtained from patients with influenza-like symptoms who visited clinics in Yokohama city, Japan during the 2017-2018 influenza season, and were submitted to the Yokohama City Institute of Public Health for virus isolation. These clinical specimens were collected under the National Epidemiological Surveillance of Infectious Diseases program in Japan. Respiratory specimens were also obtained from patients with influenza-like symptoms who visited clinics in Tokyo, Japan during the 2013-2014, 2015-2016, 2016-2017, and 2017-2018 seasons, and were submitted to the Division of Virology, Department of Microbiology and Immunology, Institute of Medical Science, the University of Tokyo for virus isolation. These specimens were collected by attending physicians after informed consent was obtained. Our research protocol was approved by the Research Ethics Review Committee of the Institute of Medical Science of the University of Tokyo (approval no. 26-42-0822). Samples that were positive by real-time RT-PCR (see below) or rapid diagnostic kits were used in this study.

Viruses.

Human influenza viruses were propagated in hCK cells in MEM containing 1 ug of L-1-Tosylamide-2-phenylethyl chloromethyl ketone (TPCK)-trypsin/ml.

Real-Time RT-PCR.

RNA was extracted from clinical specimens by using the Simply RNA Tissue Kit (Promega) or RNeasy Mini Kit (Qiagen). Amplification and detection by real-time PCR were performed with the Applied Biosystems 7900HT Fast Real-Time PCR System (Applied Biosystems) or StepOne-Plus Real-Time PCR System (Applied Biosystems). RT-PCR was carried out using the QuantiTect multiplex RT-PCR kit (Qiagen) or QuantiTect Probe RT-PCR Kit (Qiagen). The probes contained oligonucleotides with the 6-carboxyfluorescein (FAM) or the hexacholoro-6-carboxyfluorescein (HEX) reporter dye at the 5' end, and the Black Hole Quencher-1 (BHQ-1) or 6-carboxytetramethyl-rhodamine (TAMRA) quencher dye at the 3' end. The list of primers and probes used is provided in Table 5.

Virus Isolation.

MDCK, AX4, and hCK cells grown in 12-well plates were inoculated with 0.2 mL per well of the clinical samples and incubated at 34° C. for at least 30 minutes. One microliter of MEM containing 2.5 μg/mL acetylated trypsin was then added to cells. The cultures were then incubated for up to 7 days, until CPE was evident. Cell culture supernatants were harvested and subjected to hemagglutination assays using guinea pig red blood cells (see below).

Hemagglutination Assay.

Viruses (50 μL) were serially diluted with 50 μL of PBS in a microtiter plate. An equal volume (i.e., 50 μL) of a 0.75% (vol/vol) guinea pig red blood cell suspension was added to each well. The plates were kept at 4° C. and hemagglutination was assessed after a 90-minute incubation.

RT-PCR and Sequencing of Viral Genes.

Viral RNA was extracted from 140 ul of culture supernatants using the QIAamp Viral RNA Mini kit (Qiagen). Samples were amplified using the SuperScript III One-step RT-PCR System with Platinum Taq High Fidelity DNA Polymerase (Invitrogen) and specific primers of HA or NA genes. PCR products were then analyzed by means of 1.5% agarose gel electrophoresis in tris-buffer, and target bands were visualized by staining with GelRed (Biotium). The PCR products were purified and subjected to direct sequencing. The level of mutation frequencies were examined based on the height of the waves at each position on the sequencing chromatogram. The detection limit for a minor population was 10%-20%. The list of primers used is provided in Table 5.

Serial Passages of Human Influenza Viruses.

Ten-fold serial dilutions ($10^1$ to $10^6$) of viruses were prepared in MEM. Each dilution was inoculated into MDCK, AX4, and hCK cell monolayers in 24-well culture plates using one well per dilution. The plates were incubated at 33° C. for 3 days. The end point was taken as the highest dilution of the sample showing CPE. Culture supernatants were harvested from wells inoculated with the 10-fold higher concentration of dilution than the end point dilution, and were used for the next round of infection. Viruses sampled after the first and sixth passages in the supernatants of each cell were subjected to sequence analysis.

Statistical Analysis.

Data are expressed as the mean±SD. For the analysis of the growth curve data, we performed a linear mixed effects analysis. As fixed effects, the different cell lines, and the time of the measurement (with an interaction term between those fixed effects), were used. As random effects, intercepts for the individual animals were used. The virus titer values were transformed to the log 10 scale, and the R statistical package (www.r-project.org), lme4 (Bates et al., 2015), and the lsmeans package (Lenth, 2016) for the group comparisons, were used. The p-values were adjusted using Holm's method and considered significant if less than 0.05.

Figure 2B:
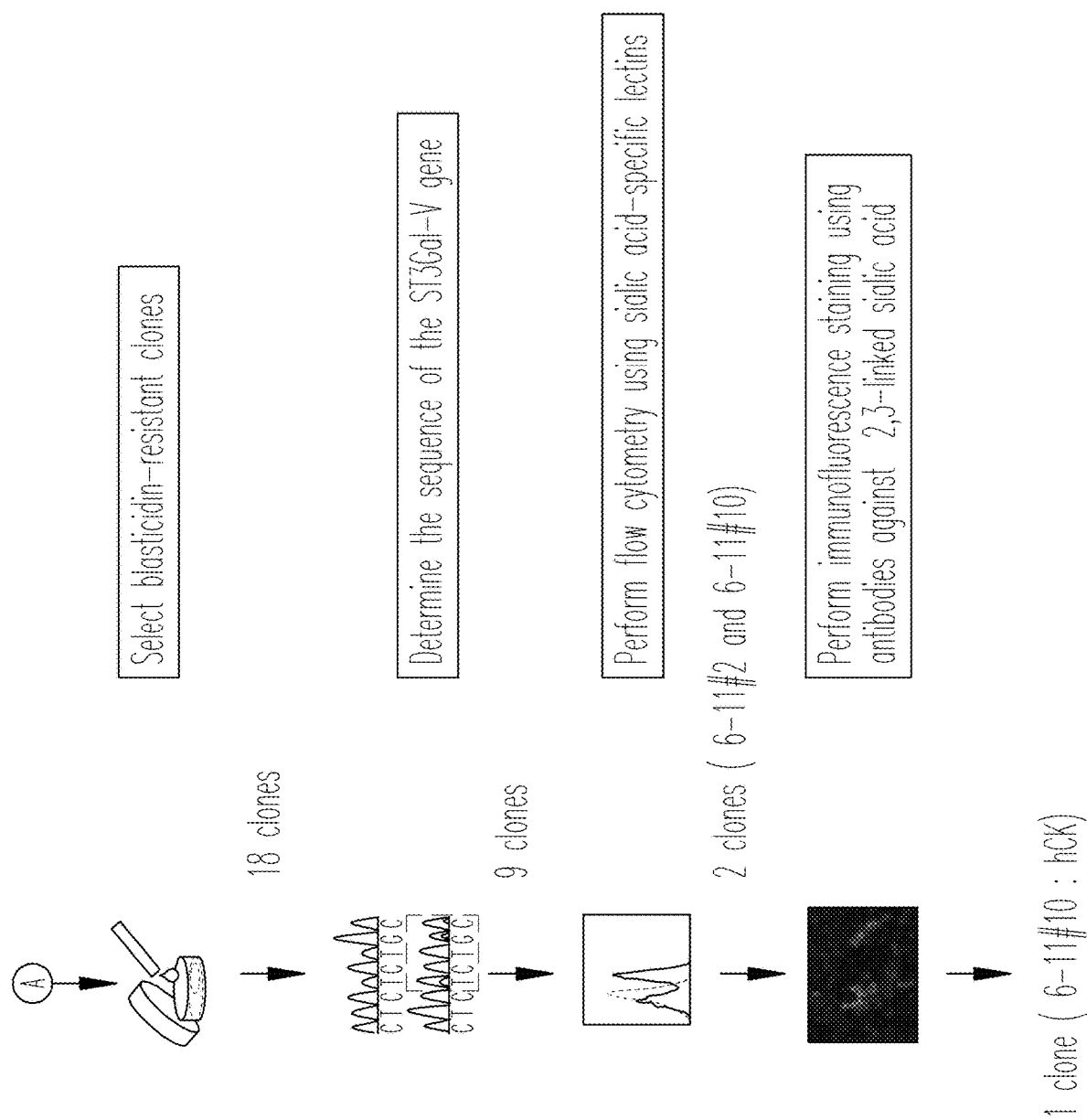
Figure 3A:
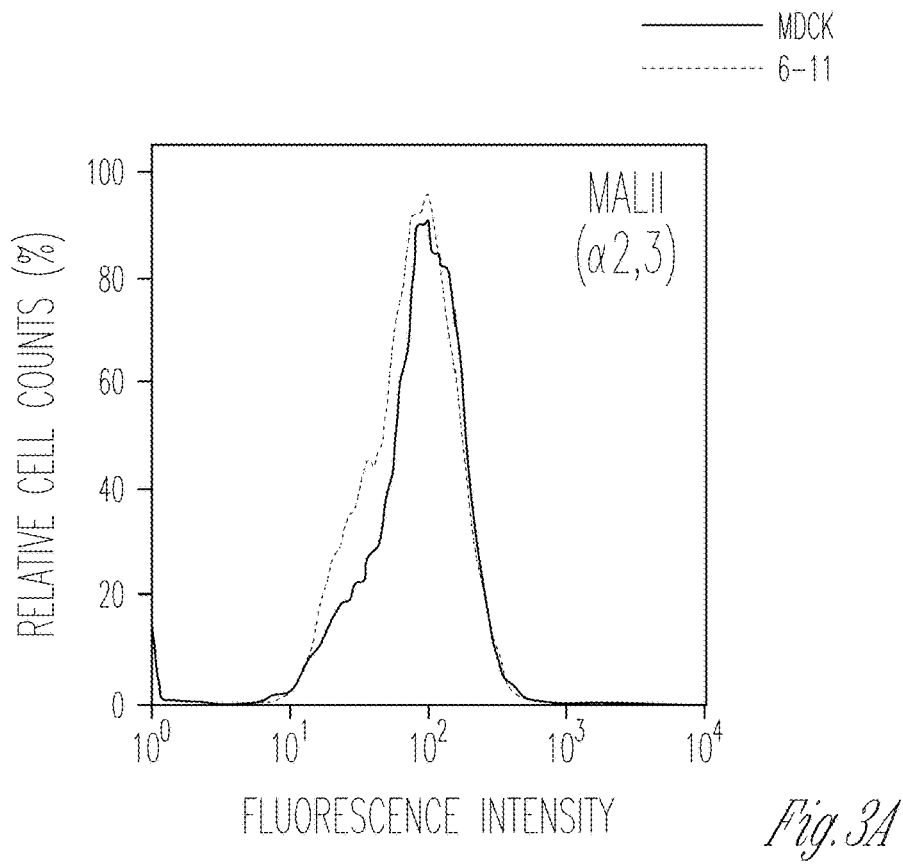
Figure 3B:
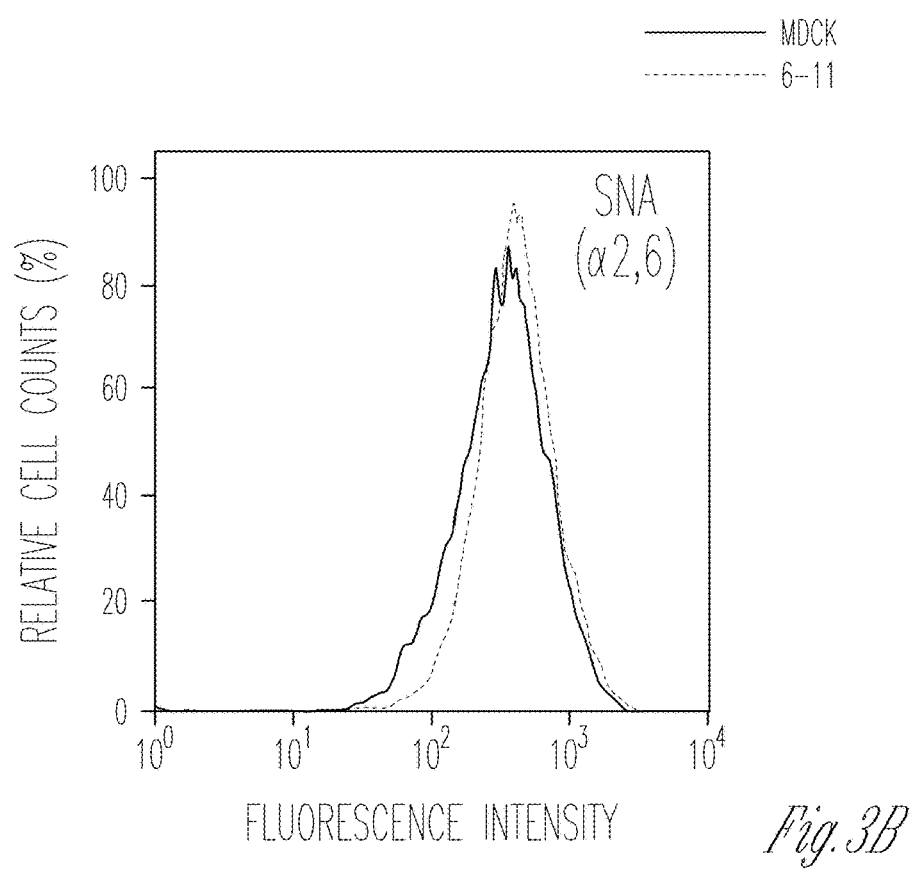
Figure 3C:
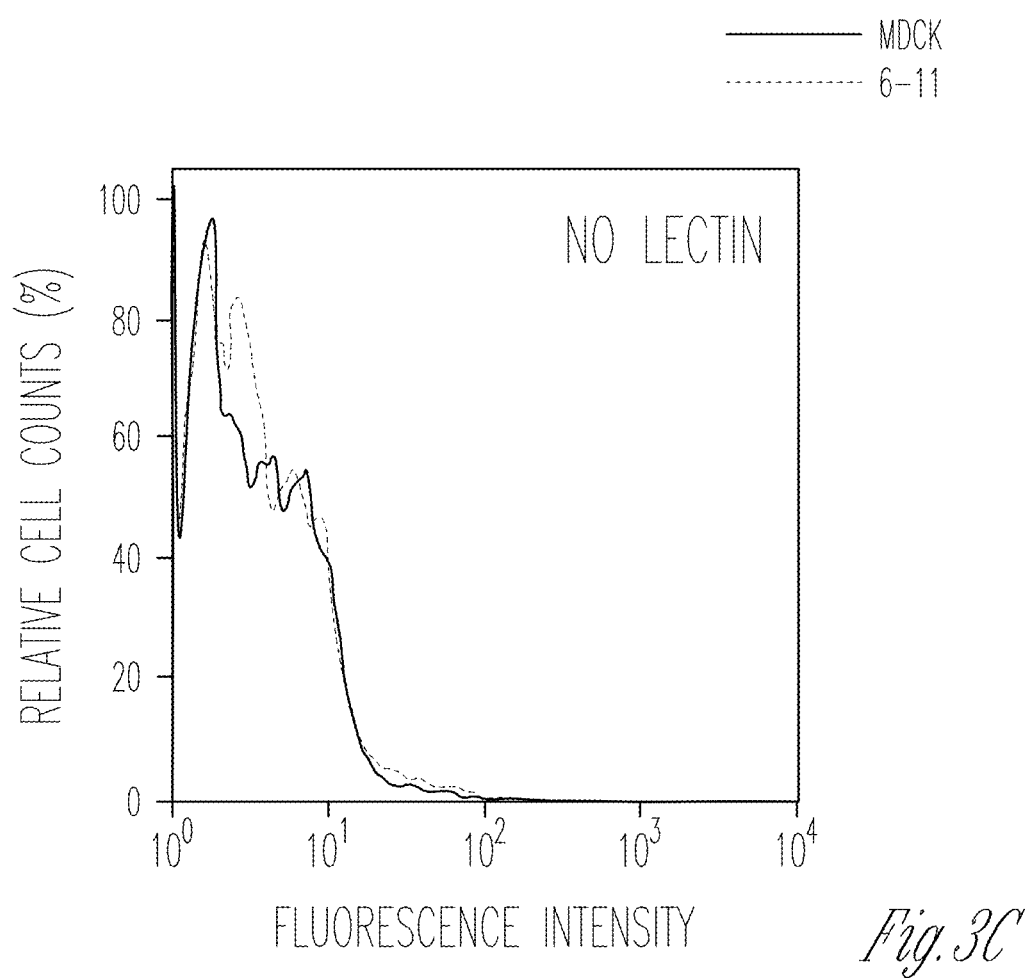

Generation of MDCK Cells Expressing Markedly Low Levels of α2,3-Linked Sialic Acid and High Levels of α2,6-Linked Sialic Acid To mimic the expression pattern of sialic acid (Sia) molecules on the surface of human upper airway epithelial cells, we first attempted to knockout the β-galactoside α2,3 sialyltransferase (ST3Gal) genes, whose products catalyze the transfer of Sia with an α2,3-linkage to terminal galactose (Gal) residues, by using the clustered regularly interspaced short palindromic repeats (CRISPR)/CRISPR-associated protein 9 (Cas9) gene editing system (Cong et al., 2013; Jinek et al., 2012; Han et al., 2018; Shalem et al., 2014). Dogs have seven different ST3Gal proteins (ST3Gal-I, -II, -III, -IV, -V, -VI, and ST3Gal-II-like protein) each of which is encoded by a distinct gene. ST3Gal-I, -II, -III, -IV, and -VI use oligosaccharides on glycoproteins, or on glycoproteins and glycolipids, as acceptor substrates, whereas ST3Gal-V utilizes oligosaccharides on glycolipids only (Takashima and Tsuji, 2011). A previous study reported that N-linked glycoprotein is required for productive entry of influenza viruses into host cells (Chu and Whittaker, 2004). Therefore, to inhibit the transfer of α2,3-linked Sias to glycoproteins, MDCK cells were transfected with a mixture of six plasmids, each containing a Cas9 gene expression cassette and an expression cassette for the individual guide RNA (gRNA) targeting the ST3Gal-I, -II, -III, -IV, -VI, or ST3Gal-II-like protein gene (FIG. 2). After transfection, puromycin was added to the cells, and 33 drug-resistant clones were randomly picked up. Genomic DNA analysis revealed that only one clone (6-11) contained mutations in the gRNA target regions for the six ST3Gal genes (data not shown). Cell surface Sias was measured by flow cytometry using the *Maackia Amurensis* II agglutinin (MAL II) lectin specific for α2,3-linked Sias and the *Sambucus nigra* agglutinin (SNA) lectin specific for α2,6-linked Sias. Unexpectedly, the reactivity with MALII was very similar between the parental MDCK cells and clone 6-11, indicating that the clone still expressed high levels of α2,3-linked Sias (FIG. 3). This may have been due to the compensatory activity of ST3Gal-V.

Figure 4A:
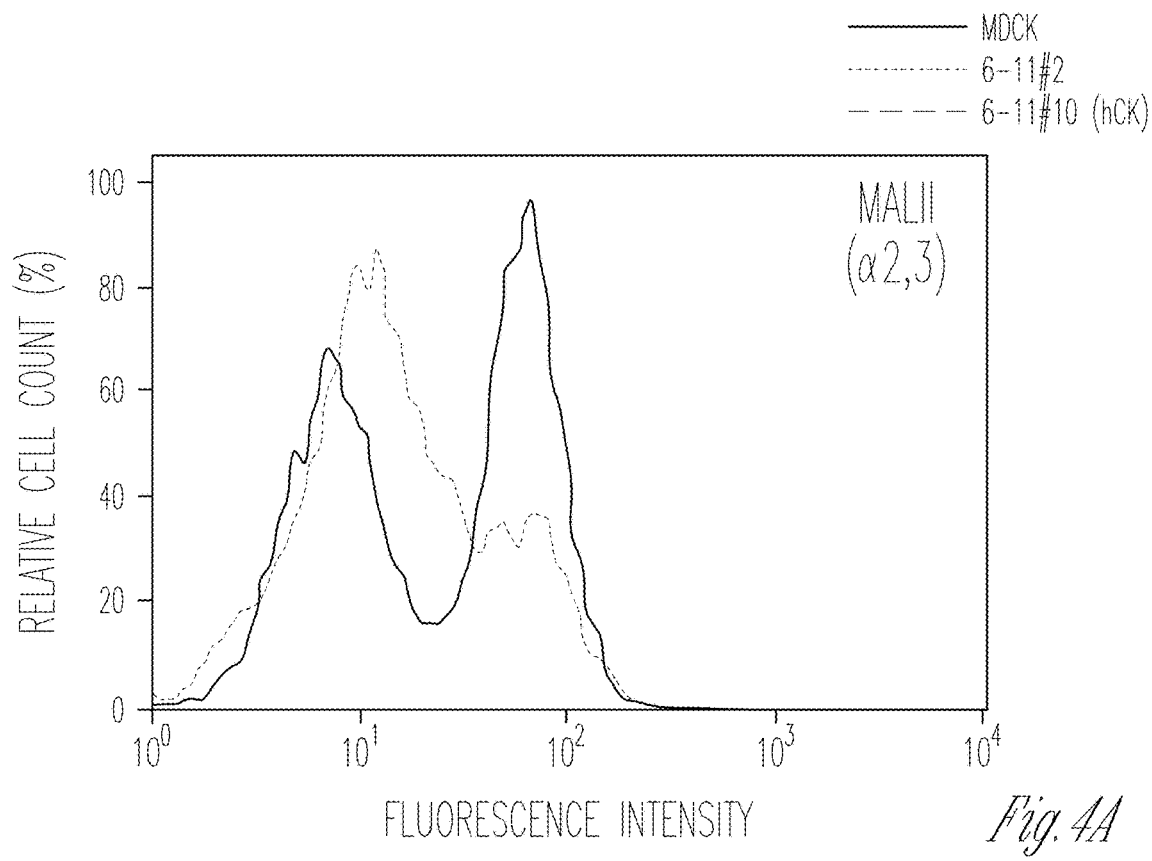
Figure 4B:
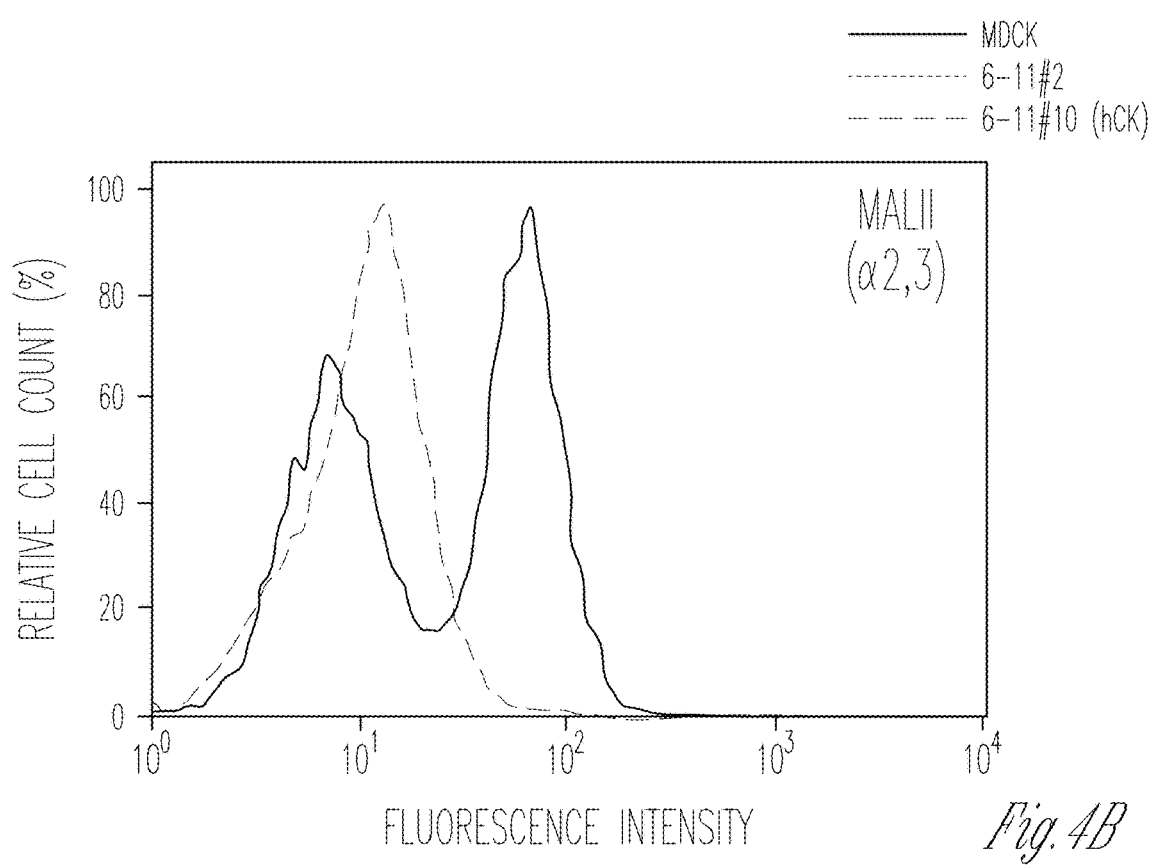
Figure 4C:
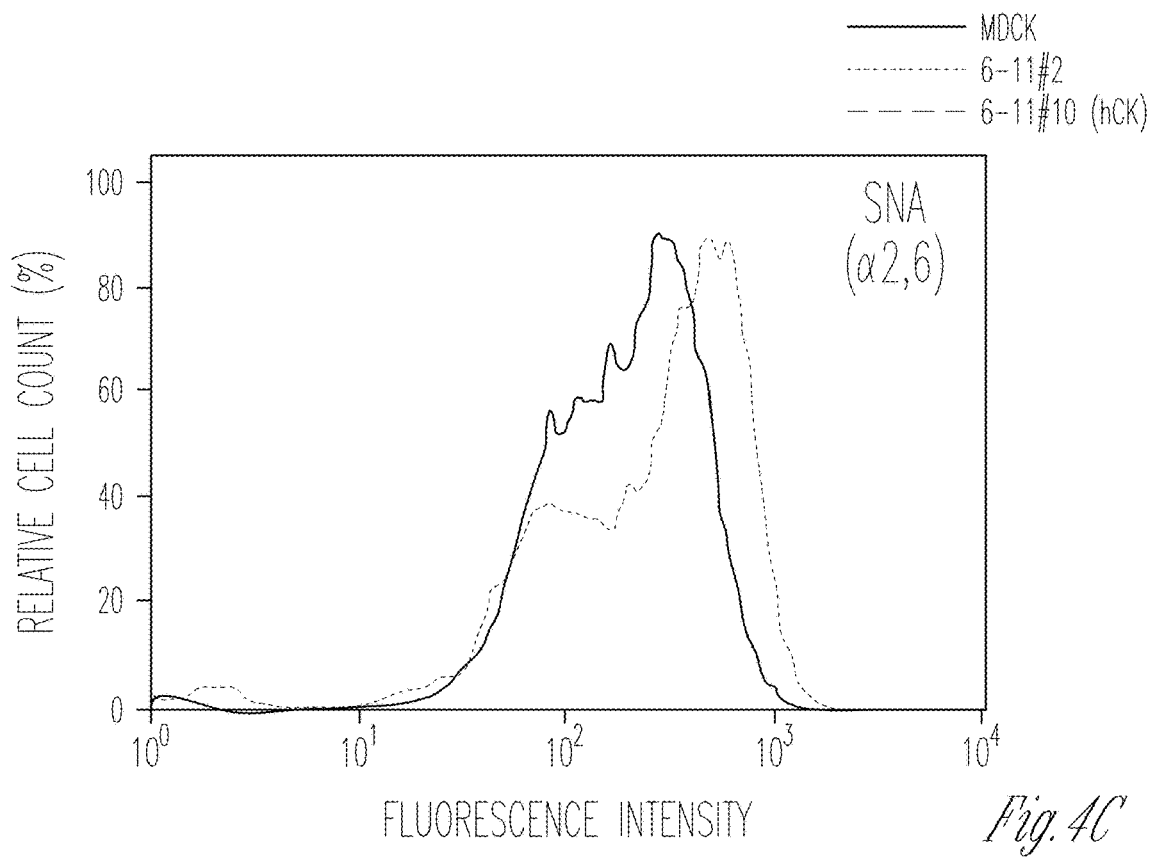
Figure 4D:
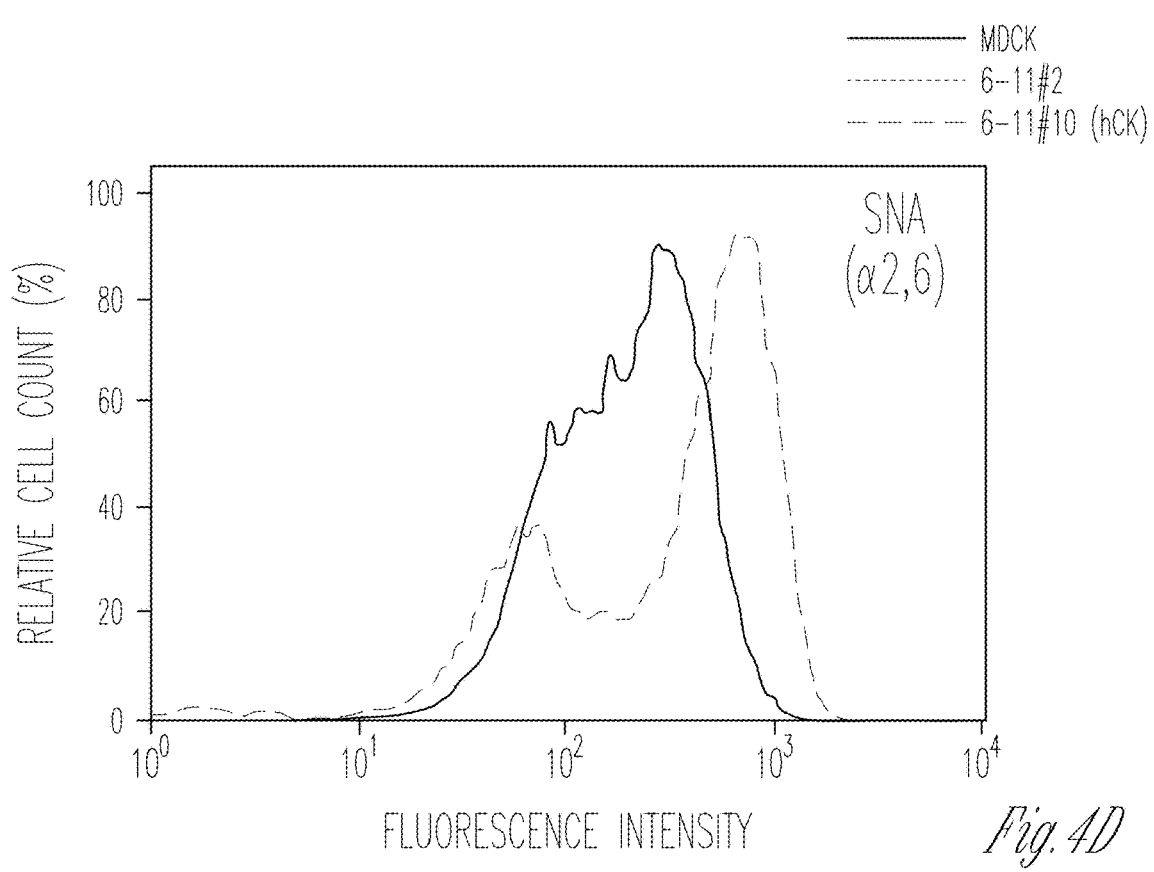
Figures 4E, 4F, 4G:
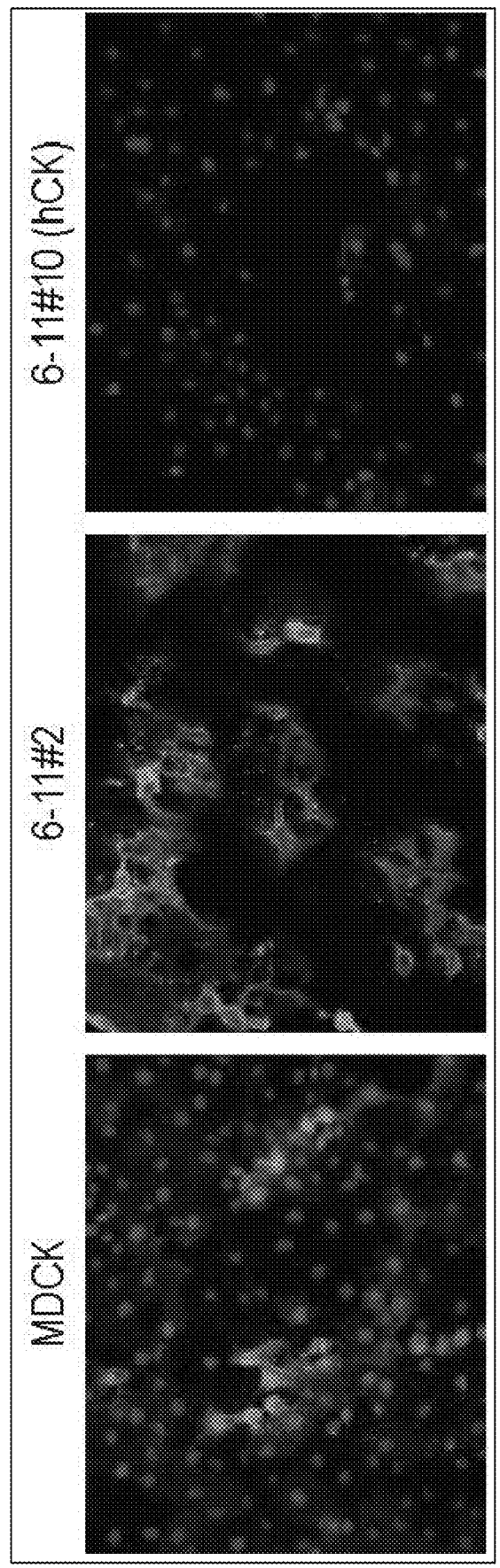
Figure 4H:
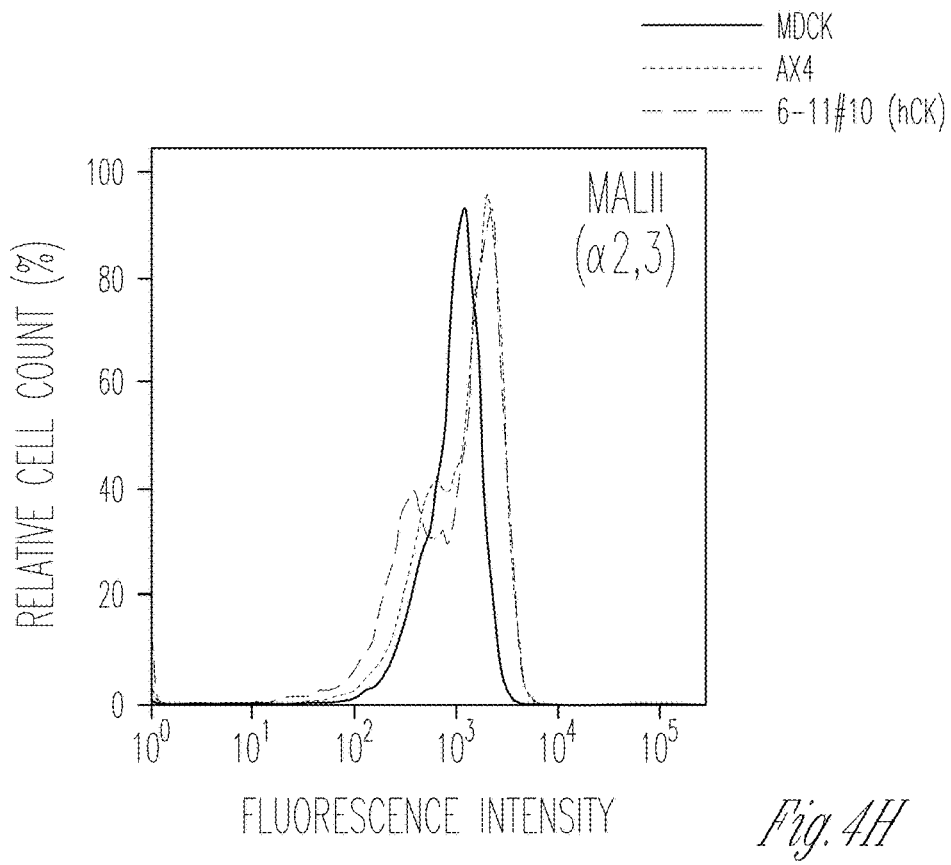
Figure 4I:
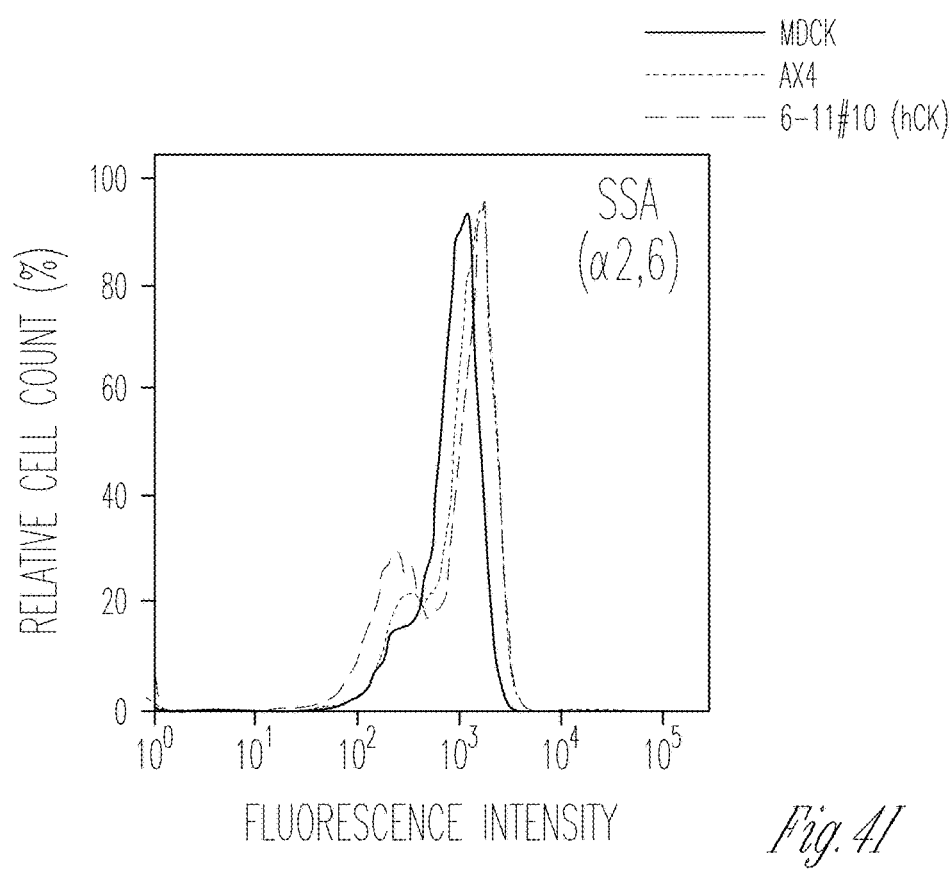
Figure 4J:
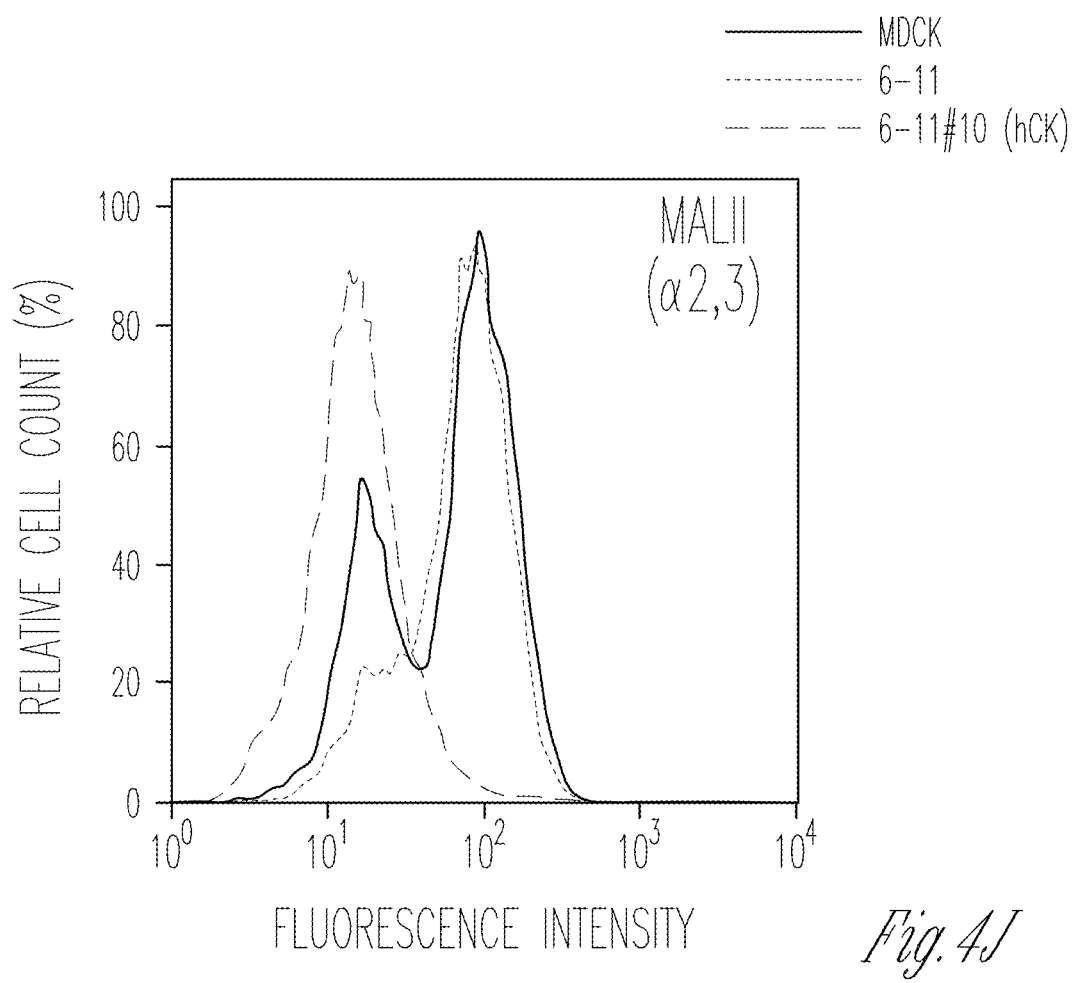

To inhibit the transfer of α2,3-linked Sias more efficiently and to express high levels of α2,6-linked Sias on the cell surface, clone 6-11 was co-transfected with a plasmid encoding human β-galactoside α2,6 sialyltransferase I (ST6Gal-I), which catalyzes the addition of α2,6-linked Sia to Gal-containing glycans, and a plasmid containing expression cassettes for Cas9 and a gRNA targeting ST3Gal-V. Eighteen cell clones were selected with blasticidin and subjected to genomic DNA analysis. Among the drug-resistant clones, 9 possessed a mutation in the gRNA target region for the ST3Gal-V gene (data not shown). Flow cytometric analysis using the MAL II and SNA lectins revealed that two (clones 6-11 #2 and 6-11 #10) of the nine clones had markedly decreased expression of α2,3-linked Sias compared with the parental MDCK cells and higher expression levels of α2,6-linked Sias than those of the parental cells (Sy FIG. 4a; data for only clones 6-11 #2 and 6-11 #10 are shown). Terminal Sia is attached to several types of oligosaccharide structures on glycoproteins or glycolipids, such as Galβ1,4GlcNAc (GlcNAc; N-acetylglucosamine), Galβ1,3GalNAc (GalNAc; N-acetylgalactosamine), and Galβ1,4Glc (Glc; glucose) (Takashima and Tsuji, 2011). The MAL II lectin preferentially recognizes the Siaα2,3Galβ1,3GalNAc structure (Hidari et al., 2013). To assess whether the two clones express different types of α2,3-linked oligosaccharide structures on the cell surface, an indirect immunofluorescence assay (IFA) analysis was performed using a monoclonal antibody against Siaα2, 3Galβ1,4GlcNAc7. IFA showed that levels of Siaα2,3Gal1, 4GlcNAc were undetectable or markedly low in one (6-11 #10) of these two clones (FIG. 4b), suggesting that in clone 6-11 #10, multiple types of oligosaccharides containing terminal α2,3-linked Sias are expressed at lower levels than in the parental cells. Next, the cell surface expression levels of α2,6-linked Sias on AX4 cells and clone 6-11 #10 were compared by using the SNA and Sambucus sieboldiana (SSA) lectins, both of which recognize the Siaα2,6Gal or Siaα2,6GalNAc structure (Shibuya et al., 1989). Flow cytometric analysis indicated that there were no differences in the expression level of α2,6-linked Sias between AX4 cells and clone 6-11 #10 (FIG. 4c). However, the expression level of α2,3-linked Sias, as measured by using the MAL II lectin, was markedly lower in clone 6-11 #10 compared to AX4 cells (FIG. 4d). It was confirmed that clone 6-11 #10 contained the desired mutations in the gRNA target regions for the seven ST3Gal genes (Table 1). These results show that clone 6-11 #10 expresses mainly human virus receptors and limited amounts of avian virus receptors. The resulting clone, 6-11 #10, was designated hCK, and subsequently expanded for further analysis.

TABLE 1

Amino acid changes in the HA and NA of viruses analyzed after passages in MDCK, AX4, or hCK cells[a].

| Virus type | Sample ID | Cell | HA[b] P1 | HA[b] P6 | HA[b] P10 | NA[c] P1 | NA[c] P6 | NA[c] P10 |
|---|---|---|---|---|---|---|---|---|
| H1N1pdm | BB139 | MDC | —[d] | — | T167T/I[e] | — | — | — |
| | | AX4 | — | — | — | — | — | — |
| | | hCK | N296N/S[f] | N296N/S[f] | N296S | S153G | S153G | S153G |
| | BB131 | MDC | — | — | N446N/S | — | — | H411cH/ |
| | | AX4 | — | — | — | — | — | C53C/Y[i] |
| | | hCK | — | — | — | — | — | — |
| | HP79 | MDC | — | — | — | — | — | — |
| | | AX4 | — | — | — | — | — | — |
| | | hCK | — | — | D27N | — | — | — |
| H3N2 | DA30[j] | AX4 | — | N158N/K | N158K | — | — | — |
| | | hCK | — | — | — | — | — | — |
| | DA29-1[j] | AX4 | — | — | — | — | T148K | T148K |
| | | hCK | — | — | D408D/N | — | — | — |
| | DA23-1[j] | AX4 | — | — | — | — | — | — |
| | | hCK | — | — | — | — | — | — |
| B/Yamagata | HP70-2 | MDC | — | — | — | — | — | — |
| | | AX4 | — | — | — | — | — | — |
| | | hCK | — | S148S/N | S148N | — | — | — |
| | BB005 | MDC | — | — | — | — | — | — |
| | | AX4 | — | — | — | — | — | — |
| | | hCK | — | — | — | — | — | — |
| | DA09-2 | MDC | — | — | — | — | — | — |
| | | AX4 | — | — | — | — | — | — |
| | | hCK | — | — | — | — | — | — |
| B/Victoria | HP015 | MDC | — | — | — | — | — | D459D/N |
| | | AX4 | — | — | — | G208G/R | G208G/R | G208G/R |
| | | hCK | — | — | — | — | — | — |
| | WD28 | MDC | — | — | N196N/S | — | — | — |
| | | AX4 | — | — | — | — | — | — |
| | | hCK | — | — | — | — | L72L/F[q] | L72F |

TABLE 1-continued

Amino acid changes in the HA and NA of viruses analyzed
after passages in MDCK, AX4, or hCK cells[a].

| Virus type | Sample ID | Cell | HA[b] | | | NA[c] | | |
|---|---|---|---|---|---|---|---|---|
| | | | P1 | P6 | P10 | P1 | P6 | P10 |
| | DA25-2 | MDC | — | — | — | — | — | — |
| | | AX4 | — | — | — | — | — | — |
| | | hCK | — | — | — | — | — | — |

[a]Influenza viruses isolated form the clinical specimens were passaged ten times in MDCK, AX4, or hCK cells. The sequences of the HA and NA genes of the viruses were determined after a single passage (P1), the sixth passage (P6), and tenth passage (P10).
[b]Mutations of influenza A viruses are shown with H3 numbering.
[c]All mutations are shown with N2 numbering.
d—, No mutation was detected compared to the sequences from the original clinical specimens.
[e]T/I, mixture of threonine and isoleucine at position 167
[f]N/S, mixture of asparagine and serine at position 296.
[g]N/S, mixture of asparagine and serine at position 446.
[h]H/Y, mixture of histidine and tyrosine at position 411c.
[i]C/Y, mixture of cysteine and tyrosine at position 53.
[j]Influenza viruses were not isolated from the clinical specimens in MDCK cells.
[k]N/K, mixture of asparagine and lysine at position 158.
[l]D/N, mixture of aspartic acid and asparagine at position 408.
[m]S/N, mixture of serine and asparagine at position 148.
[n]D/N, mixture of aspartic acid and asparagine at position 459.
[o]G/R, mixture of glycine and arginine at position 208.
[p]N/S, mixture of asparagine and serine at position 196.
[q]L/F, mixture of leucine and phenylalanine at position 72.

Establishment of a Stable Cell Line Possessing Mutations in its ST3Gal Genes and Expressing the ST6Gal-1 and HAT Genes.

gRNA sequences each targeting the ST3Gal-I, -II, -III, -IV, V, -VI, and ST3Gal-II-like protein genetic loci were designed using the sgRNA Design Tool from the Michael Boutros lab, see www.e_crisp.org/E_CRISP. The oligo DNA for the gRNA was cloned into the Cas9/gRNA dual expression vector pSpCas9(BB)-2APuro(PX459), encoding puromycin resistance (addgene). The resulting constructs were designated PX459-ST3Gal-I, PX459-ST3Gal-II, PX459-ST3Gal-III, PX459-ST3Gal-IV, PX459-ST3Gal-V, PX459-ST3Gal-VI, and PX459-ST3Gal-II-like, which express gRNA targeting ST3Gal-I, -III, -IV, V, -VI, and ST3Gal-II-like protein genes, respectively. Human ST6Gal-I genes were amplified by PCR from the pCAGGS-FLAG-PUR-ST6Gal-I plasmid (Hatakeyama et al., 2005) and were then digested with NotI and XhoI. The digested fragment was cloned between the NotI and XhoI sites of the eukaryotic expression vector pCAG-Bsd, which encodes blasticidin resistance (Wako). The resulting construct was designated pCAG-Bsd-ST6Gal-I, which expresses ST6Gal-I. All constructs were sequence verified by Sanger sequencing. Cycle sequencing was performed using BigDye Terminator version 3.1 Cycle Sequencing Kits (Thermo Fisher Scientific), and sequences were analyzed on an ABI Prism 3130x1 Genetic Analyzer (Thermo Fisher Scientific).

Electroporation was performed using the AMAXA Nucleofector II machine (Lonza) according to the manufacturer's instructions. Briefly, 5×10$^5$ MDCK cells were resuspended in 100 μL of the desired electroporation buffer and mixed with either 5 μg of Cas9/gRNA dual expression vectors (1 μg PX459-ST3Gal-I, 1 μg PX459-ST3Gal-II, 1 μg PX459-ST3Gal-III, 1 μg PX459-ST3Gal-IV, 1 μg PX459-ST3Gal-VI, and 1 μg PX459-ST3Gal-II-like) or 1.7 μg of PX459-ST3Gal-V and 1.7 μg of pCAG-Bsd-ST6Gal-I. The resuspended cells were transferred to cuvettes and immediately electroporated using the program A-024. The cells were cultured in the presence of 2 μg/mL puromycin or 10 μg/ml blasticidin in MEM supplemented with 5% NCS to select for transfected cells. Clones were isolated using cloning rings, dissociated using trypsin and EDTA, and expanded. Genomic DNA was isolated using a genome isolation kit (Promega) according to the manufacturer's instructions. The target region was amplified by PCR using primers surrounding each target site, and amplification products were cloned by using a Zero Blunt TOPO PCR Cloning Kit (Invitrogen). At least eight clones were randomly selected for each gene and the isolated plasmids were sequenced. The list of primers used is provided in Table 5.

Flow Cytometric Analysis.

Cells were detached by incubation for 10 min in PBS containing 0.125% Trypsin-20 mM EDTA (Dojindo). After being washed with PBS, the cells were blocked with Carbo-Free Blocking Solution (Vector) at 4° C. for 15 minutes. The cells were incubated with either biotinylated MAL II, SNA, or SSA at 4° C. for 30 minutes. The cells were then rinsed with PBS before being incubated with Alexa 488-conjugated streptavidin for 30 minutes at 4° C. (Invitrogen). Fluorescence was measured using a FACS Calibur or a FACS Verse (Becton Dickinson) and analyzed using FlowJo software (Becton Dickinson).

To confirm sialic acid-specific lectin binding, cells were treated, before incubation with lectin, with *Clostridium perflingense* (Roche) for 1 h at 37° C. Lectins bound to cells were detected as described above.

Immunofluorescence Staining.

Cells grown in 24-well plates were incubated with a mouse monoclonal antibody, which recognizes Siaα2,3Galβ1,4GlcNAc (HYB4: Wako) at 4° C. After incubation, the cells were fixed with 10% trichloroacetic acid for 10 minutes at −20° C. Cells were then washed with PBS and incubated for 30 minutes with Alexa 488-conjugated goat anti-mouse immunoglobulin G (IgG) (Invitrogen). Cell nuclei were counterstained with Hoechst 33342, trihydrochloride, trihydrate (Molecular Probes). The samples were examined by using Zeiss fluorescence microscopy (model Imager Z1; Carl Zeiss).

TABLE A

Sequence analysis of the CRISPR/Cas9 target sites in hCK cells[a].

| α2,3-sialyltransferase gene | Mutation type |
|---|---|
| ST3Gal-I | 2 nucleotide deletion |
| ST3Gal-II | 1 nucleotide insertion |
| ST3Gal-III | 1 nucleotide deletion, 1 nucleotide insertion |
| ST3Gal-IV | 1 nucleotide deletion, 236 nucleotide insertion |
| ST3Gal-V | 8 nucleotide deletion, 1 nucleotide insertion, 2 nucleotide deletion, 1 nucleotide insertion |
| ST3Gal-VI | 1 nucleotide deletion |
| ST3Gal-II like | 1 nucleotide deletion |

[a]PCR products of each gene were cloned into blunt-end vectors and subjected to sequencing analysis.

TABLE 2

Isolation of human influenza viruses from clinical specimens[a].

| | | Number of virus isolates recovered (isolation efficiency)[b] | | |
|---|---|---|---|---|
| Virus type | Total number of specimens | MDCK cells | AX4 cells | hCK cells |
| A/H1N1pdm | 30 | 30 (100%) | 30 (100%) | 30 (100%) |
| A/H3N2 | 30 | 25 (83%) | 28 (93%) | 30 (100%) |
| B | 30 | 30 (100%) | 30 (100%) | 30 (100%) |

[a]Clinical specimens shown to be influenza virus-positive by real-time RT-PCR or rapid diagnostic kits were used for virus isolation.
[b]Clinical specimens were inoculated into MDCK, AX4, and hCK cells. Cells were observed for the development of cytopathic effect (CPE) for 7 days. Supernatants from CPE-negative cell culture samples were tested by using rapid diagnostic kits and hemagglutination assays with guinea pig red blood cells at 7 days after inoculation.

TABLE B

Mutations in α2,3-sialyltransferase genes caused by each gRNA

| Target gene | Sequence |
|---|---|
| ST3Gal-I | CCTCCTTCTTCCTGAATTACTCCCACACC<br>CCTCCTT--TTCTGAATTACTCCCACACC<br>CCTCCT---TTCCTGAATTACTCCCACACC(SEQ ID NO: 20) |
| ST3Gal-II | CTTTACCTACTCCCACCACAGCATGGCCA<br>CTTTACCTACTCCCACCACAAGCATGGCCA(SEQ ID NO: 21) |
| ST3Gal-III | CTCCCCCGCGGCTGTGGCGGCCGCCCGCG<br>CTCCCCCGCGGGCTGTGGCGGCCGCCCGCG<br>CTCCCCCGC-GCTGTGGCGGCCGCCCGCG(SEQ ID NO: 22) |
| ST3Gal-IV | TCCCCAGGAACCCTGCTACCCTCTGAGAA<br>TCCCCAGGA-CCCTGCTACCCTCTGAGAA<br>TCCCCAGGACGATGGTGGTGTCAAAGTACTTGAAGGCGGCAGGGGCT<br>CCCAGATTGGTCAGGGTAAACAGGTGGATGATATTCTCGGCCTGCTCT<br>CTGATGGGCTTATCCCGGTGCTTGTTGTAGGCGGACAGCACTTTGTCC<br>AGATTAGCGTCGGCCAGGATCACTCTCTTGGAGAACTCGCTGATCTGC<br>TCGATGATCTCGTCCAGGTAGTGCTTGTGCTGTTCCACAAACAGCTGTTTC<br>ACCCTGCTACCCTCTGAGAA (SEQ ID NO: 23) |
| ST3Gal-V | ATCGCTCAAGACCCTCTCTGCAATGGTAC<br>ATCGCTCAAGACCCTCTCTG--ATGGTAC<br>ATCGCTCAAGAC----CAATGGTAC<br>ATCGCTCAAGACCCTCTCTGGCAATGGTAC<br>ATCGCTCAAGACCCTCTCT-CAATGGTAC (SEQ ID NO: 24) |
| ST3Gal-VI | AGCGATAAGTTTGATCTGCCCTATGGGATA<br>AGCGATAAGTTTGATCTGCC-TATGGGATA(SEQ ID NO: 25) |
| ST3Gal-II-like | CGCCCCGTCCAAGGATTTGAGATGGATGT<br>GCCCCCGTC-AAGGATTTGAGATGGATGT(SEQ ID NO: 26) |

The sequence of sgRNA is shown by bold letters. The underlined sequence shows the PAM sequence.
[1]The sequence matched some sequence of the PX459 vector.

TABLE 3

| Sample ID | Virus | Cell | Amino acid substitutions HA | Amino acid substitutions NA |
|---|---|---|---|---|
| I-1202 | A/Yokohama/146/2017 | MDCK | —[b] | D399G |
|  |  | AX4 | — | — |
|  |  | hCK | — | — |
| I-1205 | A/Yokohama/147/2017 | MDCK | — | D151N |
|  |  | AX4 | — | — |
|  |  | hCK | — | — |
| I-1218 | A/Yokohama/160/2017 | MDCK | — | — |
|  |  | AX4 | — | — |
|  |  | hCK | — | — |
| I-1221 | A/Yokohama/181/2017 | MDCK | — | D151D/G[c] |
|  |  | AX4 | — | — |
|  |  | hCK | — | — |
| P-9211 | A/Yokohama/199/2017 | MDCK | N158K | R394K/R[d] |
|  |  | AX4 | — | — |
|  |  | hCK | — | — |
| I-1250 | A/Yokohama/240/2017 | MDCK | — | — |
|  |  | AX4 | — | — |
|  |  | hCK | — | — |
| I-1244 | A/Yokohama/1/2018 | MDCK | — | — |
|  |  | AX4 | — | — |
|  |  | hCK | — | — |
| I-1248 | A/Yokohama/8/2018 | MDCK | — | D151D/N[e] |
|  |  | AX4 | — | — |
|  |  | hCK | — | — |
| P-9256 | A/Yokohama/10/2018 | MDCK | P221S/P[f], N246D/N[g] | — |
|  |  | AX4 | — | — |
|  |  | hCK | — | — |
| P-9265 | A/Yokohama/14/2018 | MDCK | T248I | — |
|  |  | AX4 | — | D151D/N[e] |
|  |  | hCK | — | — |
| P-9279 | A/Yokohama/15/2018 | MDCK | T160K/I[h] | — |
|  |  | AX4 | — | — |
|  |  | hCK | — | — |
| P-9281 | A/Yokohama/16/2018 | MDCK | — | — |
|  |  | AX4 | — | — |
|  |  | hCK | — | — |
| P-9288 | A/Yokohama/20/2018 | MDCK | T160K/T[i] | D151D/N[e] |
|  |  | AX4 | — | — |
|  |  | hCK | — | — |
| P-9291 | A/Yokohama/21/2018 | MDCK | — | D151D/N[e] |
|  |  | AX4 | — | — |
|  |  | hCK | — | — |
| P-9301 | A/Yokohama/29/2018 | MDCK | — | — |
|  |  | AX4 | — | T148K/T[j], D151D/N[e] |
|  |  | hCK | — | — |
| I-1271 | A/Yokohama/33/2018[k] | hCK | — | — |
| I-1275 | A/Yokohama/32/2018 | MDCK | — | — |
|  |  | AX4 | — | — |
|  |  | hCK | — | — |
| P-9307 | A/Yokohama/34/2018 | MDCK | — | — |
|  |  | AX4 | — | — |
|  |  | hCK | — | — |
| P-9315 | A/Yokohama/36/2018[l] | AX4 | — | — |
|  |  | hCK | — | — |
| I-1279 | A/Yokohama/37/2018[l] | AX4 | — | — |
|  |  | hCK | — | — |
| I-1280 | A/Yokohama/38/2018[l] | AX4 | — | — |
|  |  | hCK | — | — |
| P-9328 | A/Yokohama/40/2018 | MDCK | — | — |
|  |  | AX4 | — | T148T/I[m] |
|  |  | hCK | — | — |
| I-1288 | A/Yokohama/41/2018 | MDCK | — | — |
|  |  | hCK | — | — |
| P-9330 | A/Yokohama/43/2018 | MDCK | — | D151D/G[c] |
|  |  | AX4 | — | E433E/K[n] |
|  |  | hCK | — | — |
| P-9333 | A/Yokohama/44/2018 | MDCK | — | D151D/N[e] |
|  |  | AX4 | — | D151D/N[e] |
|  |  | hCK | — | — |
| P-9334 | A/Yokohama/45/2018 | MDCK | — | — |
|  |  | AX4 | — | D151D/G[c] |
|  |  | hCK | — | — |
| P-9352 | A/Yokohama/48/2018 | MDCK | — | — |
|  |  | AX4 | — | — |
|  |  | hCK | — | — |
| P-9356 | A/Yokohama/49/2018[k] | hCK | — | S44S/P[o] |
| I-1295 | A/Yokohama/50/2018 | MDCK | T160K | — |
|  |  | AX4 | — | D151D/N[e] |
|  |  | hCK | — | — |
| I-1296 | A/Yokohama/51/2018 | MDCK | N158K | — |
|  |  | AX4 | — | — |
|  |  | hCK | — | — |

[a] Influenza viruses isolated from the clinical specimens in MDCK, AX4, or hCK cells. The sequences of the HA and NA genes of the viruses were determined after isolation in MDCK, AX4, or hCK cells.
[b] —, No mutation was detected compared to the sequences from the original clinical specimens.
[c] D/G, mixture of aspartic acid and glycine at position 151.
[d] K/R, mixture of Lysine and arginine at position 394.
[e] D/N, mixture of aspartic acid and asparagine at position 151.
[f] S/P, mixture of serine and proline at position 221.
[g] D/N, mixture of aspartic acid and asparagine at position 246.
[h] K/I, mixture of lysine and isoleucine at position 160.
[i] K/T, mixture of lysine and threonine at position 160.
[j] K/T, mixture of lysine and threonine at position 148.
[k] Influenza viruses were not isolated from the clinical specimens in MDCK and AX4 cells.
[l] Influenza viruses were not isolated from the clinical specimens in MDCK cells.
[m] T/I, mixture of threonine and isoleucine at position 148.
[n] E/K, mixture of glutamic acid and lysine at position 433.
[o] S/P, mixture of serine and proline at position 44.

TABLE 4

Comparison of the sensitivity of hCK and AX4 cells to human influenza viruses[a].

| Virus type | Influenza season | Sample ID | Highest dilution of clinical sample showing CPE observed in[b] AX4 cells | Highest dilution of clinical sample showing CPE observed in[b] hCK cells | Ration (hCK highest dilution/AX4 highest dilution) |
|---|---|---|---|---|---|
| A/H1N1pdm | 2017-18 | BB139 | 8192 | 32768 | 4 |
|  |  | UT001-1 | 16 | 512 | 32 |
|  |  | HP79 | 65536 | 16384 | 0.25 |
|  | 2016-17 | P-8848 | 8192 | 8192 | 1 |
|  |  | BB131 | 524288 | 524288 | 1 |
|  | 2013-14 | IMS1 | 8192 | 16384 | 2 |
| A/H3N2 | 2017-18 | DA29-1 | <2 | 64 | >64 |
|  |  | DA30 | <2 | 2048 | >2048 |
|  |  | HP62 | 32 | 4096 | 128 |
|  | 2016-17 | DA23-1 | 16 | 2048 | 128 |
|  |  | DA16-2 | <2 | 16 | >16 |
|  |  | DA19-2 | 256 | 2048 | 8 |
| B/Yamagata | 2017-18 | BB140 | 16384 | 16384 | 1 |
|  |  | HP70-2 | 512 | 4096 | 8 |
|  |  | BB152 | 262144 | 262144 | 1 |
|  | 2016-17 | BB005 | 128 | 256 | 2 |
|  | 2015-16 | DA09-2 | 65536 | 524288 | 8 |
|  |  | DA07-2 | 64 | 64 | 1 |
| B/Victoria | 2017-18 | WD28 | 16384 | 131072 | 8 |
|  | 2016-17 | DA25-2 | 8192 | 32768 | 4 |
|  |  | BB078 | 524288 | 524288 | 1 |
|  |  | BB130 | 4096 | 4096 | 1 |
|  | 2015-16 | HP015 | 2048 | 16384 | 8 |
|  |  | HP009 | 262144 | 262144 | 1 |

[a] Clinical specimens shown to be influenza virus-positive by real-time RT-PCR were used for virus isolation.
[b] Serial 2-fold dilutions ($2^1$ to $2^{20}$) of clinical samples were prepared and inoculated into AX4 and hCK cells. Cells were observed for the development of CPE for 7 days. Three wells were used to infect with the same dilutions of virus, and the highest dilution showing CPE in all three wells is shown.

TABLE 5

List of primers used.

| Primer or probe | Target gene | Sequence (5'-3')[a] | Orientation |
|---|---|---|---|
| ST3Gal-I-F | Canis lupus familiaris ST3Gal-I | CCCTCCTCGTCCTCTTCATC (SEQ ID NO: 27) | Forward |
| ST3Gal-I-R | Canis lupus familiaris ST3Gal-I | AGGCAGAGAGAGACCAGAGA (SEQ ID NO: 28) | Reverse |
| ST3Gal-II-F | Canis lupus familiaris ST3Gal-II | CCAAACCATGAAGTGCTCCC (SEQ ID NO: 29) | Forward |
| ST3Gal-II-R | Canis lupus familiaris ST3Gal-II | AGGGGCTTGAAGAGTGACTC (SEQ ID NO: 30) | Reverse |
| ST3Gal-III-F | Canis lupus familiaris ST3Gal-III | ATGAGACTTGCTTGCATCCC (SEQ ID NO: 31) | Forward |
| ST3Gal-III-R | Canis lupus familiaris ST3Gal-III | CTTTGGTTGGCCTCTCTGTCTC (SEQ ID NO: 32) | Reverse |
| ST3Gal-III-seq-R | Canis lupus familiaris ST3Gal-III | CGTTAGCCGCGCACAG (SEQ ID NO: 33) | Reverse |
| ST3Gal-IV-F | Canis lupus familiaris ST3Gal-IV | CCGGGATGACAGCTCTC (SEQ ID NO: 34) | Forward |
| ST3Gal-IV-R | Canis lupus familiaris ST3Gal-IV | ACATGGAAGCTGGACTCAC (SEQ ID NO: 35) | Reverse |
| ST3Gal-V-F | Canis lupus familiaris ST3Gal-V | CATCATCACAAGGATCCTGC (SEQ ID NO: 36) | Forward |
| ST3Gal-V-R | Canis lupus familiaris ST3Gal-V | CTCTCCCATGAAAACCTGG (SEQ ID NO: 37) | Reverse |
| ST3Gal-VI-F | Canis lupus familiaris ST3Gal-VI | GTTTTAAATTTGGGAGCGGCC (SEQ ID NO: 38) | Forward |
| ST3Gal-VI-R | Canis lupus familiaris ST3Gal-VI | TGGCTCACATCAAACACCAC (SEQ ID NO: 39) | Reverse |
| ST3Gal-II-like-F | Canis lupus familiaris ST3Gal-II-like | GGTTGGAAACTCAAGGTGCC (SEQ ID NO: 40) | Forward |
| ST3Gal-II-like-R | Canis lupus familiaris ST3Gal-II-like | TGACTCCTTCCCCTTTTCCC (SEQ ID NO: 41) | Reverse |
| RT/PCR-A/H1N1pdm-HA-F | A/H1N1pdm virus HA | GTTACGCGCCAGCAAAAGCAGGG GAAAACAAAAGCAA (SEQ ID NO:42) | Forward |
| RT/PCR-A/H1N1pdm-HA-R | A/H1N1pdm virus HA | GTTACGCGCCAGTAGAAACAAGGG TGTTTTTCTCATGC (SEQ ID NO: 43) | Reverse |
| RT/PCR-A/H1N1pdm-NA-F | A/H1N1pdm virus NA | GTTACGCGCCAGCAAAAGCAGGA GTTTAAAAT (SEQ ID NO: 44) | Forward |

TABLE 5-continued

List of primers used.

| Primer or probe | Target gene | Sequence (5'-3')[a] | Orientation |
|---|---|---|---|
| RT/PCR-A/H1N1pdm-NA-R | A/H1N1pdm virus NA | GTTACGCGCCAGTAGAAACAAGGA GTTTTTTGAACAAC (SEQ ID NO: 45) | Reverse |
| RT/PCR-A/H3N2-HA-F | A/H3N2 virus HA | GTTACGCGCCAGCAAAAGCAGGG GATAATTCTATTAA (SEQ ID NO: 46) | Forward |
| RT/PCR-A/H3N2-HA-R | A/H3N2 virus HA | GTTACGCGCCAGTAGAAACAAGGG TGTTTTTTAATTAATG (SEQ ID NO: 47) | Reverse |
| RT/PCR-A/H3N2-NA-F | A/H3N2 virus NA | GTTACGCGCCAGCAAAAGCAGGA GTAAAGATG (SEQ ID NO: 48) | Forward |
| RT/PCR-A/H3N2-NA-R | A/H3N2 virus NA | GTTACGCGCCAGTAGAAACAAGGA GTTTTTTCTAAAATTGC (SEQ ID NO: 49) | Reverse |
| RT/PCR-IBV-HA-F | Influenza B virus HA | GTTACGCGCCAGCAGAAGCAGAGC ATTTTCTAATATCC (SEQ ID NO: 50) | Forward |
| RT/PCR-IBV-HA-R | Influenza B virus HA | GTTACGCGCCAGTAGTAACAAGAG CATTTTTCAATAACGTTTC (SEQ ID NO: 51) | Reverse |
| RT/PCR-IBV-NA-F | Influenza B virus NA | GTTACGCGCCAGCAGAAGCAGAGC ATCTTCTCAAAACTG (SEQ ID NO: 52) | Forward |
| RT/PCR-IBV-NA-R | Influenza B virus NA | GTTACGCGCCAGTAGTAACAAGAG CATTTTTCAGAAAC (SEQ ID NO: 53) | Reverse |
| qPCR-A/H1N1pdm-F | A/H1N1pdm virus HA | AGAAAAGAATGTAACAGTAACAC ACTCTGT (SEQ ID NO: 54) | Forward |
| qPCR-A/H1N1pdm-R | A/H1N1pdm virus HA | TGTTTC CAC AATGTARGAC CAT (SEQ ID NO: 55) | Reverse |
| qPCR-A/H3N2-F | A/H3N2 virus HA | CTATTGGACAATAGTAAAACCGGG RGA (SEQ ID NO: 56) | Forward |
| qPCR-A/H3N2-R | A/H3N2 virus HA | GTCATTGGGRATGCTTCCATTTGG (SEQ ID NO: 57) | Reverse |
| qPCR-B/Victoria-HA-F | B/Victoria virus HA | CCTGTTACATCTGGGTGCTTTCCTA TAATG (SEQ ID NO: 59) | Forward |
| qPCR-B/Victoria-HA-R | B/Victoria virus HA | GTTGATARCCTGATATGTTCGTATC CTCKG (SEQ ID NO: 60) | Reverse |
| qPCR-B/Yamagata-HA-F | B/Yamagata virus HA | CCTGTTACATCCGGGTGCTTYCCTA TAATG (SEQ ID NO: 61) | Forward |
| qPCR-B/Yamagata-HA-R | B/Yamagata virus HA | GTTGATAACCTKATIVITTTTCATAT CCTCTG (SEQ ID NO: 62) | Reverse |
| MP-39-67 For | Type A virus M | CCMAGGTCGAAACGTAYGTTCTCT CTATC (SEQ ID NO: 63) | Forward |
| MP-183-153 Rev | Type A virus M | TGACAGRATYGGTCTTGTCTTTAG CCAYTCCA (SEQ ID NO: 64) | Reverse |

TABLE 5-continued

List of primers used.

| Primer or probe | Target gene | Sequence (5'-3')[a] | Orientation |
|---|---|---|---|
| NIID-TypeB TM Primer-F1 | Type B virus NS | GGAGCAACCAATGCCAC (SEQ ID NO: 65) | Forward |
| NIID-TypeB TM Primer-R1 | Type B virus NS | GTKTAGGCGGTCTTGACCAG (SEQ ID NO: 66) | Reverse |
| FAM-A/H1N1pdm-HA-Probe | A/H1N1pdm virus HA | (FAM)CAGCCAGCAATRTTRCATTTACC(BHQ-1) (SEQ ID NO: 67) | |
| NIID-swH1 Probe2 | A/H1N1pdm virus HA | (FAM)CAGCCAGCAATRTTRCATTTACC(MGB/TAMRA) (SEQ ID NO: 68) | |
| HEX-A/H3N2-HA-Probe | A/H3N2 virus HA | (HEX)AAGTAACCCCKAGGAGCAATTAG(BHQ-1) (SEQ ID NO: 69) | |
| NIID-H3 Probe1 | A/H3N2 virus HA | (FAM)AAGTAACCCCKAGGAGCAATTAG(NIGB/TAMRA) (SEQ ID NO: 70) | |
| FAM-B/Victoria-HA-Probe | B/Victoria virus HA | (FAM)TTAGACAGCTGCCTAACC(BHQ-1) (SEQ ID NO: 71) | |
| FAM-Type B HA | Victoria B/Victoria virus HA | (FAM)TTAGACAGCTGCCTAACC(MGB/TAMRA) (SEQ ID NO: 72) | |
| HEX-B/Yamagata-HA-Probe | B/Yamagata virus HA | (HEX)TCAGGCAACTASCCAATC(BHQ-1) (SEQ ID NO: 73) | |
| FAM-Type B HA | Yamagata B/Yamagata virus HA | (FAM)TCAGGCAACTASCCAATC(MGB/TAMRA) (SEQ ID NO: 74) | |
| MP-96-75 Probe | As Type A virus M | (FAM)ATYTCGGCTTTGAGGGGGCCTG(MGB/TAMRA) (SEQ ID NO: 75) | |
| NIID-TypeB Probe1 | Type B virus NS | (FAM)ATAAACTTTGAAGCAGGAAT(MGB/TAMRA) (SEQ ID NO: 76) | |

[a]FAM, 6-carboxyfluorescein;
HEX, hexacholoro-6-carboxyfluorescein;
BHQ-1, black hole quencher;
MGB, minor groove binder;
TAMRA, 6-carboxytetramethylrhodamine.

Results

A new MDCK cell line (designated hCK) was prepared that overexpresses α2,6-sialoglycans and expresses extremely low levels of α2,3-sialoglycans to mimic the sialic acid expression pattern of human upper respiratory epithelial cells (see FIGS. 2-4 and Table A).

To determine whether hCK cells could support efficient replication of human influenza viruses, the growth kinetics of viruses [3 A/H1N1 2009 pandemic (A/H1N1pdm), 3 A/H3N2, 3 B/Yamagatalineage, and 3 B/Victoria-lineage] were examined in hCK cells. The three A/H1N1pdm isolates grew efficiently in MDCK, AX4, and hCK cells, and no substantial differences in titers were observed (FIG. 1A). The six influenza B isolates also replicated with similar efficiency in all three cell lines. By contrast, for A/H3N2 viruses, all three isolates grew much faster and to higher titers (2.03 to 2.91 log units higher at 48 h post-infection) in hCK cells than in AX4 cells. As reported elsewhere (Chambers et al., 2014), in MDCK cells, these recent A/H3N2 isolates replicate poorly. These findings demonstrate that hCK cells, which express very low levels of α2,3-sialoglycans and high levels of α2,6-sialoglycans, more efficiently support the replication of recent A/H3N2 viruses than do either MDCK or AX4 cells.

To evaluate the susceptibility of hCK cells for isolation of human influenza viruses, aliquots of 90 respiratory specimens (30 A/H1N1pdm, 30 A/H3N2, and 30 B/Yamagata-lineage) were inoculated into MDCK, AX4, and hCK cells. The cells were observed for the development of cytopathic effect (CPE) for 7 days. For MDCK, AX4, and hCK cells, A/H1N1pdm viruses were successfully recovered from all of the RT-PCR-positive samples without the need for blind passages (100% isolation efficiency) (Table 2). Similarly, these three cell lines showed 100% efficiency for the isolation of influenza B viruses. For the A/H3N2-positive samples, 5 and 2 viruses were not recovered from MDCK and AX4 cells, respectively. These results are consistent with previous reports (Oh et al., 2008; Hatakeyama et al., 2005) that conventional MDCK cells have relatively low sensitivity for the detection of recent A/H3N2 viruses.

The agglutination of red blood cells by influenza viruses is thought to be due to the virus binding to sialic acids on the surface of the cell. Since 2005, A/H3N2 isolates have lost their ability to agglutinate turkey red blood cells (Lin et al., 2013). In addition, current A/H3N2 isolates show reduced or no agglutination of guinea pig red blood cells (Lin et al., Influenza Other Respir Viruses, 2017), indicating a change in their avidity for sialic acid receptors. Indeed, Lin et al. (2013) measured the avidity of recent A/H3N2 viruses for α2,6-linked sialic acid receptors and showed that it has decreased drastically. Glycan array analysis has revealed that recent A/H3N2 isolates prefer binding to branched sialylated N-linked glycans with extended poly-N acetyllactosamine chains (Peng et al., Cell Host Microbe., 2017).

By contrast, virus isolation from hCK cells was successful with all samples without any subsequent blind passage, suggesting that this cell line is more effective than AX4 or MDCK cells for the isolation of human A/H3N2 viruses from clinical specimens.

During replication of recent A/H3N2 human isolates in MDCK cells, the viruses rapidly acquired amino acid changes at positions 148 and 151 of the NA protein (e.g., T148I and D151G), which affect the biological properties of NA. To examine whether the A/H3N2 viruses isolated from the three cell lines possessed mutations in their HA and NA proteins, the nucleotide sequences of the HA and NA segments of the isolates were determined by means of Sanger sequencing (Table 3). Sequence analysis revealed that 7 out of 25 MDCK-grown isolates contained an amino acid change at position 151 of NA compared with the sequence from the original specimens: NA-151N, NA-151D/G, and NA-151D/N (mixed populations of amino acids at position 151). Amino acid changes leading to the loss of the glycosylation site at position 158 of HA were found among virus populations of some other MDCK-grown isolates: HA-158K, HA-160K, HA-160K/I, and HA-160K/T. These changes are known to alter the antigenic properties of HA (Lin et al., 2017; Chambers et al., 2015; Skowronski et al., 2016). Importantly, cell culture-adaptive mutations were also found in the NA protein of several isolates propagated in AX4 cells: NA-148K/T, NA-148T/I, NA-151D/N, and NA-151D/G. Strikingly, no mutations were detected in hCK-grown isolates, except for only one isolate that possessed an S44P mutation in its NA stalk. These findings strongly suggest that hCK cells support the efficient growth of A/H3N2 viruses without accompanying cell culture-adaptive mutations.

Figure 1B:
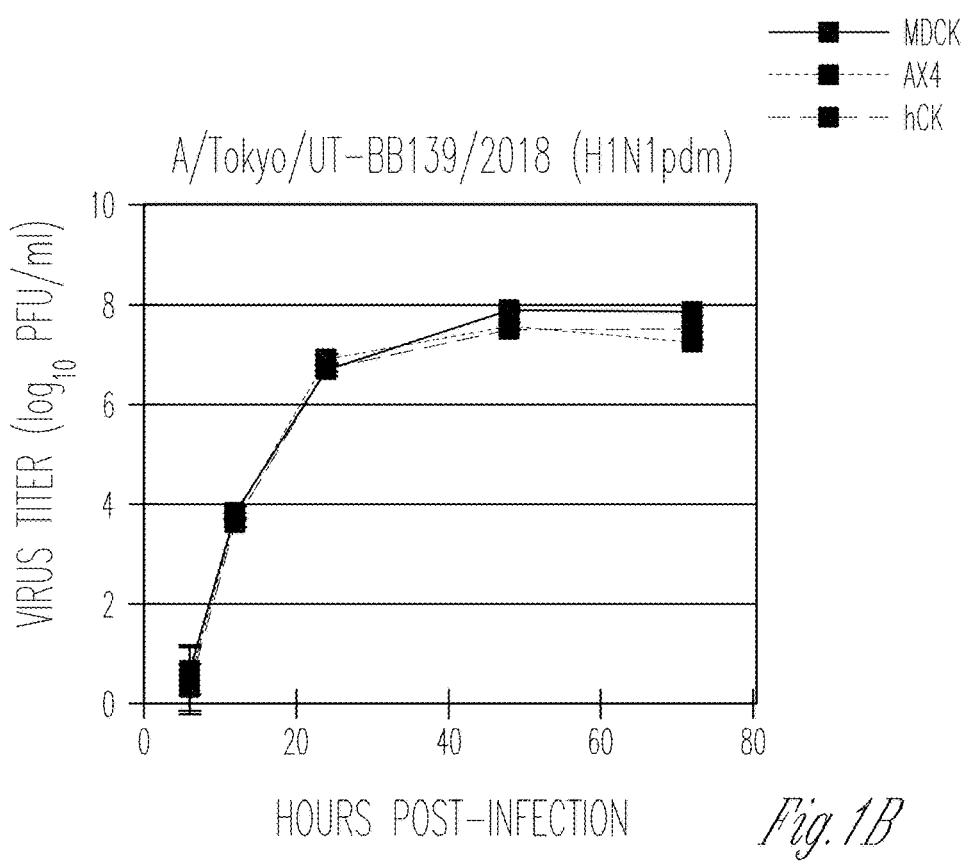
Figure 1C:
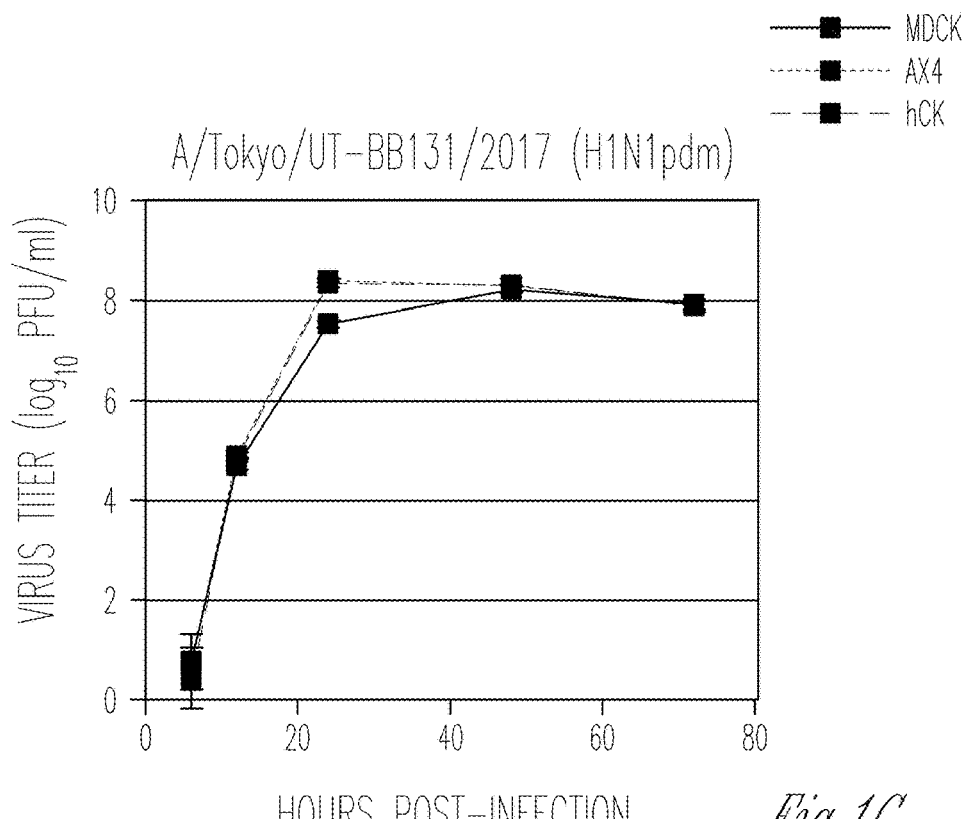
Figure 1D:
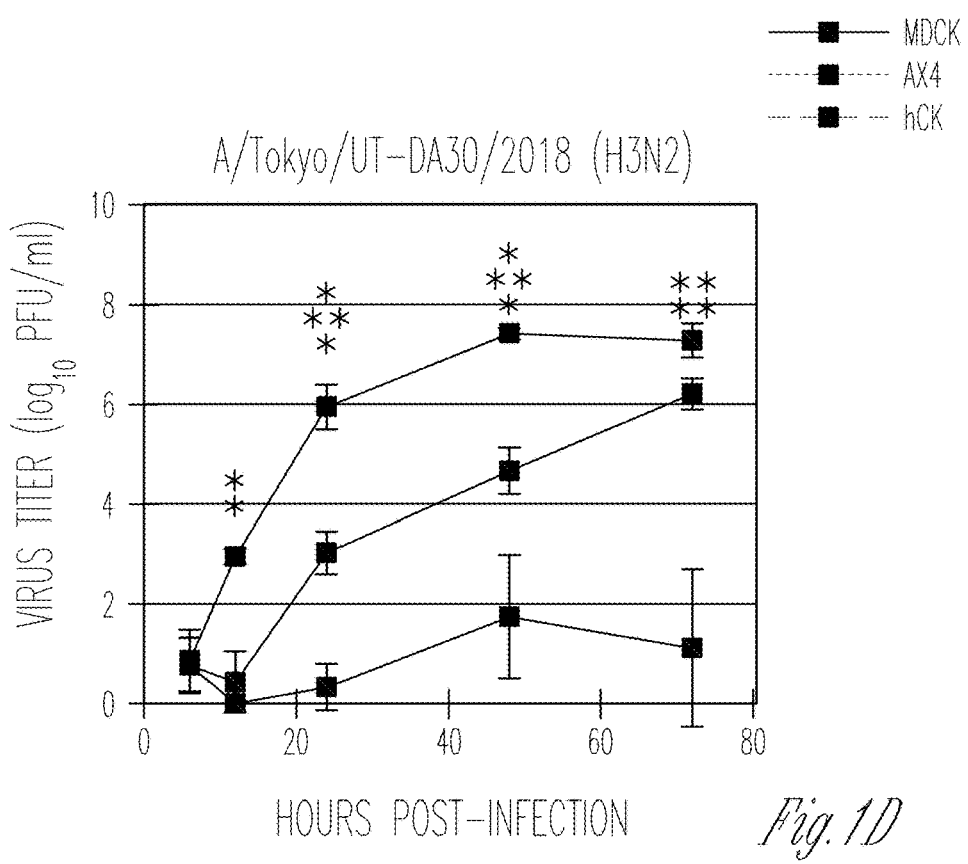
Figure 1E:
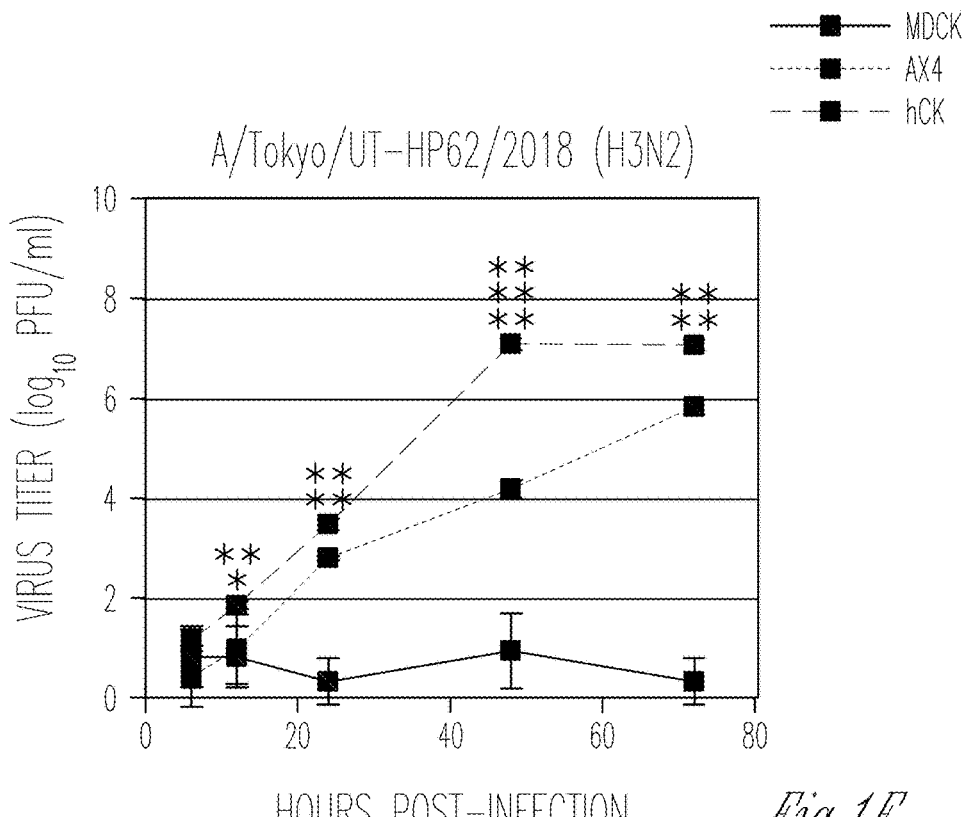
Figure 1F:
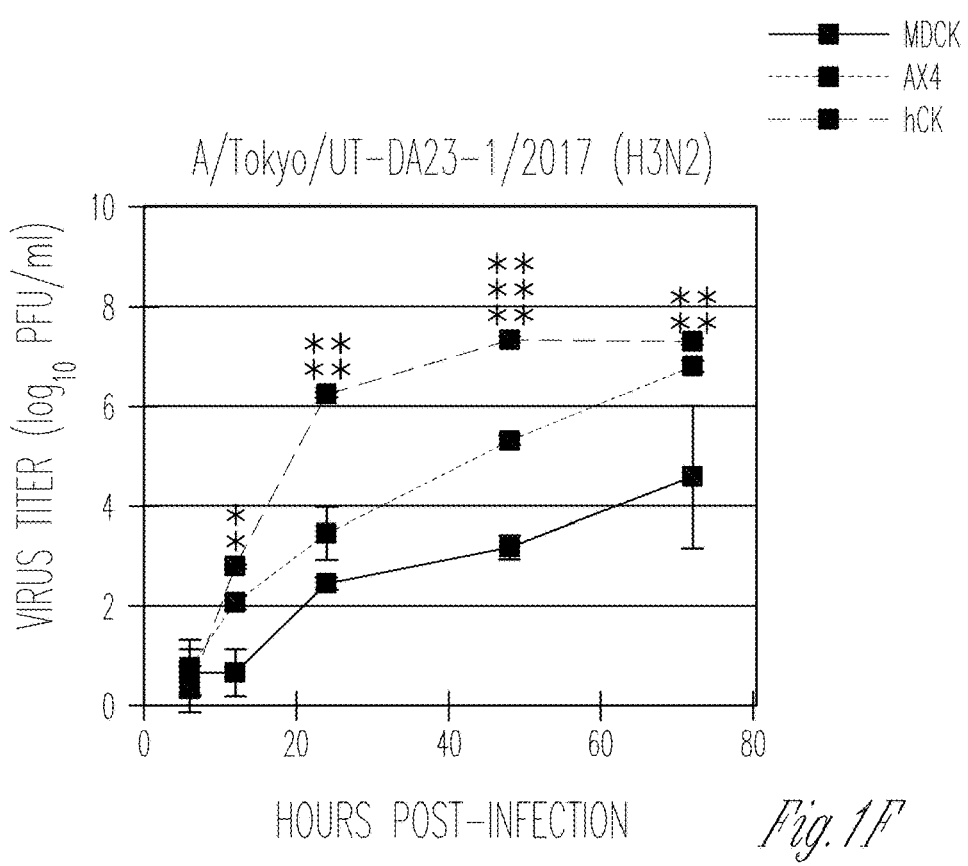
Figure 1G:
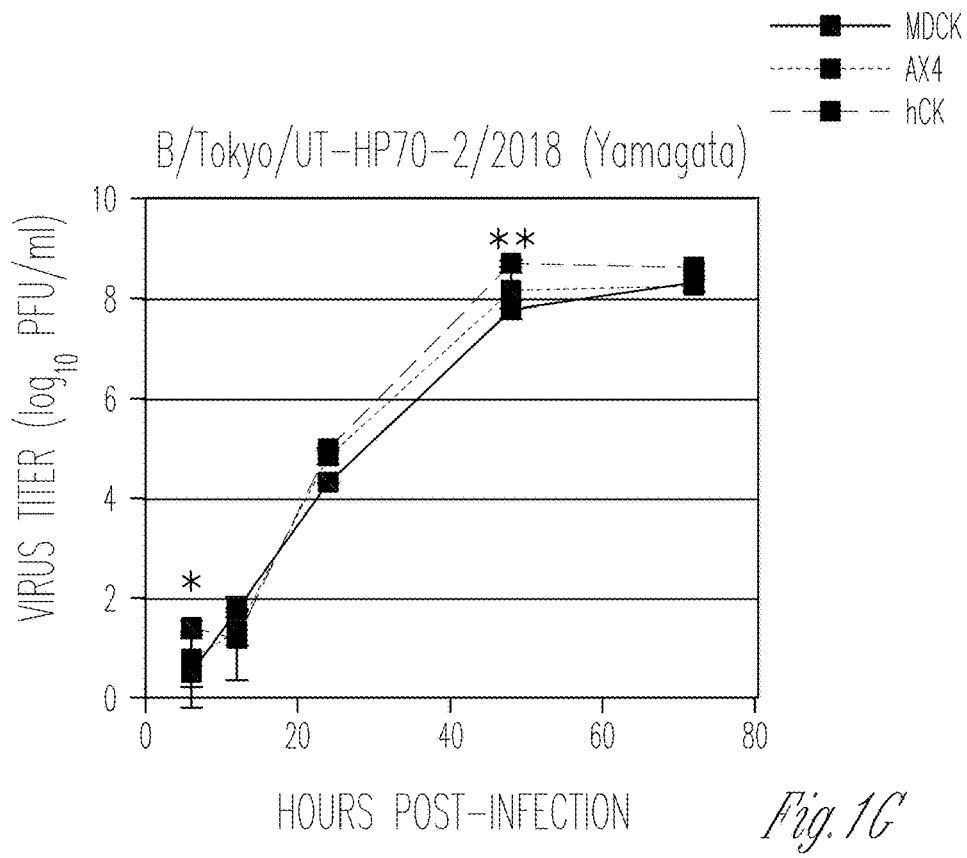
Figure 1H:
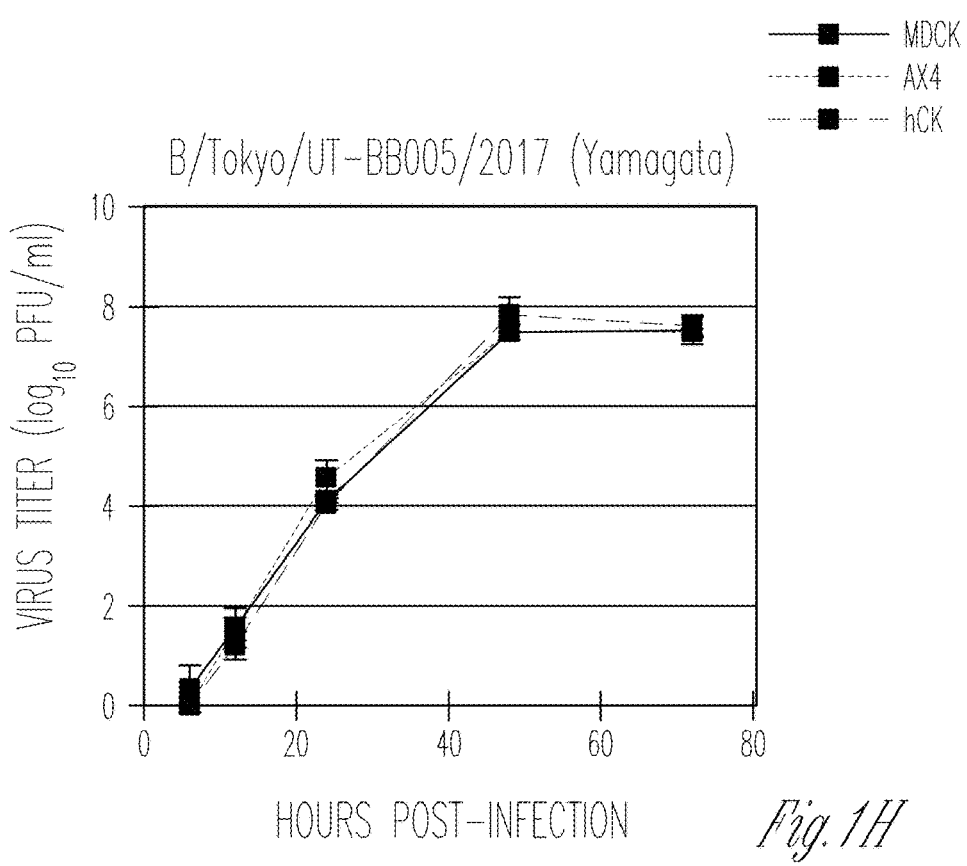
Figure 1I:
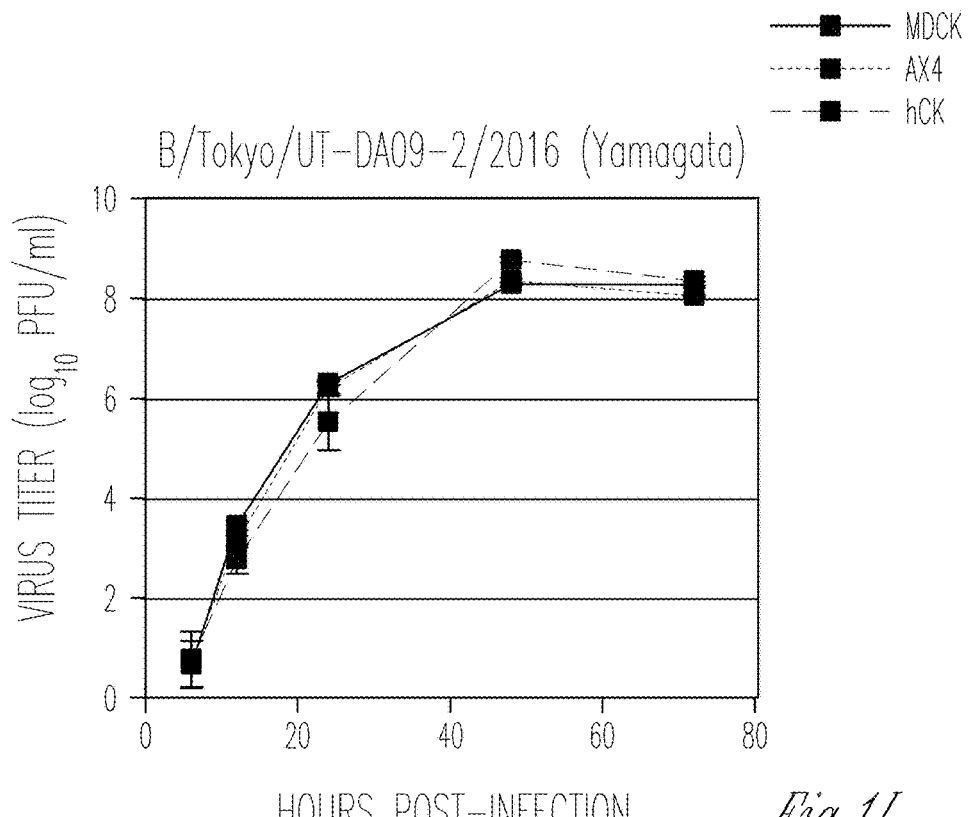
Figure 1J:
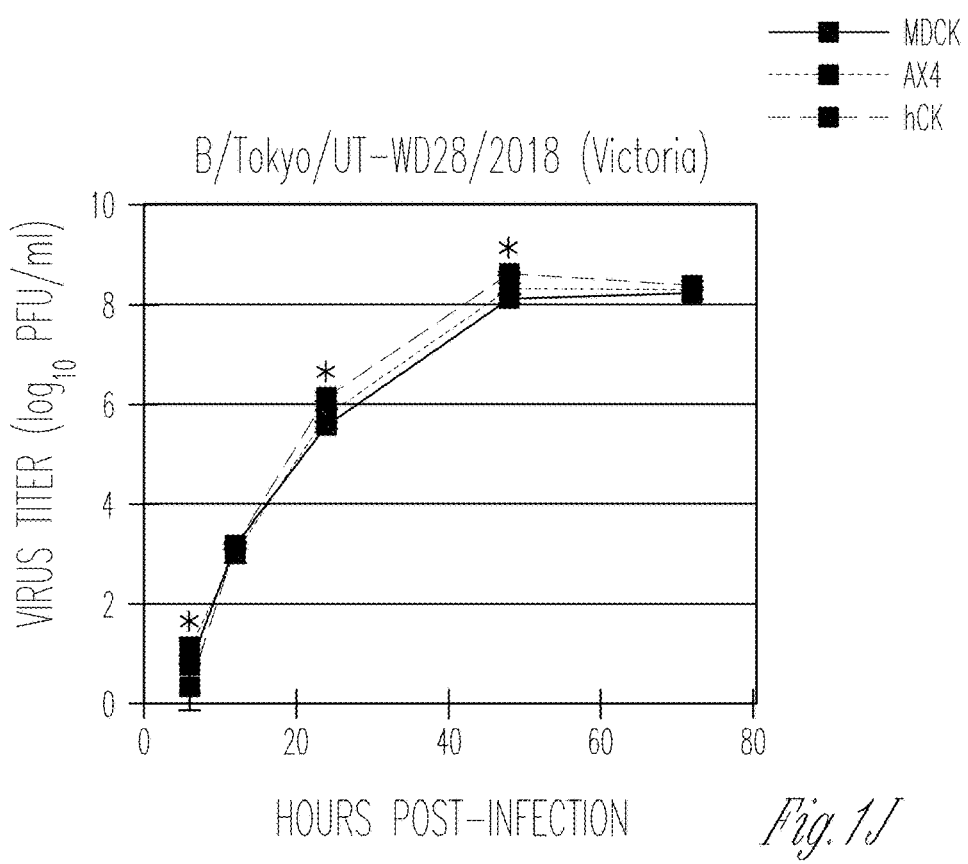
Figure 1K:
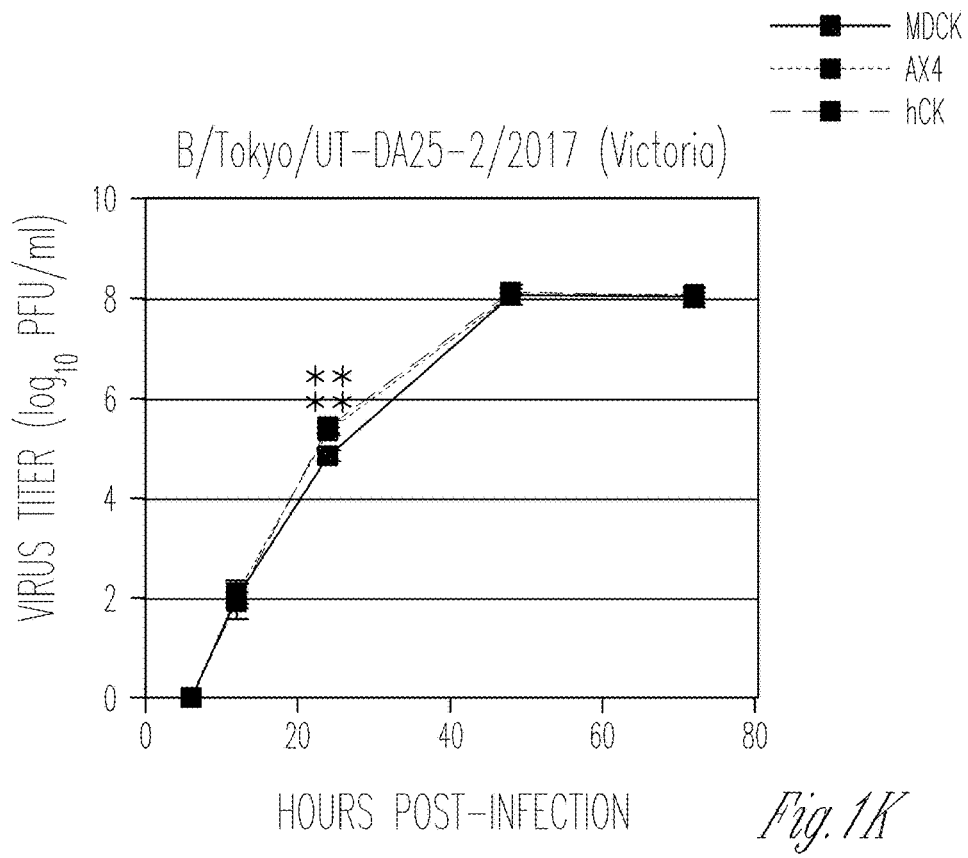
Figure 1L:
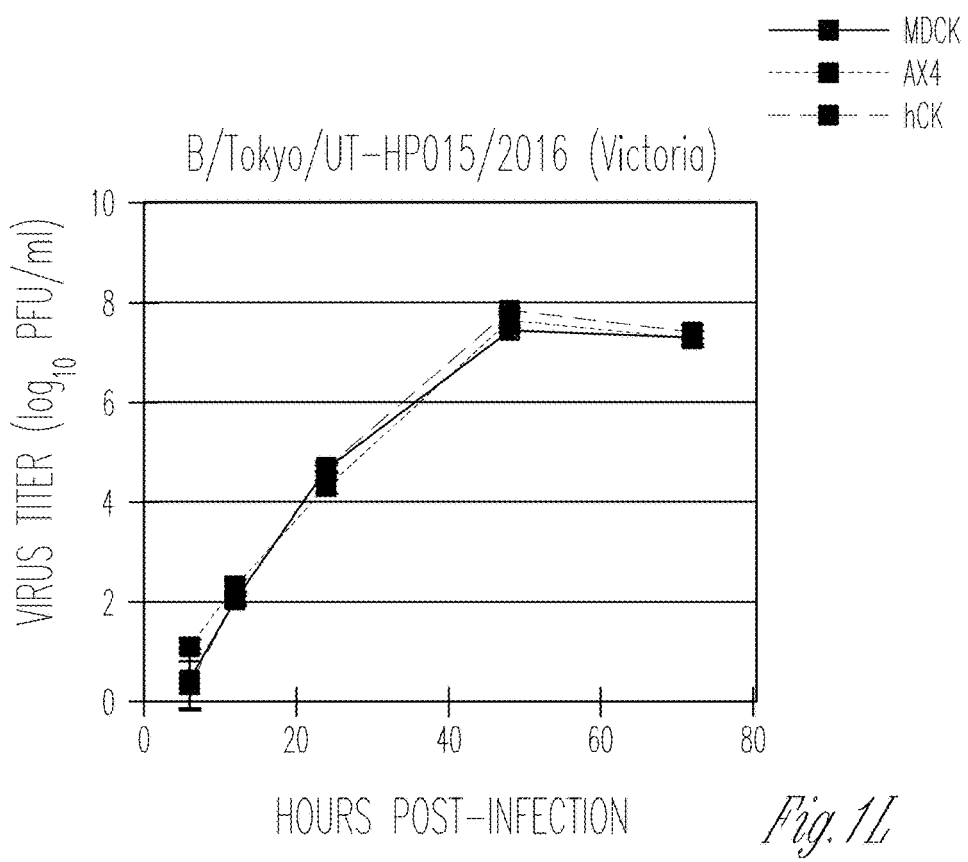
Figure 1M:
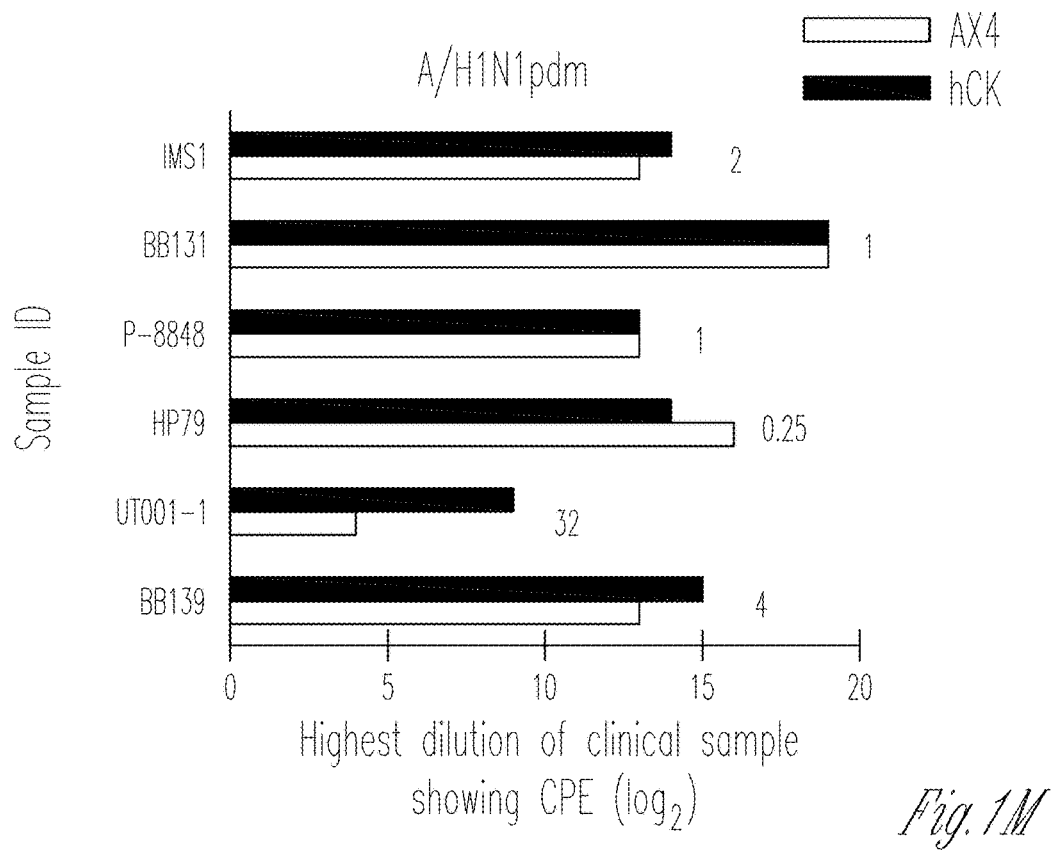
Figure 1N:
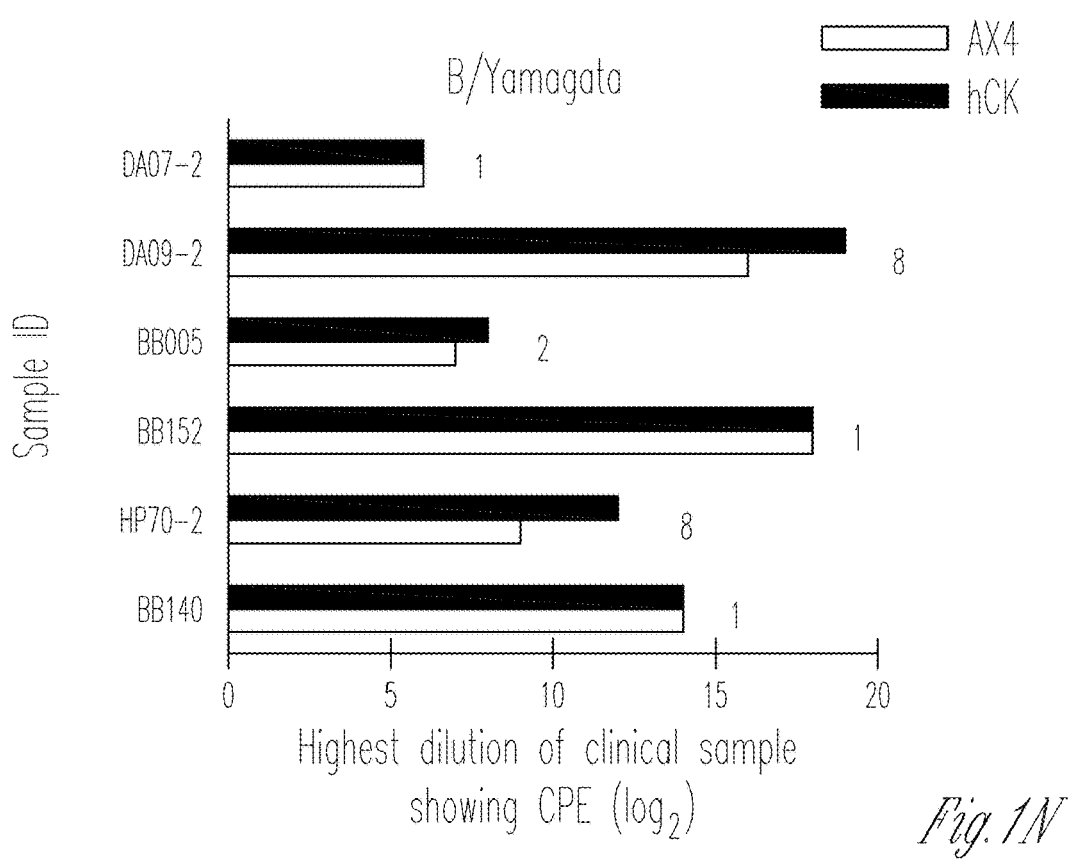
Figure 1O:
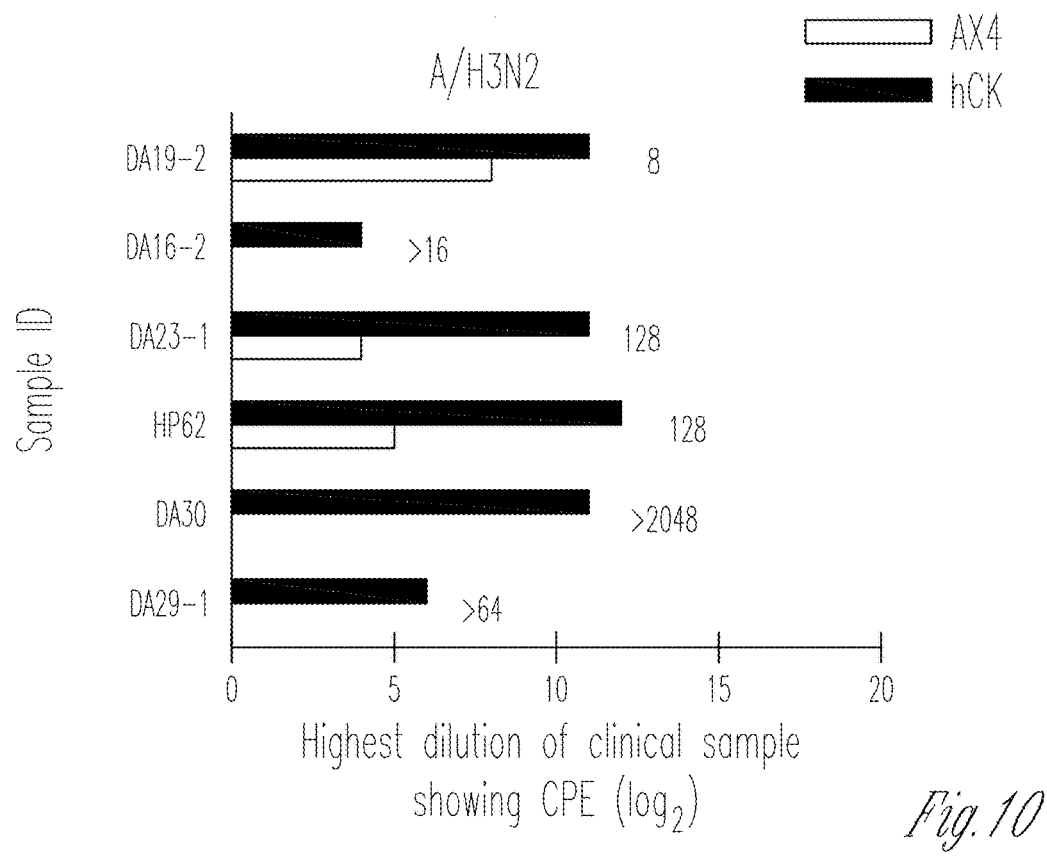
Figure 1P:
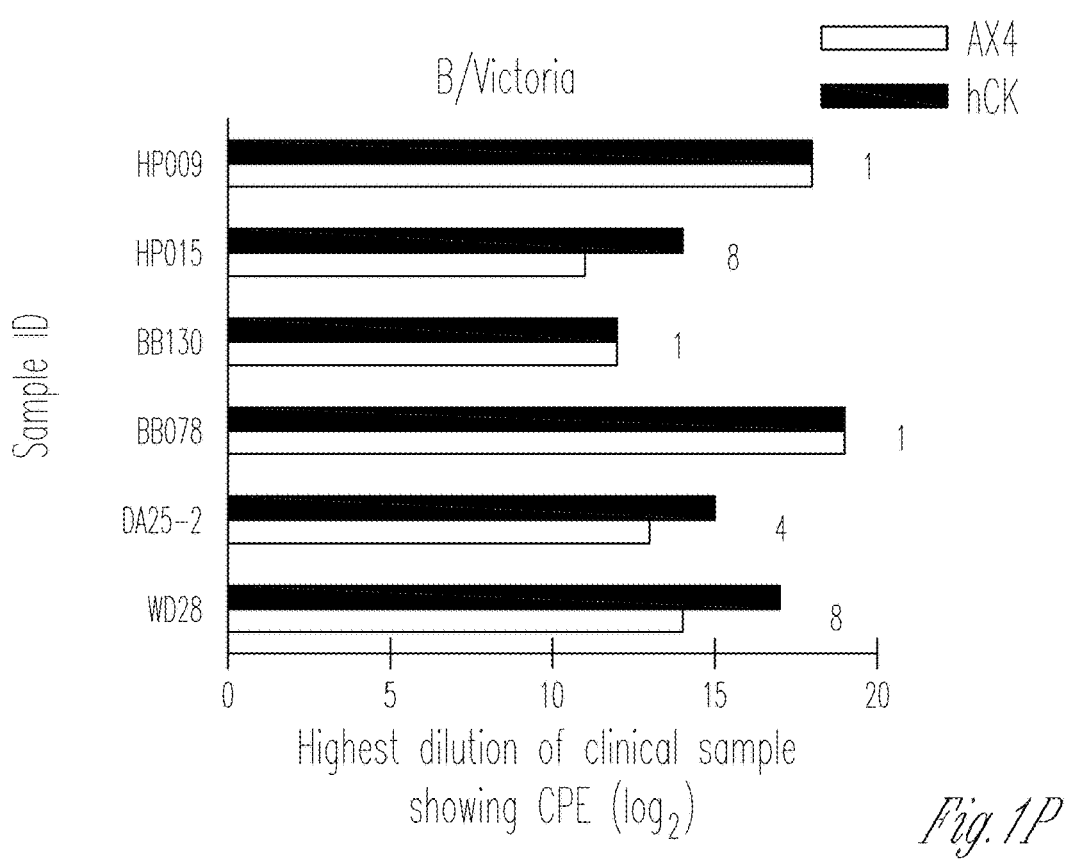

Seasonal influenza viruses from clinical specimens grow better in AX4 cells than in MDCK cells (Hatakeyama et al., 2005). To determine whether hCK cells are superior to AX4 cells for virus isolation, the sensitivity of hCK and AX4 cells were compared by testing serial 2-fold dilutions of specimens. Aliquots of 24 specimens (6 A/H1N1pdm, 6 A/H3N2, 6 B/Yamagata-lineage, and 6 B/Victoria-lineage) were inoculated into AX4 and hCK cells in triplicate. All culture wells were examined for CPE on day 7 post-inoculation, and the ratios of the highest dilutions showing CPE observed in hCK cells to those in AX4 cells were determined. For one of the six A/H1N1pdm-positive samples (sample ID, HP79), hCK cells were slightly less sensitive than AX4 cells (FIG. 1B and Table 4). For the remaining samples, however, the sensitivity of hCK cells was similar to or greater than that of AX4 cells. For the B/Yamagata- and B/Victoria-lineage-positive samples, hCK cells showed sensitivities equal to or somewhat greater than that of AX4 cells. For all of the A/H3N2-positive samples, hCK cells showed greater sensitivity than AX4 cells; for some samples, hCK cells were approximately 100- to 2,000-fold more sensitive than AX4 cells. Taken together, these results indicate that hCK cells are more suitable than AX4 or MDCK cells for the primary isolation of recent seasonal A/H3N2 viruses.

To evaluate the genetic stability of the HA and NA genes of viruses isolated in hCK cells, aliquots of 12 clinical specimens (3 A/H1N1pdm, 3 A/H3N2, and 3 B/Yamagata-lineage, and 3 B/Victoria-lineage) were inoculated into MDCK, AX4, and hCK cells, and the isolates were sequentially passaged ten times. After the first, sixth, and tenth passages, the HA and NA sequences of the viruses were determined by Sanger sequencing, and the sequences were compared to those in the clinical specimens. For A/H1N1pdm-positive specimens, a mixed viral population encoding either N or S at position 296 of HA was detected in one out of the three hCK-grown viruses (BB139) after the first passage (Table 1). The hCK-grown virus also possessed an S153G substitution mutation in its NA. Another hCK-grown virus (HP79) encoded a D27N substitution in its HA after the tenth passage. A mixed population encoding either T or I at position 167 of HA was found in one MDCK-grown virus after the tenth passage (BB139). Another MDCK-grown virus (BB131) had a mixed population encoding HA-446N and HA-446S at passage ten. The MDCK-grown virus also contained a mixed population encoding either H or Y at position 411c of NA. A mixture of C53Y/C in NA was observed in one AX4-grown virus after the tenth passage (BB131).

For A/H3N2-positive samples, viruses that were recovered from AX4 and hCK, but not MDCK, cells were serially passaged. After the sixth passage, a mixed population encoding HA-158N and HA-158K (leading to the loss of the glycosylation site at position 158 of HA) was detected in one of the three AX4-grown viruses (DA30). In addition, another AX4-grown virus (DA29-1) encoded a T148K substitution in its NA after the sixth passage. A mixed population encoding HA-408D and HA-408N was detected in one hCK-grown virus after the tenth passage (DA29-1).

For B/Yamagata-lineage viruses, no changes were detected in any isolates after the first, sixth, or tenth passages, with the exception of a mixed population encoding HA-148S and HA-148N detected in one hCK-grown virus at passage six (HP70-2). For B/Victoria lineage viruses, a mixed population encoding NA-208G and NA-208R was found in one of the three AX4-grown viruses (BB139) after the first passage. After the sixth passage, one hCK-grown viruses encoded a mixture of L72L/F in its NA (WD28). At passage ten, one MDCK-grown virus (WD28) contained an N196S mutation known to lead to the loss of the glycosylation site at position 196 of HA (B/Victoria-lineage), which can significantly alter the antigenicity of influenza B viruses. Another MDCK-grown virus (HP015) had a mixture of D459D/N in its NA.

Overall, A/H1N1pdm and B viruses were slightly more variable when passaged in MDCK or hCK cells than in AX4 cells. In contrast, A/H3N2 viruses propagated in hCK cells maintained higher genetic stability than those in AX4 cells.

In conclusion, a cell line derived from MDCK cells, hCK, expresses large amounts of α2,6-sialoglycans and small amounts of α2,3-sialoglycans that will be useful for influenza virus research, particularly studies involving human A/H3N2 influenza viruses and possibly for vaccine production.

REFERENCES

Bates et al., *J. Stat. Softw.,* 61:1 (2015).
Chambers et al., *Cell Rep.,* 12:1 (2015).
Chambers et al., *J. Viral,* 88:10986 (2014).
Chu and Whittaker, *Proc. Natl. Acad. Sci. U.S.A.,* 101:18153 (2004).
Cong et al., *Science,* 339:819 (2013).
Connor et al., *Virology,* 205:17 (1994).
Gamblin and Skehel, *J. Biol. Chem.,* 285:28403 (2010).
Han et al., *Cell Rep.,* 23:596 (2018).
Hatakeyama et al., *J. Clin. Microbiol.,* 43:4139 (2005).
Hegde, *Hum. Vaccine Immunother.,* 11:1223 (2015).
Hidari et al., *Biochem. Biophys. Res. Commun.,* 436:394 (2013).
Jinek et al., *Science,* 337:816 (2012).
Lee et al., *PLoS One* 8 (2013).
Lenth, *J. Stat. Softw.,* 69 (2016)
Li et al., *J. Clin. Microbial.,* 47:466 (2009).
Lin et al., *Influenza Other Respir Viruses,* 11:263 (2017).
Lin et al., *J. Viral.,* 84:6769 (2010).
Lin et al., *PLoS One,* 12, 72299 (2017).
Matrosovich et al., *Journal of Virology,* 77:8418 (2003).
Mohr et al., *Viral J.,* 12:67 (2015).
Oh et al., *J. Clin. Microbiol.,* 46:2189 (2008).
Rogers and Paulson, *Virology,* 127:361 (1983).
Shalem et al., *Science.* 343:84 (2014).
Shibuya et al., *J Biochem.,* 106:1098 (1989).
Shinya et al., *Nature,* 440:435 (2006).
Skowronski et al., *Euro. Surveill.,* 21:30112 (2016).
Stevens et al., *J. Mal. Biol.,* 355:1143 (2006).
Takashima and Tsuji, *Trends in Glycoscience and Glycotechnology,* 23:178 (2011).
Tamura et al., *Antimicrob. Agents Chemother.,* 57:6141 (2013).
van Riel et al., *Science,* 312:399 (2006).
Zhu et al., *J. Viral.,* 86:13371 (2012).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The claims are as follows:

1. An isolated recombinant canine cell, comprising a reduced amount of cell surface β-galactoside α2,3 sialyl residues relative to a corresponding non-recombinant canine cell, wherein seven different β-galactoside α2,3 sialyltransferase (ST3) genes are mutated so as to reduce the amount of the cell surface β-galactoside α2,3 sialyl residues, wherein the seven different genes include ST3Gal-I, ST3Gal-II, ST3Gal-III, ST3Gal-IV, ST3Gal-V, ST3Gal-VI, and ST3Gal-II-like genes, and wherein the recombinant canine cell comprises an expression cassette encoding human β-galactoside α2,6 sialyltransferase I (ST6Gal-I) or ST6Gal-II, wherein the reduced amount of cell surface 3-galactoside α2,3 sialyl residues is the result of recombinase knock out mutation of the plurality of ST3 genes in the recombinant cell, and wherein the recombinant canine cell provides for increased human influenza virus replication relative to the corresponding non-recombinant canine cell.

2. The isolated recombinant cell of claim 1 further comprising an increased amount of human β-galactoside α2,6 sialyl residues relative to a corresponding non-recombinant canine cell.

3. The isolated recombinant cell of claim 1 which comprises an expression cassette encoding human β-galactoside α2,6 sialyltransferase I (ST6Gal-I).

4. A method of modifying the amount of cell surface β-galactoside α2,3 sialyl residues and human β-galactoside α2,6 sialyl residues on a canine cell, comprising:
   mutating seven different β-galactoside α2,3 sialyltransferase (ST3Gal) genes, wherein the seven different genes include ST3Gal-I, ST3Gal-II, ST3Gal-III, ST3Gal-IV, ST3Gal-V, ST3Gal-VI, and ST3Gal-II-like genes, and overexpressing a human β-galactoside α2,6 sialyltransferase (ST6Gal) gene, in a parental canine cell so as to result in a modified canine cell having a reduced amount of cell surface β-galactoside α2,3 sialyl residues and an increased amount of human β-galactoside α2,6 sialyl residues on the surface of the modified cell relative to the corresponding parental canine cell.

5. The method of claim 4 wherein the mutations include one or more nucleotide insertions or one or more nucleotide deletions, or both, in the seven different ST3 genes.

6. The method of claim 4 wherein the modified cell comprises an expression cassette comprising a ST6Gal open reading frame.

7. A method of detecting or propagating an influenza virus, comprising:
   infecting the recombinant cell of claim 2 with a sample having or suspected of having an influenza virus.

8. The method of claim 7 further comprising collecting progeny virus.

9. The method of claim 7 wherein the sample is from an avian or a mammal suspected of being infected with an influenza virus.

10. The method of claim 7 wherein the influenza virus is a human influenza virus.

11. The method of claim 7 wherein the influenza virus is an influenza A or B virus.

12. The method of claim 7 wherein the influenza virus is a H3 virus.

13. The method of claim 7 wherein the influenza virus is A/H1N1, A/H3N2, a B/Yamagata-lineage influenza B virus or a B/Victoria-lineage influenza B virus.

14. The method of claim 7 further comprising detecting whether the sample is infected with an influenza virus.

15. The method of claim 14 further comprising identifying the HA and/or NA subtype of the virus.

16. An isolated recombinant MDCK cell comprising a reduced amount of cell surface β-galactoside α2,3 sialyl residues relative to a parental MDCK cell, wherein seven β-galactoside α2,3 sialyltransferase (ST3) genes are mutated so as to reduce the amount of the cell surface β-galactoside α2,3 sialyl residues, and wherein the recombinant MDCK cell comprises an expression cassette encoding human β-galactoside α2,6 sialyltransferase I (ST6Gal-I) or ST6Gal-II, wherein the reduced amount of cell surface β-galactoside α2,3 sialyl residues is the result of recombinase knock out mutation of ST3Gal-I, ST3Gal-II, ST3Gal-III, ST3Gal-IV, ST3Gal-V, ST3Gal-VI, and ST3Gal-II-like genes in the recombinant MDCK cell.

17. The isolated recombinant canine cell of claim 1 which is infected with human influenza virus.

* * * * *

SEQUENCE LISTING

```
<160> NUMBER OF SEQ ID NOS: 151

<210> SEQ ID NO 1
<211> LENGTH: 406
<212> TYPE: PRT
<213> ORGANISM: Homo sapiens

<400> SEQUENCE: 1

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
        115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
```

```
                145                 150                 155                 160
Asn Thr Ser Glu Trp Glu Gly Tyr Leu Pro Lys Glu Ser Ile Arg Thr
                165                 170                 175

Lys Ala Gly Pro Trp Arg Cys Ala Val Val Ser Ser Ala Gly Ser
                180                 185                 190

Leu Lys Ser Ser Gln Leu Gly Arg Glu Ile Asp Asp His Asp Ala Val
                195                 200                 205

Leu Arg Phe Asn Gly Ala Pro Thr Ala Asn Phe Gln Gln Asp Val Gly
    210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Tyr Gln Asn
    260                 265                 270

Pro Asp Tyr Asn Phe Phe Asn Asn Tyr Lys Thr Tyr Arg Lys Leu His
                275                 280                 285

Pro Asn Gln Pro Phe Tyr Ile Leu Lys Pro Gln Met Pro Trp Glu Leu
    290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
                340                 345                 350

Cys Tyr Tyr Tyr Gln Lys Phe Phe Asp Ser Ala Cys Thr Met Gly Ala
                355                 360                 365

Tyr His Pro Leu Leu Tyr Glu Lys Asn Leu Val Lys His Leu Asn Gln
                370                 375                 380

Gly Thr Asp Glu Asp Ile Tyr Leu Leu Gly Lys Ala Thr Leu Pro Gly
385                 390                 395                 400

Phe Arg Thr Ile His Cys
                405

<210> SEQ ID NO 2
<211> LENGTH: 529
<212> TYPE: PRT
<213> ORGANISM: Homo sapiens

<400> SEQUENCE: 2

Met Lys Pro His Leu Lys Gln Trp Arg Gln Arg Met Leu Phe Gly Ile
1                   5                   10                  15

Phe Ala Trp Gly Leu Leu Phe Leu Leu Ile Phe Ile Tyr Phe Thr Asp
                20                  25                  30

Ser Asn Pro Ala Glu Pro Val Pro Ser Ser Leu Ser Phe Leu Glu Thr
                35                  40                  45

Arg Arg Leu Leu Pro Val Gln Gly Lys Gln Arg Ala Ile Met Gly Ala
        50                  55                  60

Ala His Glu Pro Ser Pro Pro Gly Gly Leu Asp Ala Arg Gln Ala Leu
65                  70                  75                  80

Pro Arg Ala His Pro Ala Gly Ser Phe His Ala Gly Pro Gly Asp Leu
                85                  90                  95

Gln Lys Trp Ala Gln Ser Gln Asp Gly Phe Glu His Lys Glu Phe Phe
                100                 105                 110
```

```
Ser Ser Gln Val Gly Arg Lys Ser Gln Ser Ala Phe Tyr Pro Glu Asp
        115                 120                 125

Asp Asp Tyr Phe Phe Ala Ala Gly Gln Pro Gly Trp His Ser His Thr
130                 135                 140

Gln Gly Thr Leu Gly Phe Pro Ser Pro Gly Glu Pro Gly Pro Arg Glu
145                 150                 155                 160

Gly Ala Phe Pro Ala Ala Gln Val Gln Arg Arg Val Lys Lys Arg
                165                 170                 175

His Arg Arg Gln Arg Arg Ser His Val Leu Glu Glu Gly Asp Asp Gly
        180                 185                 190

Asp Arg Leu Tyr Ser Ser Met Ser Arg Ala Phe Leu Tyr Arg Leu Trp
        195                 200                 205

Lys Gly Asn Val Ser Ser Lys Met Leu Asn Pro Arg Leu Gln Lys Ala
        210                 215                 220

Met Lys Asp Tyr Leu Thr Ala Asn Lys His Gly Val Arg Phe Arg Gly
225                 230                 235                 240

Lys Arg Glu Ala Gly Leu Ser Arg Ala Gln Leu Leu Cys Gln Leu Arg
                245                 250                 255

Ser Arg Ala Arg Val Arg Thr Leu Asp Gly Thr Glu Ala Pro Phe Ser
        260                 265                 270

Ala Leu Gly Trp Arg Arg Leu Val Pro Ala Val Pro Leu Ser Gln Leu
        275                 280                 285

His Pro Arg Gly Leu Arg Ser Cys Ala Val Val Met Ser Ala Gly Ala
        290                 295                 300

Ile Leu Asn Ser Ser Leu Gly Glu Glu Ile Asp Ser His Asp Ala Val
305                 310                 315                 320

Leu Arg Phe Asn Ser Ala Pro Thr Arg Gly Tyr Glu Lys Asp Val Gly
                325                 330                 335

Asn Lys Thr Thr Ile Arg Ile Ile Asn Ser Gln Ile Leu Thr Asn Pro
        340                 345                 350

Ser His His Phe Ile Asp Ser Ser Leu Tyr Lys Asp Val Ile Leu Val
        355                 360                 365

Ala Trp Asp Pro Ala Pro Tyr Ser Ala Asn Leu Asn Leu Trp Tyr Lys
        370                 375                 380

Lys Pro Asp Tyr Asn Leu Phe Thr Pro Tyr Ile Gln His Arg Gln Arg
385                 390                 395                 400

Asn Pro Asn Gln Pro Phe Tyr Ile Leu His Pro Lys Phe Ile Trp Gln
                405                 410                 415

Leu Trp Asp Ile Ile Gln Glu Asn Thr Lys Glu Lys Ile Gln Pro Asn
        420                 425                 430

Pro Pro Ser Ser Gly Phe Ile Gly Ile Leu Ile Met Met Ser Met Cys
        435                 440                 445

Arg Glu Val His Val Tyr Glu Tyr Ile Pro Ser Val Arg Gln Thr Glu
450                 455                 460

Leu Cys His Tyr His Glu Leu Tyr Tyr Asp Ala Ala Cys Thr Leu Gly
465                 470                 475                 480

Ala Tyr His Pro Leu Leu Tyr Glu Lys Leu Leu Val Gln Arg Leu Asn
                485                 490                 495

Met Gly Thr Gln Gly Asp Leu His Arg Lys Gly Lys Val Val Leu Pro
        500                 505                 510

Gly Phe Gln Ala Val His Cys Pro Ala Pro Ser Pro Val Ile Pro His
        515                 520                 525

Ser
```

<210> SEQ ID NO 3
<211> LENGTH: 353
<212> TYPE: PRT
<213> ORGANISM: Homo sapiens

<400> SEQUENCE: 3

Ala Ala Met Gly Ser Asp Ser Gln Ser Val Ser Ser Ser Thr Gln
1               5                   10                  15

Asp Pro His Arg Gly Arg Gln Thr Leu Gly Ser Leu Arg Gly Leu Ala
                20                  25                  30

Lys Ala Lys Pro Glu Ala Ser Phe Gln Val Trp Asn Lys Asp Ser Ser
            35                  40                  45

Ser Lys Asn Leu Ile Pro Arg Leu Gln Lys Ile Trp Lys Asn Tyr Leu
50                  55                  60

Ser Met Asn Lys Tyr Lys Val Ser Tyr Lys Gly Pro Gly Pro Gly Ile
65                  70                  75                  80

Lys Phe Ser Ala Glu Ala Leu Arg Cys His Leu Arg Asp His Val Asn
                85                  90                  95

Val Ser Met Val Glu Val Thr Asp Phe Pro Phe Asn Thr Ser Glu Trp
            100                 105                 110

Glu Gly Tyr Leu Pro Lys Glu Ser Ile Arg Thr Lys Ala Gly Pro Trp
        115                 120                 125

Gly Arg Cys Ala Val Val Ser Ser Ala Gly Ser Leu Lys Ser Ser Gln
130                 135                 140

Leu Gly Arg Glu Ile Asp Asp His Asp Ala Val Leu Arg Phe Asn Gly
145                 150                 155                 160

Ala Pro Thr Ala Asn Phe Gln Gln Asp Val Gly Thr Lys Thr Thr Ile
                165                 170                 175

Arg Leu Met Asn Ser Gln Leu Val Thr Thr Glu Lys Arg Phe Leu Lys
            180                 185                 190

Asp Ser Leu Tyr Asn Glu Gly Ile Leu Ile Val Trp Asp Pro Ser Val
        195                 200                 205

Tyr His Ser Asp Ile Pro Lys Trp Tyr Gln Asn Pro Asp Tyr Asn Phe
210                 215                 220

Phe Asn Asn Tyr Lys Thr Tyr Arg Lys Leu His Pro Asn Gln Pro Phe
225                 230                 235                 240

Tyr Ile Leu Lys Pro Gln Met Pro Trp Glu Leu Trp Asp Ile Leu Gln
                245                 250                 255

Glu Ile Ser Pro Glu Glu Ile Gln Pro Asn Pro Pro Ser Ser Gly Met
            260                 265                 270

Leu Gly Ile Ile Ile Met Met Thr Leu Cys Asp Gln Val Asp Ile Tyr
        275                 280                 285

Glu Phe Leu Pro Ser Lys Arg Lys Thr Asp Val Cys Tyr Tyr Tyr Gln
290                 295                 300

Lys Phe Phe Asp Ser Ala Cys Thr Met Gly Ala Tyr His Pro Leu Leu
305                 310                 315                 320

Tyr Glu Lys Asn Leu Val Lys His Leu Asn Gln Gly Thr Asp Glu Asp
                325                 330                 335

Ile Tyr Leu Leu Gly Lys Ala Thr Leu Pro Gly Phe Arg Thr Ile His
            340                 345                 350

Cys

<210> SEQ ID NO 4

-continued

```
<211> LENGTH: 529
<212> TYPE: PRT
<213> ORGANISM: Homo sapiens

<400> SEQUENCE: 4

Met Lys Pro His Leu Lys Gln Trp Arg Gln Arg Met Leu Phe Gly Ile
1               5                   10                  15

Phe Ala Trp Gly Leu Leu Phe Leu Leu Ile Phe Ile Tyr Phe Thr Asp
            20                  25                  30

Ser Asn Pro Ala Glu Pro Val Pro Ser Ser Leu Ser Phe Leu Glu Thr
        35                  40                  45

Arg Arg Leu Leu Pro Val Gln Gly Lys Gln Arg Ala Ile Met Gly Ala
50                  55                  60

Ala His Glu Pro Ser Pro Gly Gly Leu Asp Ala Arg Gln Ala Leu
65                  70                  75                  80

Pro Arg Ala His Pro Ala Gly Ser Phe His Ala Gly Pro Gly Asp Leu
                85                  90                  95

Gln Lys Trp Ala Gln Ser Gln Asp Gly Phe Glu His Lys Glu Phe Phe
            100                 105                 110

Ser Ser Gln Val Gly Arg Lys Ser Gln Ser Ala Phe Tyr Pro Glu Asp
        115                 120                 125

Asp Asp Tyr Phe Phe Ala Ala Gly Gln Pro Gly Trp His Ser His Thr
130                 135                 140

Gln Gly Thr Leu Gly Phe Pro Ser Pro Gly Glu Pro Gly Pro Arg Glu
145                 150                 155                 160

Gly Ala Phe Pro Ala Ala Gln Val Gln Arg Arg Val Lys Lys Arg
                165                 170                 175

His Arg Arg Gln Arg Arg Ser His Val Leu Glu Glu Gly Asp Asp Gly
            180                 185                 190

Asp Arg Leu Tyr Ser Ser Met Ser Arg Ala Phe Leu Tyr Arg Leu Trp
        195                 200                 205

Lys Gly Asn Val Ser Ser Lys Met Leu Asn Pro Arg Leu Gln Lys Ala
210                 215                 220

Met Lys Asp Tyr Leu Thr Ala Asn Lys His Gly Val Arg Phe Arg Gly
225                 230                 235                 240

Lys Arg Glu Ala Gly Leu Ser Arg Ala Gln Leu Leu Cys Gln Leu Arg
                245                 250                 255

Ser Arg Ala Arg Val Arg Thr Leu Asp Gly Thr Glu Ala Pro Phe Ser
            260                 265                 270

Ala Leu Gly Trp Arg Arg Leu Val Pro Ala Val Pro Leu Ser Gln Leu
        275                 280                 285

His Pro Arg Gly Leu Arg Ser Cys Ala Val Val Met Ser Ala Gly Ala
290                 295                 300

Ile Leu Asn Ser Ser Leu Gly Glu Glu Ile Asp Ser His Asp Ala Val
305                 310                 315                 320

Leu Arg Phe Asn Ser Ala Pro Thr Arg Gly Tyr Glu Lys Asp Val Gly
                325                 330                 335

Asn Lys Thr Thr Ile Arg Ile Ile Asn Ser Gln Ile Leu Thr Asn Pro
            340                 345                 350

Ser His His Phe Ile Asp Ser Ser Leu Tyr Lys Asp Val Ile Leu Val
        355                 360                 365

Ala Trp Asp Pro Ala Pro Tyr Ser Ala Asn Leu Asn Leu Trp Tyr Lys
370                 375                 380

Lys Pro Asp Tyr Asn Leu Phe Thr Pro Tyr Ile Gln His Arg Gln Arg
```

```
                385                 390                 395                 400
Asn Pro Asn Gln Pro Phe Tyr Ile Leu His Pro Lys Phe Ile Trp Gln
            405                 410                 415
Leu Trp Asp Ile Ile Gln Glu Asn Thr Lys Glu Lys Ile Gln Pro Asn
            420                 425                 430
Pro Pro Ser Ser Gly Phe Ile Gly Ile Leu Ile Met Met Ser Met Cys
            435                 440                 445
Arg Glu Val His Val Tyr Glu Tyr Ile Pro Ser Val Arg Gln Thr Glu
        450                 455                 460
Leu Cys His Tyr His Glu Leu Tyr Tyr Asp Ala Ala Cys Thr Leu Gly
465                 470                 475                 480
Ala Tyr His Pro Leu Leu Tyr Glu Lys Leu Leu Val Gln Arg Leu Asn
                485                 490                 495
Met Gly Thr Gln Gly Asp Leu His Arg Lys Gly Lys Val Val Leu Pro
            500                 505                 510
Gly Phe Gln Ala Val His Cys Pro Ala Pro Ser Pro Val Ile Pro His
            515                 520                 525
Ser

<210> SEQ ID NO 5
<211> LENGTH: 6830
<212> TYPE: DNA
<213> ORGANISM: Canis familiaris

<400> SEQUENCE: 5
```

| | | | | | |
|---|---|---|---|---|---|
| gtcaggtctc | agaaaagtct | agaataaggc | ttacaggcac | tttgttcagt | tgtggaacac | 60 |
| atggaaactt | catacaccgc | ccccctcctt | gcagaccgga | gagctctctg | ctctaatttg | 120 |
| ggcacaggcg | cccaaccttg | ggccccagag | gaagcctgtt | ctactcccag | ggccaacgct | 180 |
| caattgcttg | gtaacttggc | acccacactg | ttccaggctc | tggtctcagt | ttcactctct | 240 |
| gcaaaatgag | aggctcagag | ttccgctgac | atggcctcgg | ggccgttaaa | accttctttc | 300 |
| atgaagacag | cctgcaccct | tcctgcttct | gctccaggtc | catcctcaga | accttccaga | 360 |
| aagtcctggc | acgtcagata | cagggccaa | cccggcagtg | atgccccacc | cccacccct | 420 |
| tcccttactc | atagagcctg | ctccagactc | tcagagccca | cccacttg | gtgaagtcat | 480 |
| ttgccagtaa | ttcttcgcac | tggacattga | gaggtttcag | accccagaag | tctcaggcgc | 540 |
| tgggtctgaa | agtgggcaga | gcccaggtga | catttgtgga | gactctcagt | ggtgcgtata | 600 |
| gccgccggga | ccattttcag | actcaacctt | tctgacctgg | aaatgccaat | agaagtaatc | 660 |
| atcatcgcca | ggggctgtgg | tgagcaaatg | cttggagctc | tgtggccagg | gcagtttcat | 720 |
| ttgaggacca | gagatggaca | atccctcagc | ctactgagat | gaagaaactg | agtctcagag | 780 |
| aggttaagga | actcccccga | ggttgcacca | ctgaggaaga | ttgacctgac | ttcccaagac | 840 |
| catacatctg | gtaaaccgga | acctgcacct | gcgccatctc | aagcctactc | tggaggcccg | 900 |
| aggctaattg | gcagagtttg | agggctgaga | tgacagacaa | ccctcagtgc | cttcatcggg | 960 |
| cgggctgctt | acctgcacat | ccctggtgac | agcatgggaa | agaccgcttc | taattaagcg | 1020 |
| tcatcacaca | tcacccttt | ccggaggaag | agaggcaaag | acagctcccc | tctatcctgc | 1080 |
| actgtgaacc | ttcctccgag | gtcctcccct | cacccccgag | agtccttgcc | ctgtcaccaa | 1140 |
| gattaattac | ccctcaaccc | ctttggatgg | caaaggcagt | catttatta | agtttgatta | 1200 |
| aagcttcaag | agacattgcc | ggatgtttca | ggactgctga | caaagcagcc | tgcttgtttc | 1260 |
| ctgaaaagac | caattatatg | caagaagcgt | cagccccact | cccgaggg | tccacttagc | 1320 |

```
ctccgaccac cacagggtga tgtccagcgc accggtgtgg ccatcacctg gcgggagtga    1380
ggtcggccgt agcaggtctg gaggcccccc tgcaagtccc tgcctcaccc tgtgactgag    1440
cctctcgtct ctgggaattt tgttccaaat tccccgtcta ccaggtgtga tttcctccag    1500
ccccaccagc cctgggaggc gcccatccag agagcagaga tggtgaccat gagaaagagg    1560
actctcaaag tgctcaccct cctcgtcctc ttcatcttcc tcacctcctt cttcctgaat    1620
tactcccaca ccatggtgac caccacctgg tttcccaagc agatggttgt cgagctctca    1680 gagaactttta agaagttcat gaaatacact cacaggcctt gcacctgtgc ccgctgcatc    1740
gggcagcaga gggtctcggc ctggttcgat gagaggttca accggtccat gcagccgctg    1800
ctgaccgccc agaacgccct cttggaggag acacctaca gctggtggct gaggctccag    1860
cgggagaagc aacccaacaa cttgaacgat accatcaggg agctgttcca ggtggtgccc    1920
gggaacgtgg accccctgct ggagaagagg tcggtgggct gccggcgctg cgcagtcgtg    1980
ggcaactctg gcaacctccg agagtcctgg tacgggcctc agatcgacag ccacgacttc    2040
gtgctcagga tgaacaaggc ccccacggcg ggcttcgaga tggatgtcgg gagcaagacc    2100
acccaccacc tggtgtaccc cgagagcttc agggagctgg cggagaatgt cagcatggtc    2160
ctggtgccct tcaagaccac cgacctggag tgggtggtca gtgccaccac cacaggcacc    2220
atctctcaca cctatgttcc tgttcctgca aagatcaaag tgaaaaagga taagatcctc    2280
atctaccacc cggccttcat caagtacgtc ttcgacagct ggctgcaggg ccacgggcgg    2340
tacccgtcca ccggcatcct ctccgtcatc ttctcgctgc acatctgcga cgaggtggac    2400
ttgtacggct tcggggcaga cagtaagggg aactggcatc actactggga gaacaatcca    2460
tcggcggggg ctttccgcaa gaccggggtg cacgacggag actttgagtc caacgtgacg    2520
gccaccttgg cgtccatcaa taagatccgg atatttaagg ggagatgacg ctgccgagga    2580
gcaccggagc ccgcctcttt ggccagcccc agcctctgct ggagccgatc tgtgctgggg    2640
gctttgaggg ccagcctcgg gggcgtgttc aggtgcccct cgtgccccct cgcacccga    2700 catttggcag catcgactca gcaaggcccc agagccccgc tgggtctgca gagcgagtgt    2760
cagaactggt cttggatggg gacacccccc ctccacctcc ctgcaccgcc actgctgtcc    2820
tggagcaggg ggcaggtggg gagacgcggg aggaggtccg gtctccaaac gctcaagtca    2880
tttcggcttt gggggcaga gggggagata tcgaagactc tgtgttctaa agtgaaggac    2940
actggccctg gcagagggg tcccgggctg actctctgac tctgatgctt gctgggtgag    3000
gacgacctcg ggacagagcc acatcgggcc acgtggacgc tggggtgag aaggcacctt    3060 cctctgcacg atgcccggcc cctccctcac cgcctctgcg gtcttcccga agctcctccg    3120
tggcggccag gagaggcgcc ctgcgccgag gtcctcaca gatgcttggc caagtgtttc    3180
agactccagc aggtgtcttc ttcgcaagct gaggctccct tgagtgatcg atctttgtgg    3240
ccataaatga tggctgagag cagatctgac tacttccacg tgccttttgtg tctggggag    3300 agctgtgcgc attggctgaa ataaggcaaa agccttaatt cgggagtggg gagctccccc    3360
ctctccccgc cccagcaatg ccacccccct tgctctggag ctgggtaaca tctttactag    3420
tttcctgagg cggtgccgga gctggaatga agctaggatg atgctcaacg gcgtccagag    3480
gtgcgtcagc cgcggcacgt cattcttagg ttcacagact gatggatttg gggcccgtga    3540
ccttccaagg ccacacacag aacctccacc agccagcact ttgccccagg agcccaccct    3600
ccaggccaag tccctccggg ccacctgcac agtgtcctgg ggtttgtggg gccatcccag    3660
```

```
gaacatgacc ctcggagcgg gagaagacat acctcatcct ctcacttctg ggctgctctg    3720
attcctcctc atgattattt attgattttt ttttaattca gctgacattg cgtgcacttt    3780
gtggctccgt ggctggtcct gatgttttaa ttaagcttgc tctcgcttca cctggcagcc    3840
ggggcatggg gggcttaagt caaggtttgc aggagtcctc agacttggga gggggatgca    3900
tatctagggc ttgggggctc gtcggtgggc aaatgccagg gtttcaggtt ggtaggttct    3960
ccgagtgctc tgtacctcct tcccctcagc tctgcctccc ttctccatca ttgcgggttg    4020
ggatcattct caggctaaga atctgcaaaa cccagtgaga cggccttggg gccaggtggg    4080
gagtggagtc acacaggcag ggcagcgatg gttggctccg gttgctgaca ctgaatcaga    4140
aaatccacgt ttcctattga gagcatttcc taacaggcca ctgctacttc gaggaggtgt    4200
gacagtgtcc tggctgtcac gggggcccgt ctcctgtgct ccttgcagca gcactccggc    4260
aagttctgct ctcctggctt cagtctctgc ctctgcaaac ggagagggag gcatttgggg    4320
agctcagggg gccacaggtg gtttcagggg gttcacaagc gtcccagag agagcacacc     4380 acgcccgtgt tttaccccaa gcctgtgtgt atgagcatat attcctgggg agcggtgccg    4440
tagcgttcat tcaattgtca gaggttcaga acccagacaa tggtttacaa aaacacgaaa    4500
cgacagcaag caaacaaaaa cccgttcgag ctttaaaatc ctccaacact tagactctct    4560 tgaccccctaa aggctcataa atcactacga ggtcagcaag ctgatcataa atcccaaaga    4620
ctatatagca ggcatctgtg ggttggctga tgaatccgct gagagaagtg ggtgcggagc    4680
ggcctccgag ctcctccccg agtcctggaa gagccgagtc cagtcagagc tgatgggtcc    4740
agagcgctca gcctgcgtcg gggctgtgct gagtcaggac aggtccccag agtaagggg    4800 ggggtctctc tccctcccca ccccactgag ccgtccaggc tgttgagagg acttcccacc    4860
tgccttccca tgtaacactt gagaaaagcg aggcccggag aagggaagtg gcttgcaaag    4920
tgaacccgtg gtgctggaca acgcaagtca gacccttga gcaaagatag agcacgattg     4980
ctacatgttg aacacacctc gaggtgggct ttcccagccg gcttccatcc agcctcccca    5040
aggactgtga ccgggcacag gtgggctcct caggctgcac gtggtggccc ccgcaagctc    5100
cggtgtctgc cttttccccc catccctcca gtgagggaga cacccttgct cttccctcag    5160
ccccagcaaa cttgtctttg tgttcgttgg cttagcaaag gggtctgacc cgaatgcacc    5220
aacgggcttc agcccctgg catctgtacc tggggtaagg gtggctgaga atccaaccag     5280
agtatttccc ccagagctcg tggctgtggg caggttaacg agaaccaccc gccccccca     5340 ctcggaggag gctcctgaat gcccaccca gtgttgggct cccagcctag ggccctgctt     5400
gctcctcaag cacagagctc ccttggaggc cagtcctgga cccctgggca gggagcagag    5460
gcatccctgc ctctctcagt gctgagcccg aagccaggaa gaccagggcc gaggagggag    5520
agagagattt taacaccctc cccggccctg gggagccagg agctggagtc acctgccgca    5580
aatgcaaggc ctggttccac gtgccccct ccgcccctgt cctcacccc ttgttagggt      5640 gggtttgtag cgtctggctc ccagagccat caggcaaaaa agaaagttct taagagatg     5700 cttttagggg cctgtgctta gtgggagaag ccagattcaa gaaaatggga cttaaaacgg    5760
ggaagccaga cgagaaggtg ggggggggt tgtccgggtg tgattcttac aagtgctgag    5820
gccagaagga tggaccctct ccaggtccag agtagagtgg agtcaacggg gaatatttag    5880
gactgtgatg tttgcagtaa tggtcctctt caaggcagcc tggacacaaa gcaaaatcgg    5940
aaacagaaaa gaactcacca tcccttgcgt gggtaggacc aaaacagctt tctccaggga    6000
ggcgcaagcc ctgagtggcc gccgtctggc caaagccggc ctcgtgccat cgggaaccgg    6060
```

```
ccaccgccca tgcccctccg gagagctcgg ggtcgtcatc gtgtccacca cgggcatctg      6120
gtcggaagca aacgttccca caggccactg gctggtcatc gtcccctgtg gtctgggctg      6180
accggtttga gaccaagtcc gctgccttgc tccggcctgt cctgaagaca ccagcgcccc      6240
ggcctgtggg gtgccccgtg atgcctccat gcagggaaga gcaggggacc agggaggaag      6300
agcagagaca ggtgaagcga cagtccccgc gtcccagcct cagcattcgc atcctcttgg      6360
cccctacttt tcctctccgc ccagcagaca tctgccctgc ccttgccctt gaccccattg      6420
ctgcgcttcc ctcaaggacg ggcctggcct tggtggccac ctgcggacag ccctgcgccc      6480
gacgcccgct tcaccccggg gcccgggtct ggaggggccg ccccaggac gaacgcggct       6540 gccccacggg gccggcccct caccggcttc gcgtccaagc caaagtttct cgagcacttt      6600
tttgttcttt gcaatcatgt tgggttcatt gttggtgttt taaaattttg cttccctctc      6660
cctctggcct cgctcctgtg tgtgttttgt agccgagcgc taacctggat gcttttttga      6720
atgacctttg caagagcctg ccttcctcgg cctctgctct gttttattta ttgttgaata      6780
tttccaatga tccaaatcaa agtgaattaa acaaagcta ttttatcgtt               6830
```

<210> SEQ ID NO 6
<211> LENGTH: 342
<212> TYPE: PRT
<213> ORGANISM: Canis familiaris

<400> SEQUENCE: 6

```
Met Val Thr Met Arg Lys Arg Thr Leu Lys Val Leu Thr Leu Leu Val
1               5                   10                  15

Leu Phe Ile Phe Leu Thr Ser Phe Phe Leu Asn Tyr Ser His Thr Met
            20                  25                  30

Val Thr Thr Thr Trp Phe Pro Lys Gln Met Val Val Glu Leu Ser Glu
        35                  40                  45

Asn Phe Lys Lys Phe Met Lys Tyr Thr His Arg Pro Cys Thr Cys Ala
    50                  55                  60

Arg Cys Ile Gly Gln Gln Arg Val Ser Ala Trp Phe Asp Glu Arg Phe
65                  70                  75                  80

Asn Arg Ser Met Gln Pro Leu Leu Thr Ala Gln Asn Ala Leu Leu Glu
                85                  90                  95

Glu Asp Thr Tyr Ser Trp Trp Leu Arg Leu Gln Arg Glu Lys Gln Pro
            100                 105                 110

Asn Asn Leu Asn Asp Thr Ile Arg Glu Leu Phe Gln Val Val Pro Gly
        115                 120                 125

Asn Val Asp Pro Leu Leu Glu Lys Arg Ser Val Gly Cys Arg Arg Cys
    130                 135                 140

Ala Val Val Gly Asn Ser Gly Asn Leu Arg Glu Ser Trp Tyr Gly Pro
145                 150                 155                 160

Gln Ile Asp Ser His Asp Phe Val Leu Arg Met Asn Lys Ala Pro Thr
                165                 170                 175

Ala Gly Phe Glu Met Asp Val Gly Ser Lys Thr Thr His His Leu Val
            180                 185                 190

Tyr Pro Glu Ser Phe Arg Glu Leu Ala Glu Asn Val Ser Met Val Leu
        195                 200                 205

Val Pro Phe Lys Thr Thr Asp Leu Glu Trp Val Val Ser Ala Thr Thr
    210                 215                 220

Thr Gly Thr Ile Ser His Thr Tyr Val Pro Val Pro Ala Lys Ile Lys
225                 230                 235                 240
```

Val Lys Lys Asp Lys Ile Leu Ile Tyr His Pro Ala Phe Ile Lys Tyr
            245                 250                 255

Val Phe Asp Ser Trp Leu Gln Gly His Gly Arg Tyr Pro Ser Thr Gly
            260                 265                 270

Ile Leu Ser Val Ile Phe Ser Leu His Ile Cys Asp Glu Val Asp Leu
            275                 280                 285

Tyr Gly Phe Gly Ala Asp Ser Lys Gly Asn Trp His His Tyr Trp Glu
            290                 295                 300

Asn Asn Pro Ser Ala Gly Ala Phe Arg Lys Thr Gly Val His Asp Gly
305                 310                 315                 320

Asp Phe Glu Ser Asn Val Thr Ala Thr Leu Ala Ser Ile Asn Lys Ile
            325                 330                 335

Arg Ile Phe Lys Gly Arg
            340

<210> SEQ ID NO 7
<211> LENGTH: 4577
<212> TYPE: DNA
<213> ORGANISM: Canis familiaris

<400> SEQUENCE: 7
cggctcgctc cgggagggca gagccggcaa gggcgggact ggcctgctgc gggcggacgg      60
gggagccgcg gagctaacgg gtccggacgt cgccagcggc ggagcttcct gcacgggcgg     120
aggcggcggc aggagcggca agcatggccc gcgcggcgcc cggcgctgac tgagggtcat     180
gctgcggcag cctggcgcct gacgagtgag ggggaacctg ccaggggatt actgctagca     240
cgagctaaca gcaggacagc aggcctcagg ggagtgggga tgggcatagc agcctgcctg     300
caacgctggg ccagtggcac caaggaggcc caggccctgg cagggagctc ggcacacgct     360
cagctgaccc agacagcatt caaagcaggt ccctgctgag cagcagctgt cccaggccc     420 tggaggaccg caaacgcctc agcaaccaca tttggggctg tgaccatcag gagaagggac     480
caacacctcg aatgggaagc agaagggcag aacctgctgc aggaggatc ttggtctctg     540 cagcaaagtc ttccgacacc cgtggagctt cttgggtttc tcctctcagg actggggcct     600
tgtttcctcc tctggtggag ggggtaggcc aggagggcca gctgaggtgg ggacgactct     660
cggatggaat ccaggccact tgaagcccat gggctctctg ctgtgattgg ggttcgaggg     720
cttccccact gcaggggacg aggggccgcc tccgtgtctg ctcatgaacc acaaggaccc     780
cgaatgctcc agactggacc atttcgagcc accaaagagt ggggccccca gagctggcag     840
ccagcagctc caagggacta gagagctggg atggactgac ctccccctca ccagggcatt     900
aggagagtca gagcctctgt ggcccagcta gtgacagaga gacccgatga ggccataagc     960
tggcacccga gtgactcagg acaggagag ccactcctgc ctactgtgct ttctctttac    1020
attgagggag ggtgtggtaa gggacccctg cctctgttcc ctcctcagca cgtgcccta    1080 tgccctttgc acgtggtgcc aggagacgca ggctacactg tggctggccc atcagtgggc    1140
tgggaaggga gtggccacgg tgacacccac ccgcccacca ggctggtggt ctagccccc    1200 ggggcgccaa accatgaagt gctccctgcg ggtgtggttc ctctctgtgg ccttcctgct    1260
ggtgttcatc atgtcactgc tctttaccta ctcccaccac agcatggcca ccttgcccta    1320
cctggactca ggggccctgg gcggtaccca ccgggtgaag ctggtgcctg gctatgctgg    1380
tctgcagcgc ctcagcaagg aggggctcac cggtaagagc tgtgcctgcc gccgctgcat    1440
gggtgacact ggcgcctctg actggtttga cagccacttc aacagcaaca tttcccctgt    1500

```
gtggacccga gagaatatgg atctgcctcc agatgtccag aggtggtgga tgatgctgca    1560
gccccagttc aagtcacaca acaccaacga ggtactggaa agctgttcc agatagtacc     1620 aggcgagaac ccctaccgtt tccgggaccc ccaccagtgc cggcgctgtg cggtagtggg    1680
gaactcaggc aacctgcggg gctctggcta cggcccagat gtggatgggc ataacttcat    1740
catgaggatg aatcaggcgc caaccgtggg cttttgagcag gatgttggca gccgaactac   1800
ccaccatttc atgtaccccg agagtgccaa gaaccttcct gccaacgtca gctttgtgtt    1860
ggtgcccttc aaagctctgg acctactatg gattgccagc gctttgtcca cagggcaaat    1920
cagattcacc tatgcgccag tgaagtcctt ccttcgagtg gacaaagaaa aggttcagat    1980
ctacaacccg gcattcttca agtacatcca cgaccggtgg acagagcatc acgggcggta    2040
cccttccaca gggatgctgg tgctcttctt tgccctgcat gtttgtgatg aggtgaacgt    2100
gtacgggttc ggggccgaca gccggggcaa ctggcaccac tactgggaga ataaccggta    2160
tgcgggcgag ttccggaaga cgggagtgca cgacgccgac ttcgaggccc acatcatcga    2220
catgctggcc aaggccagca agatcgaggt ctaccgaggc aactgagccc ggcctcgccg    2280
cgacccttcc ggcccagccg cgaggctgcg acgctcgctc cgcagccggg actcccggcc    2340
agcccgaggg cggcggcctt ggcgagggcg cggcgcccgg ttgggcgtct ccagccctgg    2400
gagcgacgcc aagtcgcggt ctggaccaat catgctgcaa gtccagcgag cgccggctgt    2460
cccccgccaa tcaggagact ttgggggctg gcccaggcct ggcacccaat cagcgctgca    2520
gtgggagcgg aggctctttc tcccagccaa tcatgcgact caaggagaac ttccggcgct    2580
gggcccggtc tcctccaatc aatggccttc ggaggcgggc cggccgccgc tgaatcccca    2640
ctcccctatg ctttgggtag gattttattt tatgcttttt aaggagtagt ggttggttcc    2700
ggcctcagtg gagtactttc tcaggctct gcggaggag tgttggtggc ctgtcggcgg     2760
tactcggcca ggggcaccga ggaggaagcg gggggggaagg tgcggggcag cagcggctgg   2820
gcctcccttg gccggggggcc cctcgcgacc tcggggcggg cgggggggcg ggggcgttgg    2880
cctcccgctt ctggaggtcc gggggggaatc aggtggtttc cggggagcgc gctttcatcc   2940
ccgggaagag ctagatccct ctcaaacctt ttcaggcctc agagcactct agaccgcgta    3000
tttcctttat ctgtcgggcc cagatggggtg agtgtaaacc caccaaagaa aggcagtgga   3060
gcgtgggtcc cctcgtcctc ccttgtcccc atccccacct ttggccaccc tatgggatgg    3120
ccttcctgac cagggcattg agcatcccac ctggaaacta gaactgtatt caccccgttgc   3180 tagggctcgg agttcgccga tggcctaact cgagcgcagg ggtaaggaac agggcagggg    3240 accccggaagc cccgtcactt cagatgtaag gtgcttctca ctctcgtgta ctctcgcggc   3300
cccttactgt tcgcccacaa cttttttagt gtcccttctt aagccctggg cctcctcacc    3360
agcctgctcg tcctgggatt gggggtgggg ggtgggcac tgctggcttc tccaaccccc     3420
tacccctcct cgctcgtctt tagccggctc tagggagagg aaggcaggct ggagatgggg    3480
agcccagctg cctggtgcat gcaccgttt cctccgccca tcaccccaaa gaggagtagg     3540
aaacctcttg cttggggggtg gaatttgctt tggtctccta atttagttaa cttgaggtta    3600
ccagggatgg ctgaccaaca aagattcttt taaaattcca ggctggccat gcaaattgct    3660
gggatcctag ctgggggagga gtcgactgac ttgcccgcct tgcatgtctc ctctcctgcc   3720
cctgcgtccc ctccctctgc cacgctcact tcctgcctca tctctccaac ccatttttcca   3780 ttttcagctc tagaagggca gggacgctta caaacaggag ttacatctgg aagttacttc    3840
```

-continued

```
caagactgaa cccagcttaa gtccctagag gaagctgctg atgatattct caccttcaa    3900
ggttggggaa gtttcggagg gggaaagtgc ttctgtgaag cttccaaacc actaatagga    3960
tccccttcc caacaatgag gaacacaaac accaccttt atcttagttg ataccaccaa      4020
gcagcctcct ggccattggg gtaattcctg cagctggctg gggtaaccag caggggagta    4080
tattagagga ggattggggc agggcagtgg gcacccctaa agttaatata ttgagaactt    4140
agcttaagcc taagtcttag ttccttccca attccaaaag taggaggagc aacgagtggg    4200
ggtggatttg gggggccta tcctggaatg cctctctcag ggcttccccc accattttag     4260
agagtcaagg caccagccat tcatgccagt ctcctctcag tgcttcctga agaggctgtt    4320
tggagtgttc ggaaaatgaa aaaacaatg caattatgcc aaacagtatt gagcagaata     4380
atttatttct tttttgttcc tttttcttct tttgttttg tttaaaacat taataaatcc     4440
cctttctgga agaggtaggt cccagcatcc agcccagatc tccttttctg caatagttat    4500
ttaaacaaat gtttgtttgt ttttttattt tcttcccttt ctctctcttt ctgaattaaa    4560
aaaaaagaaa actccta                                                   4577
```

<210> SEQ ID NO 8
<211> LENGTH: 350
<212> TYPE: PRT
<213> ORGANISM: Canis familiaris

<400> SEQUENCE: 8

```
Met Lys Cys Ser Leu Arg Val Trp Phe Leu Ser Val Ala Phe Leu Leu
1               5                   10                  15

Val Phe Ile Met Ser Leu Leu Phe Thr Tyr Ser His His Ser Met Ala
                20                  25                  30

Thr Leu Pro Tyr Leu Asp Ser Gly Ala Leu Gly Gly Thr His Arg Val
            35                  40                  45

Lys Leu Val Pro Gly Tyr Ala Gly Leu Gln Arg Leu Ser Lys Glu Gly
        50                  55                  60

Leu Thr Gly Lys Ser Cys Ala Cys Arg Arg Cys Met Gly Asp Thr Gly
65                  70                  75                  80

Ala Ser Asp Trp Phe Asp Ser His Phe Asn Ser Asn Ile Ser Pro Val
                85                  90                  95

Trp Thr Arg Glu Asn Met Asp Leu Pro Pro Asp Val Gln Arg Trp Trp
                100                 105                 110

Met Met Leu Gln Pro Gln Phe Lys Ser His Asn Thr Asn Glu Val Leu
            115                 120                 125

Glu Lys Leu Phe Gln Ile Val Pro Gly Glu Asn Pro Tyr Arg Phe Arg
        130                 135                 140

Asp Pro His Gln Cys Arg Arg Cys Ala Val Val Gly Asn Ser Gly Asn
145                 150                 155                 160

Leu Arg Gly Ser Gly Tyr Gly Pro Asp Val Asp Gly His Asn Phe Ile
                165                 170                 175

Met Arg Met Asn Gln Ala Pro Thr Val Gly Phe Glu Gln Asp Val Gly
            180                 185                 190

Ser Arg Thr Thr His His Phe Met Tyr Pro Glu Ser Ala Lys Asn Leu
        195                 200                 205

Pro Ala Asn Val Ser Phe Val Leu Val Pro Phe Lys Ala Leu Asp Leu
    210                 215                 220

Leu Trp Ile Ala Ser Ala Leu Ser Thr Gly Gln Ile Arg Phe Thr Tyr
225                 230                 235                 240
```

```
Ala Pro Val Lys Ser Phe Leu Arg Val Asp Lys Glu Lys Val Gln Ile
                245                 250                 255
Tyr Asn Pro Ala Phe Phe Lys Tyr Ile His Asp Arg Trp Thr Glu His
            260                 265                 270
His Gly Arg Tyr Pro Ser Thr Gly Met Leu Val Leu Phe Phe Ala Leu
        275                 280                 285
His Val Cys Asp Glu Val Asn Val Tyr Gly Phe Gly Ala Asp Ser Arg
    290                 295                 300
Gly Asn Trp His His Tyr Trp Glu Asn Asn Arg Tyr Ala Gly Glu Phe
305                 310                 315                 320
Arg Lys Thr Gly Val His Asp Ala Asp Phe Glu Ala His Ile Ile Asp
                325                 330                 335
Met Leu Ala Lys Ala Ser Lys Ile Glu Val Tyr Arg Gly Asn
                340                 345                 350

<210> SEQ ID NO 9
<211> LENGTH: 1782
<212> TYPE: DNA
<213> ORGANISM: Canis familiaris

<400> SEQUENCE: 9
```

| | | | | | |
|---|---|---|---|---|---|
| ttggtggtcg | cgctccgccc | gccgctgcgt | ccccaccatg | gcggcgcccg | tgcagcccac | 60 |
| cgcgtcgtgg | gcgcccgccg | ggctcccccg | cggctgtggc | ggccgcccgc | gcctcggcct | 120 |
| ccgcctcccc | gcccgcgccg | gccgggcgc | cgcctcccg | ctgcctccgt | ctccgctgcg | 180 |
| gtcatgtagg | aaatcgtaaa | tcatgtgaag | atgggactct | tggtatttgt | acgcaatctg | 240 |
| ctgctagccc | tctgccttt | tctggtactg | ggattttgt | attattctgc | gtggaagctg | 300 |
| catttactcc | agtgggagga | ctccaattca | gtggttcttt | cctttgactc | cgctggacaa | 360 |
| acactaggct | cagagtatga | tcggttgggt | ttcctcctga | agctggactc | taaactgcct | 420 |
| gctgagttag | ccaccaagta | tgcaaacttt | tcagagggag | cttgcaagcc | tggctatgct | 480 |
| tcggccttga | tgactgccat | ctttccccgg | ttctccaagc | cagcacccat | gttcctggat | 540 |
| gactctttcc | gcaagtgggc | taggattcgg | gagtttgtgc | cgccttttgg | gatcaaaggt | 600 |
| caagacaatc | tgatcaaagc | catcttgtca | gtcaccaaag | agtaccgcct | gacccctgcc | 660 |
| ttggacagcc | tcagctgccg | ccgctgcatc | atcgtgggca | acggaggtgt | cctagccaac | 720 |
| aagtctctgg | ggtcacgaat | tgatgactat | gacattgtgg | tcagactgaa | ctccgcacca | 780 |
| gtgaaaggct | ttgagaagga | cgtgggcagc | aaaactacac | tgcgcatcac | ctaccctgag | 840 |
| ggcgccatga | gcggcctga | gcaatatgaa | cgcgattctc | tatttgtcct | cgctggcttc | 900 |
| aagtggcagg | acttcaagtg | gttgaagtac | atcgtctaca | aggagagagt | gctctgggcc | 960 |
| cgcagggata | cctgccaatc | tgtctgggcc | catccccctc | tccctccac | cagctgtcac | 1020 |
| cagccacccc | aggggagggg | tcctgcagag | ttcaggccat | tcttcttcca | atacccgagc | 1080 |
| ctcctactgg | aggagaatga | tgacagacag | cctctggcga | caagtgcatc | agatggcttc | 1140 |
| tggaaatccg | tggccacacg | agtgcccaag | gagcccctg | agattcgcat | cctcaacccg | 1200 |
| tacttcatcc | aggaggccgc | cttcaccctc | atcggactgc | ccttcaacaa | cggcctcatg | 1260 |
| ggccgcggga | catcccgac | ccttggcagt | gtggcagtga | ccatgcgct | acacggctgt | 1320 |
| gatgaggtgg | cagtcgcagg | ctttggctac | gacatgagca | cacccaacgc | gcccctgcac | 1380 |
| tactatgaga | ccgtgcgcat | ggcagccatc | aaagaggtca | ccagcgactc | agctcaaggc | 1440 |
| tgccaaatcc | agtggacaca | tggaagcctc | atcttcctg | acctcccaga | aatgcttttt | 1500 |

-continued

```
ctgttgacca ctccttcctc tttgaaactt ttcctgctca gactgtcctg gacacacaat    1560
atccagcgag agaaagagtt tctgcgcaag ctggtgaagg cgcgcgtcat caccgaccta    1620
accagcggca tctgaggtgg gcccagcaca tggccacgga ggtcctggca ccgccaagag    1680
gaagccgcag ccactgccac ctgtccactt cattggcctc ggtctggctc tgcctgaaag    1740
gcgcaggagt cttcagaccc agagaaggac agtgccaagg gg                      1782
```

<210> SEQ ID NO 10
<211> LENGTH: 474
<212> TYPE: PRT
<213> ORGANISM: Canis familiaris

<400> SEQUENCE: 10

```
Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Asp Ser Asn Ser Val Val Leu Ser Phe Asp Ser Ala
        35                  40                  45

Gly Gln Thr Leu Gly Ser Glu Tyr Asp Arg Leu Gly Phe Leu Leu Lys
    50                  55                  60

Leu Asp Ser Lys Leu Pro Ala Glu Leu Ala Thr Lys Tyr Ala Asn Phe
65                  70                  75                  80

Ser Glu Gly Ala Cys Lys Pro Gly Tyr Ala Ser Ala Leu Met Thr Ala
                85                  90                  95

Ile Phe Pro Arg Phe Ser Lys Pro Ala Pro Met Phe Leu Asp Asp Ser
            100                 105                 110

Phe Arg Lys Trp Ala Arg Ile Arg Glu Phe Val Pro Pro Phe Gly Ile
        115                 120                 125

Lys Gly Gln Asp Asn Leu Ile Lys Ala Ile Leu Ser Val Thr Lys Glu
    130                 135                 140

Tyr Arg Leu Thr Pro Ala Leu Asp Ser Leu Ser Cys Arg Arg Cys Ile
145                 150                 155                 160

Ile Val Gly Asn Gly Gly Val Leu Ala Asn Lys Ser Leu Gly Ser Arg
                165                 170                 175

Ile Asp Asp Tyr Asp Ile Val Val Arg Leu Asn Ser Ala Pro Val Lys
            180                 185                 190

Gly Phe Glu Lys Asp Val Gly Ser Lys Thr Thr Leu Arg Ile Thr Tyr
        195                 200                 205

Pro Glu Gly Ala Met Gln Arg Pro Glu Gln Tyr Glu Arg Asp Ser Leu
    210                 215                 220

Phe Val Leu Ala Gly Phe Lys Trp Gln Asp Phe Lys Trp Leu Lys Tyr
225                 230                 235                 240

Ile Val Tyr Lys Glu Arg Val Leu Trp Ala Arg Arg Asp Thr Cys Gln
                245                 250                 255

Ser Val Trp Ala His Pro Pro Leu Pro Ser Thr Ser Cys His Gln Pro
            260                 265                 270

Pro Gln Gly Arg Gly Pro Ala Glu Phe Arg Pro Phe Phe Gln Tyr
        275                 280                 285

Pro Ser Leu Leu Leu Glu Glu Asn Asp Asp Arg Gln Pro Leu Ala Thr
    290                 295                 300

Ser Ala Ser Asp Gly Phe Trp Lys Ser Val Ala Thr Arg Val Pro Lys
305                 310                 315                 320

Glu Pro Pro Glu Ile Arg Ile Leu Asn Pro Tyr Phe Ile Gln Glu Ala
```

```
                    325                 330                 335
Ala Phe Thr Leu Ile Gly Leu Pro Phe Asn Asn Gly Leu Met Gly Arg
            340                 345                 350
Gly Asn Ile Pro Thr Leu Gly Ser Val Ala Val Thr Met Ala Leu His
        355                 360                 365
Gly Cys Asp Glu Val Ala Val Ala Gly Phe Gly Tyr Asp Met Ser Thr
    370                 375                 380
Pro Asn Ala Pro Leu His Tyr Tyr Glu Thr Val Arg Met Ala Ala Ile
385                 390                 395                 400
Lys Glu Val Thr Ser Asp Ser Ala Gln Gly Cys Gln Ile Gln Trp Thr
                405                 410                 415
His Gly Ser Leu Ile Phe Pro Asp Leu Pro Glu Met Leu Phe Leu Leu
            420                 425                 430
Thr Thr Pro Ser Ser Leu Lys Leu Phe Leu Leu Arg Leu Ser Trp Thr
        435                 440                 445
His Asn Ile Gln Arg Glu Lys Glu Phe Leu Arg Lys Leu Val Lys Ala
    450                 455                 460
Arg Val Ile Thr Asp Leu Thr Ser Gly Ile
465                 470
```

<210> SEQ ID NO 11
<211> LENGTH: 1819
<212> TYPE: DNA
<213> ORGANISM: Canis familiaris

<400> SEQUENCE: 11

| | | | | | |
|---|---|---|---|---|---|
| ccctacaggc | ccgagctgcc | ggggtcgggc | ctccccgggt | tcccgctccc | gggtcctcct | 60 |
| ggacacaccg | gcctggcctg | gctcccgggg | aactctcgtc | tgctagcggg | gagcctccct | 120 |
| ccgcctcgcc | cacgggcacc | cctcccaccc | agtatccttg | gcctcttgca | ggtggcccga | 180 |
| ggcagccggg | atgacagctc | tccccaggaa | ccctgctacc | ctctgagaaa | catgatcagc | 240 |
| aagtcccgct | ggaagctcct | ggccatgttg | gctctggtcc | tggtcgtcat | ggtgtggtat | 300 |
| tccatctccc | gagaagacag | gtacattgag | cttttttatt | ttcccatccc | agagaagaag | 360 |
| gaaccgtgct | tccagggtga | ggcagagaga | aaggcctcta | agctctttgg | caactactcc | 420 |
| cgagatcagc | ccatcttcct | gcagatgaag | gattatttct | gggtcaagac | accgtctgcc | 480 |
| tacgagctgc | cctatgggac | caaggggagc | gaagacctgc | tcctccgggt | tctagccatc | 540 |
| accagctact | ccattccaga | gagcatccag | agtctcaagt | gtcgccgctg | cgtggtggtg | 600 |
| ggcaatgggc | atcggctgcg | caacagctcg | ctgggagatg | ccatcaacaa | gtacgacgtg | 660 |
| gtcatcagac | tgaacaacgc | ccccgtggct | ggctacgagg | gtgacgtggg | ctcgaagacc | 720 |
| accatgcgtc | tcttctaccc | ggagtcagcc | cacttcaacc | ccaaagtgga | gaacaaccca | 780 |
| gacacacttc | tcgtcctggt | ggccttcaag | gcaatggact | tccactggat | tgagaccatc | 840 |
| ctgagtgata | agaagagggt | acgaaagggc | ttctggaagc | agcctcccct | catcctggga | 900 |
| gtcaaccccca | ggcaggttcg | gattctcaac | cctttcttta | tggagattgc | agctgacaaa | 960 |
| ctgctgaacc | tgccaatgaa | acagccacgc | aagatttccc | agaagcccac | cacgggcctg | 1020 |
| ctggccatca | cgctggctct | ccacctctgc | gacctggtgc | acatcgccgg | cttcggctac | 1080 |
| ccggacgccc | acaacaggaa | gcagaccatt | cactactatg | aacagatcac | gctcaagtcc | 1140 |
| atggcggggt | caggccacaa | cgtctcccag | gaggccctgg | ccatcaagcg | gatgctggag | 1200 |
| atcggagcag | tcaagaacct | cacgttcttc | tgacgggggac | aggagctcta | gccgtcagtc | 1260 |

-continued

```
tgcccgccct gccgcctgag cgaccaacca cggctgtggg ggcgccggcg tgacctgctt    1320
ggattccccc tccccgtgtg gagagggggc ctggtacagg cggggcctga gatggggccg    1380
cgcccctggc tgctcttggg gcggccggat ccagtcaggg tggaggcccc gggtggcggg    1440
aggccttccg aggcgcgggg tgtgtggctg aggcaccccct tctcaccagc ccgggagct    1500
```

```
tatttaatgg gctatttaat taaaagggta ggaatgtgcc tcgggctggt cccatggcat    1560
ccggaaacgg gggcatagca cagtggtctg cccactgtgg ataaaaacac acaagtgctt    1620
ggcccactag agcctagagc cagagcaggc ctcccaggag ggcaggggcg tctggagcgg    1680
gtgggtgccc tccagagagg ggctgctacc tcccagcggg catggaaaga gcattgggat    1740
gaggtcccac ggagaatggg acctcatgta gaaaagaggt ttgaaaccta acattaaact    1800
attttttcct aaaacggaa                                                  1819
```

<210> SEQ ID NO 12
<211> LENGTH: 333
<212> TYPE: PRT
<213> ORGANISM: Canis familiaris

<400> SEQUENCE: 12

```
Met Ile Ser Lys Ser Arg Trp Lys Leu Leu Ala Met Leu Ala Leu Val
1               5                   10                  15

Leu Val Val Met Val Trp Tyr Ser Ile Ser Arg Glu Asp Arg Tyr Ile
            20                  25                  30

Glu Leu Phe Tyr Phe Pro Ile Pro Glu Lys Lys Glu Pro Cys Phe Gln
        35                  40                  45

Gly Glu Ala Glu Arg Lys Ala Ser Lys Leu Phe Gly Asn Tyr Ser Arg
    50                  55                  60

Asp Gln Pro Ile Phe Leu Gln Met Lys Asp Tyr Phe Trp Val Lys Thr
65                  70                  75                  80

Pro Ser Ala Tyr Glu Leu Pro Tyr Gly Thr Lys Gly Ser Glu Asp Leu
                85                  90                  95

Leu Leu Arg Val Leu Ala Ile Thr Ser Tyr Ser Ile Pro Glu Ser Ile
            100                 105                 110

Gln Ser Leu Lys Cys Arg Arg Cys Val Val Gly Asn Gly His Arg
        115                 120                 125

Leu Arg Asn Ser Ser Leu Gly Asp Ala Ile Asn Lys Tyr Asp Val Val
    130                 135                 140

Ile Arg Leu Asn Asn Ala Pro Val Ala Gly Tyr Glu Gly Asp Val Gly
145                 150                 155                 160

Ser Lys Thr Thr Met Arg Leu Phe Tyr Pro Glu Ser Ala His Phe Asn
                165                 170                 175

Pro Lys Val Glu Asn Asn Pro Asp Thr Leu Leu Val Leu Val Ala Phe
            180                 185                 190

Lys Ala Met Asp Phe His Trp Ile Glu Thr Ile Leu Ser Asp Lys Lys
        195                 200                 205

Arg Val Arg Lys Gly Phe Trp Lys Gln Pro Pro Leu Ile Trp Asp Val
    210                 215                 220

Asn Pro Arg Gln Val Arg Ile Leu Asn Pro Phe Phe Met Glu Ile Ala
225                 230                 235                 240

Ala Asp Lys Leu Leu Asn Leu Pro Met Lys Gln Pro Arg Lys Ile Ser
                245                 250                 255

Gln Lys Pro Thr Thr Gly Leu Leu Ala Ile Thr Leu Ala Leu His Leu
            260                 265                 270
```

```
Cys Asp Leu Val His Ile Ala Gly Phe Gly Tyr Pro Asp Ala His Asn
            275                 280                 285

Arg Lys Gln Thr Ile His Tyr Tyr Glu Gln Ile Thr Leu Lys Ser Met
    290                 295                 300

Ala Gly Ser Gly His Asn Val Ser Gln Glu Ala Leu Ala Ile Lys Arg
305                 310                 315                 320

Met Leu Glu Ile Gly Ala Val Lys Asn Leu Thr Phe Phe
                325                 330
```

<210> SEQ ID NO 13
<211> LENGTH: 1385
<212> TYPE: DNA
<213> ORGANISM: Canis familiaris

<400> SEQUENCE: 13

```
cgctctggaa ccacttacag ccacctggtg catcctcctt tggggtgcgt ttggagggcc     60
tggttcctgc tcagccacat cttctgccac tttcaccagc aatgcccagt gagtataact    120
atgtaaaact gagaagcgat cgctcaagac cctctctgca atggtacacc cgagctcaaa    180
acaagatgag aagacccaac ttgttgttaa aagacatcct taagtgtaca ttgcttgtgt    240
ttggagtgtg gatcctttat attctcaagt taaattatac tactgaagaa tgtgacatga    300
aaaaaatgca ttatgtggac ccagaccgtg taaagagagc tcagaaatat gctcagcaag    360
tcttgcaaaa ggagtgccga cccaagtttg cgaagaagtc gatggcgcag ttgttcgagc    420
acaggtacag cacggacttg ccacctttcg tgaaggagac ccccaaaatg aatgaagccg    480
agtacaagta tgatcctcct tttggattcc gaaagttctc cagtgaagtc cagaccctgt    540
tggaaatact gcccgagcat gacatgcccg aacacttgag agcaaagagc tgtaggcgtt    600
gtgtggtcat cggaagcggt ggcatactcc acggactagc actgggccag gccctcaacc    660
agttcgatgt ggtgataagg ttaaacagtg caccagttga gggatattct gagcatgttg    720
gtaataaaac tactataagg atgacttatc cagagggcgc gccactgtct gaccttgaat    780
attattccaa tgacttgttt gttgctgttt tattcaagag tgttgacttc aactggcttc    840
aagcaatggt aaaaaatgaa accctgccat tttgggtgcg gctcttcttt tggaagcagg    900
tggcggaaaa aatcccacta cagccaaaac atttcaggat tttgaatcca gttattatca    960
aagagactgc ctttgacatc cttcaatact cagagcccca gtcaaggttc tggggccgag   1020
ataagaacgt gcccaccatt ggtgtcattg ccgttgtctt agccacacat ctgtgtgatg   1080
aagtcagctt ggcaggcttt ggatatgacc tcaatcaacc caaaacacct ttgcactact   1140
ttgacaatct ctgcatggct gccatgaact ttcaaaccat gcataatgtg acaacggaga   1200
ccaggttcct cctcaagctg gtcaaagagg gcgtggtgaa ggatctcagc ggaggcatcc   1260
attgtgaatt ttgaacacag ggaaacctca tgtgacaatg caactctgac tctgaaggct   1320
gttttttcgta gccttctcga tgcagcgcat cctgcaaaat acttagaggt gcagctgggg   1380
ttttt                                                               1385
```

<210> SEQ ID NO 14
<211> LENGTH: 390
<212> TYPE: PRT
<213> ORGANISM: Canis familiaris

<400> SEQUENCE: 14

```
Met Pro Ser Glu Tyr Asn Tyr Val Lys Leu Arg Ser Asp Arg Ser Arg
1               5                   10                  15
```

```
Pro Ser Leu Gln Trp Tyr Thr Arg Ala Gln Asn Lys Met Arg Arg Pro
            20                  25                  30

Asn Leu Leu Leu Lys Asp Ile Leu Lys Cys Thr Leu Leu Val Phe Gly
            35                  40                  45

Val Trp Ile Leu Tyr Ile Leu Lys Leu Asn Tyr Thr Thr Glu Glu Cys
 50                  55                  60

Asp Met Lys Lys Met His Tyr Val Asp Pro Asp Arg Val Lys Arg Ala
 65                  70                  75                  80

Gln Lys Tyr Ala Gln Gln Val Leu Gln Lys Glu Cys Arg Pro Lys Phe
                 85                  90                  95

Ala Lys Lys Ser Met Ala Gln Leu Phe Glu His Arg Tyr Ser Thr Asp
            100                 105                 110

Leu Pro Pro Phe Val Lys Glu Thr Pro Lys Met Asn Glu Ala Glu Tyr
            115                 120                 125

Lys Tyr Asp Pro Pro Phe Gly Phe Arg Lys Phe Ser Ser Glu Val Gln
            130                 135                 140

Thr Leu Leu Glu Ile Leu Pro Glu His Asp Met Pro Glu His Leu Arg
145                 150                 155                 160

Ala Lys Ser Cys Arg Arg Cys Val Val Ile Gly Ser Gly Ile Leu
                165                 170                 175

His Gly Leu Ala Leu Gly Gln Ala Leu Asn Gln Phe Asp Val Val Ile
            180                 185                 190

Arg Leu Asn Ser Ala Pro Val Glu Gly Tyr Ser Glu His Val Gly Asn
            195                 200                 205

Lys Thr Thr Ile Arg Met Thr Tyr Pro Glu Gly Ala Pro Leu Ser Asp
210                 215                 220

Leu Glu Tyr Tyr Ser Asn Asp Leu Phe Val Ala Val Leu Phe Lys Ser
225                 230                 235                 240

Val Asp Phe Asn Trp Leu Gln Ala Met Val Lys Asn Glu Thr Leu Pro
                245                 250                 255

Phe Trp Val Arg Leu Phe Phe Trp Lys Gln Val Ala Glu Lys Ile Pro
            260                 265                 270

Leu Gln Pro Lys His Phe Arg Ile Leu Asn Pro Val Ile Ile Lys Glu
            275                 280                 285

Thr Ala Phe Asp Ile Leu Gln Tyr Ser Glu Pro Gln Ser Arg Phe Trp
290                 295                 300

Gly Arg Asp Lys Asn Val Pro Thr Ile Gly Val Ile Ala Val Val Leu
305                 310                 315                 320

Ala Thr His Leu Cys Asp Glu Val Ser Leu Ala Gly Phe Gly Tyr Asp
                325                 330                 335

Leu Asn Gln Pro Lys Thr Pro Leu His Tyr Phe Asp Asn Leu Cys Met
            340                 345                 350

Ala Ala Met Asn Phe Gln Thr Met His Asn Val Thr Thr Glu Thr Arg
            355                 360                 365

Phe Leu Leu Lys Leu Val Lys Glu Gly Val Val Lys Asp Leu Ser Gly
            370                 375                 380

Gly Ile His Cys Glu Phe
385                 390

<210> SEQ ID NO 15
<211> LENGTH: 3159
<212> TYPE: DNA
<213> ORGANISM: Canis familiaris

<400> SEQUENCE: 15
```

```
ggtcgattgc cccttggctg ctgtggaggc tgtgatgacc tccagggccg cggccctccg    60
ggcgatgctt ctccagggge tgaggccaac gcagaactcc cgtggcaccc actcggactc   120
gcggcgtgtt cacatgtggg gttttattaa atcctcccac caaccgtgtg agacaggaac   180
agttagcccc ggtgtgtccg ccaagattgc cccgcacaag tggctccgga tggatcacac   240
gaagcacttg caagtgaaga agcagcacag ccctttatct tgggctattt cctgtggaga   300
gactccaaca atttagcagc caggctcctg ggcctctggg accctcacca catcacatcc   360
ttcaccttca ggagcagagc gcctttggga aacagacttc taaaagtgca ggtgggccag   420
ccatgagagg gtacctagtg gccatattcc tgagtgctgt ctttctctat tatgtgctgc   480
attgtatatt gtggggaaca acatctatt gggtgccacc tgtggaaatg aagcggagaa    540
ataagatcca gccttgttta gcgaagccag cttttgcctc tctcctgagg tttcatcagt   600 ttcaccctt tctgtgtgca gctgattta aaaagattgc ttccttgtat ggtagcgata    660
agtttgatct gccctatggg ataagaacat cagcggaata ttttcgactc gctctttcaa   720
aactgcagag ttgtgatctc tttgatgagt ttgacaatgt gccgtgtaaa aagtgcgtgg   780
tggttggtaa tggaggagtt ctgaagaata agacattagg agaaaaaatt gactcctatg   840
atgtcataat aagaatgaat aatggtcctg ttttaggaca tgaagaggaa gttgggagaa   900
ggacaacctt ccgactttt tatccagaat ctgtttttc agatcccaat cacaatgatc    960
ctaatactac agcgattctc actgctttta agccgcttga cttaaagtgg ctgtgggaag  1020
tgttgacggg tggcaaaata aacactaatg gttttggaa gaaaccagct ttaaacttga   1080
tctacaaacc ttatcaaatc agaatattag atcctttcat tatcagaatg gcagcttatg  1140
aactgcttca cttcccaaaa gtgtttccca aaaccagaa acccaaacac ccaacaacag    1200
gaattattgc catcacgctg gcctttcaca tatgtcacga agttcacctt gctggtttta  1260
aatacaattt ttctgacctc aagagcccctt tacactatta tgggaacgcg accatgtctt  1320
tgatgaataa gaatgcgtat cacaatgtga cagcggaaca gctcttttg aaggacattc   1380 tagaaaaaaa ctttgtaatc aacttgactg aagattgacc ctacagactc tgcagatgat  1440
gctaagagta ttagttttat ttttatactg caatttttag tttatttta aatatgttgg   1500 atgcacttgt caaaaaattg tgtatagtca gtctgttgct gcctggtgat tcataaccac  1560
cagcttaatt tctgtgaata tatttaattt ataaaaacca agaagatatg cttagatatc  1620
cgggaagttt tgattgcgtt ggttttaaaa caaccttagt tctctgaagt gttttaaac    1680 atctttttta atagttactt catctttgac ttctgagggc atgtgacgtc caagtaaggg  1740
gctttagctt gaccaccaca aactctgaac agagttggtg gcggattcgg ctactgtaaa  1800
ttggtgggga atagccatgt gattgtgcaa actggaaccg gttaggcaa gtatcgagtt    1860 cctttttact gaacccgagg aaacggattt gaatcttaaa gcaggcccaa ccatagcagt   1920
aggtacggtt atgaaatcta agatcataat ggtttcatta agcttttttt cctgtaagta   1980
aaccagatta taaatgaaa ggtgtttgtt tttaaggtgg aggaaacagg ctacatgtga    2040
aattctggat gagtaaacaa cctaggaatg caattactaa agtctggtgg ctgcattatt   2100
ttaaagttca tacaaagaag cagagctagg ccacctcaag gagacagttc ttaaacgtca   2160
tcttttgcct gccttaatat gttaaaattt ggaagtttac tatttgaaat aggaaagatg   2220
aatacggcac agtaggtaaa tccttcagac tcctcaggct gttttggat ttaaatggtc    2280 ctttcgtgaa aaatctcact tgtccacggt gaaatcccat cttcaaggg aaggcttacc    2340
```

```
cggctaccta gggtgcatca gagaagagtc ctgctggatg cagacaagtc aaaaccagcc    2400
tgtccaacaa acgtgcgccc gtctctcttc tcaaagaggg atggaatgaa cagctctcag    2460
aagaggtaag agttgaagga cttgttatcc tctgagcgat aatcgtcatg gagagacact    2520
gctggtgttc ctgaaaacca gcctgcctct gagtctcaga gacaaaatat gagagcagcc    2580
actgggataa atcgtgaagc acggcataag gggggagaag cctcgtagtt gattgaaccc    2640
atgtctacgt ggcttcagct gattcccctg taacggaggt ggaaagttcc cgcacgtaca    2700
cagctgcacg ctgcagcctg cggctgggga ttccatgggt ggactcattc agggtacaaa    2760
gacagtcctg gctgcaaagt gaaaaacccc aggtggcatt ttcaagtgtt tatggactga    2820
aataatggct gtacggtatc tggcggatgc tcaacttgag gaatcggcat ttttgtacag    2880
tgggagctga ggctataaac ctcagcgtgg cttcacataa gccagaagaa actctcagcc    2940
cgatacatat gtacaattta ttaaaaacac atgaacacgt taaaatctca ctatttatac    3000
aatctacatt ctagcaacat atacaaatac cgagtgacta cagtacatgc cgaggtaaga    3060
aaagtacatt cggggagact atcactgaca ctcaagccat ttttatttcc aatatgtttt    3120
gctttcacct ttcccagtgc caaaaaaaaa aaaaaaaa                            3159
```

<210> SEQ ID NO 16
<211> LENGTH: 331
<212> TYPE: PRT
<213> ORGANISM: Canis familiaris

<400> SEQUENCE: 16

```
Met Arg Gly Tyr Leu Val Ala Ile Phe Leu Ser Ala Val Phe Leu Tyr
1               5                   10                  15

Tyr Val Leu His Cys Ile Leu Trp Gly Thr Asn Ile Tyr Trp Val Pro
            20                  25                  30

Pro Val Glu Met Lys Arg Arg Asn Lys Ile Gln Pro Cys Leu Ala Lys
        35                  40                  45

Pro Ala Phe Ala Ser Leu Leu Arg Phe His Gln Phe His Pro Phe Leu
    50                  55                  60

Cys Ala Ala Asp Phe Lys Lys Ile Ala Ser Leu Tyr Gly Ser Asp Lys
65                  70                  75                  80

Phe Asp Leu Pro Tyr Gly Ile Arg Thr Ser Ala Glu Tyr Phe Arg Leu
                85                  90                  95

Ala Leu Ser Lys Leu Gln Ser Cys Asp Leu Phe Asp Glu Phe Asp Asn
            100                 105                 110

Val Pro Cys Lys Lys Cys Val Val Gly Asn Gly Gly Val Leu Lys
        115                 120                 125

Asn Lys Thr Leu Gly Glu Lys Ile Asp Ser Tyr Asp Val Ile Arg
    130                 135                 140

Met Asn Asn Gly Pro Val Leu His Glu Glu Val Gly Arg Arg
145                 150                 155                 160

Thr Thr Phe Arg Leu Phe Tyr Pro Glu Ser Val Phe Ser Asp Pro Asn
                165                 170                 175

His Asn Asp Pro Asn Thr Thr Ala Ile Leu Thr Ala Phe Lys Pro Leu
            180                 185                 190

Asp Leu Lys Trp Leu Trp Glu Val Leu Thr Gly Gly Lys Ile Asn Thr
        195                 200                 205

Asn Gly Phe Trp Lys Lys Pro Ala Leu Asn Leu Ile Tyr Lys Pro Tyr
    210                 215                 220

Gln Ile Arg Ile Leu Asp Pro Phe Ile Ile Arg Met Ala Ala Tyr Glu
```

```
             225                 230                 235                 240
Leu Leu His Phe Pro Lys Val Phe Pro Lys Asn Gln Lys Pro Lys His
                245                 250                 255

Pro Thr Thr Gly Ile Ile Ala Ile Thr Leu Ala Phe His Ile Cys His
                260                 265                 270

Glu Val His Leu Ala Gly Phe Lys Tyr Asn Phe Ser Asp Leu Lys Ser
                275                 280                 285

Pro Leu His Tyr Tyr Gly Asn Ala Thr Met Ser Leu Met Asn Lys Asn
                290                 295                 300

Ala Tyr His Asn Val Thr Ala Glu Gln Leu Phe Leu Lys Asp Ile Leu
305                 310                 315                 320

Glu Lys Asn Phe Val Ile Asn Leu Thr Glu Asp
                325                 330

<210> SEQ ID NO 17
<211> LENGTH: 1337
<212> TYPE: DNA
<213> ORGANISM: Canis familiaris

<400> SEQUENCE: 17
```

| | | | | | |
|---|---|---|---|---|---|
| aaagacttca | ctgggtatca | gtctcctttg | ggagaccaca | ggacacgtgt | cacctctccc | 60 |
| atcctctcag | cctccagccc | agaccttggc | agagttcctt | ttaggagtta | gcaagtggct | 120 |
| gaggaggcaa | gaggtgccag | agccaatcta | ctatctgctg | ggggatgatt | gccagggcca | 180 |
| gagatgaggg | ctcaatactt | gaagtgggt | ctggtagctg | cctgtatagt | tacgttatgg | 240 |
| ctgatgatga | tgaacttcct | ggaccaggag | ttcaaacaga | atgacttccc | taaaaagaca | 300 |
| agaatacaat | tatgccactg | ccccaggaac | tctttcagaa | agtgtaggtg | ttcgtttgag | 360 |
| atccgcaagt | gctctgcctg | cctccgcgta | cgtggaacgt | ctgtctggtt | tgatgaacgc | 420 |
| ttcgaaacgg | ctattgagcc | tgtgcagaga | ccagaagatc | ccatatcctc | tgatgctctg | 480 |
| atattgtggt | tgggtgtcca | atcaaagagg | gagtttgaga | ctcagaagcc | aatagaagag | 540 |
| cctcctgggc | aaccactggg | ctacgtggag | tccagttgtc | ggacctgtgc | agtggttgga | 600 |
| aactcaaggt | gcctacgggg | ctctggccat | ggattcagga | ttaaccaaaa | tgacatggtc | 660 |
| ctcaggatga | accaggcccc | cgtccaagga | tttgagatgg | atgtggggaa | cacaaccacc | 720 |
| atgcgcataa | tgtaccccga | tatggctagc | acgcagaatc | ctggcaccaa | attgctgctg | 780 |
| cttcctctga | attcatctgg | tctaaagtgg | tttatggaag | tactacagga | acagagcttc | 840 |
| agaaagccca | taaaccctgg | atttcagata | gtccagtttc | ctggtggaag | taacacgagc | 900 |
| aaagacgagg | tcttggtgat | cagcctcacc | tttcttcagt | acatccagga | tcattggctg | 960 |
| cgaaaacgtc | atcgtttcc | atccttgggg | tttgtgggtc | tgttatatgc | cctgcacact | 1020 |
| tgtgaccagg | tatccttatt | tggttttggg | acagatcagc | tcatgaggtg | gtcccattac | 1080 |
| tgggatgata | aatatcggtt | cgagagtaac | atgcacagtt | tcaaagaaga | gcagaagctc | 1140 |
| atcctccagc | tgcaatgtga | ggggaagatt | gttatctaca | gctgacatgt | ttctgtcctg | 1200 |
| ttcagcccac | tggaggcccc | aggaggctga | caggtagtca | aggggaccac | agagtgtcag | 1260 |
| agagggactg | gggcttcaag | tggaccctgg | atatagatca | gtctgctgct | aaataaaact | 1320 |
| acagcttatt | tctccca | | | | | 1337 |

```
<210> SEQ ID NO 18
<211> LENGTH: 333
<212> TYPE: PRT
<213> ORGANISM: Canis familiaris
```

<400> SEQUENCE: 18

Met Arg Ala Gln Tyr Leu Lys Trp Gly Leu Val Ala Ala Cys Ile Val
1               5                   10                  15

Thr Leu Trp Leu Met Met Met Asn Phe Leu Asp Gln Glu Phe Lys Gln
            20                  25                  30

Asn Asp Phe Pro Lys Lys Thr Arg Ile Gln Leu Cys His Cys Pro Arg
        35                  40                  45

Asn Ser Phe Arg Lys Cys Arg Cys Ser Phe Glu Ile Arg Lys Cys Ser
    50                  55                  60

Ala Cys Leu Arg Val Arg Gly Thr Ser Val Trp Phe Asp Glu Arg Phe
65                  70                  75                  80

Glu Thr Ala Ile Glu Pro Val Gln Arg Pro Glu Asp Pro Ile Ser Ser
                85                  90                  95

Asp Ala Leu Ile Leu Trp Leu Gly Val Gln Ser Lys Arg Glu Phe Glu
            100                 105                 110

Thr Gln Lys Pro Ile Glu Glu Pro Pro Gly Pro Leu Gly Tyr Val
        115                 120                 125

Glu Ser Ser Cys Arg Thr Cys Ala Val Val Gly Asn Ser Arg Cys Leu
130                 135                 140

Arg Gly Ser Gly His Gly Phe Arg Ile Asn Gln Asn Asp Met Val Leu
145                 150                 155                 160

Arg Met Asn Gln Ala Pro Val Gln Gly Phe Glu Met Asp Val Gly Asn
                165                 170                 175

Thr Thr Thr Met Arg Ile Met Tyr Pro Asp Met Ala Ser Thr Gln Asn
            180                 185                 190

Pro Gly Thr Lys Leu Leu Leu Pro Leu Asn Ser Ser Gly Leu Lys
        195                 200                 205

Trp Phe Met Glu Val Leu Gln Glu Gln Ser Phe Arg Lys Pro Ile Asn
210                 215                 220

Pro Gly Phe Gln Ile Val Gln Phe Pro Gly Gly Ser Asn Thr Ser Lys
225                 230                 235                 240

Asp Glu Val Leu Val Ile Ser Leu Thr Phe Leu Gln Tyr Ile Gln Asp
                245                 250                 255

His Trp Leu Arg Lys Arg His Arg Phe Pro Ser Leu Gly Phe Val Gly
            260                 265                 270

Leu Leu Tyr Ala Leu His Thr Cys Asp Gln Val Ser Leu Phe Gly Phe
        275                 280                 285

Gly Thr Asp Gln Leu Met Arg Trp Ser His Tyr Trp Asp Asp Lys Tyr
290                 295                 300

Arg Phe Glu Ser Asn Met His Ser Phe Lys Glu Glu Lys Leu Ile
305                 310                 315                 320

Leu Gln Leu Gln Cys Glu Gly Lys Ile Val Ile Tyr Ser
                325                 330

<210> SEQ ID NO 19

<400> SEQUENCE: 19

000

<210> SEQ ID NO 20
<211> LENGTH: 83
<212> TYPE: DNA
<213> ORGANISM: Artificial Sequence
<220> FEATURE:

<223> OTHER INFORMATION: A synthetic oligonucleotide

<400> SEQUENCE: 20
cctccttctt cctgaattac tcccacaccc ctccttttct gaattactcc cacacccctc    60
ctttcctgaa ttactcccac acc    83

<210> SEQ ID NO 21
<211> LENGTH: 59
<212> TYPE: DNA
<213> ORGANISM: Artificial Sequence
<220> FEATURE:
<223> OTHER INFORMATION: A synthetic oligonucleotide

<400> SEQUENCE: 21
ctttacctac tcccaccaca gcatggccac tttacctact cccaccacaa gcatggcca    59

<210> SEQ ID NO 22
<211> LENGTH: 87
<212> TYPE: DNA
<213> ORGANISM: Artificial Sequence
<220> FEATURE:
<223> OTHER INFORMATION: A synthetic oligonucleotide

<400> SEQUENCE: 22
ctcccccgcg gctgtggcgg ccgcccgcgc tcccccgcgg gctgtggcgg ccgcccgcgc    60
tcccccgcgc tgtggcggcc gcccgcg    87

<210> SEQ ID NO 23
<211> LENGTH: 319
<212> TYPE: DNA
<213> ORGANISM: Artificial Sequence
<220> FEATURE:
<223> OTHER INFORMATION: A synthetic oligonucleotide

<400> SEQUENCE: 23
tccccaggaa ccctgctacc ctctgagaat ccccaggacc ctgctaccct ctgagaatcc    60
ccaggacgat ggtggtgtca agtacttga aggcggcagg ggctcccaga ttggtcaggg   120
taaacaggtg gatgatattc tcggcctgct ctctgatggg cttatcccgg tgcttgttgt   180
aggcggacag cactttgtcc agattagcgt cggccaggat cactctcttg gagaactcgc   240
tgatctgctc gatgatctcg tccaggtagt gcttgtgctg ttccacaaac agctgtttca   300
ccctgctacc ctctgagaa    319

<210> SEQ ID NO 24
<211> LENGTH: 135
<212> TYPE: DNA
<213> ORGANISM: Artificial Sequence
<220> FEATURE:
<223> OTHER INFORMATION: A synthetic oligonucleotide

<400> SEQUENCE: 24
atcgctcaag accctctctg caatggtaca tcgctcaaga ccctctctga tggtacatcg    60
ctcaagacca atggtacatc gctcaagacc ctctctggca atggtacatc gctcaagacc   120
ctctctcaat ggtac    135

<210> SEQ ID NO 25
<211> LENGTH: 59
<212> TYPE: DNA
<213> ORGANISM: Artificial Sequence
<220> FEATURE:
<223> OTHER INFORMATION: A synthetic oligonucleotide

<400> SEQUENCE: 25
agcgataagt tgatctgcc ctatgggata agcgataagt ttgatctgcc tatgggata    59

<210> SEQ ID NO 26
<211> LENGTH: 57
<212> TYPE: DNA
<213> ORGANISM: Artificial Sequence
<220> FEATURE:
<223> OTHER INFORMATION: A synthetic oligonucleotide

<400> SEQUENCE: 26
gcccccgtcc aaggatttga gatggatgtg cccccgtcaa ggatttgaga tggatgt    57

<210> SEQ ID NO 27
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 27
ccctcctcgt cctcttcatc    20

<210> SEQ ID NO 28
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 28
aggcagagag agaccagaga    20

<210> SEQ ID NO 29
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 29
ccaaaccatg aagtgctccc    20

<210> SEQ ID NO 30
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 30
aggggcttga agagtgactc    20

<210> SEQ ID NO 31
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 31
atgagacttg cttgcatccc    20

<210> SEQ ID NO 32

```
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 32
ctttggttgg cctctctgtc tc                                             22

<210> SEQ ID NO 33
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 33
cgttagccgc gcgcacag                                                  18

<210> SEQ ID NO 34
<211> LENGTH: 17
<212> TYPE: DNA
<213> ORGANISM: Artificial Sequence
<220> FEATURE:
<223> OTHER INFORMATION: A synthetic oligonucleotide

<400> SEQUENCE: 34
ccgggatgac agctctc                                                   17

<210> SEQ ID NO 35
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 35
acatggaagc tggactcac                                                 19

<210> SEQ ID NO 36
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 36
catcatcaca aggatcctgc                                                20

<210> SEQ ID NO 37
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 37
ctctcccatg aaaacctgg                                                 19

<210> SEQ ID NO 38
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 38
```
gttttaaatt tgggagcggc c                                              21

<210> SEQ ID NO 39
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 39
tggctcacat caaacaccac                                                20

<210> SEQ ID NO 40
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 40
ggttggaaac tcaaggtgcc                                                20

<210> SEQ ID NO 41
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 41
tgactccttc ccctttccc                                                 20

<210> SEQ ID NO 42
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 42
gttacgcgcc agcaaaagca ggggaaaaca aaagcaa                             37

<210> SEQ ID NO 43
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 43
gttacgcgcc agtagaaaca agggtgtttt tctcatgc                            38

<210> SEQ ID NO 44
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 44
gttacgcgcc agcaaaagca ggagtttaaa at                                  32

<210> SEQ ID NO 45
<211> LENGTH: 38
<212> TYPE: DNA

<213> ORGANISM: Artificial Sequence
<220> FEATURE:
<223> OTHER INFORMATION: A synthetic oligonucleotide

<400> SEQUENCE: 45
gttacgcgcc agtagaaaca aggagttttt tgaacaac                               38

<210> SEQ ID NO 46
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 46
gttacgcgcc agcaaaagca ggggataatt ctattaa                                37

<210> SEQ ID NO 47
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 47
gttacgcgcc agtagaaaca agggtgtttt taattaatg                              39

<210> SEQ ID NO 48
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 48
gttacgcgcc agcaaaagca ggagtaaaga tg                                     32

<210> SEQ ID NO 49
<211> LENGTH: 41
<212> TYPE: DNA
<213> ORGANISM: Artificial Sequence
<220> FEATURE:
<223> OTHER INFORMATION: A synthetic oligonucleotide

<400> SEQUENCE: 49
gttacgcgcc agtagaaaca aggagttttt tctaaaattg c                           41

<210> SEQ ID NO 50
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 50
gttacgcgcc agcagaagca gagcattttc taatatcc                               38

<210> SEQ ID NO 51
<211> LENGTH: 43
<212> TYPE: DNA
<213> ORGANISM: Artificial Sequence
<220> FEATURE:
<223> OTHER INFORMATION: A synthetic oligonucleotide

<400> SEQUENCE: 51
gttacgcgcc agtagtaaca agagcatttt tcaataacgt ttc                         43

<210> SEQ ID NO 52
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 52
gttacgcgcc agcagaagca gagcatcttc tcaaaactg                                    39

<210> SEQ ID NO 53
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 53
gttacgcgcc agtagtaaca agagcatttt tcagaaac                                     38

<210> SEQ ID NO 54
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 54
agaaaagaat gtaacagtaa cacactctgt                                              30

<210> SEQ ID NO 55
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 55
tgtttccaca atgtargacc at                                                      22

<210> SEQ ID NO 56
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 56
ctattggaca atagtaaaac cgggrga                                                 27

<210> SEQ ID NO 57
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 57
gtcattgggr atgcttccat ttgg                                                    24

<210> SEQ ID NO 58

<400> SEQUENCE: 58

000

<210> SEQ ID NO 59
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 59
cctgttacat ctgggtgctt tcctataatg					30

<210> SEQ ID NO 60
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 60
gttgatarcc tgatatgttc gtatcctckg					30

<210> SEQ ID NO 61
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 61
cctgttacat ccgggtgctt ycctataatg					30

<210> SEQ ID NO 62
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 62
gttgataacc tkatmttttc atatcctctg					30

<210> SEQ ID NO 63
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 63
ccmaggtcga aacgtaygtt ctctctatc					29

<210> SEQ ID NO 64
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 64
tgacagraty ggtcttgtct ttagccaytc ca					32

<210> SEQ ID NO 65
<211> LENGTH: 17
<212> TYPE: DNA
<213> ORGANISM: Artificial Sequence
<220> FEATURE:

<223> OTHER INFORMATION: A synthetic oligonucleotide

<400> SEQUENCE: 65
ggagcaacca atgccac                    17

<210> SEQ ID NO 66
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 66
gtktaggcgg tcttgaccag                 20

<210> SEQ ID NO 67
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 67
cagccagcaa trttrcattt acc             23

<210> SEQ ID NO 68
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 68
cagccagcaa trttrcattt acc             23

<210> SEQ ID NO 69
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 69
aagtaacccc kaggagcaat tag             23

<210> SEQ ID NO 70
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 70
aagtaacccc kaggagcaat tag             23

<210> SEQ ID NO 71
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 71
ttagacagct gcctaacc                   18

```
<210> SEQ ID NO 72
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 72
ttagacagct gcctaacc                                                 18

<210> SEQ ID NO 73
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 73
tcaggcaact asccaatc                                                 18

<210> SEQ ID NO 74
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 74
tcaggcaact asccaatc                                                 18

<210> SEQ ID NO 75
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 75
atytcggctt tgaggggggcc tg                                           22

<210> SEQ ID NO 76
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 76
ataaactttg aagcaggaat                                               20

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000
```

```
<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<400> SEQUENCE: 90
000
```

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 1221
<212> TYPE: DNA
<213> ORGANISM: Homo sapiens

<400> SEQUENCE: 100

```
atgattcaca ccaacctgaa gaaaaagttc agctgctgcg tcctggtctt tcttctgttt      60
gcagtcatct gtgtgtggaa ggagaagaag aaagggagtt actatgattc ctttaaattg     120
caaaccaagg aattccaggt gttaaagagt ctggggaaat tggccatggg gtctgattcc     180
cagtctgtat cctcaagcag cacccaggac ccccacaggg gccgccagac cctcggcagt     240
ctcagaggcc tagccaaggc caaaccagag gcctccttcc aggtgtggaa caaggacagc     300
```

```
tcttccaaaa accttatccc taggctgcaa aagatctgga agaattacct aagcatgaac    360
aagtacaaag tgtcctacaa ggggccagga ccaggcatca agttcagtgc agaggccctg    420
cgctgccacc tccgggacca tgtgaatgta tccatggtag aggtcacaga ttttcccttc    480
aatacctctg aatgggaggg ttatctgccc aaggagagca ttaggaccaa ggctgggcct    540
tggggcaggt gtgctgttgt gtcgtcagcg ggatctctga agtcctccca actaggcaga    600
gaaatcgatg atcatgacgc agtcctgagg tttaatgggg cacccacagc caacttccaa    660
caagatgtgg gcacaaaaac taccattcgc ctgatgaact ctcagttggt taccacagag    720
aagcgcttcc tcaaagacag tttgtacaat gaaggaatcc taattgtatg ggacccatct    780
gtataccacc cagatatccc aaagtggtac cagaatccgg attataattt ctttaacaac    840
tacaagactt atcgtaagct gcaccccaat cagccctttt acatcctcaa gccccagatg    900
ccttgggagc tatgggacat tcttcaagaa atctccccag aagagattca gccaaacccc    960
ccatcctctg ggatgcttgg tatcatcatc atgatgacgc tgtgtgacca ggtggatatt   1020
tatgagttcc tcccatccaa gcgcaggact gacgtgtgct actactacca gaagttcttc   1080
gatagtgcct gcacgatggg tgcctaccac ccgctgctct ttgagaagaa tttggtgaag   1140
catctcaacc agggcacaga tgaggacatc tacctgcttg aaaagccac actgcctggc    1200
ttccggacca ttcactgcta a                                              1221
```

<210> SEQ ID NO 101
<211> LENGTH: 406
<212> TYPE: PRT
<213> ORGANISM: Homo sapiens

<400> SEQUENCE: 101

```
Met Ile His Thr Asn Leu Lys Lys Phe Ser Cys Cys Val Leu Val
1               5                   10                  15

Phe Leu Leu Phe Ala Val Ile Cys Val Trp Lys Glu Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
        115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

Leu Lys Ser Ser Gln Leu Gly Arg Glu Ile Asp Asp His Asp Ala Val
        195                 200                 205
```

```
Leu Arg Phe Asn Gly Ala Pro Thr Ala Asn Phe Gln Gln Asp Val Gly
        210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Pro Asp Ile Pro Lys Trp Tyr Gln Asn
                260                 265                 270

Pro Asp Tyr Asn Phe Phe Asn Asn Tyr Lys Thr Tyr Arg Lys Leu His
            275                 280                 285

Pro Asn Gln Pro Phe Tyr Ile Leu Lys Pro Gln Met Pro Trp Glu Leu
        290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Arg Thr Asp Val
            340                 345                 350

Cys Tyr Tyr Tyr Gln Lys Phe Phe Asp Ser Ala Cys Thr Met Gly Ala
        355                 360                 365

Tyr His Pro Leu Leu Phe Glu Lys Asn Leu Val Lys His Leu Asn Gln
    370                 375                 380

Gly Thr Asp Glu Asp Ile Tyr Leu Leu Gly Lys Ala Thr Leu Pro Gly
385                 390                 395                 400

Phe Arg Thr Ile His Cys
                405

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107
```

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

-continued

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

```
<210> SEQ ID NO 130
<400> SEQUENCE: 130
000

<210> SEQ ID NO 131
<400> SEQUENCE: 131
000

<210> SEQ ID NO 132
<400> SEQUENCE: 132
000

<210> SEQ ID NO 133
<400> SEQUENCE: 133
000

<210> SEQ ID NO 134
<400> SEQUENCE: 134
000

<210> SEQ ID NO 135
<400> SEQUENCE: 135
000

<210> SEQ ID NO 136
<400> SEQUENCE: 136
000

<210> SEQ ID NO 137
<400> SEQUENCE: 137
000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
```

```
<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150
<211> LENGTH: 406
<212> TYPE: PRT
<213> ORGANISM: Homo sapiens

<400> SEQUENCE: 150

Met Ile His Thr Asn Leu Lys Lys Phe Ser Cys Cys Val Leu Val
1               5                   10                  15

Phe Leu Leu Phe Ala Val Ile Cys Val Trp Lys Glu Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60
```

-continued

```
Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Lys Asn Leu Ile Pro Arg Leu Gln Lys Ile
            100                 105                 110

Trp Lys Asn Tyr Leu Ser Met Asn Lys Tyr Val Ser Tyr Lys Gly
            115                 120                 125

Pro Gly Pro Gly Ile Lys Phe Ser Ala Glu Ala Leu Arg Cys His Leu
130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
                180                 185                 190

Leu Lys Ser Ser Gln Leu Gly Arg Glu Ile Asp Asp His Asp Ala Val
            195                 200                 205

Leu Arg Phe Asn Gly Ala Pro Thr Ala Asn Phe Gln Gln Asp Val Gly
210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Pro Asp Ile Pro Lys Trp Tyr Gln Asn
                260                 265                 270

Pro Asp Tyr Asn Phe Phe Asn Asn Tyr Lys Thr Tyr Arg Lys Leu His
            275                 280                 285

Pro Asn Gln Pro Phe Tyr Ile Leu Lys Pro Gln Met Pro Trp Glu Leu
290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Arg Thr Asp Val
                340                 345                 350

Cys Tyr Tyr Tyr Gln Lys Phe Phe Asp Ser Ala Cys Thr Met Gly Ala
            355                 360                 365

Tyr His Pro Leu Leu Phe Glu Lys Asn Leu Val Lys His Leu Asn Gln
            370                 375                 380

Gly Thr Asp Glu Asp Ile Tyr Leu Leu Gly Lys Ala Thr Leu Pro Gly
385                 390                 395                 400

Phe Arg Thr Ile His Cys
                405
```

<210> SEQ ID NO 151
<211> LENGTH: 1221
<212> TYPE: DNA
<213> ORGANISM: Homo sapiens

<400> SEQUENCE: 151
atgattcaca ccaacctgaa gaaaaagttc agctgctgcg tcctggtctt tcttctgttt     60
gcagtcatct gtgtgtggaa ggagaagaag aaagggagtt actatgattc ctttaaattg    120

-continued

```
caaaccaagg aattccaggt gttaaagagt ctggggaaat tggccatggg gtctgattcc      180
cagtctgtat cctcaagcag cacccaggac ccccacaggg gccgccagac cctcggcagt      240
ctcagaggcc tagccaaggc caaaccagag gcctccttcc aggtgtggaa caaggacagc      300
tcttccaaaa accttatccc taggctgcaa aagatctgga agaattacct aagcatgaac      360
aagtacaaag tgtcctacaa ggggccagga ccaggcatca agttcagtgc agaggccctg      420
cgctgccacc tccgggacca tgtgaatgta tccatggtag aggtcacaga tttttcccttc     480 aatacctctg aatgggaggg ttatctgccc aaggagagca ttaggaccaa ggctgggcct      540
tggggcaggt gtgctgttgt gtcgtcagcg ggatctctga agtcctccca actaggcaga      600
gaaatcgatg atcatgacgc agtcctgagg tttaatgggg cacccacagc caacttccaa      660
caagatgtgg gcacaaaaac taccattcgc ctgatgaact ctcagttggt taccacagag      720
aagcgcttcc tcaaagacag tttgtacaat gaaggaatcc taattgtatg ggacccatct      780
gtataccacc cagatatccc aaagtggtac cagaatccgg attataattt ctttaacaac      840
tacaagactt atcgtaagct gcaccccaat cagcccttt acatcctcaa gccccagatg       900
ccttgggagc tatgggacat tcttcaagaa atctccccag aagagattca gccaaacccc      960
ccatcctctg ggatgcttgg tatcatcatc atgatgacgc tgtgtgacca ggtggatatt     1020
tatgagttcc tcccatccaa gcgcaggact gacgtgtgct actactacca gaagttcttc     1080
gatagtgcct gcacgatggg tgcctaccac ccgctgctct ttgagaagaa tttggtgaag     1140
catctcaacc agggcacaga tgaggacatc tacctgcttg gaaaagccac actgcctggc     1200
ttccggacca ttcactgcta a                                               1221
```